(12) United States Patent
Dhanak et al.

(10) Patent No.: US 7,419,988 B2
(45) Date of Patent: Sep. 2, 2008

(54) AZAINDOLE INHIBITORS OF AURORA KINASES

(75) Inventors: Dashyant Dhanak, Collegeville, PA (US); Kenneth Allen Newlander, Collegeville, PA (US)

(73) Assignee: SmithKline Beecham Corp, Philadelphia, PA (US)

( * ) Notice: Subject to any disclaimer, the term of this patent is extended or adjusted under 35 U.S.C. 154(b) by 0 days.

(21) Appl. No.: 11/835,434

(22) Filed: Aug. 8, 2007

(65) Prior Publication Data

US 2008/0004308 A1  Jan. 3, 2008

Related U.S. Application Data

(62) Division of application No. 11/612,531, filed on Dec. 19, 2006, now Pat. No. 7,282,588.

(60) Provisional application No. 60/753,383, filed on Dec. 23, 2005.

(51) Int. Cl.
*A61K 31/44* (2006.01)
(52) U.S. Cl. ...................................... 514/300
(58) Field of Classification Search ................ 514/300; 546/133
See application file for complete search history.

(56) References Cited

U.S. PATENT DOCUMENTS 6,770,643 B2   8/2004   Cox et al.
7,282,588 B2 *  10/2007  Dhanak et al. ............ 546/133
2006/0211678 A1   9/2006  Ahmed et al.

FOREIGN PATENT DOCUMENTS

WO   WO2007/076423   7/2007

* cited by examiner

*Primary Examiner*—D. Margaret Seaman
*Assistant Examiner*—Nizal S Chandrakumar
(74) *Attorney, Agent, or Firm*—Reid S. Willis; William Majarian; Stephen Venetianer

(57) ABSTRACT

The present invention relates to a compound represented by Formula (I):

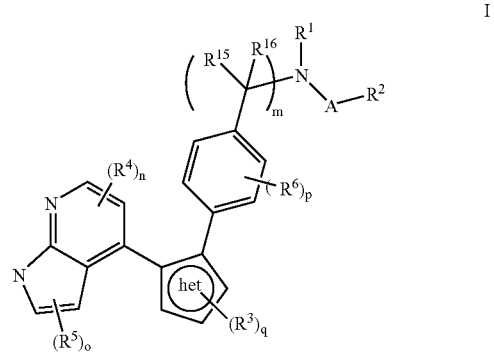

and pharmaceutically acceptable salts. Compounds of the present invention inhibit Aurora kinase, making them especially suitable for the treatment of a number of diseases, including solid tumor cancers and hematological cancers.

1 Claim, No Drawings

AZAINDOLE INHIBITORS OF AURORA KINASES

CROSS REFERENCE TO PRIOR APPLICATIONS

This application is a divisional of application Ser. No. 11/612,531, filed Dec. 19, 2006 now U.S. Pat. No. 7,282,588, which claims the benefit of U.S. Provisional Application No. 60/753,383, filed Dec. 23, 2005.

BACKGROUND OF THE INVENTION

The present invention relates to azaindole compounds, compositions, and medicaments thereof, as well as methods of treatments therefor. These azaindoles inhibit Aurora kinase.

Protein kinases catalyze the phosphorylation of hydroxylic amino acid side chains in proteins by the transfer of the γ-phosphate of ATP-$Mg^{2+}$ to form a mono-phosphate ester of serine, threonine or tyrosine. Studies have shown that protein kinases are key regulators of many cell functions, including signal transduction, transcriptional regulation, cell motility and cell division. Several oncogenes have also been shown to encode protein kinases, suggesting that kinases may play a role in oncogenesis.

The protein kinase family of enzymes is typically classified into two main subfamilies: protein tyrosine kinases and protein serine/threonine kinases, based on the amino acid residue they phosphorylate. Aberrant protein serine/threonine kinase activity has been implicated or is suspected in a number of pathologies such as rheumatoid arthritis, psoriasis, septic shock, bone loss, cancers and other proliferative diseases. Tyrosine kinases play an equally important role in cell regulation. These kinases include several receptors for molecules such as growth factors and hormones, including epidermal growth factor receptor, insulin receptor and platelet derived growth factor receptor. Studies have indicated that many tyrosine kinases are transmembrane proteins with their receptor domains located on the outside of the cell and their kinase domains on the inside. Accordingly, both kinase subfamilies and their signal transduction pathways are important targets for drug design.

Since its discovery in 1997, the mammalian Aurora family of serine/threonine kinases has been closely linked to tumorigenesis. The three known mammalian family members, Aurora-A ("2"), B ("1") and C ("3"), are highly homologous proteins responsible for chromosome segregation, mitotic spindle function and cytokinesis. Aurora expression is low or undetectable in resting cells, with expression and activity peaking during the G2 and mitotic phases in cycling cells. In mammalian cells proposed substrates for the Aurora A and B kinases include histone H3, CENP-A, myosin II regulatory light chain, protein phosphatase 1, TPX2, INCENP, p53 and survivin, many of which are required for cell division.

The Aurora kinases have been reported to be over-expressed in a wide range of human tumors. Elevated expression of Aurora-A has been detected in colorectal, ovarian and pancreatic cancers and in invasive duct adenocarcinomas of the breast. High levels of Aurora-A have also been reported in renal, cervical, neuroblastoma, melanoma, lymphoma, pancreatic and prostate tumor cell lines. Amplification/over-expression of Aurora-A is observed in human bladder cancers and amplification of Aurora-A is associated with aneuploidy and aggressive clinical behavior. Moreover, amplification of the Aurora-A locus (20q13) correlates with poor prognosis for patients with node-negative breast cancer. In addition, an allelic variant, isoleucine at amino acid position 31, is reported to be a low-penetrance tumor-susceptibility gene and displays greater transforming potential than the phenylalanine-31 variant and is associated with increased risk for advanced and metastatic disease. Like Aurora A, Aurora-B is also highly expressed in multiple human tumor cell lines, including leukemic cells. Levels of Aurora-B increase as a function of Duke's stage in primary colorectal cancers. Aurora-C, which is normally only found in germ cells, is also over-expressed in a high percentage of primary colorectal cancers and in a variety of tumor cell lines including cervical adenocarinoma and breast carcinoma cells.

It has been suggested that in vitro an inhibitor of Aurora kinase activity disrupts mitosis causing cell cycle defects and eventual cell death. Therefore, in vivo, an Aurora kinase inhibitor should slow tumor growth and induce regression. For example, Hauf et al. describe an Aurora B inhibitor, Hesperadin, that causes defects in chromosomal segregation and a block in cytokinesis, thereby resulting in polyploidy [Hauf, S et al. JCB 161(2), 281-294 (2003)]. Ditchfield et al. have described an equipotent inhibitor of Aurora A and B (ZM447439) that causes defects in chromosome alignment, chromosome segregation and cytokinesis [Ditchfield, C. et al., JCB 161(2), 267-280 (2003)]. Furthermore, the authors show that proliferating cells, but not cell-cycle arrested cells, are sensitive to the inhibitor. Efficacy of a potent Aurora A and B inhibitor in mouse and rat xenograft models was recently reported [Harrington, E. A. et al., Nature Medicine 10(3), 262-267, (2004)]. These results demonstrate that inhibition of Aurora kinases can provide a therapeutic window for the treatment of proliferative disorders such as cancer (see Nature, Cancer Reviews, Vol. 4, p 927-936, December 2004, for a review by N. Keen and S Taylor).

In view of the teachings of the art, there is a need for the discovery of kinase activity inhibitors, in particular, compounds that inhibit the activity of Aurora kinases.

SUMMARY OF THE INVENTION

In a first aspect, the present invention is a compound of formula (I):

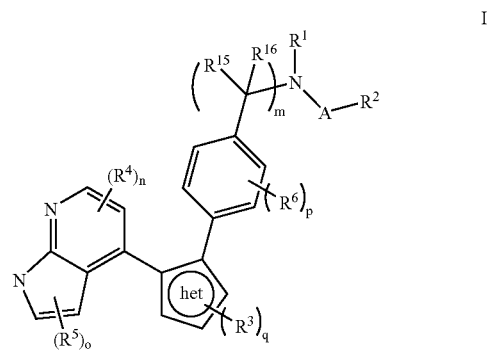

or a pharmaceutically acceptable salt thereof, wherein:

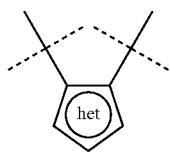

represents a 5-membered heteroaromatic ring fragment;

A is >C=Y or >S(O)$_x$ wherein Y is O, S, or N—R$^1$; wherein x is 1 or 2;

R$^1$ is independently H, C$_1$-C$_3$-alkyl, or cyclopropyl;

R$^2$ is H, C$_1$-C$_6$ alkyl, halo-C$_1$-C$_6$-alkyl, C$_3$-C$_6$-cycloalkyl, C$_1$-C$_6$ alkoxy, hydroxy-C$_1$-C$_6$-alkyl, amino-C$_1$-C$_6$ alkyl, C$_1$-C$_6$ alkoxymethyl, hydroxy, —(CH$_2$)$_y$—Ar—(R$^7$)$_z$, or NR$^8$R$^9$, with the proviso that when A is S(O)$_x$, R$^2$ is not H; wherein y is 0, 1, or 2; and z is a non-negative integer not greater than the number of positions available on Ar for substitution;

Ar is phenyl or heteroaryl;

R$^3$ is independently H, C$_1$-C$_6$-alkyl, C$_2$-C$_6$-alkenyl, halo-C$_1$-C$_6$-alkyl, hydroxy-C$_1$-C$_6$-alkyl, amino-C$_1$-C$_6$-alkyl, C$_1$-C$_6$-alkylamino-C$_1$-C$_6$-alkyl, di-C$_1$-C$_6$-alkylamino-C$_1$-C$_6$-alkyl, —(CH$_2$)$_w$—R$^{10}$; wherein w is 1 or 2;

R$^4$ is independently C$_1$-C$_6$-alkyl, halo, halo-C$_1$-C$_6$-alkyl, or Ar—(R$^7$)$_z$;

R$^5$ is independently C$_1$-C$_6$-alkyl, halo, halo-C$_1$-C$_6$-alkyl, Ar—(R$^7$)$_z$, —(CH$_2$)$_a$NR$^{13}$R$^{14}$, —Ar—(CH$_2$)$_a$NR$^{13}$R$^{14}$, -A'—NR$^1$—(CH$_2$)$_b$-A'', —CH$_2$CH$_2$C(O)-A''', or —Ar'—(C(O)(CH$_2$)$_a$NR$^{13}$R$^{14}$)$_c$;

wherein A' is C(O) or CH$_2$; A'' is H, NR$^{13}$R$^{14}$, C$_1$-C$_6$-thioalkyl, C$_1$-C$_6$-alkoxy, —SO$_2$CH$_3$, or —OH; A''' is —OH, C$_1$-C$_6$-alkoxy, or —NR$^{13}$R$^{14}$, and Ar' is a 5- or 6-membered heterocycloalkyl ring;

wherein a is independently 0, 1, or 2; b is 1, 2, or 3, with the proviso that when b is 1, A'' is H; and c is 0 or 1;

R$^6$ and each R$^7$ are each independently halo, cyano, nitro, C$_1$-C$_6$-alkyl, COOH, C$_1$-C$_6$-alkylcarbonyl, C$_1$-C$_6$-alkyl-carbonyl-C$_1$-C$_6$-alkyl, amino, C$_1$-C$_6$-alkylamino, di-C$_1$-C$_6$-alkylamino, amino-C$_1$-C$_6$-alkyl, C$_1$-C$_6$-alkylamino-C$_1$-C$_6$-alkyl, di-C$_1$-C$_6$-alkylamino-C$_1$-C$_6$-alkyl, OH, halo-C$_1$-C$_6$-alkyl, hydroxy-C$_1$-C$_6$-alkyl, C$_1$-C$_6$-alkoxy, C$_1$-C$_6$-alkoxy-C$_1$-C$_6$-alkyl, heteroaryl, or phenyl;

R$^8$ is H or C$_1$-C$_6$-alkyl;

R$^9$ is H, C$_1$-C$_6$-alkyl, halo-C$_1$-C$_6$-alkyl, C$_3$-C$_6$-cycloalkyl, C$_1$-C$_6$ alkoxy, —(CH$_2$)$_y$—Ar—(R$^7$)$_z$; or R$^8$ and R$^9$, together with the nitrogen atom to which they are attached form a 5- or 6-membered heterocycloalkyl ring optionally substituted with C$_1$-C$_6$-alkyl, halo, amino, cyano, C$_1$-C$_6$-alkoxy, or OH;

R$^{10}$ is heterocycloalkyl, Ar—(R$^7$)$_z$, COOH, or C(O)—NR$^{11}$R$^{12}$

R$^{11}$ is H or C$_1$-C$_3$-alkyl;

R$^{12}$ is H, C$_1$-C$_6$-alkyl, halo-C$_1$-C$_3$-alkyl, or hydroxy-C$_1$-C$_3$-alkyl; or R$^{11}$ and R$^{12}$, together with the nitrogen atom to which they are attached form 5- or 6-membered heterocycloalkyl ring optionally substituted with C$_1$-C$_6$-alkyl, halo, amino, cyano, C$_1$-C$_6$-alkoxy, or hydroxy;

R$^{13}$ is H, C$_1$-C$_6$-alkyl, or hydroxy-C$_1$-C$_6$-alkyl;

R$^{14}$ is H, C$_1$-C$_6$-alkyl, halo-C$_1$-C$_6$-alkyl, hydroxy-C$_1$-C$_6$-alkyl, C$_1$-C$_6$-alkylamino, or SO$_2$CH$_3$; or R$^{13}$ and R$^{14}$, together with the nitrogen atom to which they are attached form 5- or 6-membered heterocycloalkyl ring optionally substituted with C$_1$-C$_6$-alkyl, halo, amino, cyano, C$_1$-C$_6$-alkoxy, hydroxy-C$_1$-C$_6$-alkyl, or OH; and R$^{15}$ and R$^{16}$ are each independently H, C$_1$-C$_6$-alkyl, or halo, or R$^{15}$ and R$^{16}$, together with the carbon atom to which they are attached form cyclopropyl, C=O, C=S, or C=NR$^1$;

m is 0 or 1;

n, o, and q are each independently 0, 1, or 2; and p is 0, 1, 2, 3, or 4.

In another aspect, the present invention is a composition comprising the compound represented by Formula (I), or a salt thereof, in admixture with one or more pharmaceutically acceptable excipients.

In another aspect, the present invention is a method for treating a disease of cell proliferation comprising administering to a patient in need thereof a compound represented by Formula I or a salt thereof.

In another aspect the present invention is a method comprising the step of administering to a patient in need thereof an effective amount of a composition comprising (a) the compound represented by Formula (I), or a salt thereof, and (b) at least one pharmaceutically acceptable excipient.

In another aspect, the present invention relates to the compound N'-{4-[4-(2-{3-[(dimethylamino)methyl]phenyl}-1H-pyrrolo[2,3-b]pyridin-4-yl)-1-ethyl-1H-pyrazol-3-yl]phenyl}-N,N-dimethylurea or a pharmaceutically acceptable salt thereof.

In another aspect, the present invention relates to a composition comprising N'-{4-[4-(2-{3-[(dimethylamino)methyl]phenyl}-1H-pyrrolo[2,3-b]pyridin-4-yl)-1-ethyl-1H-pyrazol-3-yl]phenyl}-N,N-dimethylurea or a pharmaceutically acceptable salt thereof, and (b) at least one pharmaceutically acceptable excipient.

In another aspect, the present invention relates to a method for treating cancer comprising administering to a patient in need thereof N'-{4-[4-(2-{3-[(dimethylamino)methyl]phenyl}-1H-pyrrolo[2,3-b]pyridin-4-yl)-1-ethyl-1H-pyrazol-3-yl]phenyl}-N,N-dimethylurea or a pharmaceutically acceptable salt thereof.

In another aspect, the present invention relates to a method for treating cancer comprising the step of administering to a patient in need thereof an effective amount of a composition comprising N'-{4-[4-(2-{3-[(dimethylamino)methyl]phenyl}-1H-pyrrolo[2,3-b]pyridin-4-yl)-1-ethyl-1H-pyrazol-3-yl]phenyl}-N,N-dimethylurea or a pharmaceutically acceptable salt thereof, and (b) at least one pharmaceutically acceptable excipient.

In another aspect, m is 0.

In another aspect, n is 0; p is 0, 1, or 2, and each R$^6$ is independently halo, cyano, nitro, C$_1$-C$_6$-alkyl, C$_1$-C$_6$-alkylcarbonyl, amino, C$_1$-C$_6$-alkylamino, di-C$_1$-C$_6$-alkylamino, amino-C$_1$-C$_6$-alkyl, OH, halo-C$_1$-C$_6$-alkyl, or C$_1$-C$_6$-alkoxy.

In another aspect p is 0 and

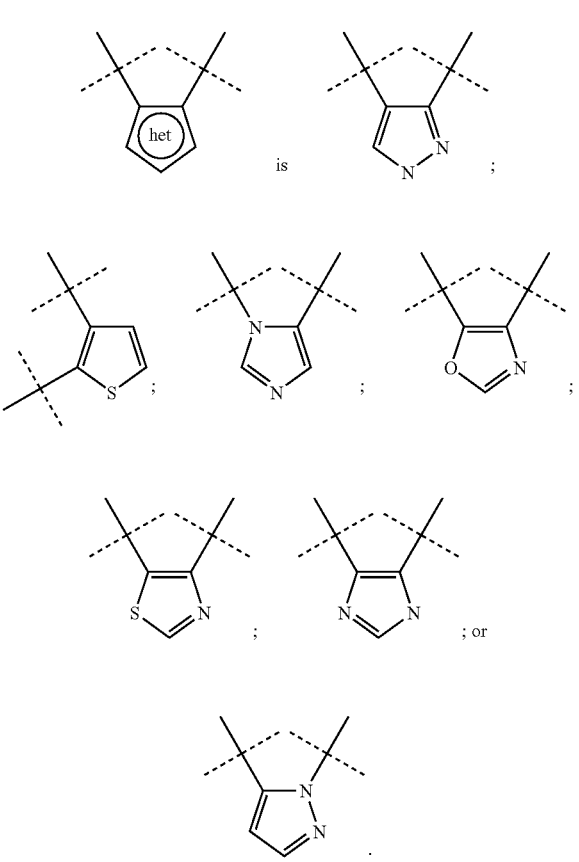

In another aspect, q is 0 or 1, and R³ is C₁-C₆-alkyl, C₂-C₆-alkenyl, halo-C₁-C₆-alkyl, hydroxy-C₁-C₆-alkyl, amino-C₁-C₆-alkyl, C₁-C₆-alkylamino-C₁-C₆-alkyl, di-C₁-C₆-alkylamino-C₁-C₆-alkyl, —(CH₂)$_w$—R¹⁰ where w is 1 or 2, R¹⁰ is heterocycloalkyl, Ar—(R⁷)$_z$, COOH, or C(O)—NR¹¹R¹² where R¹¹ is H or C₁-C₃-alkyl; R¹² is H, C₁-C₆-alkyl, halo-C₁-C₃-alkyl, or hydroxy-C₁-C₃-alkyl; or R¹¹ and R¹², together with the nitrogen atom to which they are attached form 5- or 6-membered heterocycloalkyl ring optionally substituted with C₁-C₆-alkyl, halo, amino, cyano, C₁-C₆-alkoxy, or hydroxy; and

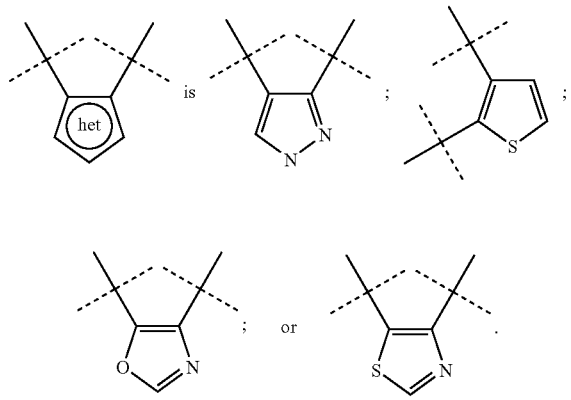

In another aspect,

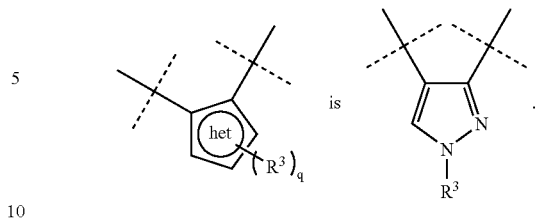

In another aspect, R¹ is H, R² is C₁-C₆-alkyl, fluoro-C₁-C₆-alkyl, phenyl, thienylmethyl, C₃-C₆-cycloalkyl, halophenyl, cyanophenyl, trifluoromethylphenyl, benzyl, methoxy, ethoxy, methoxymethyl, N-methylpyrrolyl, or NR⁸R⁹, where R⁸ is H or C₁-C₆ alkyl and R⁹ is C₁-C₆ alkyl, C₃-C₆-cycloalkyl, phenyl, halophenyl, cyanophenyl, tolyl, methoxyphenyl, trifluoromethylphenyl, biphenyl, benzyl, pyrrolyl, pyridinyl, thiazolyl, or thienyl, or R⁸ and R⁹, together with the nitrogen atom to which they are attached, form a morpholino, thiomorpholino, thiomorpholinyl-1,1-dioxide, pyrrolidinyl, hydroxypyrrolidinyl, or piperidinyl group;

R³ is C₁-C₆ alkyl, C₁-C₆-alkylamino-C₁-C₆-alkyl, trifluoromethyl, 2,2,2-trifluoroethyl, 1,1,1,3,3,3-hexafluoroisopropyl, methoxybenzyl, hydroxyethyl, hydroxypropyl, acetic acid, acetamide, morpholinyloxoethyl, methoxyphenylacetamide, hydroxyethylacetamide, or dihydroxypropyl;

R⁴ is C₁-C₆-alkyl, halo, or dimethylaminomethylphenyl; n is 0 or 1; and

R⁵ is acetanilido, dimethylaminomethylphenyl, methylaminomethylphenyl, morpholinomethylphenyl, pyrrolidinylmethylphenyl, ethyl(2-hydroxyethyl)aminomethylphenyl, 2-hydroxyethyl-1-piperazinylmethylphenyl, hydroxylmethylphenyl, 4-methyl-1-piperazinylpyrimidinyl, morpholinoethylaminomethyl, hydroxyethylaminomethyl, dimethylaminomethyl, dimethylaminoethylaminomethyl, dimethylaminomethylcarbonyltetrahydropyridinyl, tetrahydropyridinyl, morpholinopyridinyl, morpholinocarbonyltetrahydropyridinyl, methylsulfonylethylaminomethyl, 4-methylpiperazinylpropylaminomethyl, —CH₂CH₂C(O)-A‴, where A‴ is C₁-C₂-alkoxy, OH, or 4-methylpiperazinyl; or —C(O)NH(CH₂)$_r$NR¹³NR¹⁴, where R¹³ and R¹⁴, together with the nitrogen to which they are attached, form N-morpholino, N-thiomorpholino, piperazinyl, 4-methylpiperazinyl, or —SCH₃; wherein r is 2 or 3.

In another aspect, the present invention is a compound selected from the group consisting of:

N'-{4-[4-(2-{3-[(dimethylamino)methyl]phenyl}-1H-pyrrolo[2,3-b]pyridin-4-yl)-1-ethyl-1H-pyrazol-3-yl]phenyl}-N,N-dimethylurea;

N-{4-[4-(2-{3-[(dimethylamino)methyl]phenyl}-1H-pyrrolo[2,3-b]pyridin-4-yl)-1-ethyl-1H-pyrazol-3-yl]phenyl}-N'-phenylurea;

N-{4-[4-(2-{3-[(dimethylamino)methyl]phenyl}-1H-pyrrolo[2,3-b]pyridin-4-yl)-1-ethyl-1H-pyrazol-3-yl]phenyl}-N'-ethylurea;

N'-[4-(1-ethyl-4-{2-[3-(4-morpholinylmethyl)phenyl]-1H-pyrrolo[2,3-b]pyridin-4-yl}-1H-pyrazol-3-yl)phenyl]-N,N-dimethylurea;

N'-{4-[4-(2-{4-[(dimethylamino)methyl]phenyl}-1H-pyrrolo[2,3-b]pyridin-4-yl)-1-ethyl-1H-pyrazol-3-yl]phenyl}-N,N-dimethylurea;

N-{4-[4-(2-{4-[(dimethylamino)methyl]phenyl}-1H-pyrrolo[2,3-b]pyridin-4-yl)-1-ethyl-1H-pyrazol-3-yl]phenyl}-N'-ethylurea;

N'-[4-(1-ethyl-4-{2-[4-(1-pyrrolidinylmethyl)phenyl]-1H-pyrrolo[2,3-b]pyridin-4-yl}-1H-pyrazol-3-yl)phenyl]-N,N-dimethylurea;

N'-(4-{1-ethyl-4-[2-(1,2,3,6-tetrahydro-4-pyridinyl)-1H-pyrrolo[2,3-b]pyridin-4-yl]-1H-pyrazol-3-yl}phenyl)-N,N-dimethylurea;

N'-[4-(4-{2-[3-(dimethylamino)phenyl]-1H-pyrrolo[2,3-b]pyridin-4-yl}-1-ethyl-1H-pyrazol-3-yl)phenyl]-N,N-dimethylurea;

N'-{4-[4-(2-{4-[(dimethylamino)methyl]phenyl}-1H-pyrrolo[2,3-b]pyridin-4-yl)-1-methyl-1H-pyrazol-3-yl]phenyl}-N,N-dimethylurea;

N'-{4-[4-(2-{4-[(dimethylamino)methyl]phenyl}-1H-pyrrolo[2,3-b]pyridin-4-yl)-1-(1-methylethyl)-1H-pyrazol-3-yl]phenyl}-N,N-dimethylurea;

N,N-dimethyl-N'-[4-(1-methyl-4-{2-[4-(1-pyrrolidinylmethyl)phenyl]-1H-pyrrolo[2,3-b]pyridin-4-yl}-1H-pyrazol-3-yl)phenyl]urea;

N'-(4-{4-[2-(4-{[ethyl(2-hydroxyethyl)amino]methyl}phenyl)-1H-pyrrolo[2,3-b]pyridin-4-yl]-1-methyl-1H-pyrazol-3-yl}phenyl)-N,N-dimethylurea;

N'-{4-[4-(2-{4-[(dimethylamino)methyl]phenyl}-1H-pyrrolo[2,3-b]pyridin-4-yl)-1-ethyl-1H-pyrazol-3-yl]phenyl}-N,N-diethylurea;

N,N-diethyl-N'-[4-(1-ethyl-4-{2-[4-(1-pyrrolidinylmethyl)phenyl]-1H-pyrrolo[2,3-b]pyridin-4-yl}-1H-pyrazol-3-yl)phenyl]urea;

N'-(4-{1-ethyl-4-[2-(4-{[ethyl(2-hydroxyethyl)amino]methyl}phenyl)-1H-pyrrolo[2,3-b]pyridin-4-yl]-1H-pyrazol-3-yl}phenyl)-N,N-dimethylurea;

N'-{4-[4-[2-(4-{[ethyl(2-hydroxyethyl)amino]methyl}phenyl)-1H-pyrrolo[2,3-b]pyridin-4-yl]-1-(1-methylethyl)-1H-pyrazol-3-yl]phenyl}-N,N-dimethylurea;

N,N-diethyl-N'-(4-{4-[2-(4-{[4-(2-hydroxyethyl)-1-piperazinyl]methyl}phenyl)-1H-pyrrolo[2,3-b]pyridin-4-yl]-1-methyl-1H-pyrazol-3-yl}phenyl)urea;

N'-{4-[1-ethyl-4-(2-{3-[(methylamino)methyl]phenyl}-1H-pyrrolo[2,3-b]pyridin-4-yl)-1H-pyrazol-3-yl]phenyl}-N,N-dimethylurea;

N'-{4-[4-(2-{4-[(dimethylamino)methyl]phenyl}-1H-pyrrolo[2,3-b]pyridin-4-yl)-1-(1-methylethyl)-1H-pyrazol-3-yl]phenyl}-N,N-diethylurea;

N'-{4-[4-(2-{4-[(dimethylamino)methyl]phenyl}-1H-pyrrolo[2,3-b]pyridin-4-yl)-1-methyl-1H-pyrazol-3-yl]phenyl}-N,N-diethylurea;

N'-(4-{4-[2-{3-[(dimethylamino)methyl]phenyl}-1H-pyrrolo[2,3-b]pyridin-4-yl)-1-[2-(methylamino)ethyl]-1H-pyrazol-3-yl}phenyl)-N,N-dimethylurea;

N'-(4-{4-{2-[3-(hydroxymethyl)phenyl]-1H-pyrrolo[2,3-b]pyridin-4-yl}-1-[2-(methylamino)ethyl]-1H-pyrazol-3-yl}phenyl)-N,N-dimethylurea;

N'-{4-[1-[2-(dimethylamino)ethyl]-4-(2-{3-[(dimethylamino)methyl]phenyl}-1H-pyrrolo[2,3-b]pyridin-4-yl)-1H-pyrazol-3-yl]phenyl}-N,N-dimethylurea; and N,N-dimethyl-N'-[4-(1-methyl-4-{2-[2-(4-methyl-1-piperazinyl)-5-pyrimidinyl]-1H-pyrrolo[2,3-b]pyridin-4-yl}-1H-pyrazol-3-yl)phenyl]urea;

or a pharmaceutically acceptable salt thereof.

The present invention addresses a need in the art by providing a class of azaindoles that inhibit Aurora kinase activity. Such compounds are useful in the treatment of disorders associated with inappropriate Aurora kinase family activity, for example, solid tumor cancers including lung cancer, breast cancer, colon cancer, ovarian cancer, melanoma, and pancreatic cancer, as well as hematological cancers including leukemia and B-cell lymphomas, AML and CML. Accordingly, in another aspect, the present invention is a method for treating a cancer, including any or all of the above-described cancers, comprising administering to a patient in need thereof a compound of Formula I, including any of the compounds specifically named herein and pharmaceutically acceptable salts thereof.

DETAILED DESCRIPTION OF THE INVENTION

In a first aspect, the present invention is a compound of formula (I):

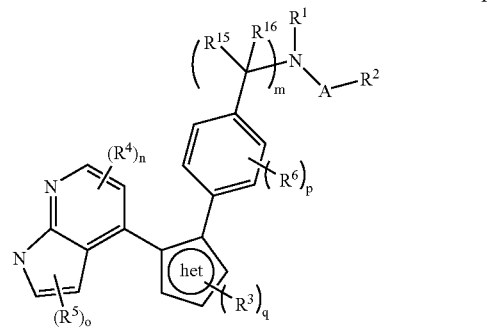

or a pharmaceutically acceptable salt thereof, wherein:

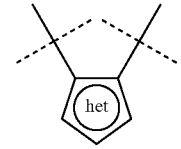

represents a 5-membered heteroaromatic ring fragment;

A is >C=Y or >S(O)$_x$ wherein Y is O, S, or N—R$^1$; wherein x is 1 or 2;

R$^1$ is independently H, C$_1$-C$_3$-alkyl, or cyclopropyl;

R$^2$ is H, C$_1$-C$_6$ alkyl, halo-C$_1$-C$_6$-alkyl, C$_3$-C$_6$-cycloalkyl, C$_1$-C$_6$ alkoxy, hydroxy-C$_1$-C$_6$-alkyl, amino-C$_1$-C$_6$ alkyl, C$_1$-C$_6$ alkoxymethyl, hydroxy, —(CH$_2$)$_y$—Ar—(R$^7$)$_z$, or NR$^8$R$^9$, with the proviso that when A is S(O)$_x$, R$^2$ is not H; wherein y is 0, 1, or 2; and z is a non-negative integer not greater than the number of positions available on Ar for substitution;

Ar is phenyl or heteroaryl;

R$^3$ is independently H, C$_1$-C$_6$-alkyl, C$_2$-C$_6$-alkenyl, halo-C$_1$-C$_6$-alkyl, hydroxy-C$_1$-C$_6$-alkyl, amino-C$_1$-C$_6$-alkyl, C$_1$-C$_6$-alkylamino-C$_1$-C$_6$-alkyl, di-C$_1$-C$_6$-alkylamino-C$_1$-C$_6$-alkyl, —(CH$_2$)$_w$—R$^{10}$; wherein w is 1 or 2;

R$^4$ is independently C$_1$-C$_6$-alkyl, halo, halo-C$_1$-C$_6$-alkyl, or Ar—(R$^7$)$_z$;

R$^5$ is independently C$_1$-C$_6$-alkyl, halo, halo-C$_1$-C$_6$-alkyl, Ar—(R$^7$)$_z$, —(CH$_2$)$_a$NR$^{13}$R$^{14}$, —Ar—(CH$_2$)$_a$NR$^{13}$R$^{14}$, -A'—NR$^1$—(CH$_2$)$_b$-A", —CH$_2$CH$_2$C(O)-A'", or —Ar'—(C(O)(CH$_2$)$_a$NR$^{13}$R$^{14}$)$_c$;

wherein A' is C(O) or CH$_2$; A" is H, NR$^{13}$R$^{14}$, C$_1$-C$_6$-thioalkyl, C$_1$-C$_6$-alkoxy, —SO$_2$CH$_3$, or —OH; A''' is —OH, C$_1$-C$_6$-alkoxy, or —NR$^{13}$R$^{14}$; and Ar' is a 5- or 6-membered heterocycloalkyl ring;

wherein a is independently 0, 1, or 2; b is 1, 2, or 3, with the proviso that when b is 1, A" is H; and c is 0 or 1;

R$^6$ and each R$^7$ are each independently halo, cyano, nitro, C$_1$-C$_6$-alkyl, COOH, C$_1$-C$_6$-alkylcarbonyl, C$_1$-C$_6$-alkyl-carbonyl-C$_1$-C$_6$-alkyl, amino, C$_1$-C$_6$-alkylamino, di-C$_1$-C$_6$-alkylamino, amino-C$_1$-C$_6$-alkyl, C$_1$-C$_6$-alkylamino-C$_1$-C$_6$-alkyl, di-C$_1$-C$_6$-alkylamino-C$_1$-C$_6$-alkyl, OH, halo-C$_1$-C$_6$-alkyl, hydroxy-C$_1$-C$_6$-alkyl, C$_1$-C$_6$-alkoxy, C$_1$-C$_6$-alkoxy-C$_1$-C$_6$-alkyl, heteroaryl, or phenyl;

R$^8$ is H or C$_1$-C$_6$-alkyl;

R$^9$ is H, C$_1$-C$_6$-alkyl, halo-C$_1$-C$_6$-alkyl, C$_3$-C$_6$-cycloalkyl, C$_1$-C$_6$ alkoxy, —(CH$_2$)$_y$—Ar—(R$^7$)$_z$; or R$^8$ and R$^9$, together with the nitrogen atom to which they are attached form a 5- or 6-membered heterocycloalkyl ring optionally substituted with C$_1$-C$_6$-alkyl, halo, amino, cyano, C$_1$-C$_6$-alkoxy, or OH;

R$^{10}$ is heterocycloalkyl, Ar—(R$^7$)$_z$, COOH, or C(O)—NR$^{11}$R$^{12}$

R$^{11}$ is H or C$_1$-C$_3$-alkyl;

R$^{12}$ is H, C$_1$-C$_6$-alkyl, halo-C$_1$-C$_3$-alkyl, or hydroxy-C$_1$-C$_3$-alkyl; or R$^{11}$ and R$^{12}$, together with the nitrogen atom to which they are attached form 5- or 6-membered heterocycloalkyl ring optionally substituted with C$_1$-C$_6$-alkyl, halo, amino, cyano, C$_1$-C$_6$-alkoxy, or hydroxy;

R$^{13}$ is H, C$_1$-C$_6$-alkyl, or hydroxy-C$_1$-C$_6$-alkyl;

R$^{14}$ is H, C$_1$-C$_6$-alkyl, halo-C$_1$-C$_6$-alkyl, hydroxy-C$_1$-C$_6$-alkyl, C$_1$-C$_6$-alkylamino, or SO$_2$CH$_3$; or R$^{13}$ and R$^{14}$, together with the nitrogen atom to which they are attached form 5- or 6-membered heterocycloalkyl ring optionally substituted with C$_1$-C$_6$-alkyl, halo, amino, cyano, C$_1$-C$_6$-alkoxy, hydroxy-C$_1$-C$_6$-alkyl, or OH; and R$^{15}$ and R$^{16}$ are each independently H, C$_1$-C$_6$-alkyl, or halo, or R$^{15}$ and R$^{16}$, together with the carbon atom to which they are attached form cyclopropyl, C=O, C=S, or C=NR$^1$;

m is 0 or 1;

n, o, and q are each independently 0, 1, or 2; and p is 0, 1, 2, 3, or 4.

Definitions

As used herein, a 5-membered heteroaromatic ring fragment refers to a 5-membered heteroaromatic ring that includes at least one heteroatom selected from O, S, and N. Examples of 5-membered heteroaromatic ring fragments include the following

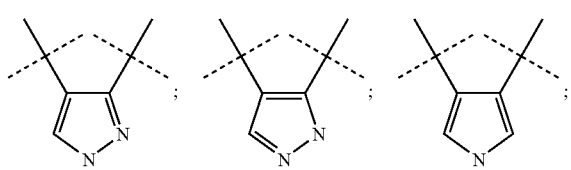

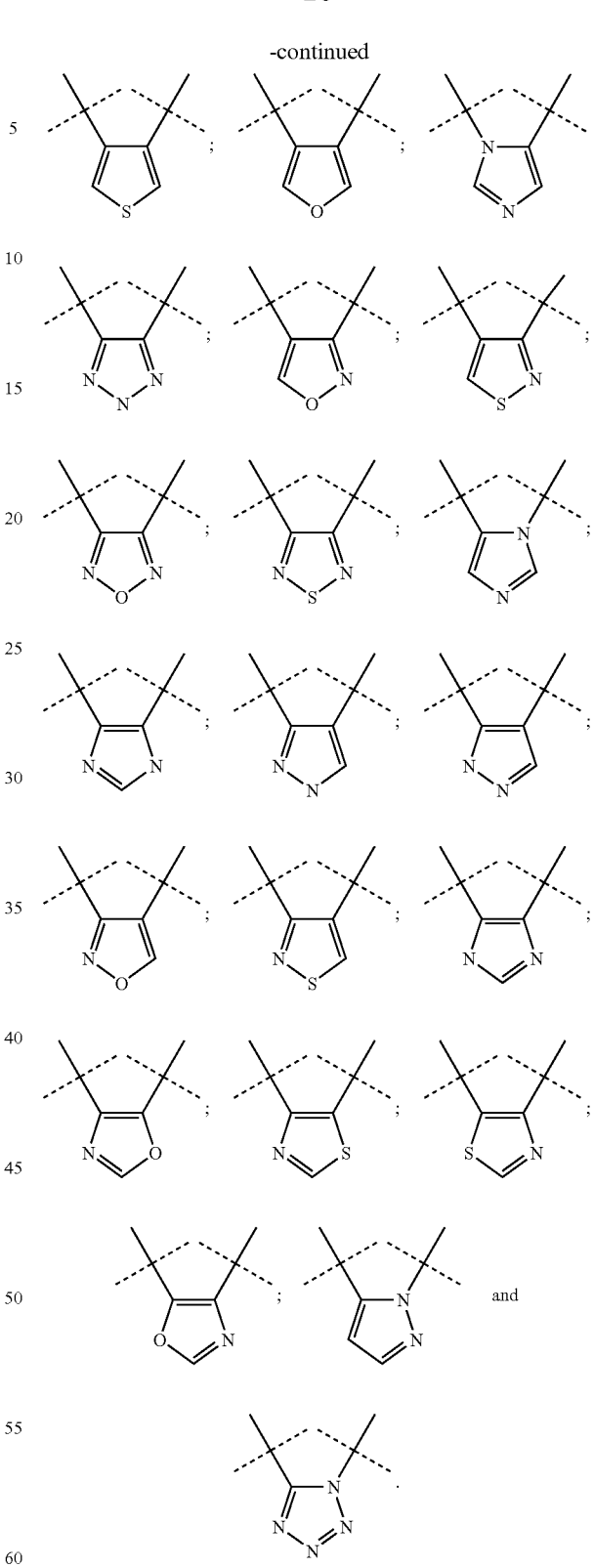

Ar may be phenyl or heteroaryl. The term "heteroaryl" refers to an aromatic group that contains at least one heteroatom selected from N, O, and S. Examples of suitable heteroaryl groups include pyridinyl, oxidopyridinyl, furyl, thienyl, imidazolyl, pyrrolyl, pyrazolyl, oxazolyl, isoxazolyl, thiazolyl, isothiazolyl, triazolyl, tetrazolyl, pyrimidinyl, and benzothiadiazolyl groups. The Ar group may be substituted with up to the number of positions available for substitution. For example, if Ar is phenyl, up to five substitutions are possible (z=0-5); if Ar is thienyl or furyl, up to three substitutions are possible (z=0-3); and if Ar is oxazolyl or thiazolyl, up to two substitutions are possible (z=0-2).

"$C_1$-$C_6$-alkyl" refers to a straight or branched chain monovalent radical of 1 to 6 carbon atoms, including, methyl, ethyl, n-propyl, isopropyl, n-butyl, isobutyl, t-butyl, n-pentyl, isopentyl, neopentyl, and n-hexyl and isomers thereof.

"$C_1$-$C_6$-alkenyl" refers to a refers to a straight or branched chain monovalent radical of 2 to 6 carbon atoms and one degree of unsaturation. Examples include vinyl and allyl groups.

Examples of suitable $C_1$-$C_6$-alkylcarbonyl groups include $CH_3C(O)$— (acetyl) and $CH_3CH_2C(O)$— (ethylcarbonyl); examples of $C_1$-$C_6$-alkyl-carbonyl-$C_1$-$C_6$-alkyl groups include $CH_3C(O)CH_2$—, $CH_3CH_2C(O)CH_2$—, and $CH_3CH_2C(O)CH_2CH_2$—; examples of $C_1$-$C_6$-alkylamino groups include $CH_3NH$— (methylamino) and $CH_3CH_2NH$— (ethylamino); examples of di-$C_1$-$C_6$-alkylamino groups include dimethylamino, diethylamino, and methylethylamino; examples of amino-$C_1$-$C_6$-alkyl groups include —$CH_2NH_2$ (aminomethyl) and —$CH_2CH_2NH_2$ (aminoethyl); examples of $C_1$-$C_6$-alkylamino-$C_1$-$C_6$-alkyl groups include methylaminomethyl ($CH_3NHCH_2$—), ethylaminomethyl ($CH_3CH_2NHCH_2$—), and ethylaminoethyl ($CH_3CH_2NHCH_2CH_2$—); examples of di-$C_1$-$C_6$-alkylamino-$C_1$-$C_6$-alkyl include dimethylaminomethyl (($CH_3)_2NCH_2$—) and dimethylaminoethyl (($CH_3)_2NCH_2CH_2$—).

Representative halo groups include fluoro, chloro, and bromo groups. Examples of halo-$C_1$-$C_6$-alkyl (including halo-$C_1$-$C_3$-alkyl) includes trifluoromethyl, 2,2,2-trifluoroethyl, and 1,1,1,3,3,3-hexafluoroisopropyl; examples of $C_1$-$C_6$-alkoxy groups include methoxy, ethoxy, n-propoxy, isopropxy, n-butoxy, isobutoxy, and t-butoxy; examples of $C_1$-$C_6$-alkoxy-$C_1$-$C_6$-alkyl groups include methyloxymethyl (i.e., $CH_3OCH_2$—) and methyloxyethyl (i.e., $CH_3OCH_2CH_2$—).

The term "heterocycloalkyl group" refers to a non-aromatic 5- or 6-membered ring that contains as least one heteroatom selected from N, O, and S. Examples include piperidinyl, pyrrolidinyl, piperazinyl, 4-methylpiperazinyl, morpholino, thiomorpholino, tetrahydrofuranyl, 1,3-dioxolan-2-yl, tetrahydropyridinyl, and tetrahydropyranyl groups. The groups $R^8$ and $R^9$ (as well as the groups $R^{11}$ and $R^{12}$ as well as $R^{13}$ and $R^{14}$) may, along with the nitrogen atom to which they are attached, form a 5- or 6-membered heterocycloalkyl ring including piperidinyl, pyrrolidinyl, piperazinyl, 4-methylpiperazinyl, morpholino, thiomorpholinyl-1,1-dioxide, and thiomorpholino groups.

As used herein, pharmaceutically acceptable refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio. The skilled artisan will appreciate that pharmaceutically acceptable salts of compounds according to Formula (I) may be prepared. These pharmaceutically acceptable salts may be prepared in situ during the final isolation and purification of the compound, or by separately reacting the purified compound in its free acid or free base form with a suitable base or acid, respectively.

In certain embodiments, compounds according to Formula (I) may contain an acidic functional group and are, therefore, capable of forming pharmaceutically acceptable base addition salts by treatment with a suitable base. Examples of such bases include a) hydroxides, carbonates, and bicarbonates of sodium, potassium, lithium, calcium, magnesium, aluminum, and zinc; and b) primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, malic acid, malonic acid, tartaric acid, citric acid, salicylic acid, benzoic acid, tannic acid, formic acid, stearic acid, lactic acid, ascorbic acid, p-toluenesulfonic acid, oleic acid, and lauric acid.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, and ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

Schemes

Compounds of the present invention can be prepared by a variety of procedures, some of which are illustrated in the schemes below (1-11). It will be recognized by those skilled in the art that the individual steps in the following schemes may be varied to provide compounds of Formula (1). The particular order of steps required to produce compounds of Formula (1) is dependent upon the particular compound being synthesized, the starting compound, the relative lability of the substituted moieties as well as the feasibility of the reaction, recognized by those skilled in the art.

Azaindolyl heteroaryls can be prepared by a variety of carbon-carbon or carbon-heteroatom cross coupling reactions of the proto, halo or boronic acid/ester of the heteroaryl partner with an appropriately functionalized 7-azaindole. An example of such an intermediate is 4-bromo-7-azaindole, the preparation of which is described in the literature (WO200382289, WO03/000690A1). This bromoazaindole can be further functionalized via the 4-bromo-2-iodo-7-azaindole (2; WO03/000690A1) by palladium catalyzed Suzuki cross coupling reactions with appropriate boronic acids or boronate esters (such as for example RB(OR')$_2$, where R is substituted heteroaryl and R' is H or $C_1$-$C_6$-alkyl), as is described in the literature (Scheme 1). Examples of functionalized heteroaryl coupling partners for the bromoazaindoles or the azaindole boronic acids include halides, boronic acids or boronate esters of furans, oxazoles, thiazoles, pyrroles, pyrazoles, thiophenes, phenyl and imidazoles.

Bromoazaindoles such as compound 2 and its precursors in Scheme 1 can be coupled via Suzuki cross-coupling reactions to suitable aryl halides, aryl boronic acids or aryl boronate esters using, for example, a palladium(0) catalyst (typically tetrakis(triphenylphosphine)palladium(0)) in a suitable solvent (e.g., 1,4-dioxane) containing a base (e.g., aqueous potassium carbonate) at elevated temperature (e.g., ~100° C.). This reaction can also be performed using azaindolyl boronic acids and aryl halides. Numerous aryl halides and aryl boronic acids/esters are commercially available. Several others are reported in the literature or can be prepared using conventional synthetic methods or literature procedures by those skilled in the art.

In the following Schemes, the R groups are all as previously defined.

Scheme 1

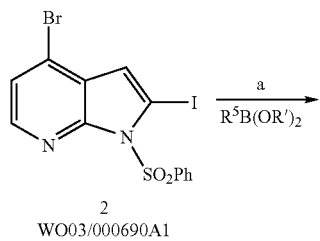

2
WO03/000690A1

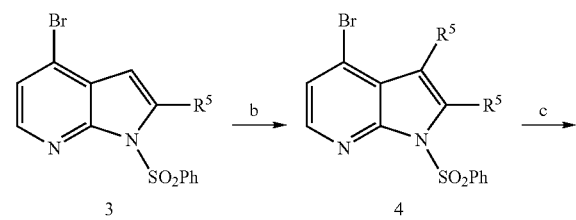

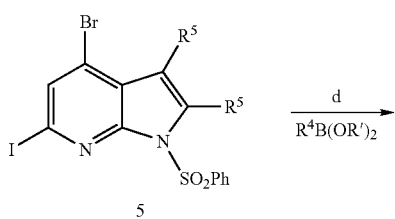

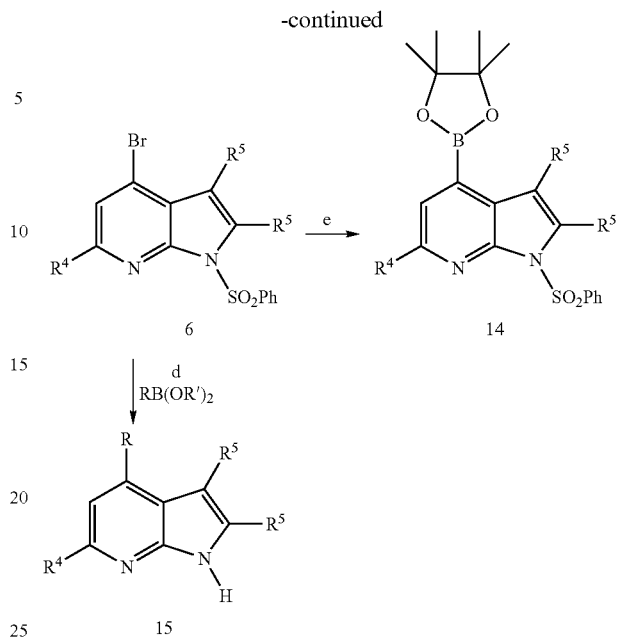

Reagents and Conditions: a) Pd(PPh$_3$)$_4$, DMF, NaHCO$_3$ (aq), 100° C.; b) i) NIS, ii) RB(OR')$_2$, Pd(PPh$_3$)$_4$, NaHCO$_3$, DMF, 100° C. c) i) mCPBA, EtOAc; ii) (MeSO$_2$)$_2$O, Me$_4$NI, DME, DMF; d) i) Pd(PPh$_3$)$_4$, NaHCO$_3$ or K$_2$CO$_3$, DMF, 100° C. ii) 6N NaOH(aq), MeOH, 70° C.; e) Pd(dppf)Cl$_2$, bis(pinacolato)diboron, KOAc, dioxane, 90° C.

Azaindolyl pyrazoles such as represented by Formula (1) can be prepared from, for example, pyrazole bromides (10) or pyrazole boronate esters (13). As outlined in Scheme 2, a substituted acetophenone may be converted to a compound of formula 7 by treatment with a dialkyl acetal of dimethylformamide, followed by reaction with hydrazine in aqueous ethanol to produce a pyrazole 8. Bromination using N-bromosuccinimide provides a compound (9) which may be reacted with an alkylating agent such as R$^3$X (where X is a leaving group, exemplified by but not restricted to halo, trifluoromethansulfonate, tosylate or mesylate) to afford an alkylated pyrazole of formula 10 or 11. This reaction may be performed in the presence of base, such as potassium tert-butoxide, potassium carbonate, or sodium hydride, in the presence of a suitable solvent, such as tetrahydrofuran or dimethylformamide, under an inert atmosphere.

Depending on the nature of the alkylating agent and the reaction conditions, the compound of formula 10 may be isolated as a pure regioisomer or a mixture of the two possible regioisomers (where the R$^3$ group is on either N atom of the pyrazole ring). Where a mixture of regioisomers (10 and 11) is obtained, these isomers may be separated by physical methods (such as crystallization or chromatographic methods) at this stage or at any later stage in the synthetic scheme. The respective pyrazoles (10 and 11) can i) react with an azaindole boronic acid to form tetracycles such as 15 which may be converted to the compound of Formula (1) according to the procedures outlined in Scheme 3, or ii) undergo borylation with a palladium(0) catalyst (such as bis(diphenylphosphino) ferrocenepalladium(II) in the presence of base (such as potassium acetate) in dioxane at elevated temperature (typically ~90° C.) to form boronate esters like 13. The compound of formula 13 can then undergo Suzuki coupling to a bromoazaindole such as 6 to furnish the tetracycle of formula 15 which may be converted to the compound of Formula (1) according to Scheme 3.

Scheme 2

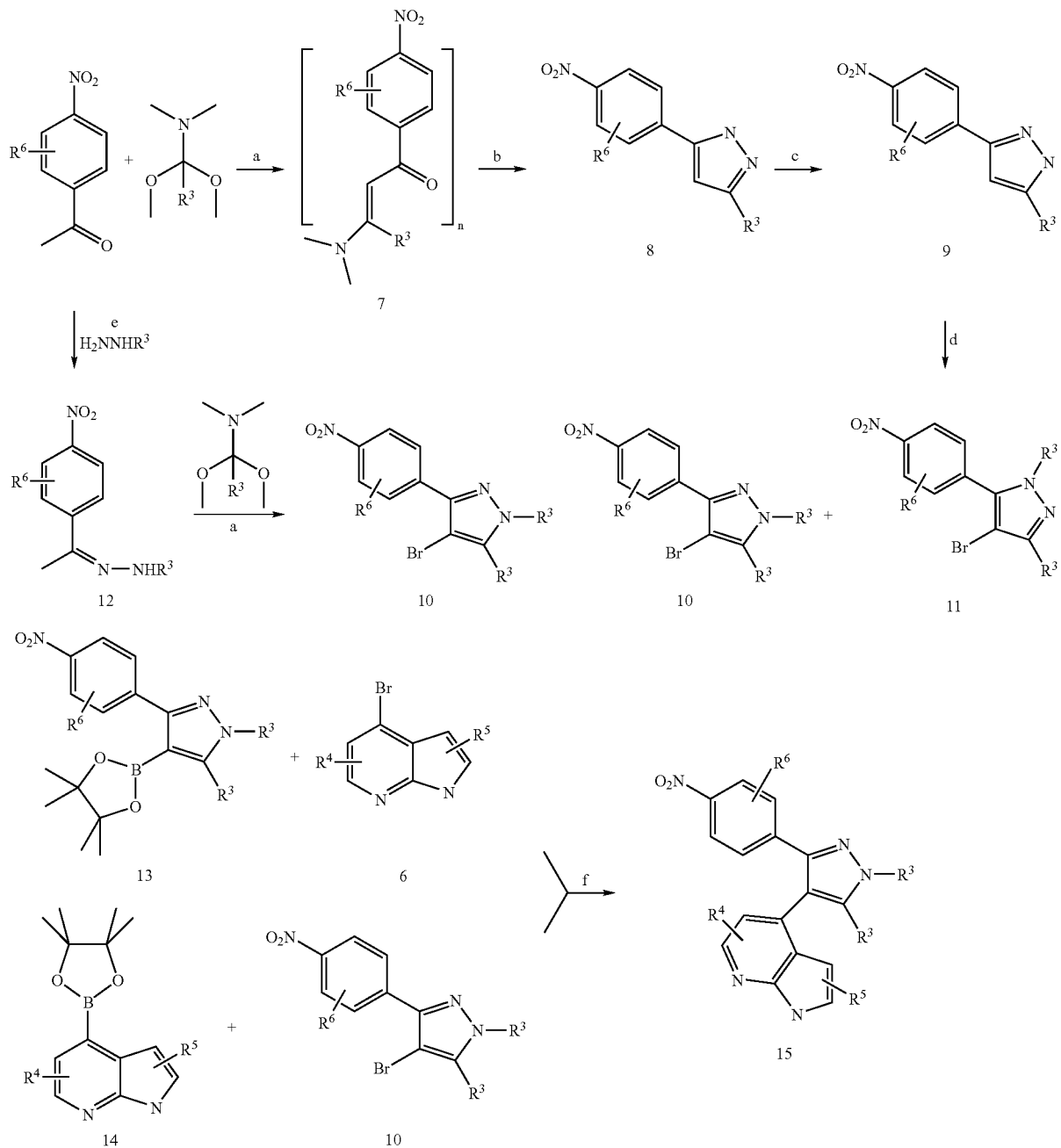

Reagents and conditions: a) DMF, 80° C.; b) hydrazine, EtOH, 70° C.; c) NBS, DMF, rt; d) $R^3X$, NaH, DMF, rt; e) KOAc, $PdCl_2(PPh_3)_2$, 1,4-dioxane, 100° C.; f) $Pd(PPh_3)_4$, 2M $K_2CO_3$: 1,4-dioxane (1:1), 100° C.

Alternatively, the regioisomer 10 may be prepared selectively by treatment of a functionalized acetophenone with the hydrazine $R^3NHNH_2$ (which is commercially available or may be synthesized using techniques conventional in the art) to yield a hydrazone of formula 12. The hydrazone (12) may then be reacted with the dialkyl acetal of dimethylformamide to generate a compound of formula 10, where $R^3$ is attached to the β-N atom of the pyrazole ring (Scheme 2).

As depicted in Scheme 3, 4-nitrophenyl derivatives such as 15 may be reduced to anilines such as 16, according to their specific chemical nature. This could include, but is not limited to, reduction of 15 (for example, by elemental tin in aqueous hydrochloric acid or by palladium on carbon in a solvent such as methanol under a hydrogen atmosphere). The resulting aniline 16 can be further functionalized depending on the nature of the electrophilic $R^1X$ and AX groups (where X is a leaving group such as, but not restricted to, halo, trifluoromethanesulfonate, mesylate, tosylate) to provide compounds of Formula 1.

The resulting compounds of Formula 1 can include, for example, anilines, amides, ureas, guanadines, sulfones, sulfonamides, sulfamides, and carbamates. Amide formation may be achieved by treating the compound of formula 16 or 17 with an acylating reagent including acyl chlorides, acid anhydrides, and carboxylic acids activated by a coupling agent such as HBTU. Urea formation may be achieved, for example, by i) treatment of the compound of formula 16 or 17 with an isocyanate in an inert solvent, or ii) treatment of the compound of formula 16 or 17 with phosgene or equivalent in an inert solvent, followed by incubation with the amine of interest, or iii) treatment of the amine of interest with phosgene or equivalent in an inert solvent, followed by incubation with the compound of formula 16 or 17.

ylethyl)silyl]-1H-pyrrolo[2,3-b]pyridine (18) (prepared as described in *Tetrahedron Lett.* 2004, 45, 2317-2319) in an inert solvent such as tetrahydrofuran by the choice of alkylating agent $R^4$. Trapping of the ortho-anion of 18, generated by treatment with sec-butyllithium in tetrahydrofuran at −78° C., with iodomethane, for example, would provide the compound of formula 19. The compound of formula 21 can likewise be prepared as described in the literature (*Tetrahedron Lett.* 2004, 45, 2317-2319). Halogen exchange of chlorine to iodine (for instance 19 to 20 or 21 to 22) can be achieved, for example, by heating the chloro-azaindole (such as 19 or 22) in an inert solvent (such as acetonitrile) containing a source of iodide (such as sodium iodide) and acetyl chloride. Suzuki coupling of 20 and 22 to an arylboronate such as 13 can be

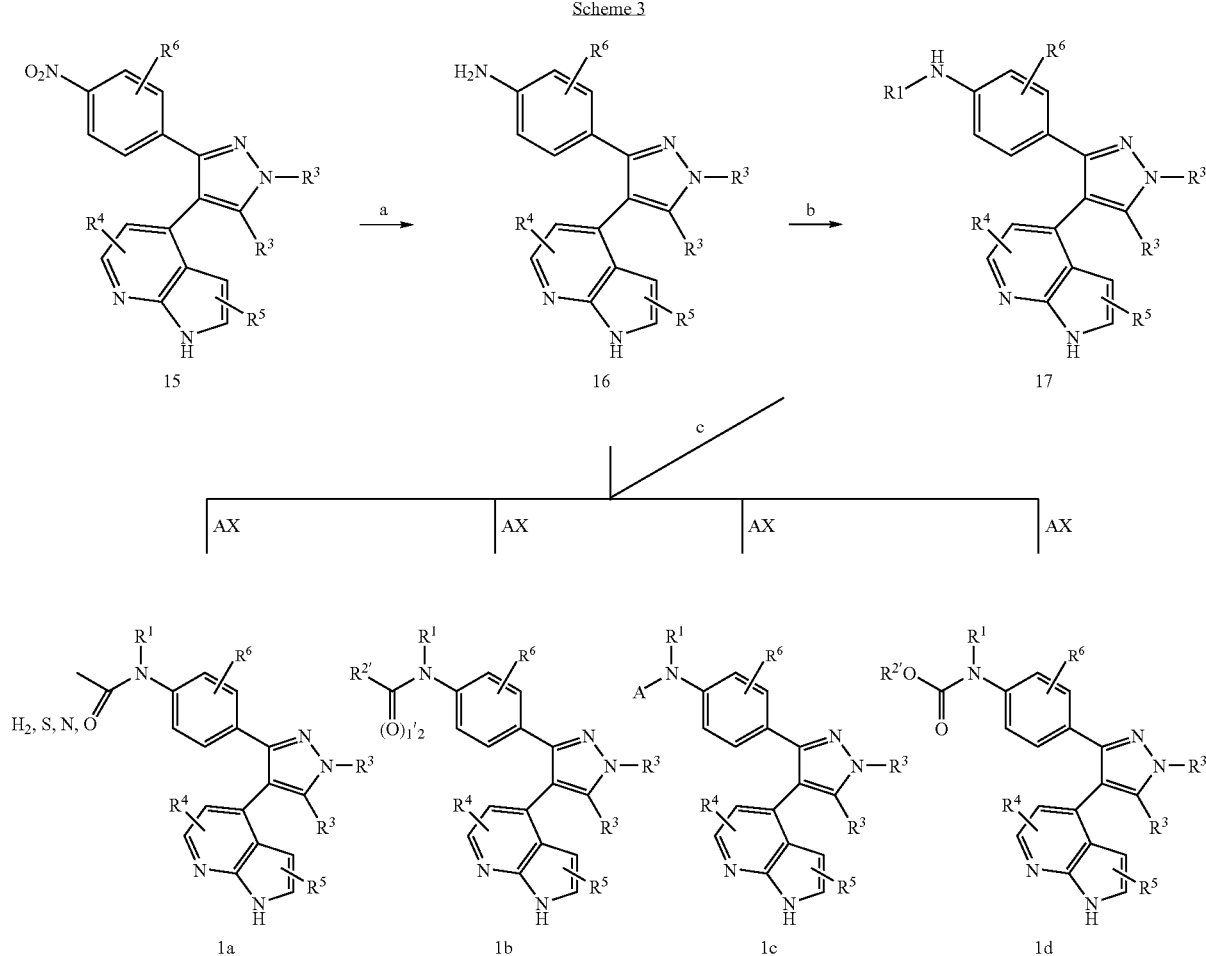

Scheme 3 where A is selected from H, C(S)$R^2$, C(O)$R^2$, C(N)$R^2$, C(O)O$R^2$, S(O)$R^2$, S(O)$_2R^2$
where X is a leaving group such as halo, trifluoromethanesulfonyl, mesyl, tosyl Reagents and conditions: a) Zn, AcOH, rt; b) $R^1$X, Et$_3$N, THF, rt; c) AX, Et$_3$N, THF, rt.

As depicted in Scheme 4, variably 5-substituted azaindoles of Formula 1 can be prepared from 4-chloro-1-[tris(1-methachieved using the conditions described in Scheme 2 to give compounds of formula 23. Such a tetracycle (23) can be converted to compounds of Formula (I) using the procedure outlined in Scheme 3.

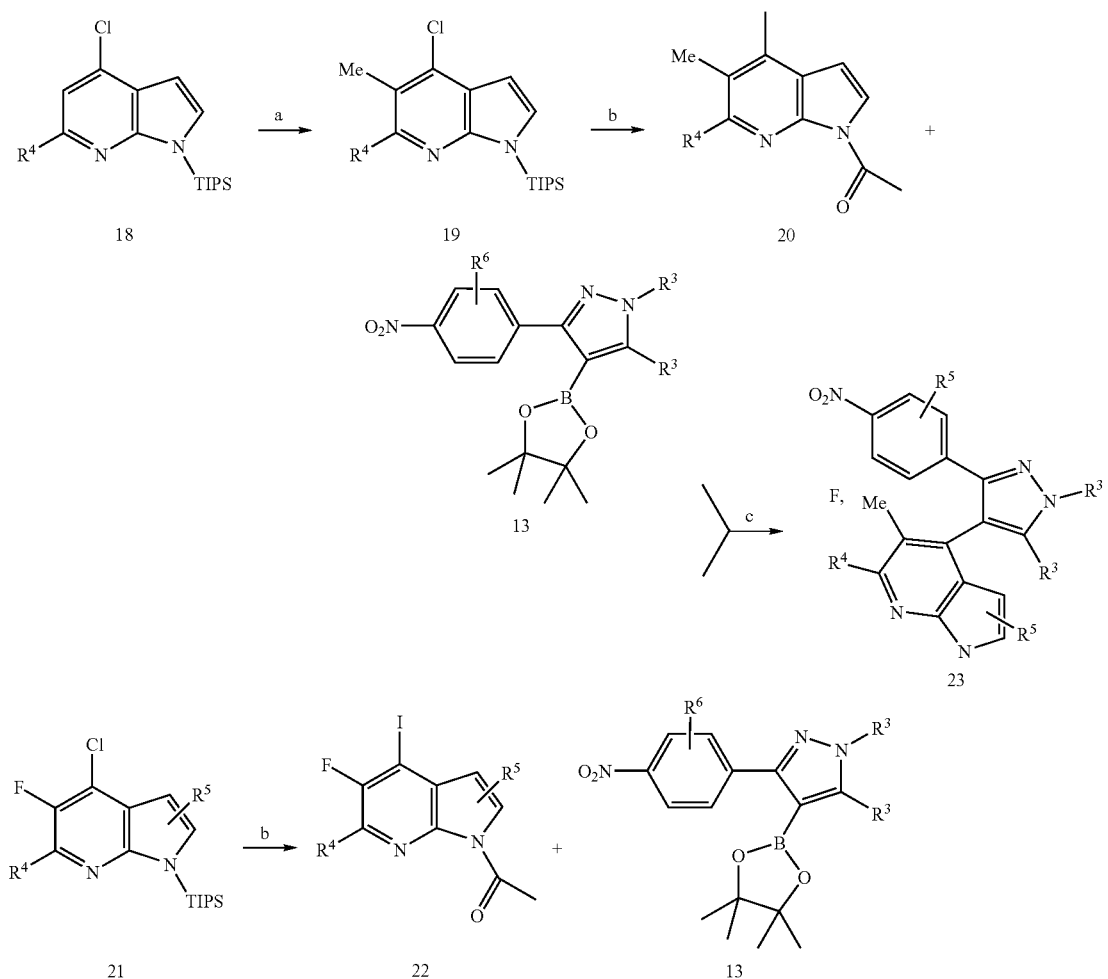

Reagents and conditions: a) sec-BuLi, THF, −78° C., then MeI; b) NaI, AcCl, MeCN, μwave, 150° C., 15 min; c) Pd(PPh$_3$)$_4$, aq. NaHCO$_3$, DMF, 100° C.

Alternatively, azaindolylpyrazole formation can occur at a later stage using more highly functionalized coupling partners as shown in Scheme 5. An optionally substituted azaindolyl pyrazole may be prepared by first installing the R$^1$ and A moieties onto an appropriate heteroaryl, as illustrated in Scheme 5 below. The compound of formula 10 may be reduced from a nitrophenyl derivative to an aniline under a variety of conditions, such as depicted in Scheme 3. Depending on the desired choice for R$^1$, the resulting aniline may be alkylated (or not) using an alkylating agent such as methyl iodide before installation of the A moiety (for example, acyl, sulfonyl, sulfamyl, carbamoyl, or guanidine) to furnish an intermediate such as 24. Alkylation of 24 with R$^3$X and Suzuki cross-coupling of the resulting compound 25 with a functionalized azaindole boronic acid such as 14 using a palladium catalyst (typically tetrakis(triphenylphosphine) palladium(0)) in the presence of a base (such as potassium carbonate aqueous solution) and a suitable solvent (such as 1,4-dioxane or N,N-dimethylformamide) at elevated temperatures (typically 100° C.) furnishes compounds of Formula 1.

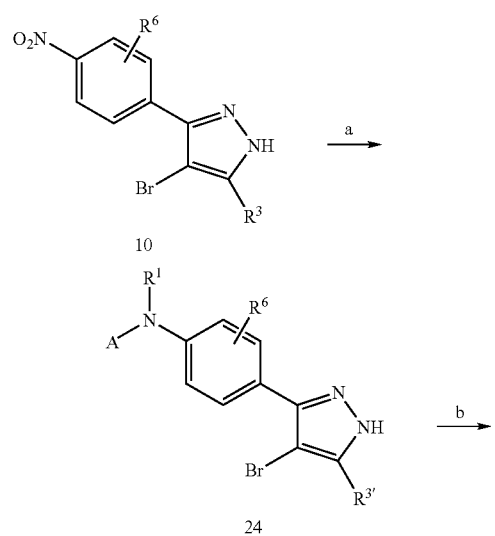

-continued

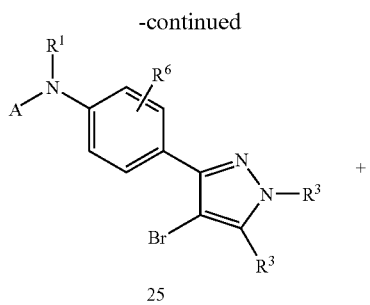

25

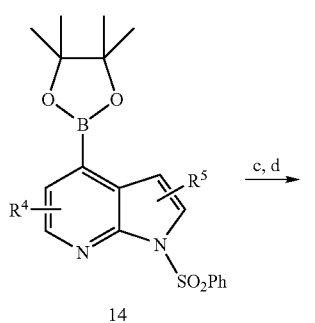

14

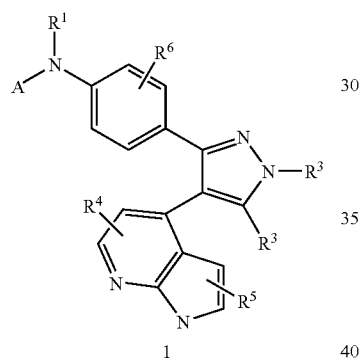

1

Reagents and conditions: a) i. Sn, 6N HCl, EtOH, 70° C.; ii. $R^1X$, pyridine, rt; iii AX, $CH_2Cl_2$, pyridine; b) KOtBu, DMF, $R^3X$ 0° C.-rt; c) $Pd(PPh_3)_4$, satd. aq. $NaHCO_3$, DMF, 100° C. d) 6N NaOH (aq), MeOH, 70° C.

Isomeric azaindolyl thiophenes, as depicted in Scheme 6, can be prepared from commercially available dihalothiophenes 26a and 26b. Selective Suzuki coupling of azaindole boronate 14 to the more activated carbon-halogen bond of the compound of formula 26a at high dilution provides intermediate 27, which further couples to a protected 4-aminophenylboronic acid to provide 28, which can be deprotected to form the aniline 29. The deprotection may be achieved under acidic conditions, e.g., heating with trifluoroacetic acid or aqueous hydrochloric acid in a solvent such as dioxane. If desired, the aniline 29 may be alkylated with an alkylating agent $R^1X$ (such as methyl iodide), followed by treatment with AX (wherein X represents a leaving group such as halide, trifluorosulfonate, mesylate or tosylate) to provide compounds of Formula 1.

Isomers of the thienyl core are easily accessed by the sequence of two successive Suzuki couplings between the dihaloaryl 26a or 26b and the azaindole boronate (14) and the phenyl boronate (N-Boc-4-aminophenylboronic acid), in either order.

Those skilled in the art will recognize that this approach can be extended to azaindolyl furans arising from 31a and 31b and azaindolyl pyrroles arising from 32a or 32b (which may be alkylated by successive treatment with sodium hydride in an inert solvent such as DMF followed by treatment with $R^3X$). The requisite aryls are all commercially available or can be prepared using methods in the literature (Scheme 6).

Scheme 6

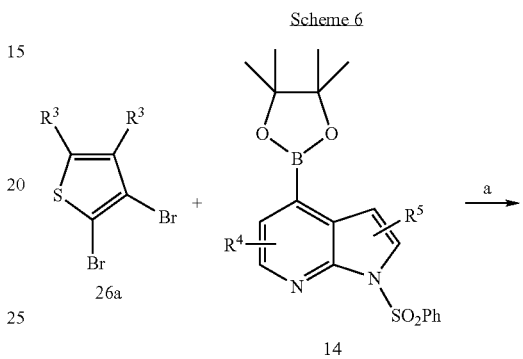

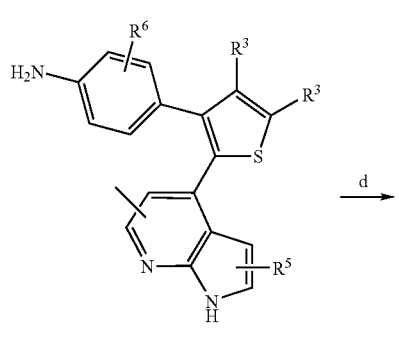

-continued

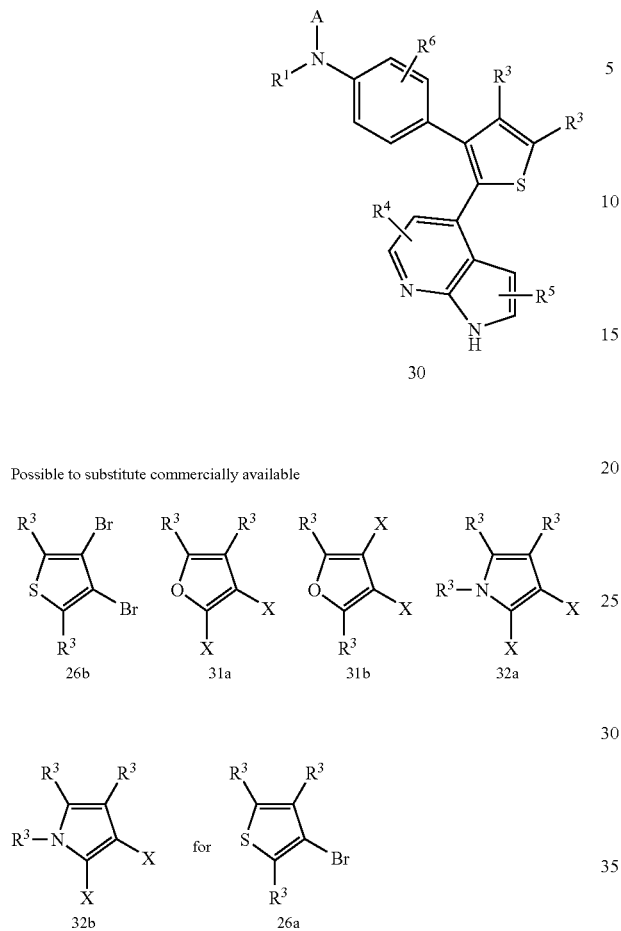

30

Possible to substitute commercially available 26b, 31a, 31b, 32a, 32b for 26a

Reagents and conditions: a) Pd(PPh$_3$)$_4$, 2M K$_2$CO$_3$, 1,4-dixoane, 90° C.; b) N-Boc-4-aminophenylboronic acid boronic acid, Pd(PPh$_3$)$_4$, Ba(OH)$_2$, 1,4-dioxane, DME, H$_2$O, 80° C.; c) i. 4M HCl, dioxane, ii. NaHCO$_3$, CH$_2$Cl$_2$, rt; d) i. R$^1$X, TEA, THF; ii. AX, where X is a leaving group such as halo.

Azaindolyl thiazoles and azaindolyl oxazoles can be prepared similarly, using either a thioacetamide (33 where X=S) or an acetamide (33 where X=O), respectively. As illustrated in Scheme 7, treating α-bromoketone 34 with a thioacetamide or an acetamide in ethanol provides in one instance a thiazole 35 (where X=S) or in another instance an oxazole 35 (where X=O), respectively. The thiazole or oxazole can be brominated with bromine in a suitable solvent such as chloroform. The brominated heterocycle 36 can undergo Suzuki coupling with an azaindolylboronate such as 14. This adduct can be advanced to thiazole and oxazole analogs of the compound of Formula 1 using analogous chemistry to that described for intermediate 15 in Scheme 3. One skilled in the art will recognize that isomers of the thiazole and oxazole described can be readily accessed depending on the choice of R$^3$ as well as the starting α-bromoketone 34.

Scheme 7

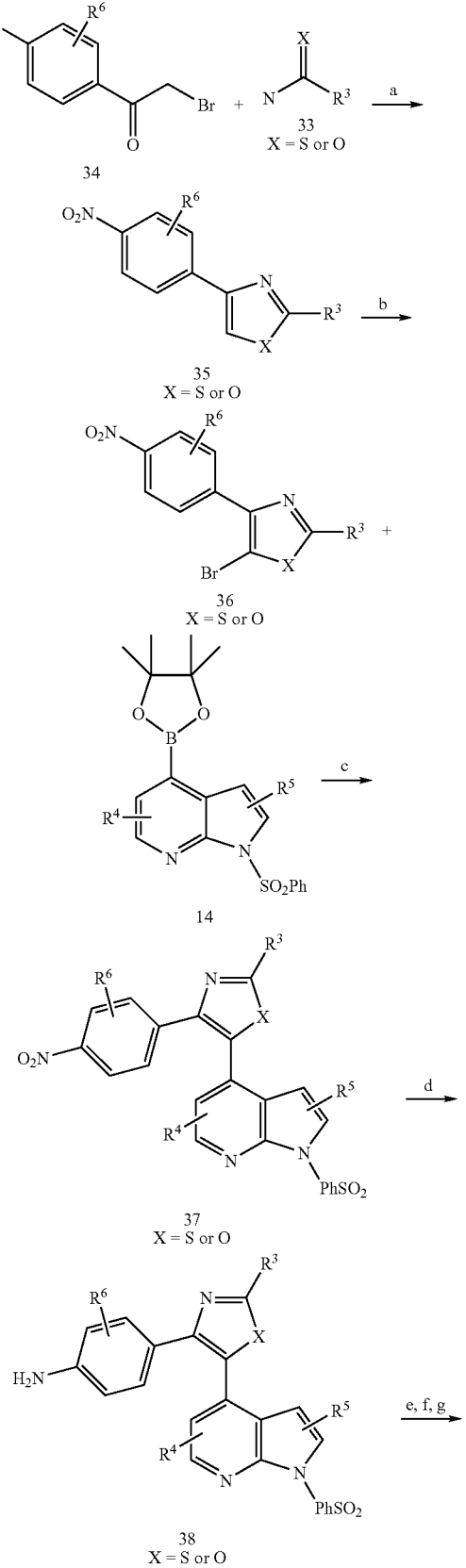

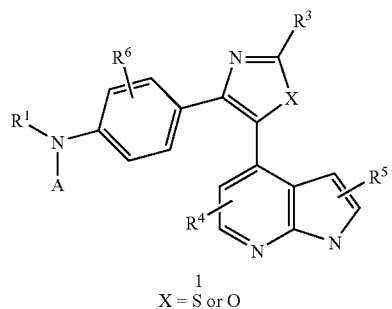

Reagents and Conditions: a) EtOH; b) Br$_2$, CH$_2$Cl$_2$; c) Pd(PPh$_3$)$_4$, 2M K$_2$CO$_3$(aq), 1,4-dioxane, 100° C.; d) Zn, AcOH, EtOH, 70° C.; e) R$^1$X, TEA, THF; f) AX, TEA, THF; g) MeOH, NaOH, 70° C.

The central phenyl moiety of these analogs can be homologated as depicted in Scheme 8. This provides access to compounds of Formula 1 wherein m=1. Using analogous chemistry to that described in Scheme 2 and starting with a functionalized 4-acetylbenzonitrile, nitrile hydrolysis of the compound of formula 44, for example using aqueous hydrochloric acid at elevated temperature, can provide access to amides represented by Formula (I) which can be further elaborated to such moieties as thioamides (treatment with Burgess reagent as known in the literature) and benzylamines (reduction with lithium aluminum hydride), using conventional chemistry known in the art. Similarly, reduction of the nitrile of compound 44 can provide access to optionally substituted amines as well as hydroxylamines as represented by Formula 1.

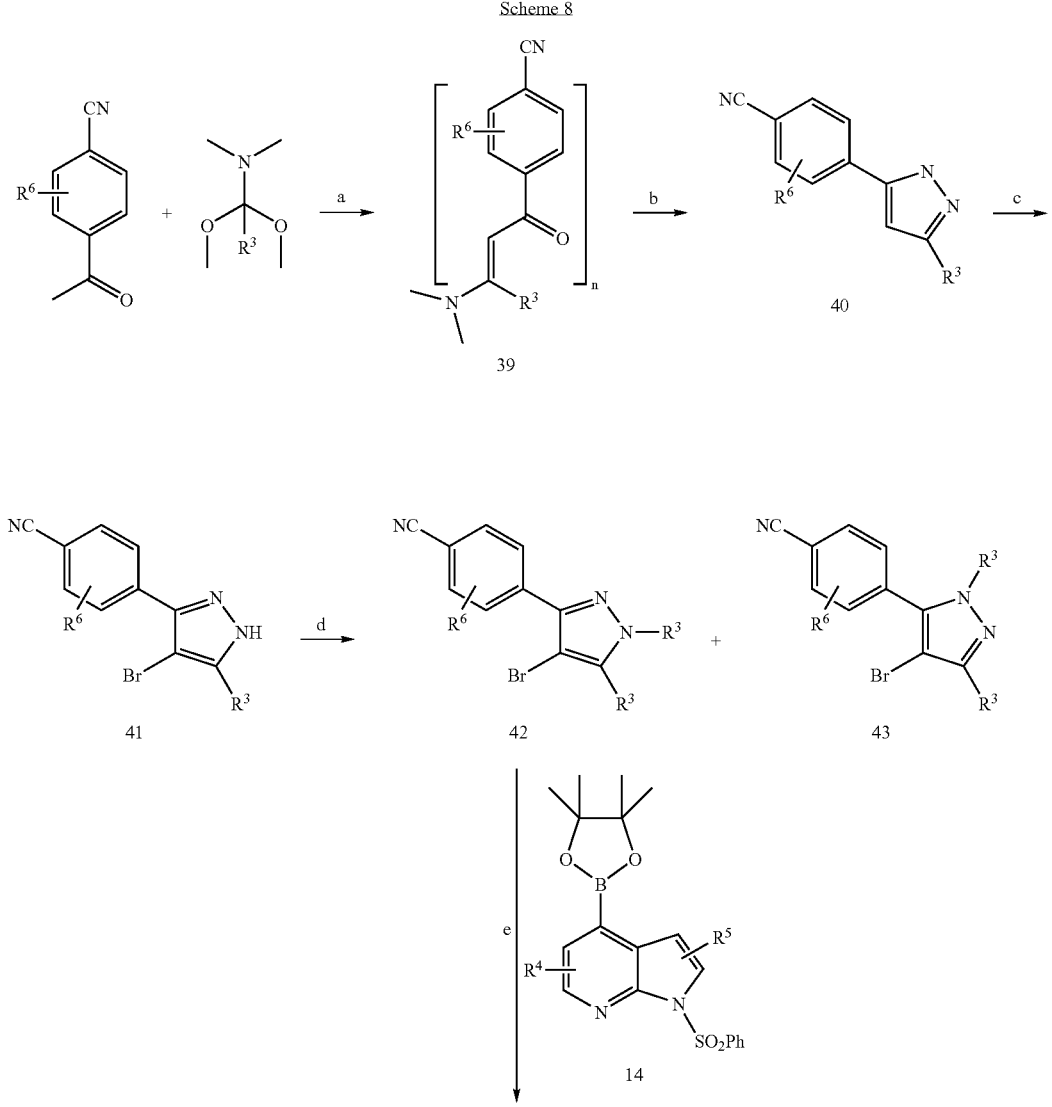

-continued

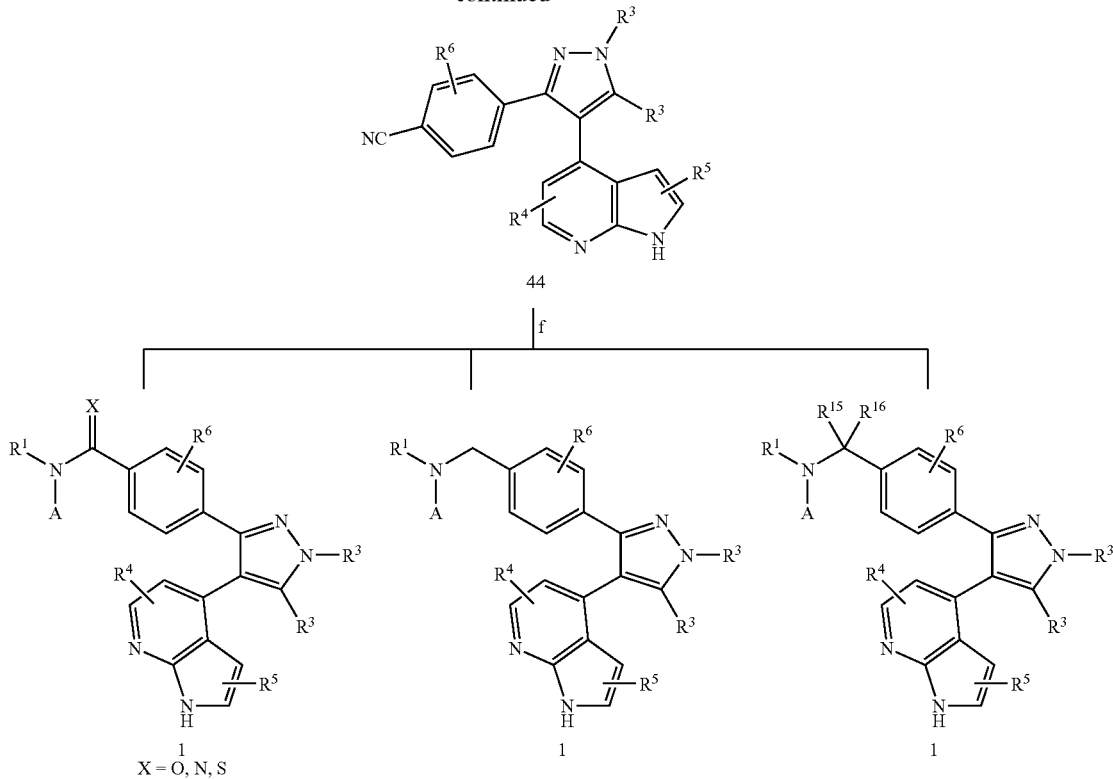

Reagents and Conditions: a) DMF, 80° C.; b) hydrazine, EtOH, 70° C.; c) NBS, DMF, rt; d) NaH, $R^3X$, DMF, rt; e) $Pd(PPh_3)_4$, $NaHCO_3$(aq), DMF, 100° C.; f) nitrile hydrolysis (HCl, $H_2O$) or nitrile reduction ($PtO_2.H_2O$, EtOH, $H_2$) followed by, if desired, $R^1X$, $Et_3N$, THF and/or AX, $Et_3N$, THF In the instance where the aryl core of the compound of Formula (I) is an imidazole, Scheme 9 outlines the conversion of a commercially available imidazole by nitration (*Heterocycles*, 1988, 27, 371-376) to 45, followed by base-mediated displacement on a compound of formula 6 (using for example cesium carbonate) at elevated temperature (typically 150° C.) to afford the tetracycle 46 as described in the literature (*Chem, Comm.* 2004 7, 778-779). This intermediate can be converted to compounds of Formula 1 by the methods described in Schemes 2 and 3.

Scheme 9

-continued

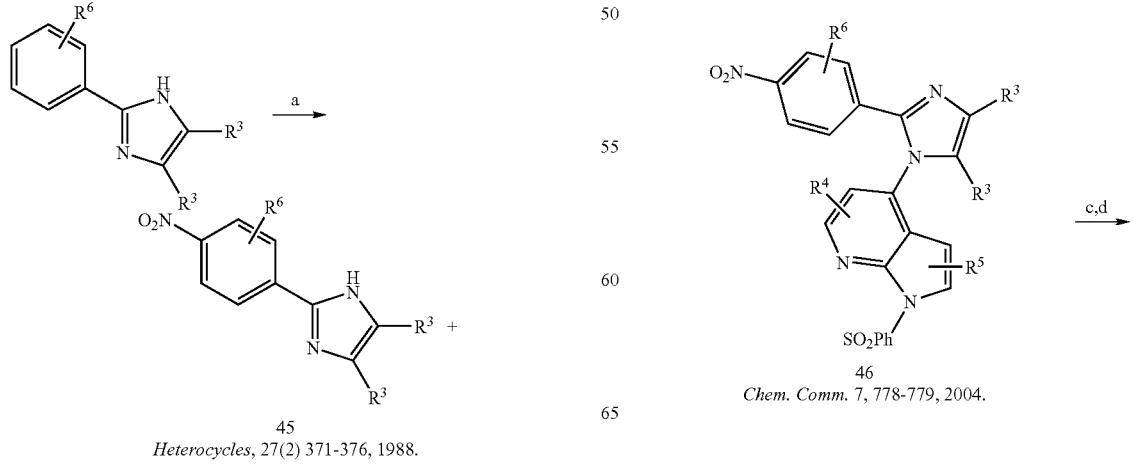

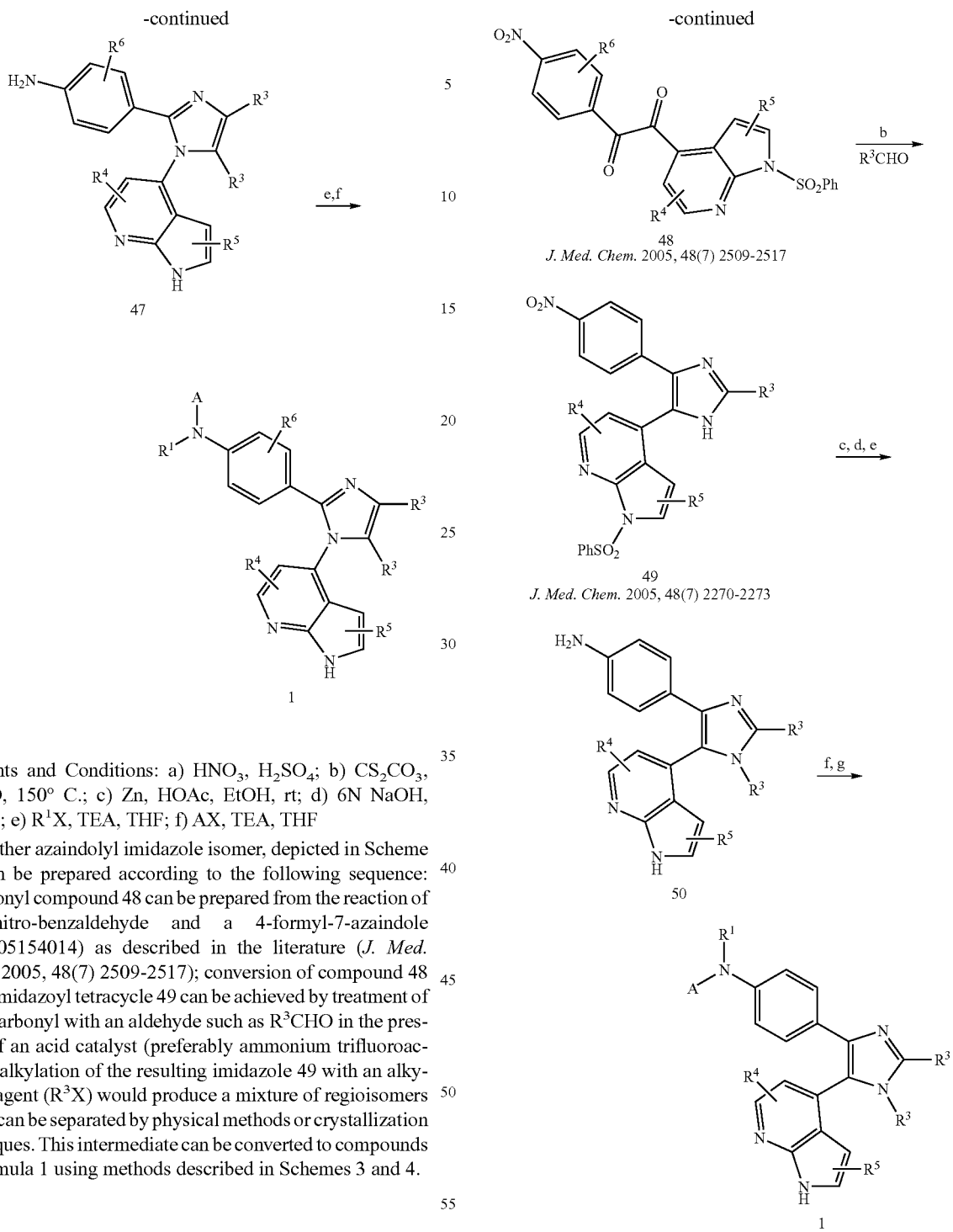

Reagents and Conditions: a) HNO$_3$, H$_2$SO$_4$; b) CS$_2$CO$_3$, DMSO, 150° C.; c) Zn, HOAc, EtOH, rt; d) 6N NaOH, MeOH; e) R$^1$X, TEA, THF; f) AX, TEA, THF Another azaindolyl imidazole isomer, depicted in Scheme 10, can be prepared according to the following sequence: dicarbonyl compound 48 can be prepared from the reaction of a 4-nitro-benzaldehyde and a 4-formyl-7-azaindole (US2005154014) as described in the literature (*J. Med. Chem.* 2005, 48(7) 2509-2517); conversion of compound 48 to the imidazoyl tetracycle 49 can be achieved by treatment of the dicarbonyl with an aldehyde such as R$^3$CHO in the presence of an acid catalyst (preferably ammonium trifluoroacetate); alkylation of the resulting imidazole 49 with an alkylating agent (R$^3$X) would produce a mixture of regioisomers which can be separated by physical methods or crystallization techniques. This intermediate can be converted to compounds of Formula 1 using methods described in Schemes 3 and 4.

Scheme 10

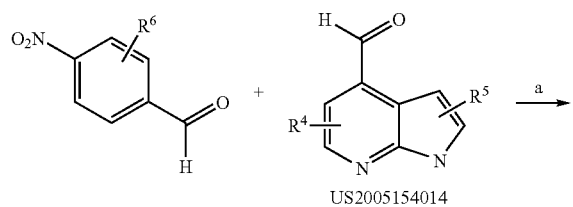

Reagents and Conditions: a) i) NaCN, H$_2$O/EtOH; ii) HNO$_3$, H$_2$O; b) CF$_3$COONH$_4$; c) NaH, R$^3$X, DMF; d) Zn, AcOH, EtOH; e) 6N NaOH(aq), MeOH, 70° C.; f) R$^1$X, Et$_3$N, THF; g) AX, Et$_3$N, THF The preparation of another pyrazole isomer according to methods described in the literature is illustrated in Scheme 11. Treatment of a functionalized ketone with the dialkyl acetal of dimethylformamide or equivalent chemical entity generates a compound of formula 51, as described in the literature (*J. Het. Chem.* 1996, 331(6), 1707-1710). Treatment of 51 with a commercially available substituted hydrazine in ethanol at elevated temperature (preferably ~70° C.) furnishes the substituted pyrazole 52 (*J. Het. Chem.* 1982, 19(6), 1355-1361). Following methods described in the literature (*Acta Chemica Scandanavia* 1992, 46(10), 972-980 and *J. Org. Chem.* 2001, 66(25) 8654-8656), oxidation to the N-oxide 53 followed by bromination to 54 and reduction over palladium metal under a hydrogen atmosphere reduces the nitro moiety and the N-oxide to provide aniline 55. The anilines illustrated in Scheme 11 can be converted to compounds of Formula 1 following the chemistry outlined in Scheme 5.

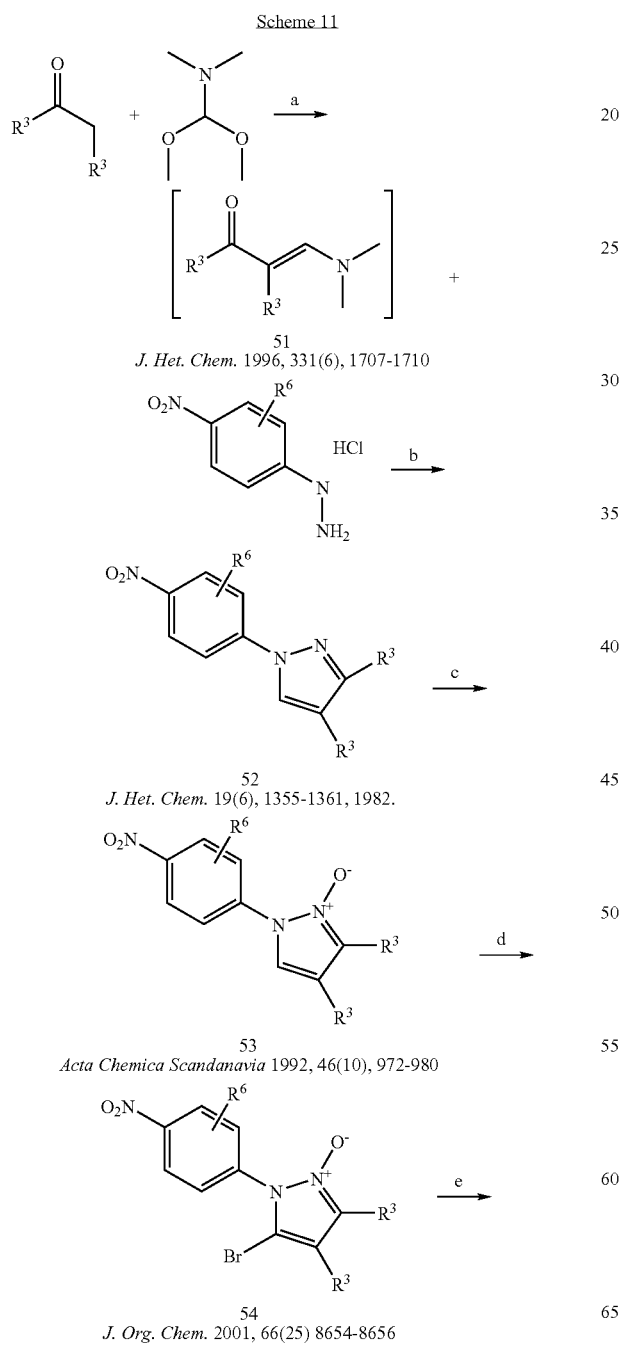

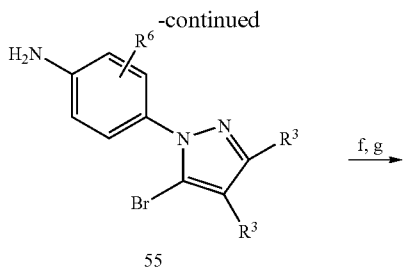

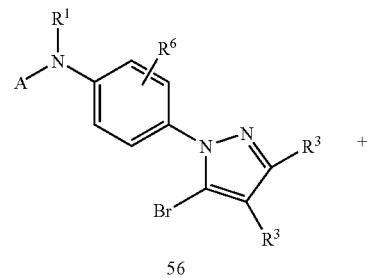

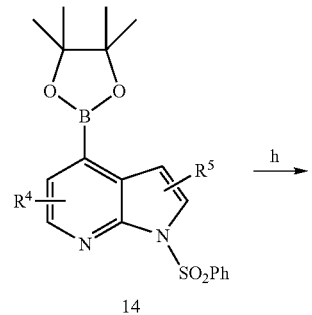

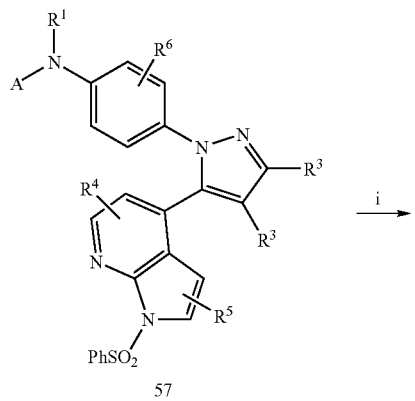

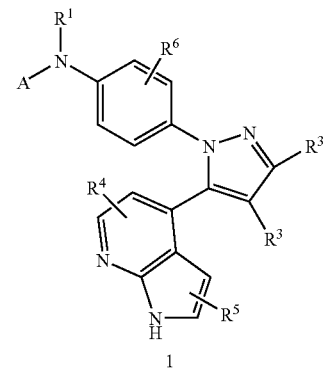

$R^1$ = H, Me

Reagents and conditions: a) DMF, 80° C.; b) EtOH, 70° C.; c) m-CPBA, $CH_2Cl_2$; d) $Br_2$, $K_2CO_3$, $CHCl_3$; e) $Pd(OH)_2/C$, MeOH, $H_2$; f) $R^1X$, TEA, THF; g) AX, TEA, THF; h) $Pd(dppf)Cl_2$, 2M $K_2CO_3$, dioxane, 100° C.; i) 6N NaOH, MeOH, 70° C.

Methods of Use

Compounds of the invention can be used to treat diseases of cellular proliferation, autoimmunity or inflammation. Disease states which can be treated by Compounds of the invention include, but are not limited to, cancer, autoimmune disease, fungal disorders, arthritis, graft rejection, inflammatory bowel disease, proliferation induced after medical procedures, including, but not limited to, surgery and angioplasty. It is appreciated that in some cases the cells may not be in a hyper- or hypoproliferation state (abnormal state) and still require treatment. Thus, in certain embodiments, the invention includes application to cells or individuals afflicted or impending affliction with any one of these disorders or states.

Proliferative Disease/Cancer

Compounds of the invention inhibit Aurora kinase. The present invention makes use of the finding that Aurora kinase serves multiple essential functions required for the completion of mitosis and that inhibition of the kinase activity of Aurora frequently results in cell cycle arrest and/or abnormal cell division, both of which can trigger cell death. Thus, by inhibiting Aurora kinase, cellular proliferation is blocked.

Compounds of the invention find use in a variety of applications. As will be appreciated by those skilled in the art, mitosis may be altered in a variety of ways; that is, mitosis can be affected either by increasing or decreasing the activity of a component in the mitotic pathway. Stated differently, mitosis may be disrupted by disturbing equilibrium, either by inhibiting or activating certain components. Similar approaches may be used to alter meiosis.

Compounds of the invention provided herein may be particularly useful for the treatment of cancer including solid tumors, such as skin, breast, brain, cervical carcinomas, testicular carcinomas and others. More particularly, cancers that may be treated using compounds of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma, serous cystadenocarcinoma, mucinous cystadenocarcinoma, unclassified carcinoma), granulosa-thecal cell tumors, Sertoli-Leydig cell tumors, dysgerminoma, malignant teratoma, vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma)), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above identified conditions.

Accordingly, compounds of the invention are administered to cells. By "administered" herein is meant administration of a therapeutically effective dose of a compound of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant any cell in which mitosis or meiosis can be altered. A "patient" for the purposes of the present invention includes both humans and other animals, particularly mammals, and other organisms. Thus the methods are applicable to both human therapy and veterinary applications. In certain embodiments the patient is a mammal, especially a human.

Compounds of the invention may be administered in a physiologically acceptable carrier to a patient, as described herein. Depending upon the manner of introduction, the compounds may be formulated in a variety of ways.

When used to treat proliferative diseases, compounds of the present invention can be administered alone or in combination with other treatments, i.e., radiation, or other therapeutic agents, such as the taxane class of agents that appear to act on microtubule formation or the camptothecin class of topoisomerase I inhibitors. When so used, other therapeutic agents may be administered before, concurrently with (whether in separate dosage forms or in a combined dosage form) or after administration of the compound of the invention.

Compositions

Compounds of the invention may be formulated into pharmaceutical compositions prior to administration to a patient. Accordingly, in another aspect the invention is directed to pharmaceutical compositions comprising a compound of the invention and one or more pharmaceutically acceptable excipients.

The pharmaceutical compositions of the invention may be prepared and packaged in bulk form wherein a safe and effective amount of a compound of the invention can be extracted and then given to the patient, such as with powders or syrups. Alternatively, the pharmaceutical compositions of the invention may be prepared and packaged in unit dosage form wherein each physically discrete unit contains a safe and effective amount of a compound of the invention.

As used herein, "pharmaceutically acceptable excipient" means a pharmaceutically acceptable material, composition or vehicle involved in giving form or consistency to the pharmaceutical composition. Each excipient is advantageously compatible with the other ingredients of the pharmaceutical composition when commingled, such that interactions which would substantially reduce the efficacy of the compound of the invention when administered to a patient and would result in pharmaceutically unacceptable compositions are avoided. In addition, each excipient is sufficiently high in purity to render it pharmaceutically acceptable.

The compound of the invention and the pharmaceutically acceptable excipient or excipients will typically be formulated into a dosage form adapted for administration to the patient by the desired route of administration. For example, dosage forms include those adapted for (1) oral administration, such as tablets, capsules, caplets, pills, troches, powders, syrups, elixers, suspensions, solutions, emulsions, sachets, and cachets; (2) parenteral administration, such as sterile solutions, suspensions, and powders for reconstitution; (3) transdermal administration, such as transdermal patches; (4) rectal administration, such as suppositories; (5) inhalation, such as aerosols and solutions; and (6) topical administration, such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *Remington: The Science and Practice of Pharmacy*, (Lippincott Williams & Wilkins), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Oral solid dosage forms such as tablets will typically comprise one or more pharmaceutically acceptable excipients, which may for example help impart satisfactory processing and compression characteristics, or provide additional desirable physical characteristics to the tablet. Such pharmaceutically acceptable excipients may be selected from diluents, binders, glidants, lubricants, disintegrants, colorants, flavorants, sweetening agents, polymers, waxes or other solubility-modulating materials.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided], and include:

- alcohol, e.g., 5% alcohol (e.g., in dextrose and water ("D/W") or D/W in normal saline solution ("NSS"), including in 5% dextrose and water ("D5/W"), or D5/W in NSS);
- synthetic amino acid such as Aminosyn, FreAmine, Travasol, e.g., 3.5 or 7; 8.5; 3.5, 5.5 or 8.5% respectively;
- ammonium chloride e.g., 2.14%;
- dextran 40, in NSS e.g., 10% or in D5/W e.g., 10%;
- dextran 70, in NSS e.g., 6% or in D5/W e.g., 6%;
- dextrose (glucose, D5/W) e.g., 2.5-50%;
- dextrose and sodium chloride e.g., 5-20% dextrose and 0.22-0.9% NaCl;
- lactated Ringer's (Hartmann's) e.g., NaCl 0.6%, KCl 0.03%, $CaCl_2$ 0.02%;
- lactate 0.3%;
- mannitol e.g., 5%, optionally in combination with dextrose e.g., 10% or NaCl e.g., 15 or 20%;
- multiple electrolyte solutions with varying combinations of electrolytes, dextrose, fructose, invert sugar Ringer's e.g., NaCl 0.86%, KCl 0.03%, $CaCl_2$ 0.033%;
- sodium bicarbonate e.g., 5%;
- sodium chloride e.g., 0.45, 0.9, 3, or 5%;
- sodium lactate e.g., 1/6 M; and sterile water for injection The pH of such IV fluids may vary, and will typically be from 3.5 to 8 as known in the art.

It will be appreciated that when compounds of the present invention are administered in combination with other therapeutic agents normally administered by the inhaled, intravenous, oral or intranasal route, that the resultant pharmaceutical composition may be administered by the same routes.

Compounds of the invention may conveniently be administered in amounts of, for example, 0.001 to 500 mg/kg body weight. The precise dose will of course depend on the age and condition of the patient and the particular route of administration chosen.

Compounds of the invention were tested for in vitro activity in accordance with the following assays.

Aurora A Enzyme Activity Assay

Compounds of the present invention were tested for Aurora A protein kinase inhibitory activity in substrate phosphorylation assays. This assay examines the ability of small molecule organic compounds to inhibit the serine phosphorylation of a peptide substrate, and was run in the LEADseeker (Amersham Bioscience, Piscataway, N.J.) scintillation proximity assay (SPA) format.

The substrate phosphorylation assays use recombinant human full-length Aurora A kinase expressed in baculovirus/Sf9 system. A N-terminal His-Thr-affinity tag was fused to the amino terminus of amino acids 2 through 403 of Aurora A. 5 nM okadaic acid was added during the last 4 hours of expression (experimentally determined to enhance Aurora A's enzymatic activity). The enzyme was purified to approximately 70% purity by metal-chelate affinity chromatography.

The method measures the ability of the isolated enzyme to catalyze the transfer of the gamma-phosphate from ATP onto the serine residue of a biotinylated synthetic peptide (Biotin-aminohexyl-RARRRLSFFFFAKKK-amide). Substrate phosphorylation was detected by the following procedure: Assays were performed in 384-well low volume white polystyrene plates (Greiner Bio-One, Longwood, Fla.). 1 nM Aurora A enzyme was added to the wells containing 0.1 µl of test compound in 100% DMSO and incubated for 30 minutes followed by the addition of reaction mixture resulting in a final assay volume of 10 µl containing 6 mM magnesium chloride, 1.5 µM ATP, 1 µM peptide substrate, 40 nM microtubule associated protein TPX2 peptide (1-43), 0.03 µCi [gamma-$P^{33}$] ATP/well, 5 mM DTT, 25 mM KCl, 0.15 mg/ml BSA and 0.01% Tween-20 in 50 mM HEPES, pH 7.2. The reaction was allowed to proceed for 120 minutes at room temperature and was terminated by the addition of 10 µl of a LEADseeker SPA bead solution containing PBS (Dulbecco's PBS without Mg2+ and Ca2+), 50 mM EDTA, 0.03 mg of Streptavidin coupled polystyrene imaging beads (Amersham Bioscience). The plate was sealed and the beads were allowed to incubate overnight. The plate was read in a Viewlux (Wallac, Turku, Finland) plate reader.

For dose response curves, data were normalized and expressed as % inhibition using the formula 100*(1−(U−C2)/(C1−C2)) where U is the unknown value, C1 is the average of the high signal (0% inhibition) and C2 is the average of the low signal (100% inhibition) control wells. Curve fitting was performed with the following equation: y=A+((B−A)/(1+(10^x/10^C)^D)), where A is the minimum response, B is the maximum response, C is the log 10(XC50), and D is the slope. The results for each compound were recorded as pIC50 values (−C in the above equation).

Aurora B Enzyme Activity Assay

Compounds of the present invention were tested for Aurora B protein kinase inhibitory activity in substrate phosphorylation assays. This assay examines the ability of small molecule organic compounds to inhibit the serine phosphorylation of a peptide substrate, and was run in the LEADseeker (Amersham Bioscience) scintillation proximity assay (SPA) format.

The substrate phosphorylation assays use recombinant human full-length Aurora B kinase expressed in baculovirus/Sf9 system. Following expression the culture is incubated with 50 nM okadaic acid for 1 hour prior to purification. A N-terminal His-affinity tag was fused to the amino terminus of amino acids 1 through 344 of Aurora B. 5 µM Aurora B was activated in 50 mM Tris-HCl pH 7.5, 0.1 mM EGTA, 0.1% 2-mercaptoethanol, 0.1 mM sodium vandate, 10 mM magnesium acetate, 0.1 mM ATP with 0.1 mg/ml GST-INCENP [826-919] at 30° C. for 30 mins. Following activation the enzyme is then dialysed into enzyme storage buffer and stored at −70° C.

The method measures the ability of the isolated enzyme to catalyze the transfer of the gamma-phosphate from ATP onto the serine residue of a biotinylated synthetic peptide (Biotin-aminohexyl-RARRRLSFFFFAKKK-amide). Substrate phosphorylation was detected by the following procedure: Assays were performed in 384-well low volume white polystyrene plates (Greiner Bio-One, Longwood, Fla.). 5 nM Aurora B enzyme was added to the wells containing 0.1 µl of test compound in 100% DMSO and incubated for 30 minutes followed by the addition of reaction mixture resulting in a final assay volume of 10 µl containing 6 mM magnesium chloride, 3 mM manganese chloride, 1.25 µM ATP, 1.25 µM peptide substrate, 0.025 µCi [gamma-$P^{33}$] ATP/well, 5 mM DTT, 0.15 mg/ml BSA, 0.01% Tween-20 in 50 mM HEPES, pH 7.5, and 0.1 µl of test compound in 100% DMSO. The reaction was allowed to proceed for 120 minutes at room temperature and was terminated by the addition of 10 µl of a LEADseeker SPA bead solution containing PBS (Dulbecco's PBS without Mg2+ and Ca2+), 50 mM EDTA, 0.03 mg of Streptavidin coupled polystyrene imaging beads (Amersham Bioscience). The plate was sealed and the beads were allowed to incubate overnight. The plate was read in a Viewlux (Wallac, Turku, Finland) plate reader.

For dose response curves, data were normalized and expressed as % inhibition using the formula 100*(1−(U−C2)/(C1−C2)) where U is the unknown value, C1 is the average of the high signal (0% inhibition) and C2 is the average of the low signal (100% inhibition) control wells. Curve fitting was performed with the following equation: y=A+((B−A)/(1+(10^x/10^C)^D)), where A is the minimum response, B is the maximum response, C is the log 10(XC50), and D is the slope. The results for each compound were recorded as pIC50 values (−C in the above equation).

Cellular Proliferation Assay:

The ability of compounds to inhibit the proliferation of human tumor or normal cells was investigated using cell proliferation assays. Briefly, cells are seeded into 96 well plates at an appropriate density for each cell type to ensure logarithmic growth throughout the assay and allowed to adhere overnight. Compounds are dissolved in 100% DMSO at approximately 10 mM and two-fold serially dilutions are made in 100% DMSO spanning twenty concentration points. Compounds are diluted 500-fold into cell culture media and incubated on cells for three to six days. Cell viability is determined using Promega's CellTiter-Glo reagent as per manufacturer's instructions. Percent growth proliferation is calculated relative to DMSO alone treated cells and IC50 values are determined by a four-parameter fit model using Xlfit (IDBS, Inc.).

General Purification and Analytical Methods

Preparative HPLC was conducted on a YMC ODS-A C18 (75×30 mm, 5 μm) using water with 0.1% trifluoroacetic acid (solvent A) and acetonitrile (solvent B) or on a YMC ODS-A C18 (250×30 mm, 15 μm) using water (solvent A) and acetonitrile (solvent B) or on an XBridge Prep C18 (19×150 mm, 5 μm) using water with 0.1% ammonium hydroxide (solvent A) and acetonitrile (solvent B). Detection: 214 or 254 nm. Examples or intermediates purified by Gilson reverse phase HPLC refer to the use of these columns.

LC-MS analysis was performed on a Perkin Elmer Sciex 100 atmospheric pressure ionization (APCI) mass spectrometer. Retention times in LC-MS are referred to as $t_R$ (time in minutes).

$^1$H NMR spectra were recorded using a Bruker DPX 400 MHz spectrometer referenced to tetramethylsilane. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), m (multiplet), br (broad).

Analogix™ chromatography refers to purification carried out using equipment sold by Analogix Corporation (IntelliFlash 280) and cartridges PuriFlash (RS or SF) pre-packed with PuriSil. TLC (thin layer chromatography) plates coated with silica gel 60 F254 were obtained from Merck.

EXAMPLES

The following examples are for illustrative purposes only and are not intended to limit the scope of this invention. As used herein, the symbols and conventions used in these processes, schemes and examples are consistent with those used in the contemporary scientific literature, for example, the Journal of the American Chemical Society or the Journal of Biological Chemistry. All temperatures are in ° C. All compounds were named using the MDL ISIS™/Draw 2.5 SP 1 naming program. Unless otherwise noted, all starting materials were obtained from commercial suppliers and used without further purification. Specifically, the following abbreviations may be used in the examples and throughout the specification:

g (grams); mg (milligrams);

L (liters); mL (milliliters);

μL (microliters); psi (pounds per square inch);

M (molar); mM (millimolar);

Hz (Hertz); MHz (megahertz);

mmol (millimoles); mol (moles);

min (minutes); h (hours);

mp (melting point); TLC (thin layer chromatography);

HPLC (high pressure liquid chromatography);

atm (atmosphere);

$t_R$ (retention time); RP (reverse phase);

MeOH (methanol); i-PrOH (isopropanol);

TEA (triethylamine); TFA (trifluoroacetic acid);

THF (tetrahydrofuran); DMSO (dimethyl sulfoxide);

AcOEt (EtOAc) (ethyl acetate); DCM ($CH_2Cl_2$) (dichloromethane);

DMF (N,N-dimethylformamide); $CH_3CN$ (acetonitrile)

HOAc (acetic acid); mCPBA (meta-chloroperbenzoic acid);

BOC (tert-butyloxycarbonyl); Ac (acetyl);

DMAP (4-dimethylaminopyridine); ICl (iodine monochloride)

ATP (adenosine triphosphate); BSA (bovine serum albumin)

HBTU (O-Benzotriazole-1-yl-N,N,N',N'-tetramethyluronium hexafluorophosphate);

HEPES (4-(2-hydroxyethyl)-1-piperazine ethane sulfonic acid);

DMF-DMA (N,N-dimethylformamide dimethylacetal).

The following compounds have an $IC_{50}$ of less than 10 μM for Aurora A or Aurora B or both as determined by the following assays described. The following table illustrates the structures and names of each of the compounds that appear in the experimental section.

| Example # | Structure | Name |
|---|---|---|
| Example 1 | 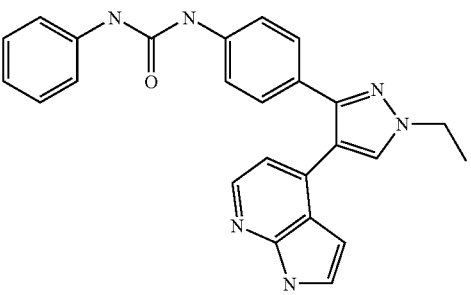 | N-{4-[1-ethyl-4-(1 H-pyrrolo[2,3-b]pyridin-4-yl)-1 H-pyrazol-3-yl]phenyl}-N'-phenylurea |

-continued

| Example # | Structure | Name |
|---|---|---|
| Example 2 | 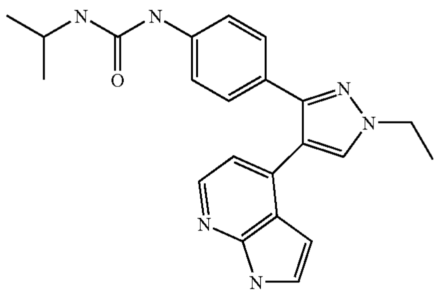 | N-{4-[1-ethyl-4-(1H-pyrrolo[2,3-b]pyridin-4-yl)-1H-pyrazol-3-yl]phenyl}-N'-(1-methylethyl)urea |
| Example 3 | 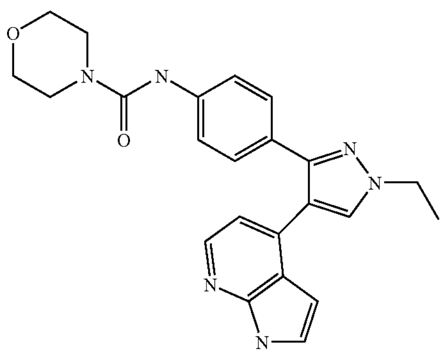 | N-{4-[1-ethyl-4-(1H-pyrrolo[2,3-b]pyridin-4-yl)-1H-pyrazol-3-yl]phenyl}-4-morpholinecarboxamide |
| Example 4a | 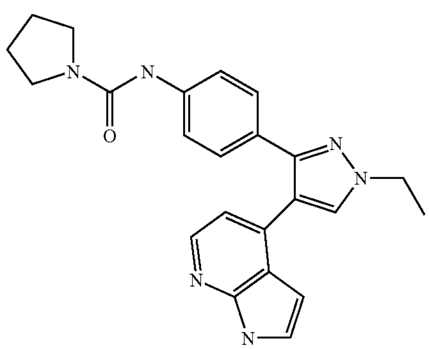 | N-{4-[1-ethyl-4-(1H-pyrrolo[2,3-b]pyridin-4-yl)-1H-pyrazol-3-yl]phenyl}-1-pyrrolidinecarboxamide |
| Example 4b | 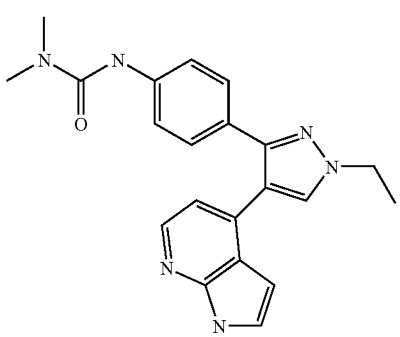 | N'-{4-[1-ethyl-4-(1H-pyrrolo[2,3-b]pyridin-4-yl)-1H-pyrazol-3-yl]phenyl}-N,N-dimethylurea |

-continued

| Example # | Structure | Name |
|---|---|---|
| Example 4c | 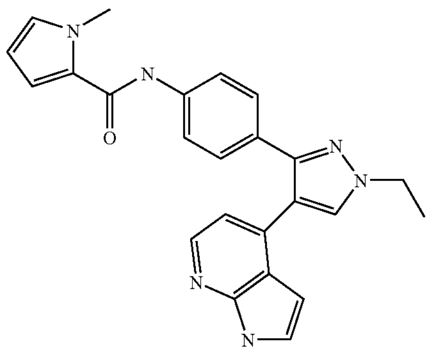 | N-{4-[1-ethyl-4-(1 H-pyrrolo[2,3-b]pyridin-4-yl)-1 H-pyrazol-3-yl]phenyl}-1-methyl-1 H-pyrrole-2-carboxamide |
| Example 4d | 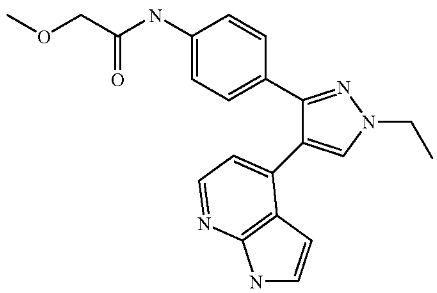 | N-{4-[1-ethyl-4-(1 H-pyrrolo[2,3-b]pyridin-4-yl)-1 H-pyrazol-3-yl]phenyl}-2-(methyloxy)acetamide |
| Example 4e | 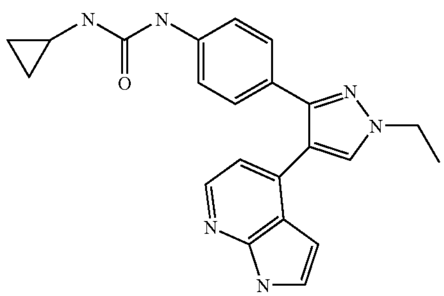 | N-cyclopropyl-N'-{4-[1-ethyl-4-(1 H-pyrrolo[2,3-b]pyridin-4-yl)-1 H-pyrazol-3-yl]phenyl}urea |
| Example 5a | 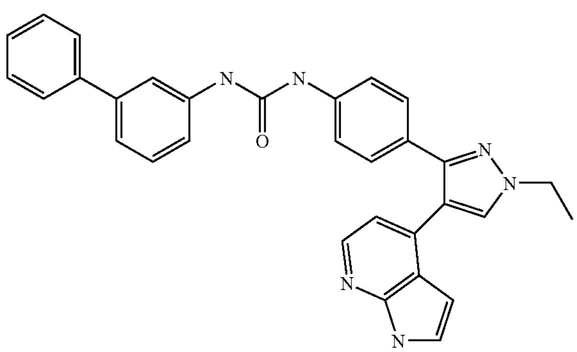 | N-3-biphenyl-N'-{4-[1-ethyl-4-(1 H-pyrrolo[2,3-b]pyridin-4-yl)-1 H-pyrazol-3-yl]phenyl}urea |
| Example 5b | 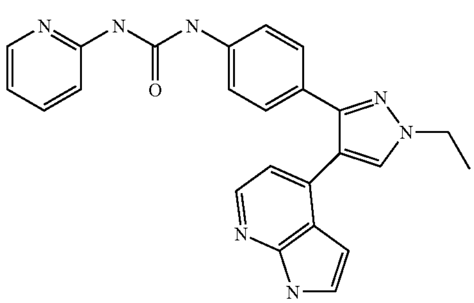 | N-{4-[1-ethyl-4-(1 H-pyrrolo[2,3-b]pyridin-4-yl)-1 H-pyrazol-3-yl]phenyl}-N'-2-pyridinylurea |

-continued

| Example # | Structure | Name |
|---|---|---|
| Example 5c | 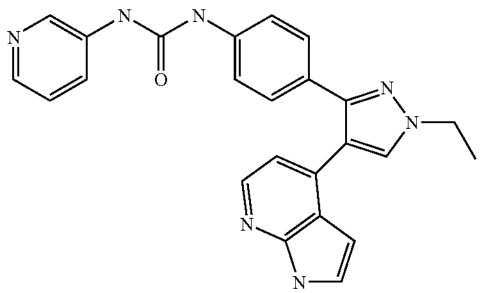 | N-{4-[1-ethyl-4-(1H-pyrrolo[2,3-b]pyridin-4-yl)-1H-pyrazol-3-yl]phenyl}-N'-3-pyridinylurea |
| Example 5d | 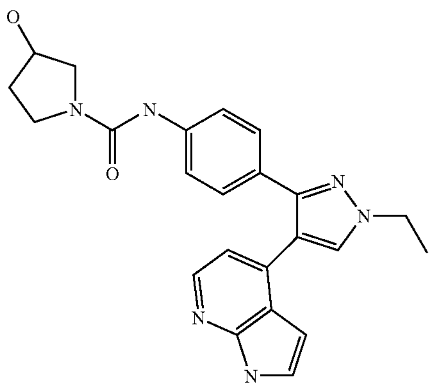 | N-{4-[1-ethyl-4-(1H-pyrrolo[2,3-b]pyridin-4-yl)-1H-pyrazol-3-yl]phenyl}-3-hydroxy-1-pyrolidinecarboxamide |
| Example 5e | 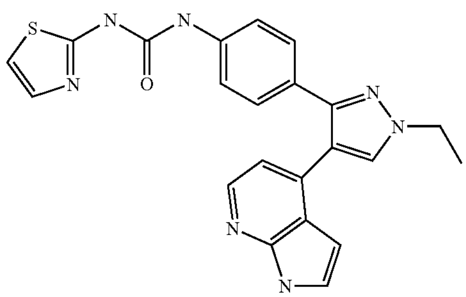 | N-{4-[1-ethyl-4-(1H-pyrrolo[2,3-b]pyridin-4-yl)-1H-pyrazol-3-yl]phenyl}-N'-1,3-thiazol-2-ylurea |
| Example 5f | 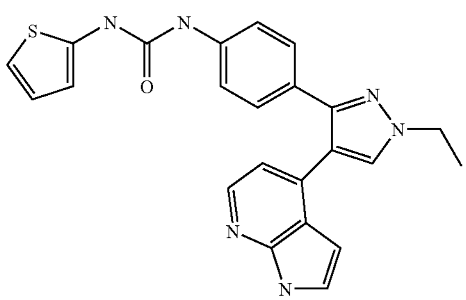 | N-{4-[1-ethyl-4-(1H-pyrrolo[2,3-b]pyridin-4-yl)-1H-pyrazol-3-yl]phenyl}-N'-2-thienylurea |
| Example 5g | 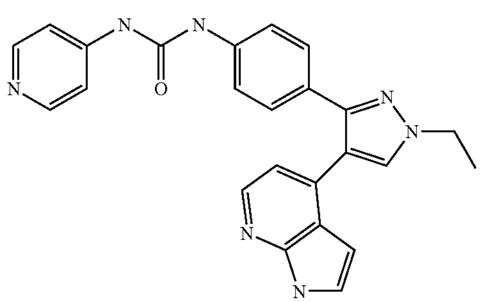 | N-{4-[1-ethyl-4-(1H-pyrrolo[2,3-b]pyridin-4-yl)-1H-pyrazol-3-yl]phenyl}-N'-4-pyridinylurea |

-continued

| Example # | Structure | Name |
|---|---|---|
| Example 5h | 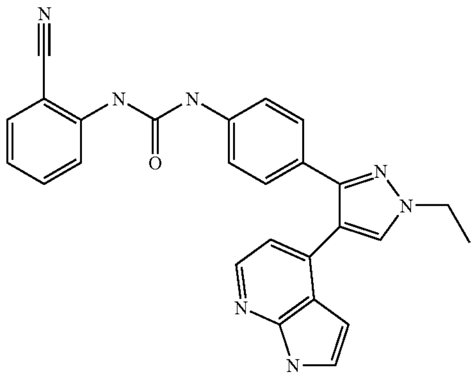 | N-(2-cyanophenyl)-N'-{4-[1-ethyl-4-(1 H-pyrrolo[2,3-b]pyridin-4-yl)-1 H-pyrazol-3-yl]phenyl}urea |
| Example 5i | 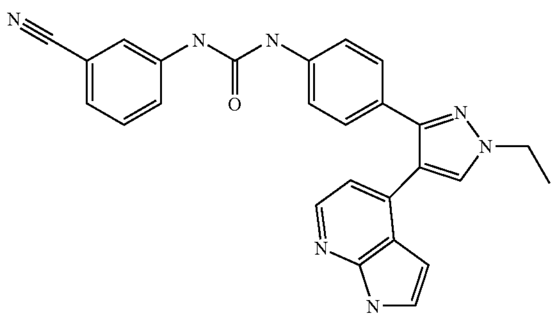 | N-(3-cyanophenyl)-N'-{4-[1-ethyl-4-(1 H-pyrrolo[2,3-b]pyridin-4-yl)-1 H-pyrazol-3-yl]phenyl}urea |
| Example 5j | 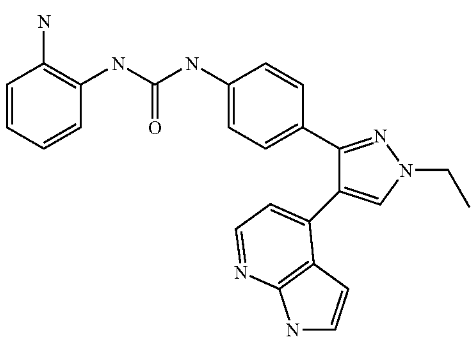 | N-(2-aminophenyl)-N'-{4-[1-ethyl-4-(1 H-pyrrolo[2,3-b]pyridin-4-yl)-1 H-pyrazol-3-yl]phenyl}urea |
| Example 5k | 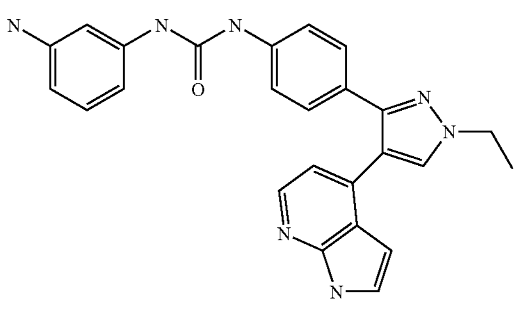 | N-(3-aminophenyl)-N'-{4-[1-ethyl-4-(1 H-pyrrolo[2,3-b]pyridin-4-yl)-1 H-pyrazol-3-yl]phenyl}urea |

-continued

| Example # | Structure | Name |
|---|---|---|
| Example 5l | 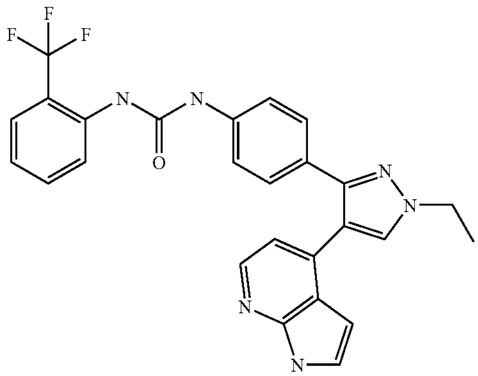 | N-{4-[1-ethyl-4-(1H-pyrrolo[2,3-b]pyridin-4-yl)-1H-pyrazol-3-yl]phenyl}-N'-[2-(trifluoromethyl)phenyl]urea |
| Example 5m | 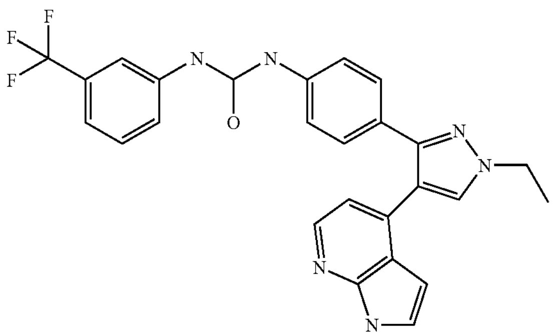 | N-{4-[1-ethyl-4-(1H-pyrrolo[2,3-b]pyridin-4-yl)-1H-pyrazol-3-yl]phenyl}-N'-[3-(trifluoromethyl)phenyl]urea |
| Example 5n | 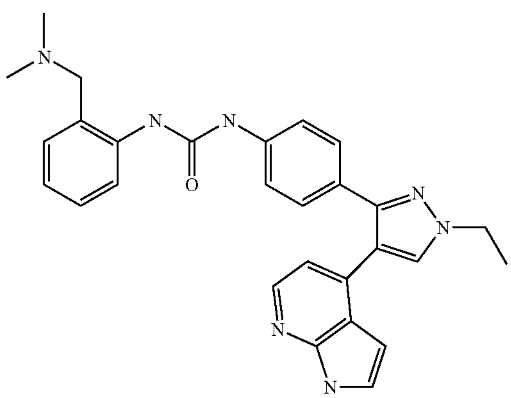 | N-{2-[(dimethylamino)methyl]phenyl}-N'-{4-[1-ethyl-4-(1H-pyrrolo[2,3-b]pyridin-4-yl)-1H-pyrazol-3-yl]phenyl}urea |
| Example 5o | 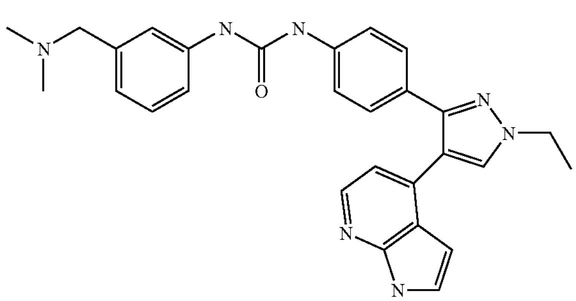 | N-{3-[(dimethylamino)methyl]phenyl}-N'-{4-[1-ethyl-4-(1H-pyrrolo[2,3-b]pyridin-4-yl)-1H-pyrazol-3-yl]phenyl}urea |

-continued

| Example # | Structure | Name |
|---|---|---|
| Example 5p | 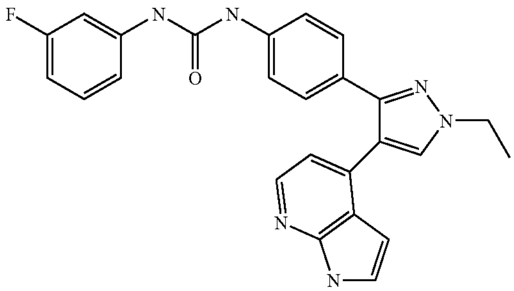 | N-{4-[1-ethyl-4-(1H-pyrrolo[2,3-b]pyridin-4-yl)-1H-pyrazol-3-yl]phenyl}-N'-(3-fluorophenyl)urea |
| Example 5q | 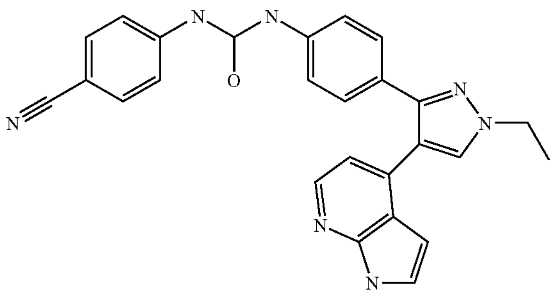 | N-(4-cyanophenyl)-N'-{4-[1-ethyl-4-(1H-pyrrolo[2,3-b]pyridin-4-yl)-1H-pyrazol-3-yl]phenyl}urea |
| Example 5r | 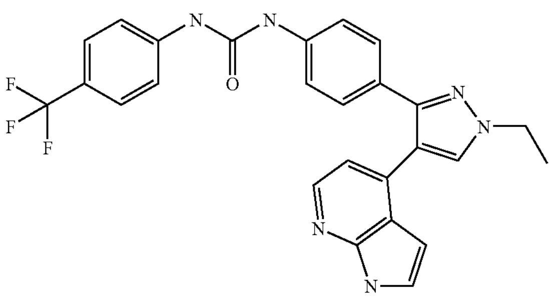 | N-{4-[1-ethyl-4-(1H-pyrrolo[2,3-b]pyridin-4-yl)-1H-pyrazol-3-yl]phenyl}-N'-[4-(trifluoromethyl)phenyl]urea |
| Example 5s | 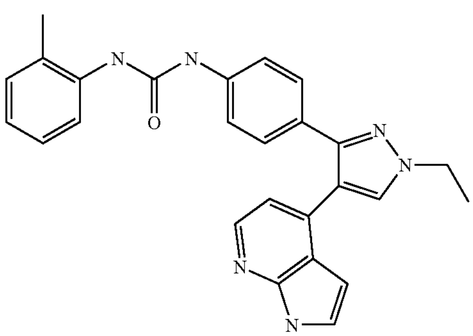 | N-{4-[1-ethyl-4-(1H-pyrrolo[2,3-b]pyridin-4-yl)-1H-pyrazol-3-yl]phenyl}-N'-(2-methylphenyl)urea |
| Example 5t | 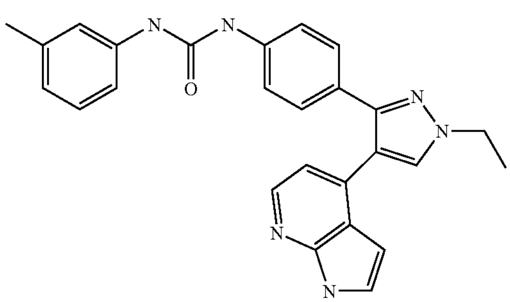 | N-{4-[1-ethyl-4-(1H-pyrrolo[2,3-b]pyridin-4-yl)-1H-pyrazol-3-yl]phenyl}-N'-(3-methylphenyl)urea |

-continued

| Example # | Structure | Name |
|---|---|---|
| Example 5u | 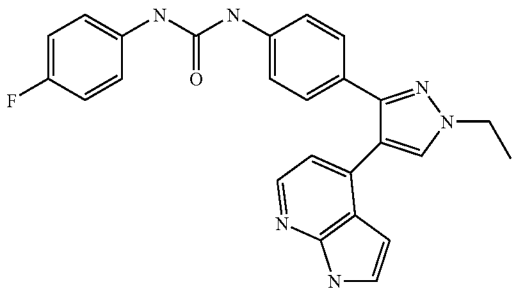 | N-{4-[1-ethyl-4-(1H-pyrrolo[2,3-b]pyridin-4-yl)-1H-pyrazol-3-yl]phenyl}-N'-(4-fluorophenyl)urea |
| Example 5v | 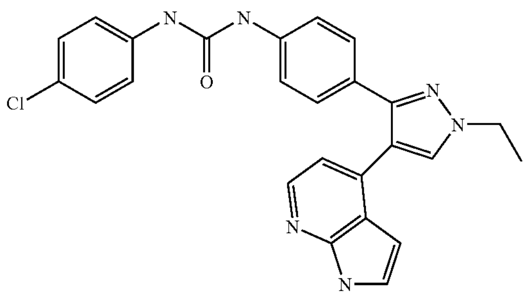 | N-(4-chlorophenyl)-N'-{4-[1-ethyl-4-(1H-pyrrolo[2,3-b]pyridin-4-yl)-1H-pyrazol-3-yl]phenyl}urea |
| Example 5w | 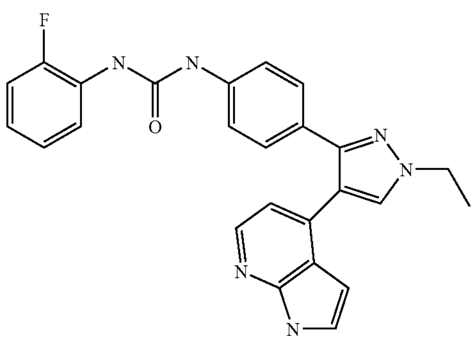 | N-{4-[1-ethyl-4-(1H-pyrrolo[2,3-b]pyridin-4-yl)-1H-pyrazol-3-yl]phenyl}-N'-(2-fluorophenyl)urea |
| Example 5x | 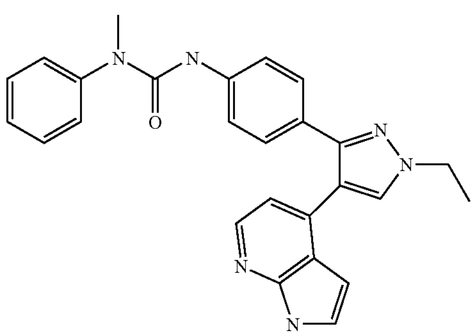 | N'-{4-[1-ethyl-4-(1H-pyrrolo[2,3-b]pyridin-4-yl)-1H-pyrazol-3-yl]phenyl}-N-methyl-N-phenylurea |
| Example 6 | 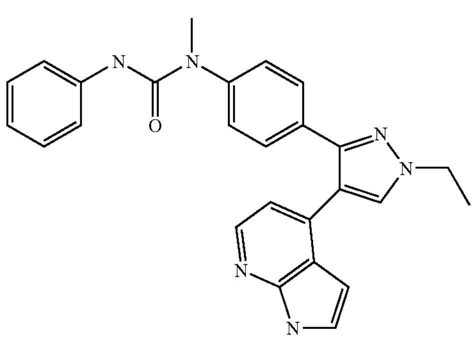 | N-{4-[1-ethyl-4-(1H-pyrrolo[2,3-b]pyridin-4-yl)-1H-pyrazol-3-yl]phenyl}-N-methyl-N'-phenylurea |

-continued

| Example # | Structure | Name |
|---|---|---|
| Example 7a | 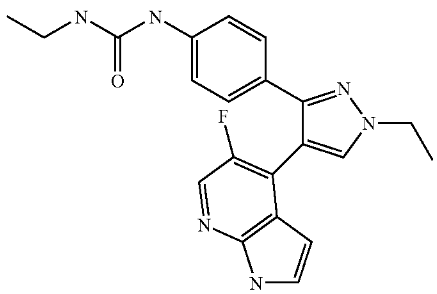 | N-ethyl-N'-{4-[1-ethyl-4-(5-fluoro-1 H-pyrrolo[2,3-b]pyridin-4-yl)-1 H-pyrazol-3-yl]phenyl}urea |
| Example 7b | 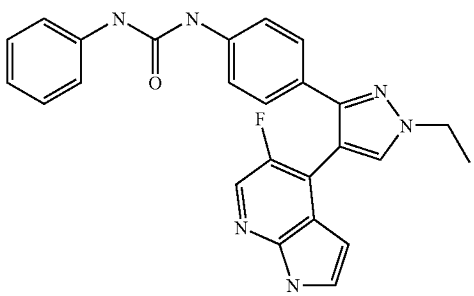 | N-{4-[1-ethyl-4-(5-fluoro-1 H-pyrrolo[2,3-b]pyridin-4-yl)-1 H-pyrazol-3-yl]phenyl}-N'-phenylurea |
| Example 8 | 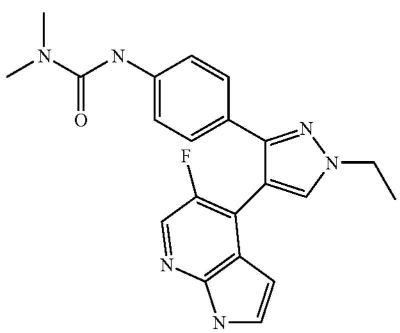 | N'-{4-[1-ethyl-4-(5-fluoro-1 H-pyrrolo[2,3-b]pyridin-4-yl)-1 H-pyrazol-3-yl]phenyl}-N,N-dimethylurea |
| Example 9a | 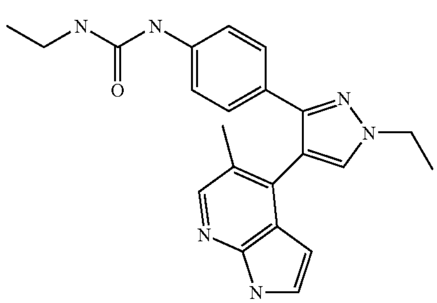 | N-ethyl-N'-{4-[1-ethyl-4-(5-methyl-1 H-pyrrolo[2,3-b]pyridin-4-yl)-1 H-pyrazol-3-yl]phenyl}urea |
| Example 9b | 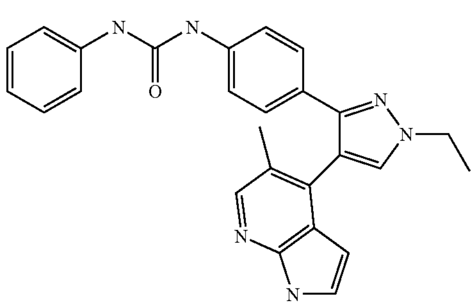 | N-{4-[1-ethyl-4-(5-methyl-1 H-pyrrolo[2,3-b]pyridin-4-yl)-1 H-pyrazol-3-yl]phenyl}-N'-phenylurea |

-continued

| Example # | Structure | Name |
|---|---|---|
| Example 10 | 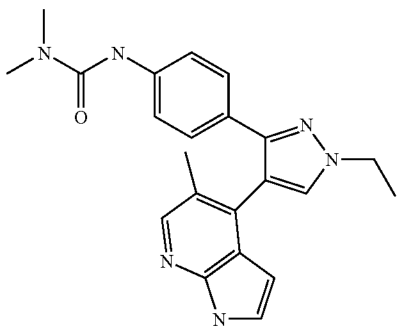 | N'-{4-[1-ethyl-4-(5-methyl-1 H-pyrrolo[2,3-b]pyridin-4-yl)-1 H-pyrazol-3-yl]phenyl}-N,N-dimethylurea |
| Example 11 | 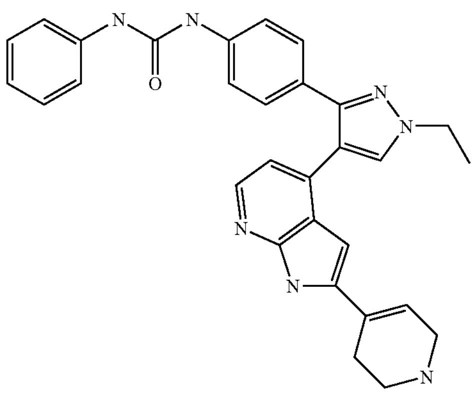 | N-(4-{1-ethyl-4-[2-(1,2,3,6-tetrahydro-4-pyridinyl)-1 H-pyrrolo[2,3-b]pyridin-4-yl]-1 H-pyrazol-3-yl}phenyl)-N'-phenylurea |
| Example 12a | 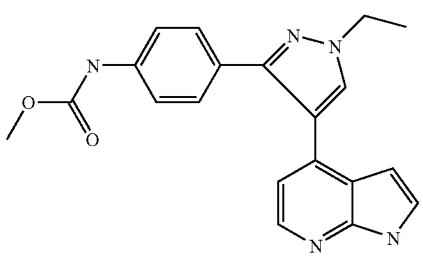 | methyl {4-[1-ethyl-4-(1 H-pyrrolo[2,3-b]pyridin-4-yl)-1 H-pyrazol-3-yl]phenyl}carbamate |
| Example 12b | 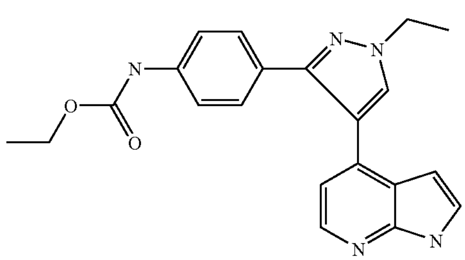 | ethyl {4-[1-ethyl-4-(1 H-pyrrolo[2,3-b]pyridin-4-yl)-1 H-pyrazol-3-yl]phenyl}carbamate |
| Example 12c | 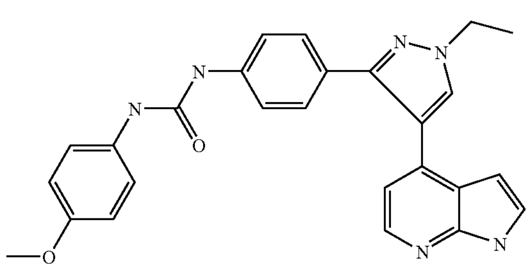 | N-{4-[1-ethyl-4-(1 H-pyrrolo[2,3-b]pyridin-4-yl)-1 H-pyrazol-3-yl]phenyl}-N'-[4-(methyloxy)phenyl]urea |

-continued

| Example # | Structure | Name |
|---|---|---|
| Example 12d | 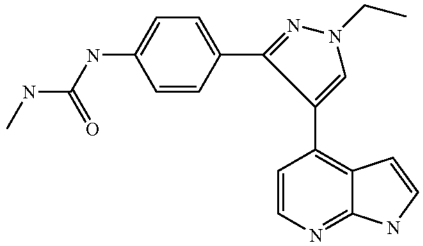 | N-{4-[1-ethyl-4-(1 H-pyrrolo[2,3-b]pyridin-4-yl)-1 H-pyrazol-3-yl]phenyl}-N'-methylurea |
| Example 12e | 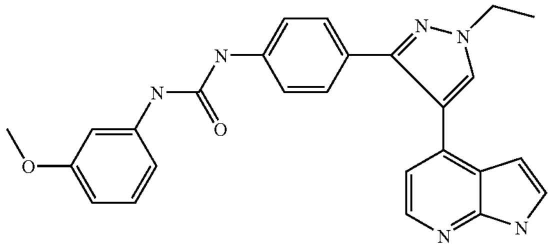 | N-{4-[1-ethyl-4-(1 H-pyrrolo[2,3-b]pyridin-4-yl)-1 H-pyrazol-3-yl]phenyl}-N'-[3-(methyloxy)pheny]urea |
| Example 13 | 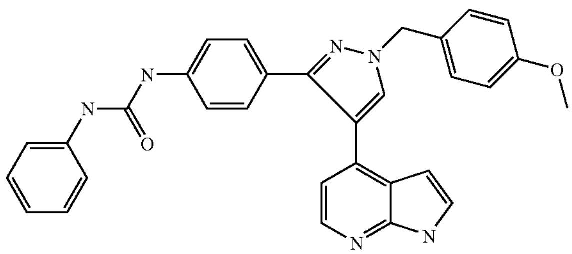 | N-{4-[1-{[4-(methyloxy)phenyl]methyl}-4-(1 H-pyrrolo[2,3-b]pyridin-4-yl)-1 H-pyrazol-3-yl]phenyl}-N'-phenylurea |
| Example 14 | 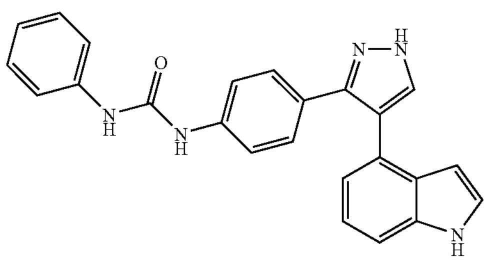 | N-phenyl-N'-{4-[4-(1 H-pyrrolo[2,3-b]pyridin-4-yl)-1 H-pyrazol-3-yl]phenyl}urea hydrochloride |
| Example 15a | 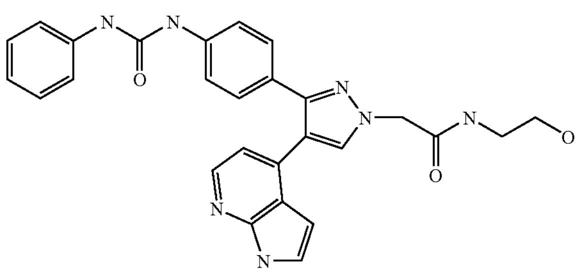 | N-(2-hydroxyethyl)-2-[3-(4-{[(phenylamino)carbonyl]amino}phenyl)-4-(1 H-pyrrolo[2,3-b]pyridin-4-yl)-1 H-pyrazol-1-yl]acetamide |
| Example 15b | 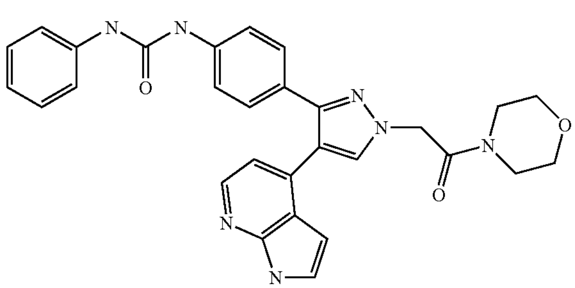 | N-{4-[1-[2-(4-morpholinyl)-2-oxoethyl]-4-(1 H-pyrrolo[2,3-b]pyridin-4-yl)-1 H-pyrazol-3-yl]phenyl}-N'-phenylurea |

| Example # | Structure | Name |
|---|---|---|
| Example 16a | 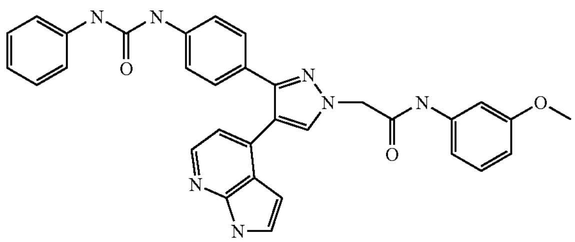 | N-[3-(methyloxy)phenyl]-2-[3-(4-{[(phenylamino)carbonyl]amino}phenyl)-4-(1 H-pyrrolo[2,3-b]pyridin-4-yl)-1 H-pyrazol-1-yl]acetamide |
| Example 16b | 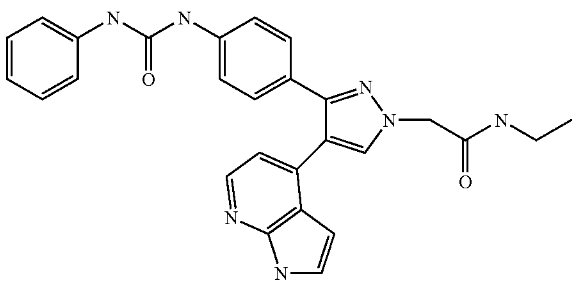 | N-ethyl-2-[3-(4-{[(phenylamino)carbonyl]amino}phenyl)-4-(1 H-pyrrolo[2,3-b]pyridin-4-yl)-1 H-pyrazol-1-yl]acetamide |
| Example 17 | 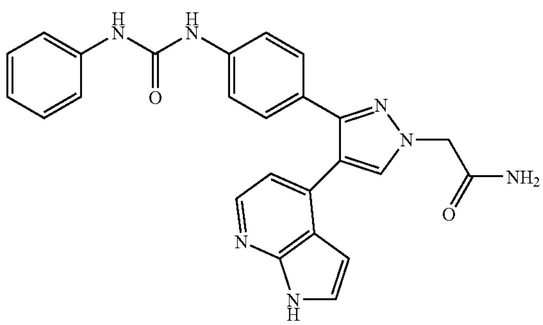 | 2-[3-(4-{[(phenylamino)carbonyl]amino}phenyl)-4-(1 H-pyrrolo[2,3-b]pyridin-4-yl)-1 H-pyrazol-1-yl]acetamide |
| Example 18 | 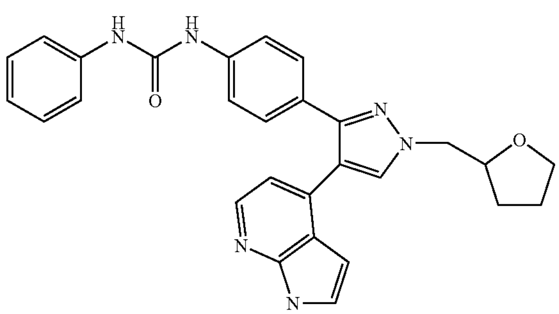 | N-phenyl-N'-{4-[4-(1 H-pyrrolo[2,3-b]pyridin-4-yl)-1-(tetrahydro-2-furanylmethyl)-1 H-pyrazol-3-yl]phenyl}urea |
| Example 19 | 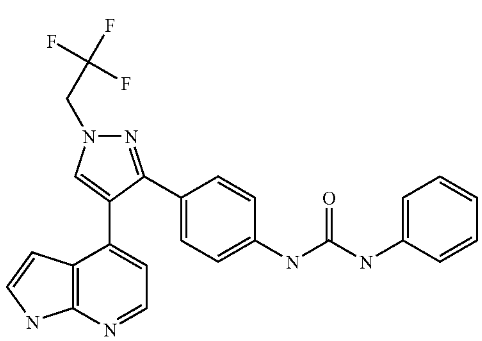 | N-phenyl-N'-{4-[4-(1 H-pyrrolo[2,3-b]pyridin-4-yl)-1-(2,2,2-trifluoroethyl)-1 H-pyrazol-3-yl]phenyl}urea |

-continued

| Example # | Structure | Name |
|---|---|---|
| Example 20 | 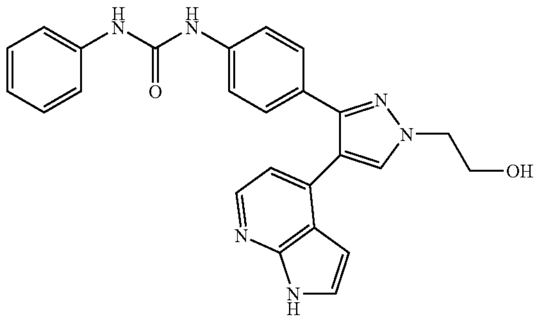 | N-{4-[1-(2-hydroxyethyl)-4-(1 H-pyrrolo[2,3-b]pyridin-4-yl)-1 H-pyrazol-3-yl]phenyl}-N'-phenylurea |
| Example 21 | 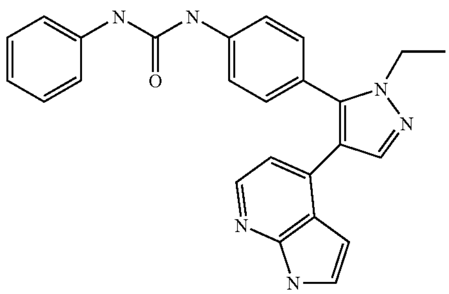 | N-{4-[1-ethyl-4-(1 H-pyrrolo[2,3-b]pyridin-4-yl)-1 H-pyrazol-5-yl]phenyl}-N'-phenylurea |
| Example 22 | 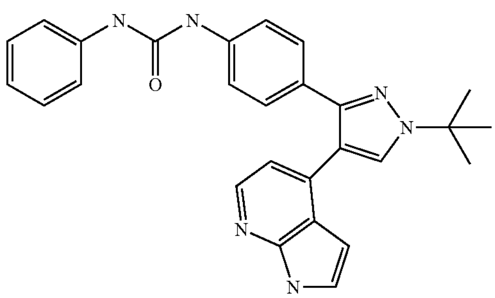 | N-{4-[1-(1,1-dimethylethyl)-4-(1 H-pyrrolo[2,3-b]pyridin-4-yl)-1 H-pyrazol-3-yl]phenyl}-N'-phenylurea |
| Example 23 | 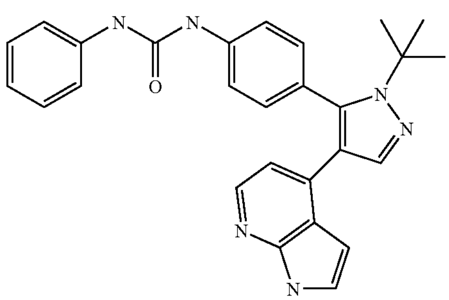 | N-{4-[1-(1,1-dimethylethyl)-4-(1 H-pyrrolo[2,3-b]pyridin-4-yl)-1 H-pyrazol-5-yl]phenyl}-N'-phenylurea |
| Example 24 | 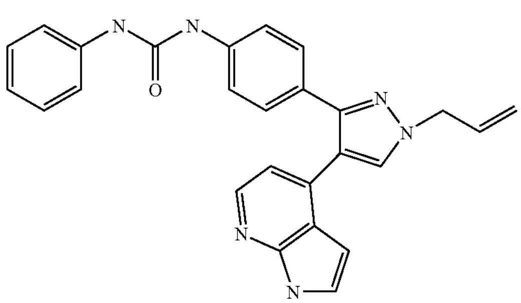 | N-phenyl-N'-{4-[1-(2-propen-1-yl)-4-(1 H-pyrrolo[2,3-b]pyridin-4-yl)-1 H-pyrazol-3-yl]phenyl}urea |

-continued

| Example # | Structure | Name |
| --- | --- | --- |
| Example 25 | 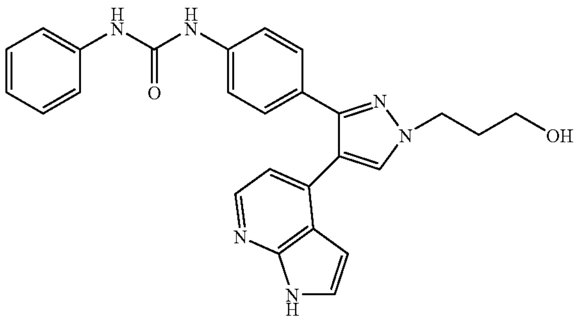 | N-{4-[1-(3-hydroxypropyl)-4-(1 H-pyrrolo[2,3-b]pyridin-4-yl)-1 H-pyrazol-3-yl]phenyl}-N'-phenylurea |
| Example 26 | 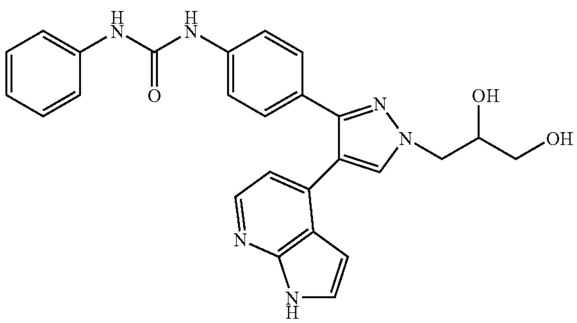 | N-{4-[1-(2,3-dihydroxypropyl)-4-(1 H-pyrrolo[2,3-b]pyridin-4-yl)-1 H-pyrazol-3-yl]phenyl}-N'-phenylurea |
| Example 27a | 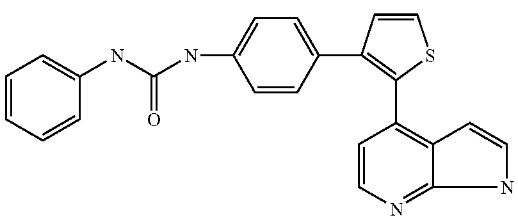 | N-phenyl-N'-{4-[2-(1 H-pyrrolo[2,3-b]pyridin-4-yl)-3-thienyl]phenyl}urea |
| Example 27b | 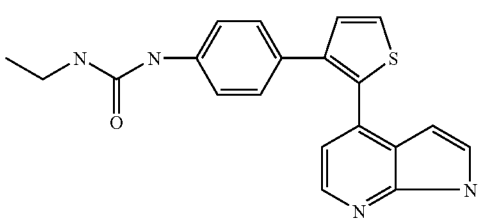 | N-ethyl-N'-{4-[2-(1 H-pyrrolo[2,3-b]pyridin-4-yl)-3-thienyl]phenyl}urea |
| Example 28 | 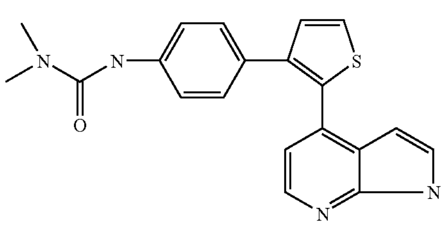 | N,N-dimethyl-N'-{4-[2-(1 H-pyrrolo[2,3-b]pyridin-4-yl)-3-thienyl]phenyl}urea |

-continued

| Example # | Structure | Name |
|---|---|---|
| Example 29 | 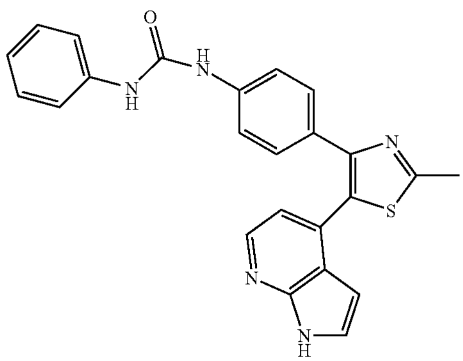 | N-{4-[2-methyl-5-(1H-pyrrolo[2,3-b]pyridin-4-yl)-1,3-thiazol-4-yl]phenyl}-N'-phenylurea |
| Example 30 | 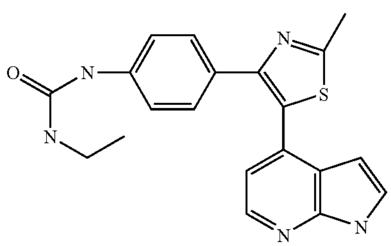 | N-ethyl-N'-{4-[2-methyl-5-(1H-pyrrolo[2,3-b]pyridin-4-yl)-1,3-thiazol-4-yl]phenyl}urea |
| Example 31 | 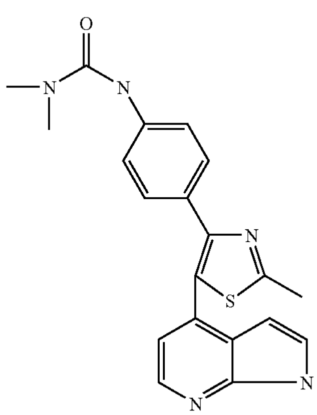 | N,N-dimethyl-N'-{4-[2-methyl-5-(1H-pyrrolo[2,3-b]pyridin-4-yl)-1,3-thiazol-4-yl]phenyl}urea |
| Example 32 | 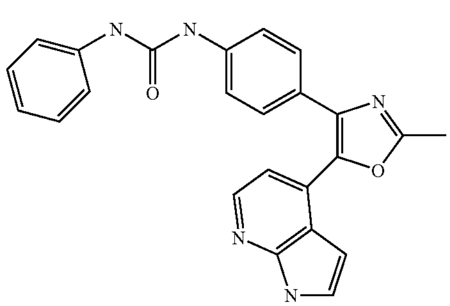 | N-{4-[2-methyl-5-(1H-pyrrolo[2,3-b]pyridin-4-yl)-1,3-oxazol-4-yl]phenyl}-N'-phenylurea |

-continued

| Example # | Structure | Name |
|---|---|---|
| Example 33 | 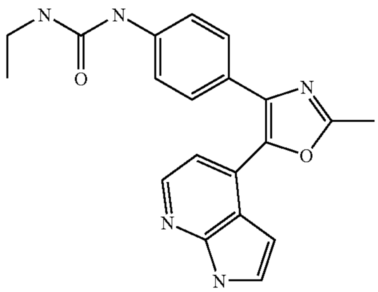 | N-ethyl-N'-{4-[2-methyl-5-(1 H-pyrrolo[2,3-b]pyridin-4-yl)-1,3-oxazol-4-yl]phenyl}urea |
| Example 34 | 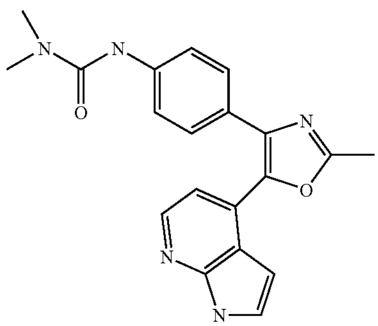 | N,N-dimethyl-N'-{4-[2-methyl-5-(1 H-pyrrolo[2,3-b]pyridin-4-yl)-1,3-oxazol-4-yl]phenyl}urea |
| Example 35 | 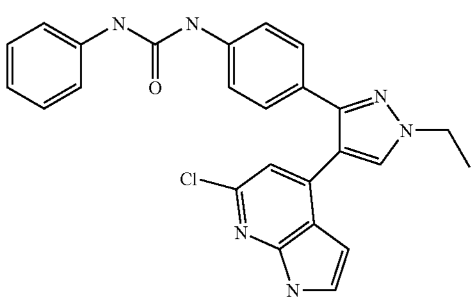 | N-{4-[4-(6-chloro-1 H-pyrrolo[2,3-b]pyridin-4-yl)-1-ethyl-1 H-pyrazol-3-yl]phenyl}-N'-phenylurea |
| Example 36 | 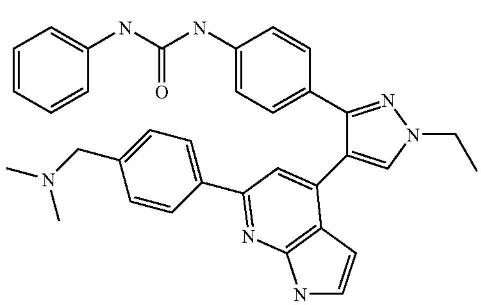 | N-{4-[4-(6-{4-[(dimethylamino)methyl]phenyl}-1 H-pyrrolo[2,3-b]pyridin-4-yl)-1-ethyl-1 H-pyrazol-3-yl]phenyl}-N'-phenylurea |

-continued

| Example # | Structure | Name |
|---|---|---|
| Example 37 | 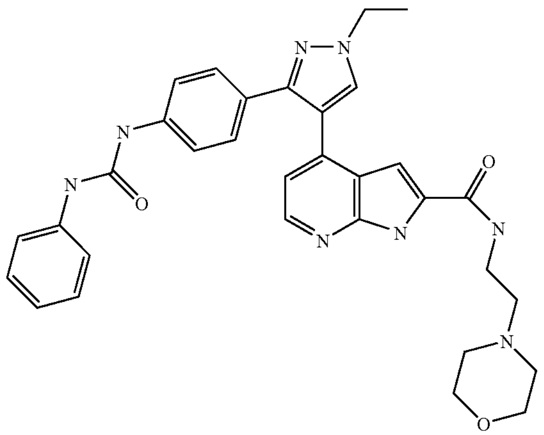 | 4-[1-ethyl-3-(4-{[(phenylamino)carbonyl]amino}phenyl)-1H-pyrazol-4-yl]-N-[2-(4-morpholinyl)ethyl]-1H-pyrrolo[2,3-b]pyridine-2-carboxamide |
| Example 38 | 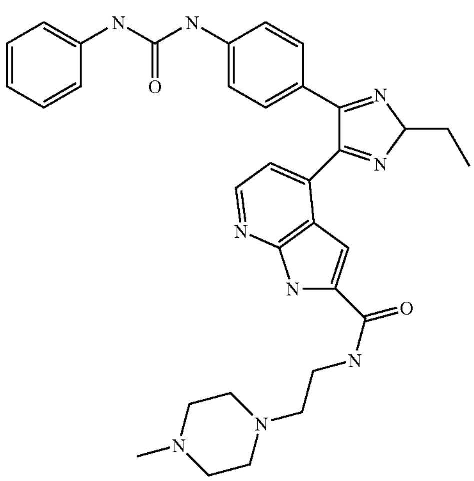 | 4-[1-ethyl-3-(4-{[(phenylamino)carbonyl]amino}phenyl)-1H-pyrazol-4-yl]-N-[2-(4-methyl-1-piperazinyl)-1H-pyrrolo[2,3-b]pyridine-2-carboxamide |
| Example 39 | 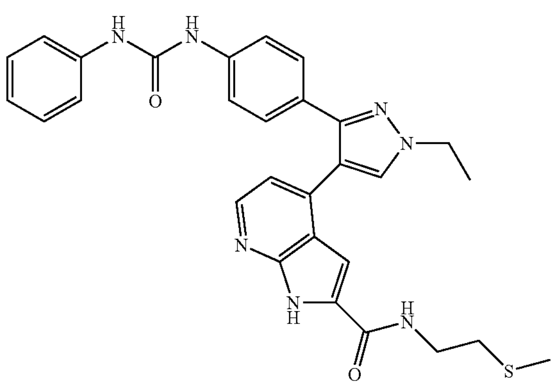 | 4-[1-ethyl-3-(4-{[(phenylamino)carbonyl]amino}phenyl)-1H-pyrazol-4-yl]-N-[2-(methylthio)ethyl]-1H-pyrrolo[2,3-b]pyridine-2-carboxamide |

-continued

| Example # | Structure | Name |
|---|---|---|
| Example 40 | 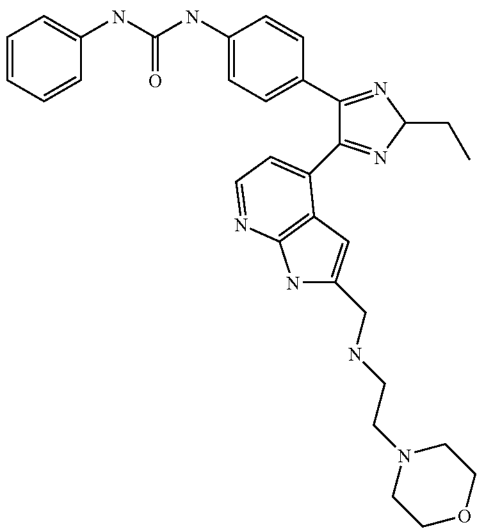 | N-(4-{1-ethyl-4-[2-({[2-(4-morpholinyl)ethyl]amino}methyl)-1H-pyrrolo[2,3-b]pyridin-4-yl]-1H-pyrazol-3-yl}phenyl)-N'-phenylurea |
| Example 41 | 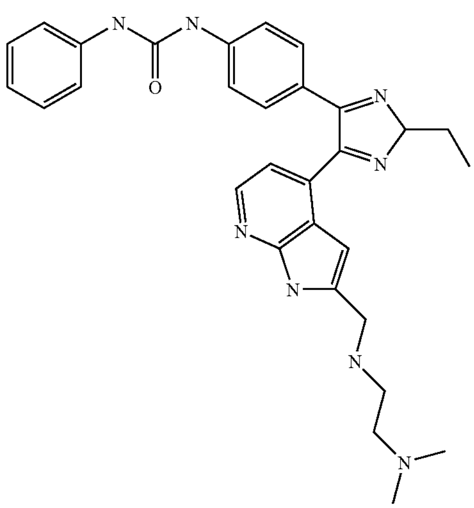 | N-(4-{4-[2-({[2-(dimethylamino)ethyl]amino}methyl)-1H-pyrrolo[2,3-b]pyridin-4-yl]-1-ethyl-1H-pyrazol-3-yl}phenyl)-N'-phenylurea |
| Example 42 | 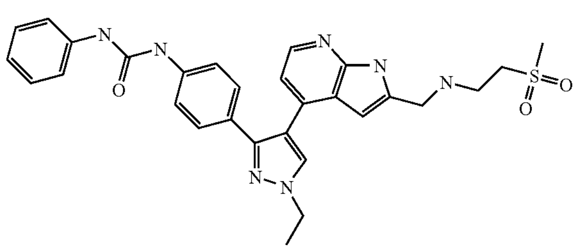 | N-(4-{1-ethyl-4-[2-({[2-(methylsulfonyl)ethyl]amino}methyl)-1H-pyrrolo[2,3-b]pyridin-4-yl]-1H-pyrazol-3-yl}phenyl)-N'-phenylurea |

-continued

| Example # | Structure | Name |
|---|---|---|
| Example 43 | 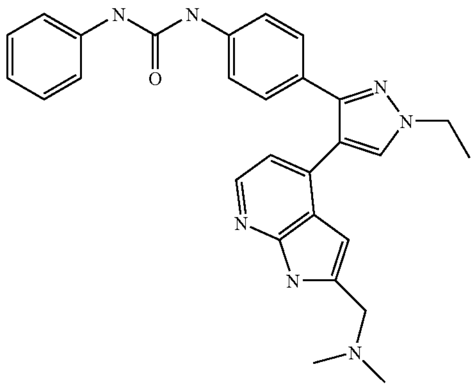 | N-[4-(4-{2-[(dimethylamino)methyl]-1 H-pyrrolo[2,3-b]pyridin-4-yl}-1-ethyl-1 H-pyrazol-3-yl)phenyl]-N'-phenylurea |
| Example 44 | 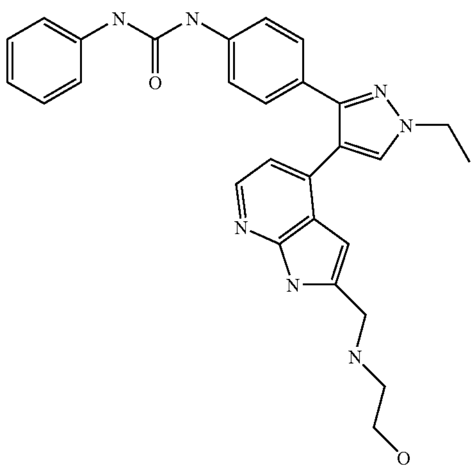 | N-{4-[1-ethyl-4-(2-{[(2-hydroxyethyl)amino]methyl}-1 H-pyrrolo[2,3-b]pyridin-4-yl)-1 H-pyrazol-3-yl]phenyl}-N'-phenylurea |
| Example 45 | 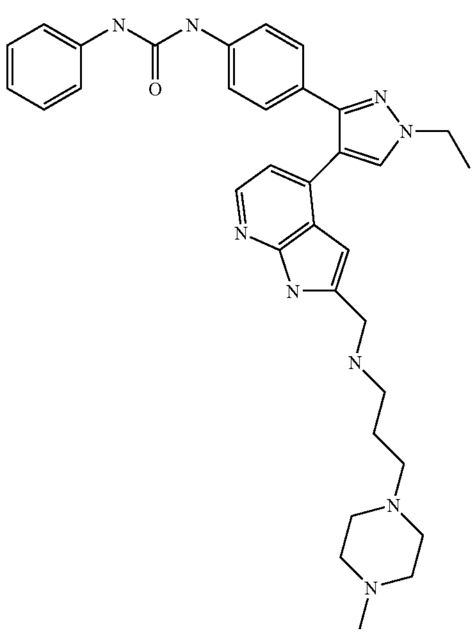 | N-(4-{1-ethyl-4-[2-({[3-(4-methyl-1-piperazinyl)propyl]amino}methyl)-1 H-pyrrolo[2,3-b]pyridin-4-yl]-1 H-pyrazol-3-yl}phenyl)-N'-phenylurea |

-continued

| Example # | Structure | Name |
|---|---|---|
| Example 46a | 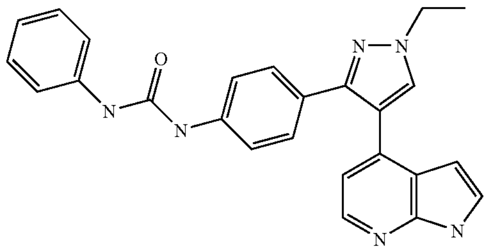 | N-{4-[1-ethyl-4-(1H-pyrrolo[2,3-b]pyridin-4-yl)-1H-pyrazol-3-yl]phenyl}-N'-phenylurea |
| Example 46b | 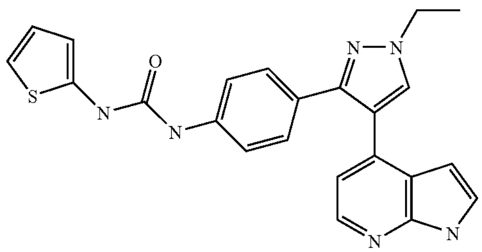 | N-{4-[1-ethyl-4-(1H-pyrrolo[2,3-b]pyridin-4-yl)-1H-pyrazol-3-yl]phenyl}-2-(2-thienyl)acetamide |
| Example 46c | 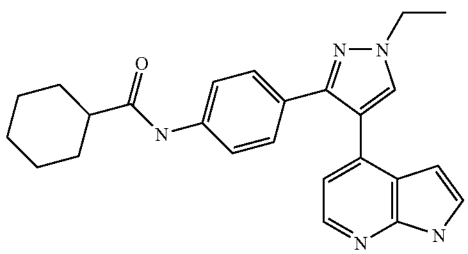 | N-{4-[1-ethyl-4-(1H-pyrrolo[2,3-b]pyridin-4-yl)-1H-pyrazol-3-yl]phenyl}cyclohexanecarboxamide |
| Example 46d | 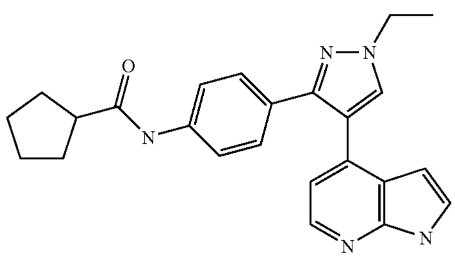 | N-{4-[1-ethyl-4-(1H-pyrrolo[2,3-b]pyridin-4-yl)-1H-pyrazol-3-yl]phenyl}cyclopentanecarboxamide |
| Example 46e | 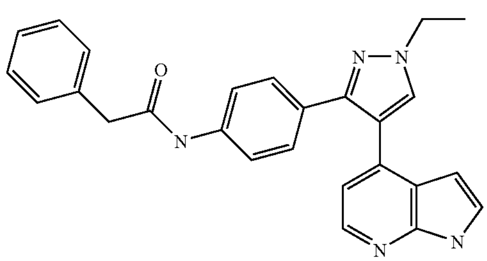 | N-{4-[1-ethyl-4-(1H-pyrrolo[2,3-b]pyridin-4-yl)-1H-pyrazol-3-yl]phenyl}-2-phenylacetamide |
| Example 46f | 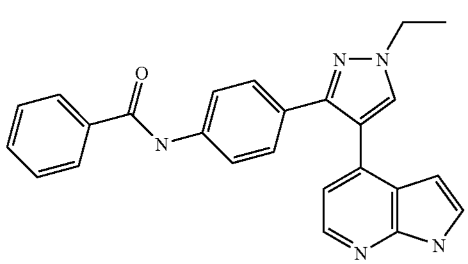 | N-{4-[1-ethyl-4-(1H-pyrrolo[2,3-b]pyridin-4-yl)-1H-pyrazol-3-yl]phenyl}benzamide |

-continued

| Example # | Structure | Name |
|---|---|---|
| Example 46g | 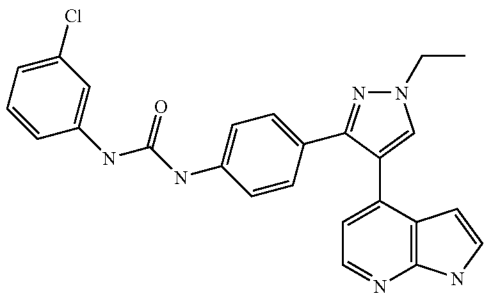 | N-(3-chlorophenyl)-N'-{4-[1-ethyl-4-(1 H-pyrrolo[2,3-b]pyridin-4-yl)-1 H-pyrazol-3-yl]phenyl}urea |
| Example 46h | 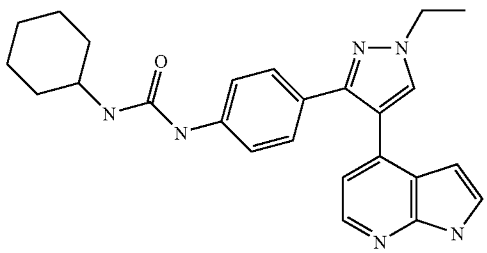 | N-cyclohexyl-N'-{4-[1-ethyl-4-(1 H-pyrrolo[2,3-b]pyridin-4-yl)-1 H-pyrazol-3-yl]phenyl}urea |
| Example 46i | 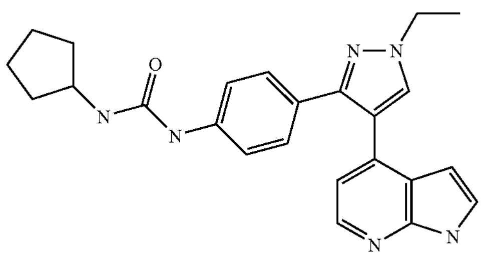 | N-cyclopentyl-N'-{4-[1-ethyl-4-(1 H-pyrrolo[2,3-b]pyridin-4-yl)-1 H-pyrazol-3-yl]phenyl}urea |
| Example 46j | 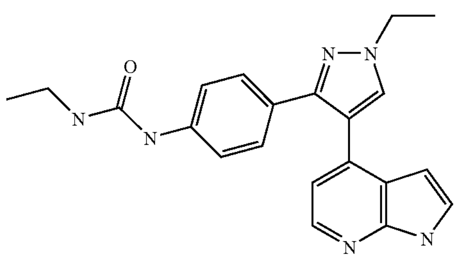 | N-ethyl-N'-{4-[1-ethyl-4-(1 H-pyrrolo[2,3-b]pyridin-4-yl)-1 H-pyrazol-3-yl]phenyl}urea |
| Example 46k | 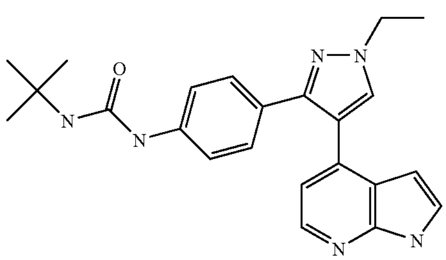 | N-(1,1-dimethylethyl)-N'-{4-[1-ethyl-4-(1 H-pyrrolo[2,3-b]pyridin-4-yl)-1 H-pyrazol-3-yl]phenyl}urea |
| Example 46l | 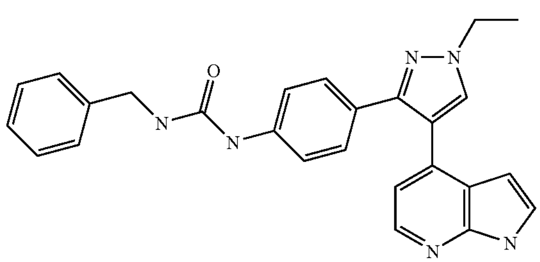 | N-{4-[1-ethyl-4-(1 H-pyrrolo[2,3-b]pyridin-4-yl)-1 H-pyrazol-3-yl]phenyl}-N'-(phenylmethyl)urea |

-continued

| Example # | Structure | Name |
|---|---|---|
| Example 47 | 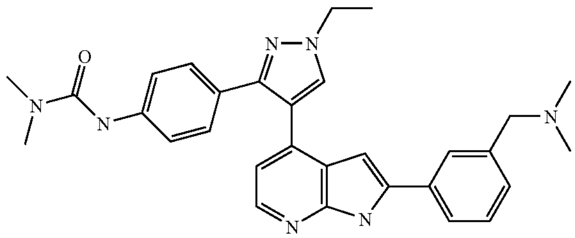 | N'-{4-[4-(2-{3-[(dimethylamino)methyl]phenyl}-1H-pyrrolo[2,3-b]pyridin-4-yl)-1-ethyl-1H-pyrazol-3-yl]phenyl}-N,N-dimethylurea |
| Example 48 | 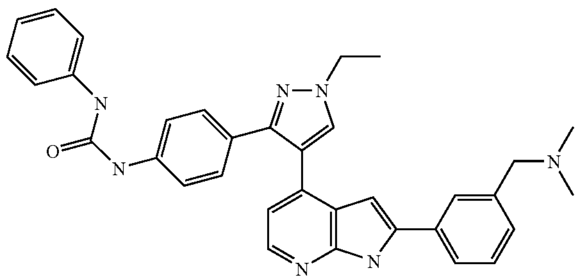 | N-{4-[4-(2-{3-[(dimethylamino)methyl]phenyl}-1H-pyrrolo[2,3-b]pyridin-4-yl)-1-ethyl-1H-pyrazol-3-yl]phenyl}-N'-phenylurea |
| Example 49 | 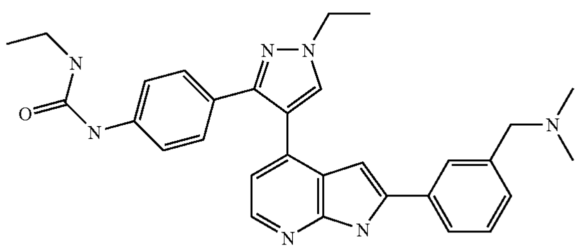 | N-{4-[4-(2-{3-[(dimethylamino)methyl]phenyl}-1H-pyrrolo[2,3-b]pyridin-4-yl)-1-ethyl-1H-pyrazol-3-yl]phenyl}-N'-ethylurea |
| Example 50 | 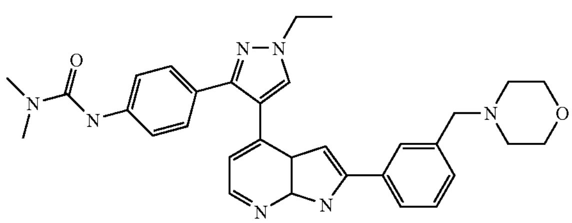 | N'-[4-(1-ethyl-4-{2-[3-(4-morpholinylmethyl)phenyl]-1H-pyrrolo[2,3-b]pyridin-4-yl}-1H-pyrazol-3-yl)phenyl]-N,N-dimethylurea |
| Example 51 | 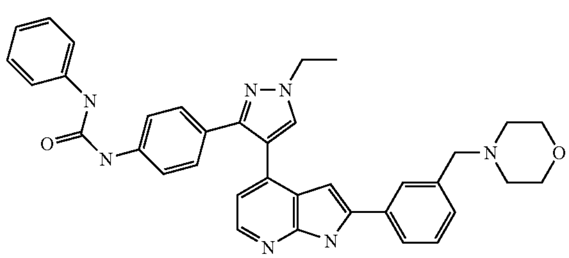 | N-[4-(1-ethyl-4-{2-[3-(4-morpholinylmethyl)phenyl]-1H-pyrrolo[2,3-b]pyridin-4-yl}-1H-pyrazol-3-yl)phenyl]-N'-phenylurea |
| Example 52 | 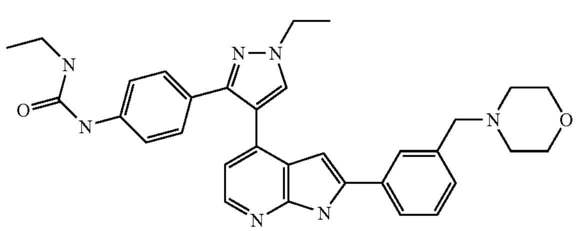 | N-ethyl-N'-[4-(1-ethyl-4-{2-[3-(4-morpholinylmethyl)phenyl]-1H-pyrrolo[2,3-b]pyridin-4-yl}-1H-pyrazol-3-yl)phenyl]urea |

-continued

| Example # | Structure | Name |
| --- | --- | --- |
| Example 53 | 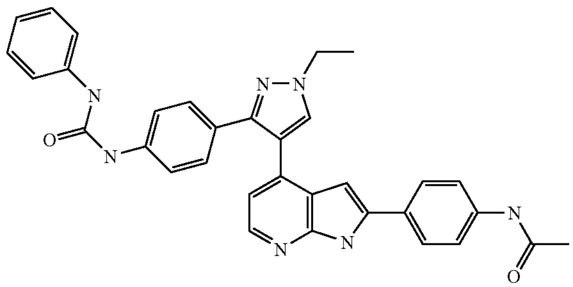 | N-(4-{4-[1-ethyl-3-(4-{[(phenylamino)carbonyl]amino}phenyl)-1 H-pyrazol-4-yl]-1 H-pyrrolo[2,3-b]pyridin-2-yl}phenyl)acetamide |
| Example 54 | 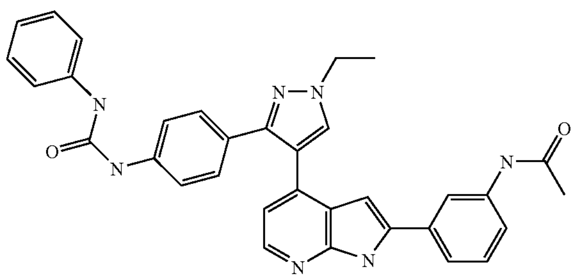 | N-(3-{4-[1-ethyl-3-(4-{[(phenylamino)carbonyl]amino}phenyl)-1 H-pyrazol-4-yl]-1 H-pyrrolo[2,3-b]pyridin-2-yl}phenyl)acetamide |
| Example 55 | 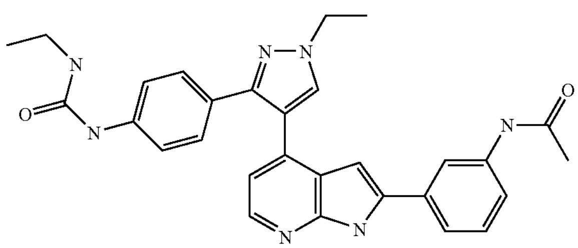 | N-(3-{4-[1-ethyl-3-(4-{[(ethylamino)carbonyl]amino}phenyl)-1 H-pyrazol-4-yl]-1 H-pyrrolo[2,3-b]pyridin-2-yl}phenyl)acetamide |
| Example 56 | 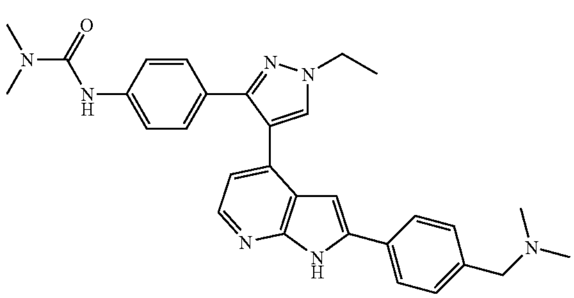 | N'-{4-[4-(2-{4-[(dimethylamino)methyl]phenyl}-1 H-pyrrolo[2,3-b]pyridin-4-yl)-1-ethyl-1 H-pyrazol-3-yl]phenyl}-N,N-dimethylurea |
| Example 57 | 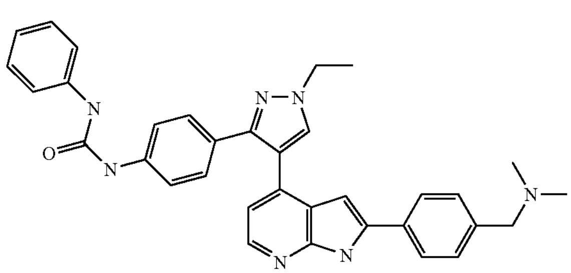 | N-{4-[4-(2-{4-[(dimethylamino)methyl]phenyl}-1 H-pyrrolo[2,3-b]pyridin-4-yl)-1-ethyl-1 H-pyrazol-3-yl]phenyl}-N'-phenylurea |

-continued

| Example # | Structure | Name |
|---|---|---|
| Example 58 | 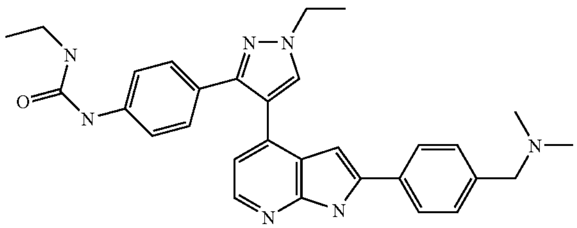 | N-{4-[4-(2-{4-[(dimethylamino)methyl]phenyl}-1H-pyrrolo[2,3-b]pyridin-4-yl)-1-ethyl-1H-pyrazol-3-yl]phenyl}-N'-ethylurea |
| Example 59 | 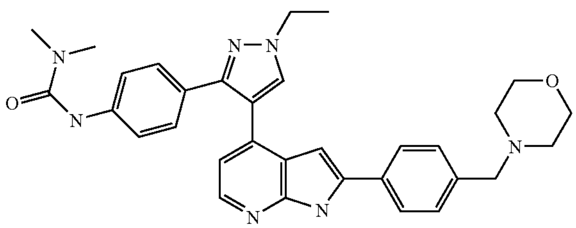 | N'-[4-(1-ethyl-4-{2-[4-(4-morpholinylmethyl)phenyl]-1H-pyrrolo[2,3-b]pyridin-4-yl}-1H-pyrazol-3-yl)phenyl]-N,N-dimethylurea |
| Example 60 | 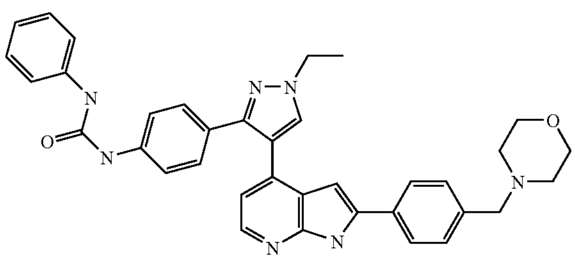 | N-[4-(1-ethyl-4-{2-[4-(4-morpholinylmethyl)phenyl]-1H-pyrrolo[2,3-b]pyridin-4-yl}-1H-pyrazol-3-yl)phenyl]-N'-phenylurea |
| Example 61 | 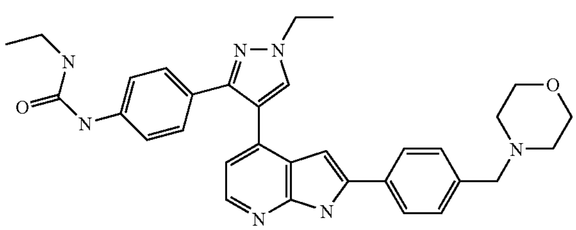 | N-ethyl-N'-[4-(1-ethyl-4-{2-[4-(4-morpholinylmethyl)phenyl]-1H-pyrrolo[2,3-b]pyridin-4-yl}-1H-pyrazol-3-yl)phenyl]urea |
| Example 62 | 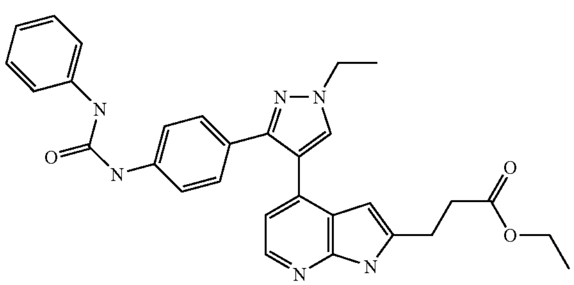 | ethyl 3-{4-[1-ethyl-3-(4-{[(phenylamino)carbonyl]amino}phenyl)-1H-pyrazol-4-yl]-1H-pyrrolo[2,3-b]pyridin-2-yl}propanoate |
| Example 63 | 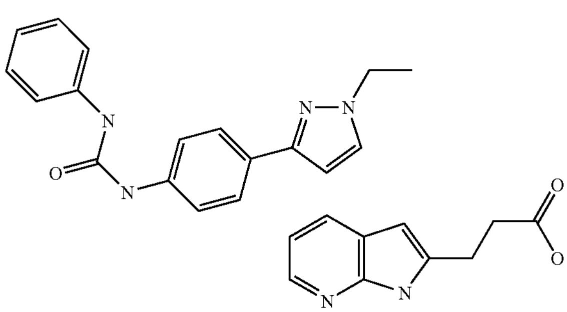 | 3-{4-[1-ethyl-3-(4-{[(phenylamino)carbonyl]amino}phenyl)-1H-pyrazol-4-yl]-1H-pyrrolo[2,3-b]pyridin-2-yl}propanoic acid |

| Example # | Structure | Name |
|---|---|---|
| Example 64 | 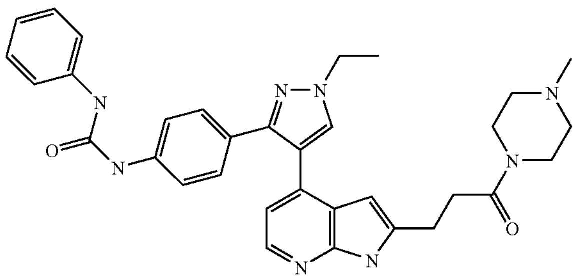 | N-[4-(1-ethyl-4-{2-[3-(4-methyl-1-piperazinyl)-3-oxopropyl]-1 H-pyrrolo[2,3-b]pyridin-4-yl}-1 H-pyrazol-3-yl)phenyl]-N'-phenylurea |
| Example 65 | 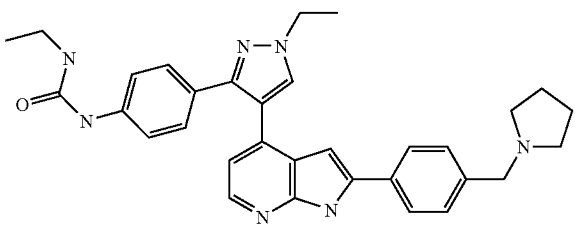 | N-ethyl-N'-[4-(1-ethyl-4-{2-[4-(1-pyrrolidinylmethyl)phenyl]-1 H-pyrrolo[2,3-b]pyridin-4-yl}-1 H-pyrazol-3-yl)phenyl]urea |
| Example 66 | 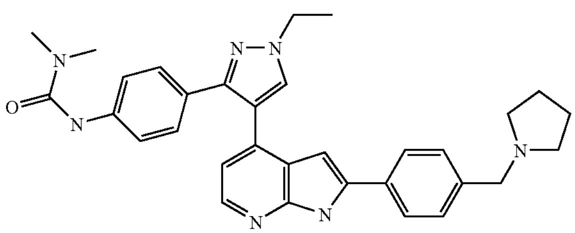 | N'-[4-(1-ethyl-4-{2-[4-(1-pyrrolidinylmethyl)phenyl]-1 H-pyrrolo[2,3-b]pyridin-4-yl}-1 H-pyrazol-3-yl)phenyl]-N,N-dimethylurea |
| Example 67 | 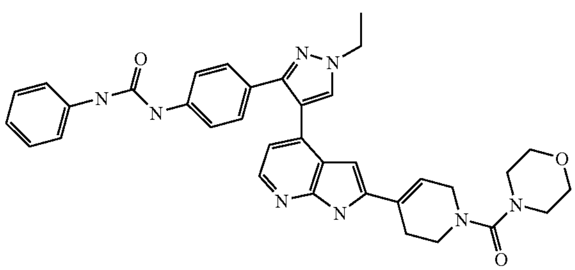 | N-[4-(1-ethyl-4-{2-[1-(4-morpholinylcarbonyl)-1,2,3,6-tetrahydro-4-pyridinyl]-1 H-pyrrolo[2,3-b]pyridin-4-yl}-1 H-pyrazol-3-yl)phenyl]-N'-phenylurea |
| Example 68 | 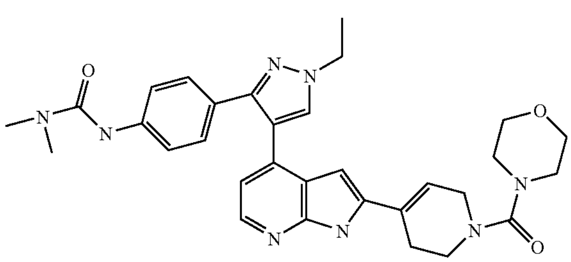 | N'-[4-(1-ethyl-4-{2-[1-(4-morpholinylcarbonyl)-1,2,3,6-tetrahydro-4-pyridinyl]-1 H-pyrrolo[2,3-b]pyridin-4-yl}-1 H-pyrazol-3-yl)phenyl]-N,N-dimethylurea |
| Example 69 | 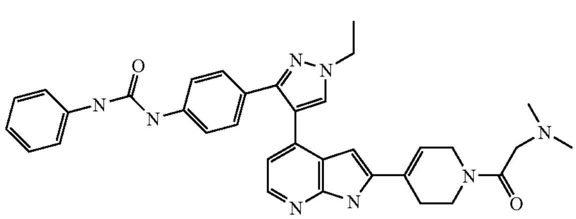 | N-[4-(4-{2-[1-(N,N-dimethylglycyl)-1,2,3,6-tetrahydro-4-pyridinyl]-1 H-pyrrolo[2,3-b]pyridin-4-yl}-1-ethyl-1 H-pyrazol-3-yl)phenyl]-N'-phenylurea |

| Example # | Structure | Name |
|---|---|---|
| Example 70 | 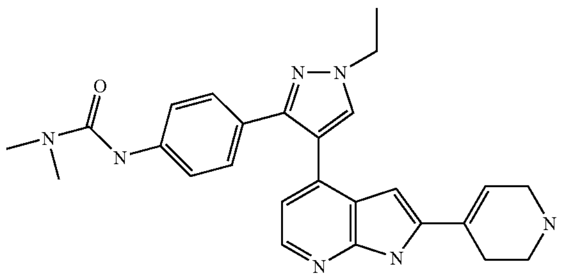 | N'-(4-{1-ethyl-4-[2-(1,2,3,6-tetrahydro-4-pyridinyl)-1H-pyrrolo[2,3-b]pyridin-4-yl]-1H-pyrazol-3-yl}phenyl)-N,N-dimethylurea |
| Example 71a | 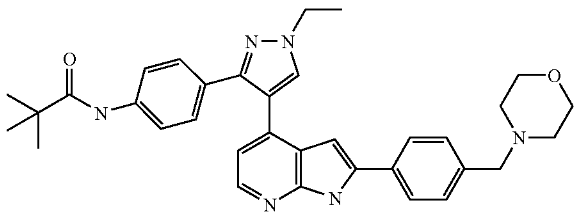 | N-[4-(1-ethyl-4-{2-[4-(4-morpholinylmethyl)phenyl]-1H-pyrrolo[2,3-b]pyridin-4-yl}-1H-pyrazol-3-yl)phenyl]-2,2-dimethylpropanamide |
| Example 71b | 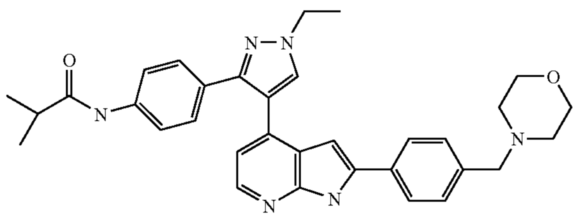 | N-[4-(1-ethyl-4-{2-[4-(4-morpholinylmethyl)phenyl]-1H-pyrrolo[2,3-b]pyridin-4-yl}-1H-pyrazol-3-yl)phenyl]-2-methylpropanamide |
| Example 72 | 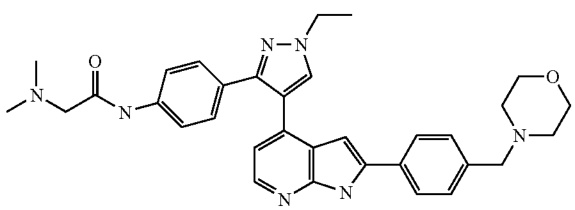 | N~1~-[4-(1-ethyl-4-{2-[4-(4-morpholinylmethyl)phenyl]-1H-pyrrolo[2,3-b]pyridin-4-yl}-1H-pyrazol-3-yl)phenyl]-N~2~,N~2~-dimethylglycinamide |
| Example 73a | 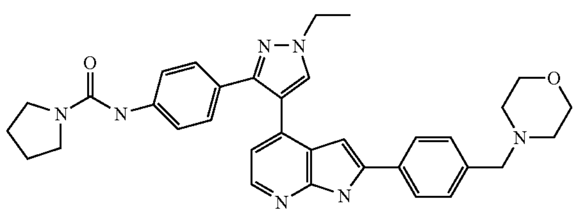 | N-[4-(1-ethyl-4-{2-[4-(4-morpholinylmethyl)phenyl]-1H-pyrrolo[2,3-b]pyridin-4-yl}-1H-pyrazol-3-yl)phenyl]-1-pyrrolidinecarboxamide |
| Example 73b | 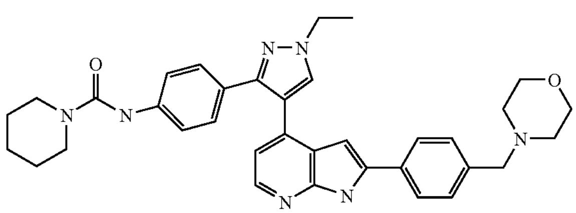 | N-[4-(1-ethyl-4-{2-[4-(4-morpholinylmethyl)phenyl]-1H-pyrrolo[2,3-b]pyridin-4-yl}-1H-pyrazol-3-yl)phenyl]-1-piperidinecarboxamide |
| Example 73c | 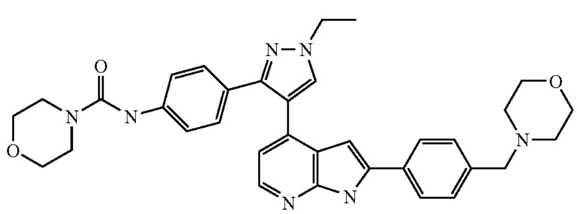 | N-[4-(1-ethyl-4-{2-[4-(4-morpholinylmethyl)phenyl]-1H-pyrrolo[2,3-b]pyridin-4-yl}-1H-pyrazol-3-yl)phenyl]-4-morpholinecarboxamide |

| Example # | Structure | Name |
|---|---|---|
| Example 73d | 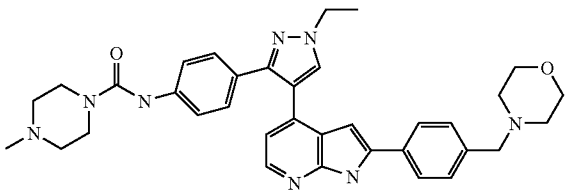 | N-[4-(1-ethyl-4-{2-[4-(4-morpholinylmethyl)phenyl]-1H-pyrrolo[2,3-b]pyridin-4-yl}-1H-pyrazol-3-yl)phenyl]-4-methyl-1-piperazinecarboxamide |
| Example 73e | 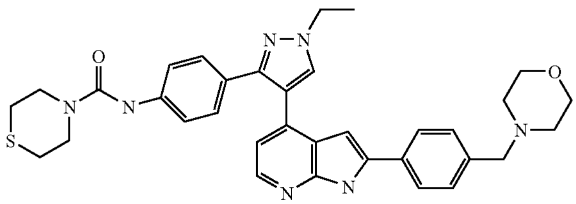 | N-[4-(1-ethyl-4-{2-[4-(4-morpholinylmethyl)phenyl]-1H-pyrrolo[2,3-b]pyridin-4-yl}-1H-pyrazol-3-yl)phenyl]-4-thiomorpholinecarboxamide |
| Example 74a | 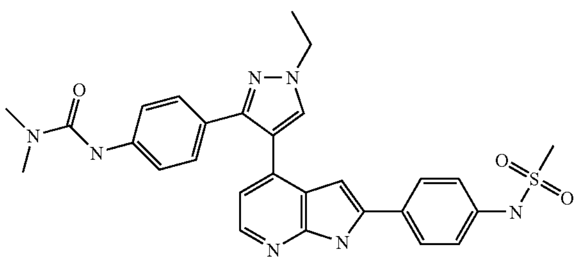 | N-(4-{4-[3-(4-{[(dimethylamino)carbonyl]amino}phenyl)-1-ethyl-1H-pyrazol-4-yl]-1H-pyrrolo[2,3-b]pyridin-2-yl}phenyl)methanesulfonamide |
| Example 74b | 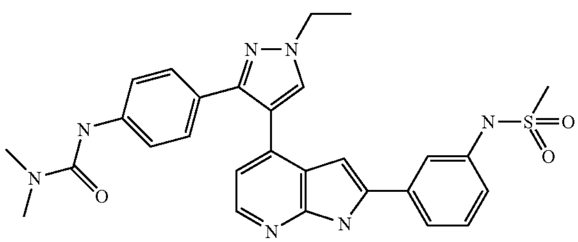 | N-(3-{4-[3-(4-{[(dimethylamino)carbonyl]amino}phenyl)-1-ethyl-1H-pyrazol-4-yl]-1H-pyrrolo[2,3-b]pyridin-2-yl}phenyl)methanesulfonamide |
| Example 74c | 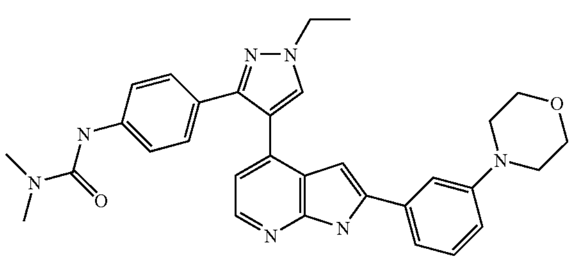 | N'-[4-(1-ethyl-4-{2-[3-(4-morpholinyl)phenyl]-1H-pyrrolo[2,3b]pyridin-4-yl}-1H-pyrazol-3-yl)phenyl]-N,N-dimethylurea |
| Example 74d | 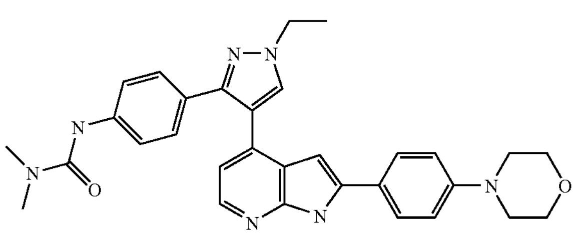 | N'-[4-(1-ethyl-4-{2-[4-(4-morpholinyl)phenyl]-1H-pyrrolo[2,3-b]pyridin-4-yl}-1H-pyrazol-3-yl)phenyl]-N,N-dimethylurea |

-continued

| Example # | Structure | Name |
|---|---|---|
| Example 74e | 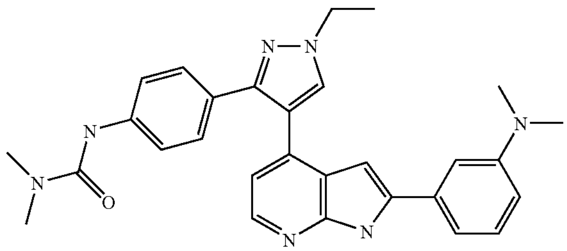 | N'-[4-(4-{2-[3-(dimethylamino)phenyl]-1 H-pyrrolo[2,3-b]pyridin-4-yl}-1-ethyl-1 H-pyrazol-3-yl)phenyl]-N,N-dimethylurea |
| Example 74f | 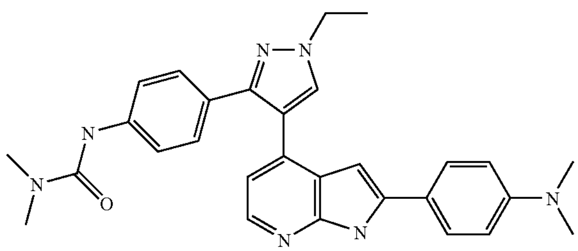 | N'-[4-(4-{2-[4-(dimethylamino)phenyl]-1 H-pyrrolo[2,3-b]pyridin-4-yl}-1-ethyl-1 H-pyrazol-3-yl)phenyl]-N,N-dimethylurea |
| Example 74g | 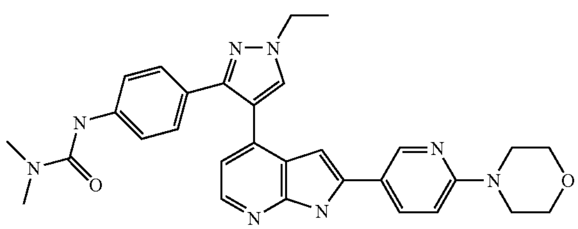 | N'-[4-(1-ethyl-4-{2-[6-(4-morpholinyl)-3-pyridinyl]-1 H-pyrrolo[2,3-b]pyridin-4-yl}-1 H-pyrazol-3-yl)phenyl]-N,N-dimethylurea |
| Example 75 | 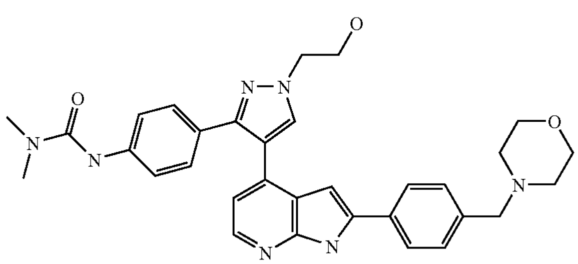 | N'-[4-(1-(2-hydroxyethyl)-4-{2-[4-(4-morpholinylmethyl)phenyl]-1 H-pyrrolo[2,3-b]pyridin-4-yl}-1 H-pyrazol-3-yl)phenyl]-N,N-dimethylurea |
| Example 76 | 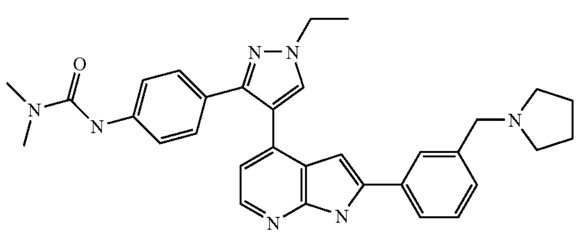 | N'-[4-(1-ethyl-4-{2-[3-(1-pyrrolidinylmethyl)phenyl]-1 H-pyrrolo[2,3-b]pyridin-4-yl}-1 H-pyrazol-3-yl)phenyl]-N,N-dimethylurea |
| Example 77 | 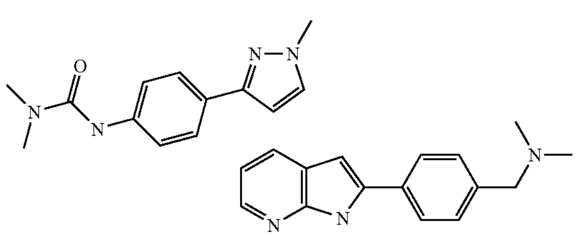 | N'-{4-[4-(2-{4-[(dimethylamino)methyl]phenyl}-1 H-pyrrolo[2,3-b]pyridin-4-yl)-1-methyl-1 H-pyrazol-3-yl]phenyl}-N,N-dimethylurea |

-continued

| Example # | Structure | Name |
|---|---|---|
| Example 78 | 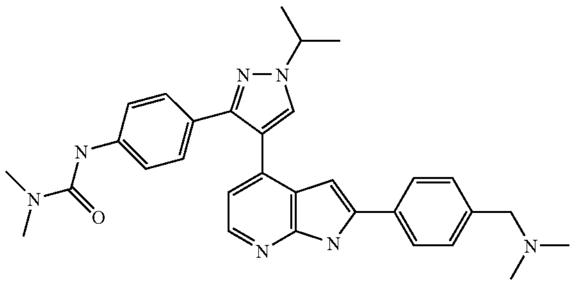 | N'-{4-[4-(2-{4-[(dimethylamino)methyl]phenyl}-1H-pyrrolo[2,3-b]pyridin-4-yl)-1-(1-methylethyl)-1H-pyrazol-3-yl]phenyl}-N,N-dimethylurea |
| Example 79 | 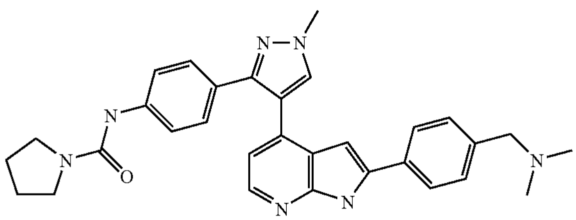 | N-{4-[4-(2-{4-[(dimethylamino)methyl]phenyl}-1H-pyrrolo[2,3-b]pyridin-4-yl)-1-methyl-1H-pyrazol-3-yl]phenyl}-1-pyrrolidinecarboxamide |
| Example 80 | 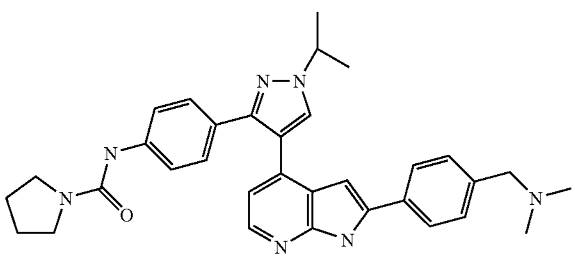 | N-{4-[4-(2-{4-[(dimethylamino)methyl]phenyl}-1H-pyrrolo[2,3-b]pyridin-4-yl)-1-(1-methylethyl)-1H-pyrazol-3-yl]phenyl}-1-pyrrolidinecarboxamide |
| Example 81 | 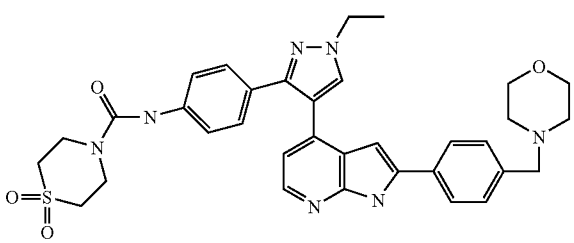 | N-[4-(1-ethyl-4-{2-[4-(4-morpholinylmethyl)phenyl]-1H-pyrrolo[2,3-b]pyridin-4-yl}-1H-pyrazol-3-yl)phenyl]-4-thiomorpholinecarboxamide 1,1-dioxide |
| Example 82 | 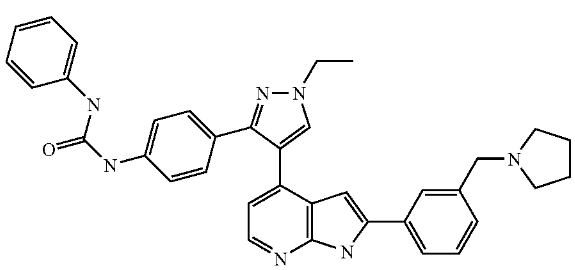 | N-[4-(1-ethyl-4-{2-[3-(1-pyrrolidinylmethyl)phenyl]-1H-pyrrolo[2,3-b]pyridin-4-yl}-1H-pyrazol-3-yl)phenyl]-N'-phenylurea |
| Example 83 | 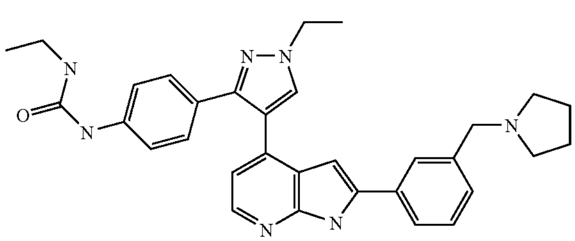 | N-ethyl-N'-[4-(1-ethyl-4-{2-[3-(1-pyrrolidinylmethyl)phenyl]-1H-pyrrolo[2,3-b]pyridin-4-yl}-1H-pyrazol-3-yl)phenyl]urea |

-continued

| Example # | Structure | Name |
|---|---|---|
| Example 84 | 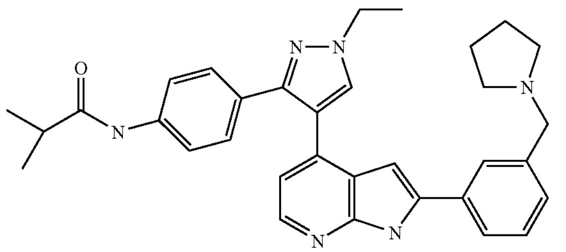 | N-[4-(1-ethyl-4-{2-[3-(1-pyrrolidinylmethyl)phenyl]-1 H-pyrrolo[2,3-b]pyridin-4-yl}-1 H-pyrazol-3-yl)phenyl]-2-methylpropanamide |
| Example 85 | 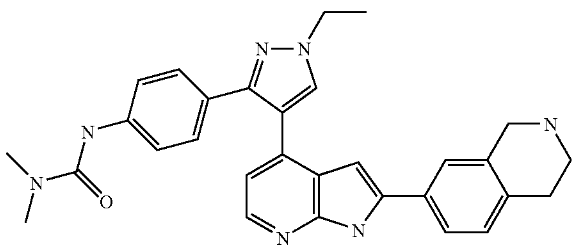 | N'-(4-{1-ethyl-4-[2-(1,2,3,4-tetrahydro-7-isoquinolinyl)-1 H-pyrrolo[2,3-b]pyridin-4-yl]-1 H-pyrazol-3-yl}phenyl)-N,N-dimethylurea |
| Example 86 | 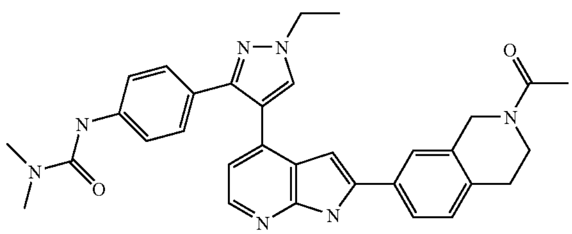 | N'-(4-{4-[2-(2-acetyl-1,2,3,4-tetrahydro-7-isoquinolinyl)-1 H-pyrrolo[2,3-b]pyridin-4-yl]-1-ethyl-1 H-pyrazol-3-yl}phenyl)-N,N-dimethylurea |
| Example 87 | 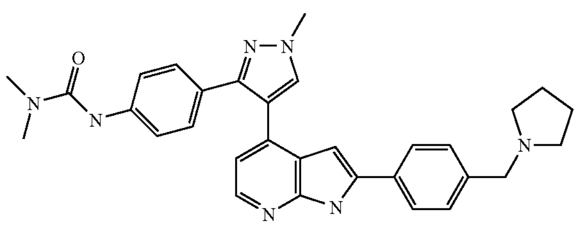 | N,N-dimethyl-N'-[4-(1-methyl-4-{2-[4-(1-pyrrolidinylmethyl)phenyl]-1 H-pyrrolo[2,3-b]pyridin-4-yl}-1 H-pyrazol-3-yl)phenyl]urea |
| Example 88 | 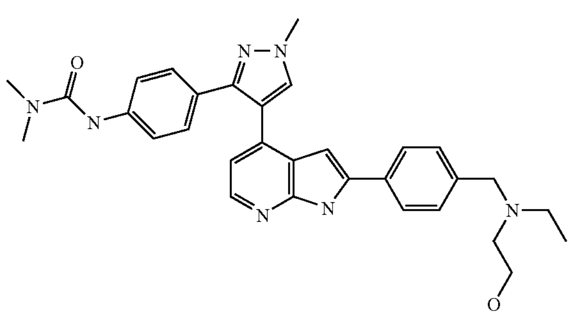 | N'-(4-{4-[2-(4-{[ethyl(2-hydroxyethyl)amino]methyl}phenyl)-1 H-pyrrolo[2,3-b]pyridin-4-yl]-1-methyl-1 H-pyrazol-3-yl}phenyl)-N,N-dimethylurea |
| Example 89 | 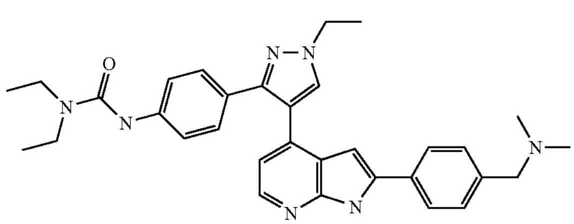 | N'-{4-[4-(2-{4-[(dimethylamino)methyl]phenyl}-1 H-pyrrolo[2,3-b]pyridin-4-yl)-1-ethyl-1 H-pyrazol-3-yl]phenyl}-N,N-diethylurea |

-continued

| Example # | Structure | Name |
|---|---|---|
| Example 90 | 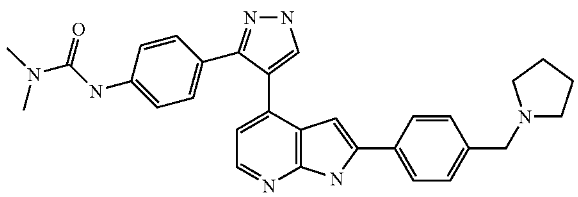 | N,N-dimethyl-N'-[4-(4-{2-[4-(1-pyrrolidinylmethyl)phenyl]-1H-pyrrolo[2,3-b]pyridin-4-yl}-1H-pyrazol-3-yl)phenyl]urea |
| Example 91 | 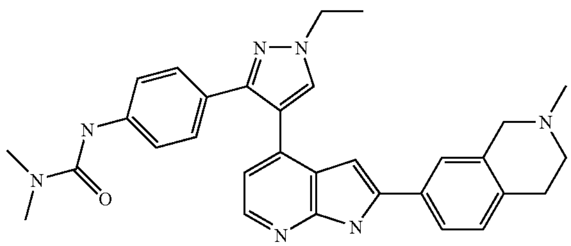 | N'-(4-{1-ethyl-4-[2-(2-methyl-1,2,3,4-tetrahydro-7-isoquinolinyl)-1H-pyrrolo[2,3-b]pyridin-4-yl]-1H-pyrazol-3-yl}phenyl)-N,N-dimethylurea |
| Example 92 | 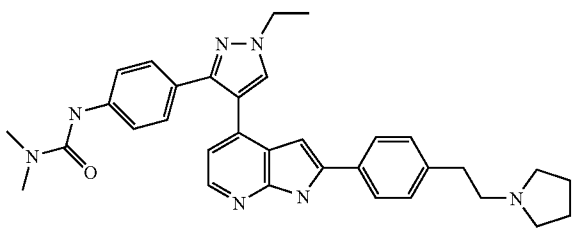 | N'-{4-[1-ethyl-4-(2-{4-[2-(1-pyrrolidinyl)ethyl]phenyl}-1H-pyrrolo[2,3-b]pyridin-4-yl)-1H-pyrazol-3-yl]phenyl}-N,N-dimethylurea |
| Example 93 | 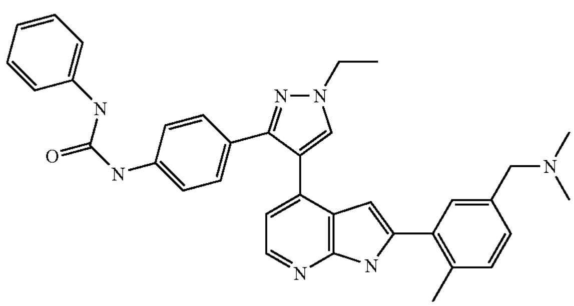 | N-{4-[4-(2-{5-[(dimethylamino)methyl]-2-methylphenyl}-1H-pyrrolo[2,3-b]pyridin-4-yl)-1-ethyl-1H-pyrazol-3-yl]phenyl}-N'-phenylurea |
| Example 94 | 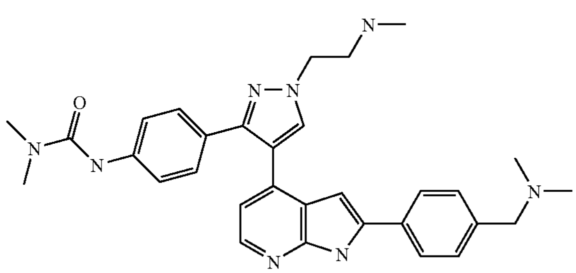 | N'-(4-{4-(2-{4-[(dimethylamino)methyl]phenyl}-1H-pyrrolo[2,3-b]pyridin-4-yl)-1-[2-(methylamino)ethyl]-1H-pyrazol-3-yl}phenyl)-N,N-dimethylurea |
| Example 95 | 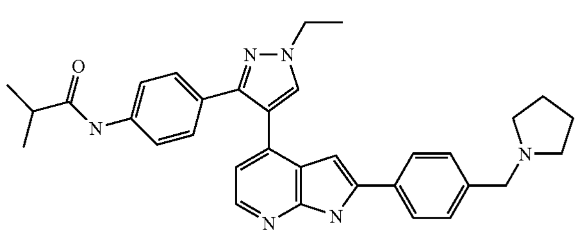 | N-[4-(1-ethyl-4-{2-[4-(1-pyrrolidinylmethyl)phenyl]-1H-pyrrolo[2,3-b]pyridin-4-yl}-1H-pyrazol-3-yl)phenyl]-2-methylpropanamide |

-continued

| Example # | Structure | Name |
| --- | --- | --- |
| Example 96 | 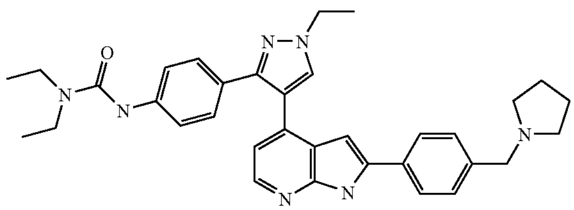 | N,N-diethyl-N'-[4-(1-ethyl-4-{2-[4-(1-pyrrolidinylmethyl)phenyl]-1 H-pyrrolo[2,3-b]pyridin-4-yl}-1 H-pyrazol-3-yl)phenyl]urea |
| Example 97 | 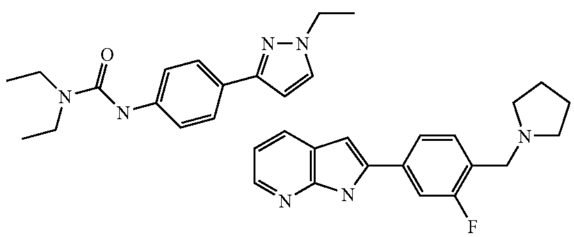 | N,N-diethyl-N'-[4-(1-ethyl-4-{2-[3-fluoro-4-(1-pyrrolidinylmethyl)phenyl]-1 H-pyrrolo[2,3-b]pyridin-4-yl}-1 H-pyrazol-3-yl)phenyl]urea |
| Example 98 | 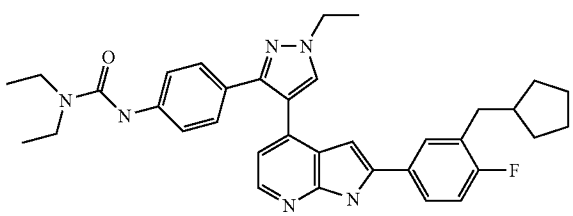 | N,N-diethyl-N'-[4-(1-ethyl-4-{2-[4-fluoro-3-(1-pyrrolidinylmethyl)phenyl]-1 H-pyrrolo[2,3-b]pyridin-4-yl}-1 H-pyrazol-3-yl)phenyl]urea |
| Example 99 | 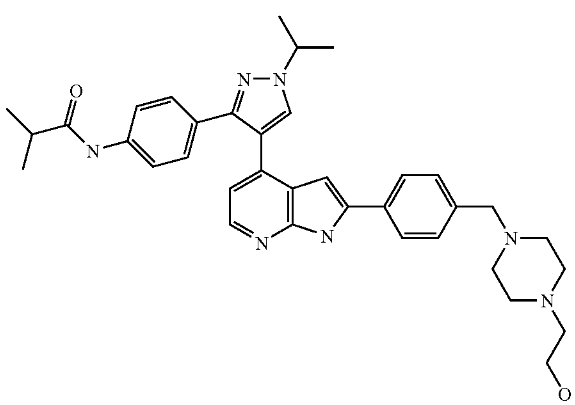 | N-{4-[4-[2-(4-{[4-(2-hydroxyethyl)-1-piperazinyl]methyl}phenyl)-1 H-pyrrolo[2,3-b]pyridin-4-yl]-1-(1-methylethyl)-1 H-pyrazol-3-yl]phenyl}-2-methylpropanamide |
| Example 100 | 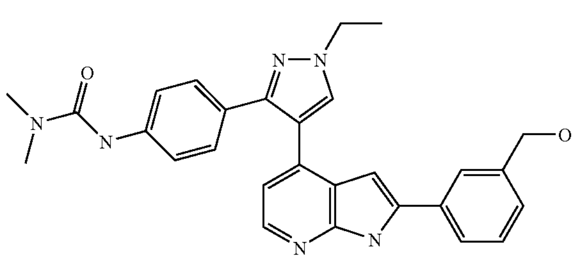 | N'-[4-(1-ethyl-4-{2-[3-(hydroxymethyl)phenyl]-1 H-pyrrolo[2,3-b]pyridin-4-yl}-1 H-pyrazol-3-yl)phenyl]-N,N-dimethylurea |

-continued

| Example # | Structure | Name |
|---|---|---|
| Example 101 | 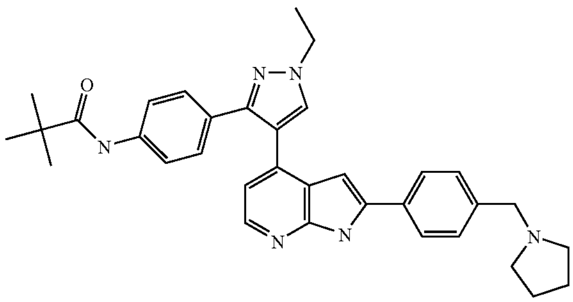 | N-[4-(1-ethyl-4-{2-[4-(1-pyrrolidinylmethyl)phenyl]-1H-pyrrolo[2,3-b]pyridin-4-yl}-1H-pyrazol-3-yl)phenyl]-2,2-dimethylpropanamide |
| Example 102 | 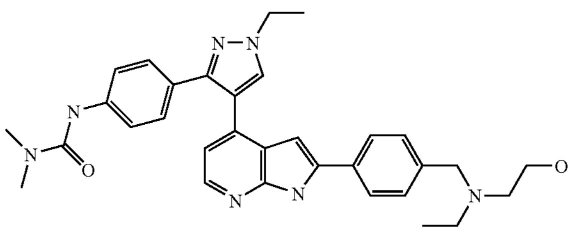 | N'-(4-{1-ethyl-4-[2-(4-{[ethyl(2-hydroxyethyl)amino]methyl}phenyl)-1H-pyrrolo[2,3-b]pyridin-4-yl]-1H-pyrazol-3-yl}phenyl)-N,N-dimethylurea |
| Example 103 | 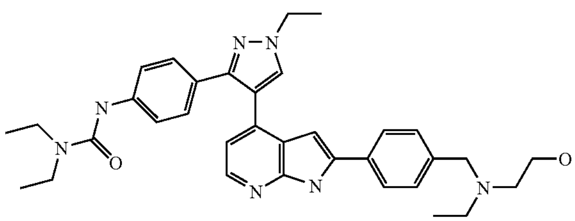 | N,N-diethyl-N'-(4-{1-ethyl-4-[2-(4-{[ethyl(2-hydroxyethyl)amino]methyl}phenyl)-1H-pyrrolo[2,3-b]pyridin-4-yl]-1H-pyrazol-3-yl}phenyl)urea |
| Example 104 | 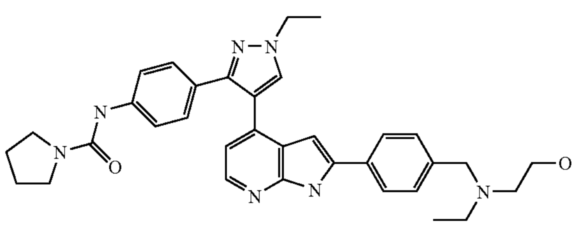 | N-(4-{1-ethyl-4-[2-(4-{[ethyl(2-hydroxyethyl)amino]methyl}phenyl)-1H-pyrrolo[2,3-b]pyridin-4-yl]-1H-pyrazol-3-yl}phenyl)-1-pyrrolidinecarboxamide |
| Example 105 | 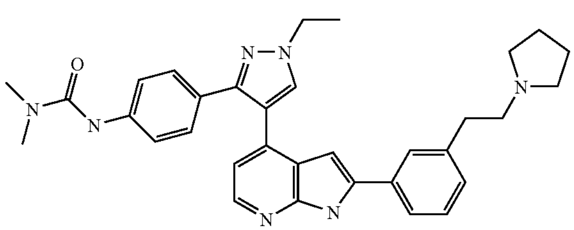 | N'-{4-[1-ethyl-4-(2-{3-[2-(1-pyrrolidinyl)ethyl]phenyl}-1H-pyrrolo[2,3-b]pyridin-4-yl)-1H-pyrazol-3-yl]phenyl}-N,N-dimethylurea |
| Example 106 | 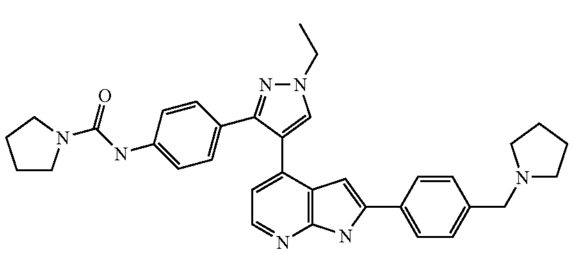 | N-[4-(1-ethyl-4-{2-[4-(1-pyrrolidinylmethyl)phenyl]-1H-pyrrolo[2,3-b]pyridin-4-yl}-1H-pyrazol-3-yl)phenyl]-1-pyrrolidinecarboxamide |

-continued

| Example # | Structure | Name |
|---|---|---|
| Example 107 | 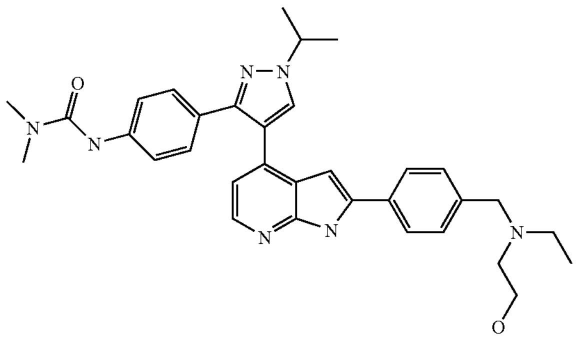 | N'-{4-[4-[2-(4-{[ethyl(2-hydroxyethyl)amino]methyl}phenyl)-1 H-pyrrolo[2,3-b]pyridin-4-yl]-1-(1-methylethyl)-1 H-pyrazol-3-yl]phenyl}-N,N-dimethylurea |
| Example 108 | 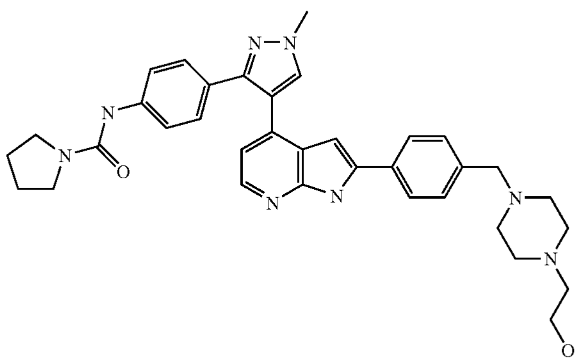 | N-(4-{4-[2-(4-{[4-(2-hydroxyethyl)-1-piperazinyl]methyl}phenyl)-1 H-pyrrolo[2,3-b]pyridin-4-yl]-1-methyl-1 H-pyrazol-3-yl}phenyl)-1-pyrrolidinecarboxamide |
| Example 109 | 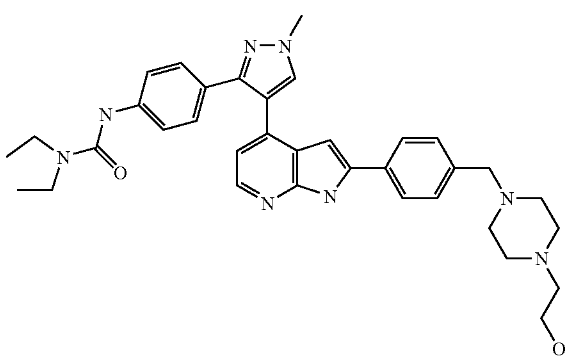 | N,N-diethyl-N'-(4-{4-[2-(4-{[4-(2-hydroxyethyl)-1-piperazinyl]methyl}phenyl)-1 H-pyrrolo[2,3-b]pyridin-4-yl]-1-methyl-1 H-pyrazol-3-yl}phenyl)urea |
| Example 110 | 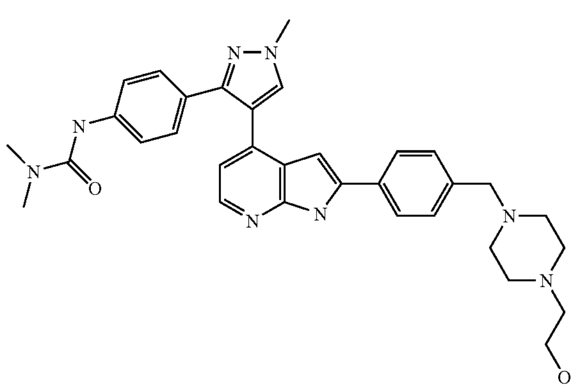 | N'-(4-{4-[2-(4-{[4-(2-hydroxyethyl)-1-piperazinyl]methyl}phenyl)-1 H-pyrrolo[2,3-b]pyridin-4-yl]-1-methyl-1 H-pyrazol-3-yl}phenyl)-N,N-dimethylurea |

-continued

| Example # | Structure | Name |
|---|---|---|
| Example 111 | 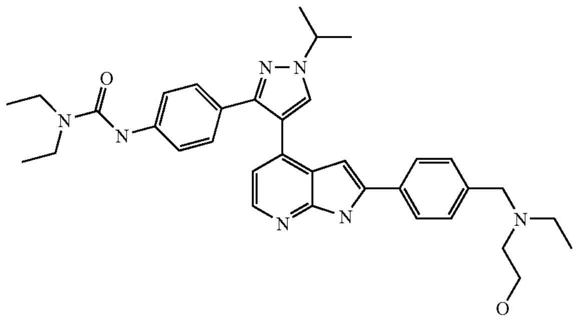 | N,N-diethyl-N'-{4-[4-[2-(4-{[ethyl(2-hydroxyethyl)amino]methyl}phenyl)-1 H-pyrrolo[2,3-b]pyridin-4-yl]-1-(1-methylethyl)-1 H-pyrazol-3-yl]phenyl}urea |
| Example 112 | 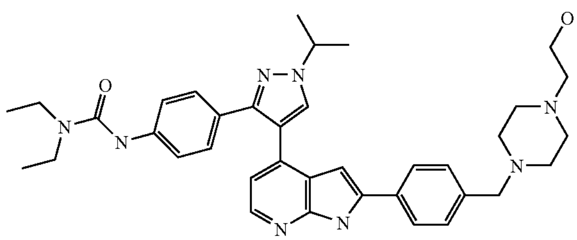 | N,N-diethyl-N'-{4-[4-[2-(4-{[4-(2-hydroxyethyl)-1-piperazinyl]methyl}phenyl)-1 H-pyrrolo[2,3-b]pyridin-4-yl]-1-(1-methylethyl)-1 H-pyrazol-3-yl]phenyl}urea |
| Example 113 | 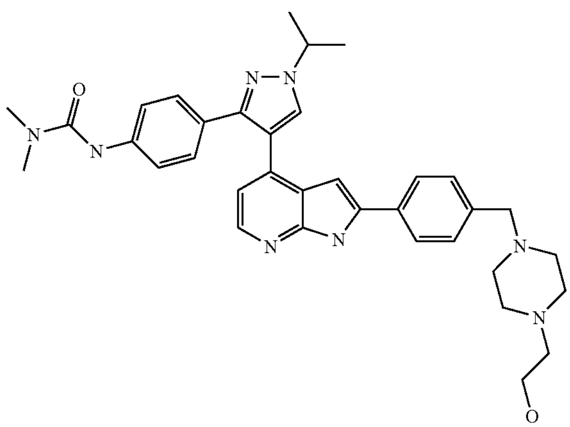 | N'-{4-[4-[2-(4-{[4-(2-hydroxyethyl)-1-piperazinyl]methyl}phenyl)-1 H-pyrrolo[2,3-b]pyridin-4-yl]-1-(1-methylethyl)-1 H-pyrazol-3-yl]phenyl}-N,N-dimethylurea |
| Example 114 | 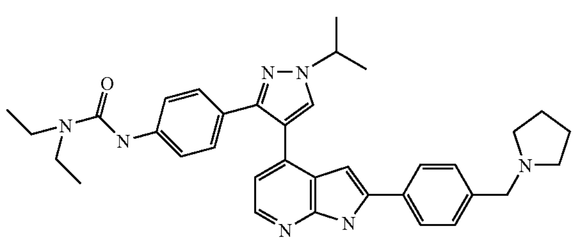 | N,N-diethyl-N'-[4-(1-(1-methylethyl)-4-{2-[4-(1-pyrrolidinylmethyl)phenyl]-1 H-pyrrolo[2,3-b]pyridin-4-yl}-1 H-pyrazol-3-yl)phenyl]urea |
| Example 115 | 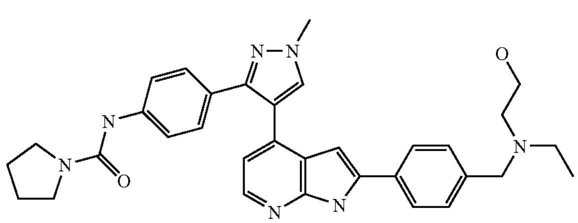 | N-(4-{4-[2-(4-{[ethyl(2-hydroxyethyl)amino]methyl}phenyl)-1 H-pyrrolo[2,3-b]pyridin-4-yl]-1-methyl-1 H-pyrazol-3-yl}phenyl)-1-pyrrolidinecarboxamide |

| Example # | Structure | Name |
|---|---|---|
| Example 116 | 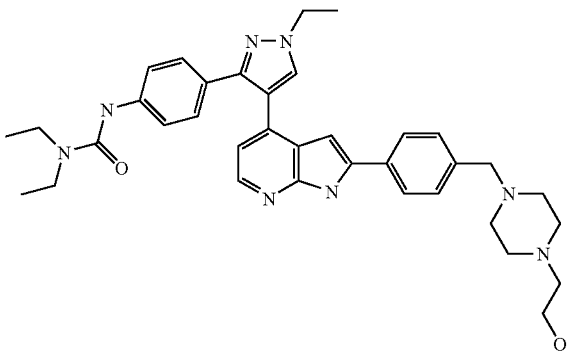 | N,N-diethyl-N'-(4-{1-ethyl-4-[2-(4-{[4-(2-hydroxyethyl)-1-piperazinyl]methyl}phenyl)-1H-pyrrolo[2,3-b]pyridin-4-yl]-1H-pyrazol-3-yl}phenyl)urea |
| Example 117 | 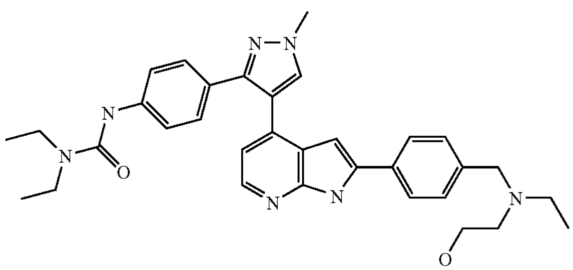 | N,N-diethyl-N'-(4-{4-[2-(4-{[ethyl(2-hydroxyethyl)amino]methyl}phenyl)-1H-pyrrolo[2,3-b]pyridin-4-yl]-1-methyl-1H-pyrazol-3-yl}phenyl)urea |
| Example 118 | 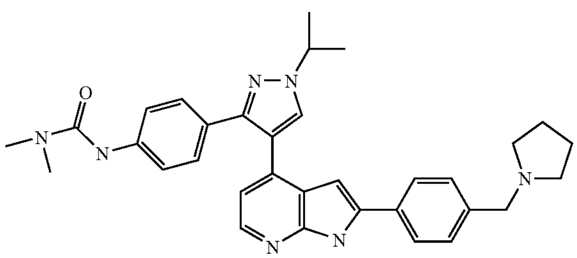 | N,N-dimethyl-N'-[4-(1-(1-methylethyl)-4-{2-[4-(1-pyrrolidinylmethyl)phenyl]-1H-pyrrolo[2,3-b]pyridin-4-yl}-1H-pyrazol-3-yl)phenyl]urea |
| Example 119 | 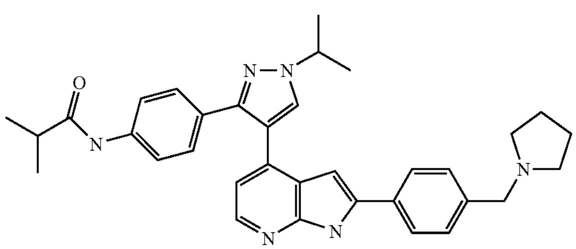 | 2-methyl-N-[4-(1-(1-methylethyl)-4-{2-[4-(1-pyrrolidinylmethyl)phenyl]-1H-pyrrolo[2,3-b]pyridin-4-yl]-1H-pyrazol-3-yl)phenyl]propanamide |
| Example 120 | 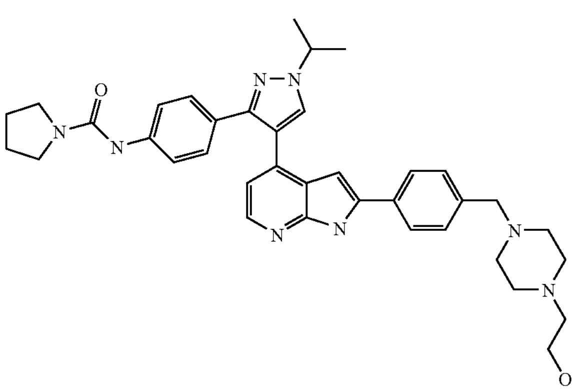 | N-{4-[4-[2-(4-{[4-(2-hydroxyethyl)-1-piperazinyl]methyl}phenyl)-1H-pyrrolo[2,3-b]pyridin-4-yl]-1-(1-methylethyl)-1H-pyrazol-3-yl]phenyl}-1-pyrrolidinecarboxamide |

-continued

| Example # | Structure | Name |
|---|---|---|
| Example 121 | 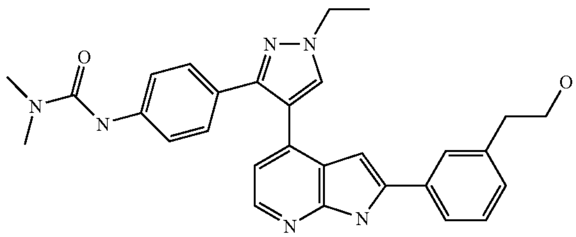 | N'-[4-(1-ethyl-4-{2-[3-(2-hydroxyethyl)phenyl]-1 H-pyrrolo[2,3-b]pyridin-4-yl}-1 H-pyrazol-3-yl)phenyl]-N,N-dimethylurea |
| Example 122 | 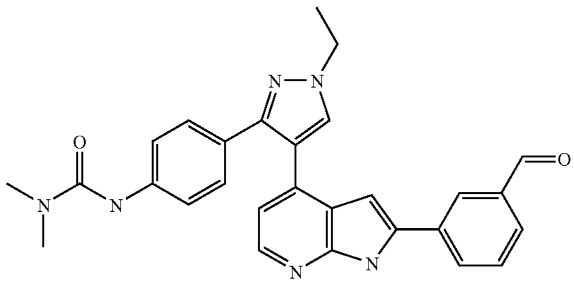 | N'-(4-{1-ethyl-4-[2-(3-formylphenyl)-1 H-pyrrolo[2,3-b]pyridin-4-yl]-1 H-pyrazol-3-yl}phenyl)-N,N-dimethylurea |
| Example 123 | 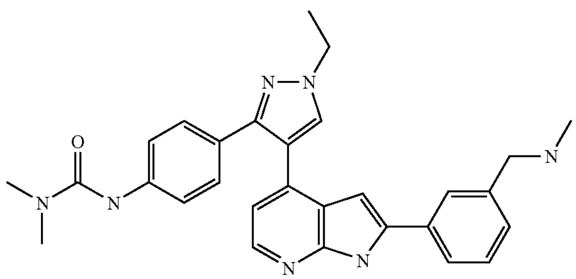 | N'-{4-[1-ethyl-4-(2-{3-[(methylamino)methyl]phenyl}-1 H-pyrrolo[2,3-b]pyridin-4-yl)-1 H-pyrazol-3-yl]phenyl}-N,N-dimethylurea |
| Example 124 | 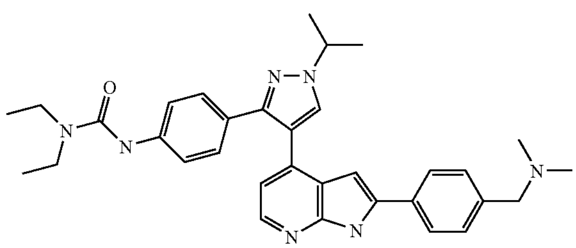 | N'-{4-[4-(2-{4-[(dimethylamino)methyl]phenyl}-1 H-pyrrolo[2,3-b]pyridin-4-yl)-1-(1-methylethyl)-1 H-pyrazol-3-yl]phenyl}-N,N-diethylurea |
| Example 125 | 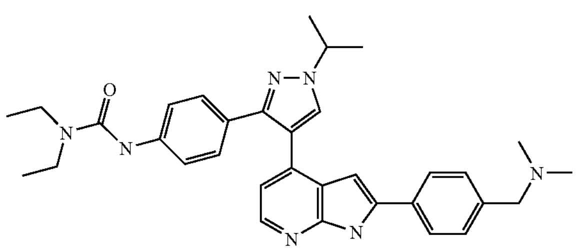 | N'-{4-[4-(2-{4-[(dimethylamino)methyl]phenyl}-1 H-pyrrolo[2,3-b]pyridin-4-yl)-1-methyl-1 H-pyrazol-3-yl]phenyl}-N,N-diethylurea |
| Example 126 | 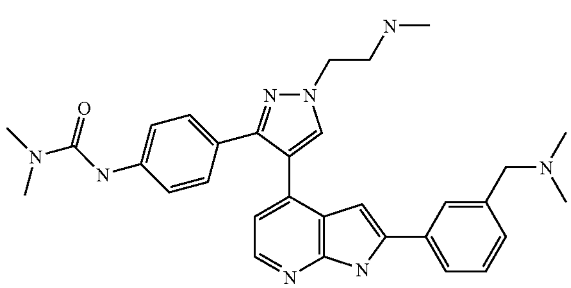 | N'-(4-{4-(2-{3-[(dimethylamino)methyl]phenyl}-1 H-pyrrolo[2,3-b]pyridin-4-yl)-1-[2-(methylamino)ethyl]-1 H-pyrazol-3-yl}phenyl)-N,N-dimethylurea |

| Example # | Structure | Name |
|---|---|---|
| Example 127 | 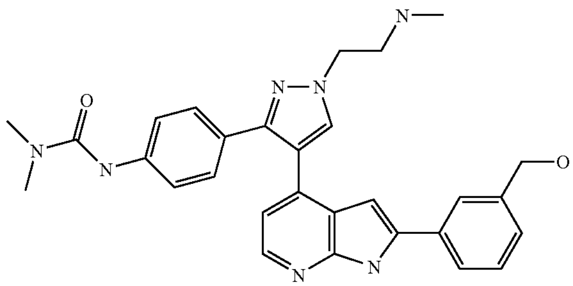 | N'-(4-{4-{2-[3-(hydroxymethyl)phenyl]-1 H-pyrrolo[2,3-b]pyridin-4-yl}-1-[2-(methylamino)ethyl]-1 H-pyrazol-3-yl}phenyl)-N,N-dimethylurea |
| Example 128 | 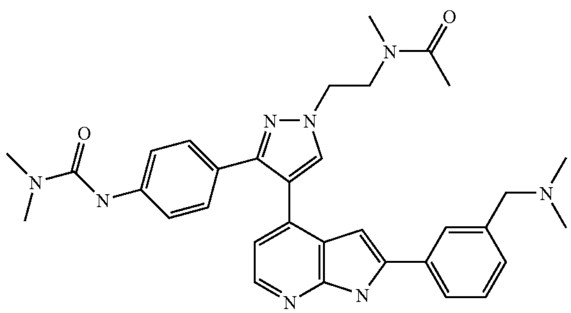 | N-{2-[3-(4-{[(dimethylamino)carbonyl]amino}phenyl)-4-(2-{3-[(dimethylamino)methyl]phenyl}-1 H-pyrrolo[2,3-b]pyridin-4-yl)-1 H-pyrazol-1-yl]ethyl}-N-methylacetamide |
| Example 129 | 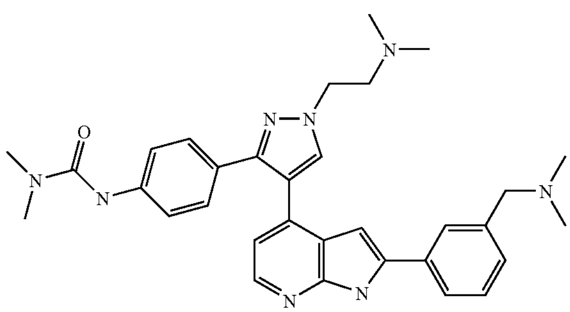 | N'-{4-[1-[2-(dimethylamino)ethyl]-4-(2-{3-[(dimethylamino)methyl]phenyl}-1 H-pyrrolo[2,3-b]pyridin-4-yl)-1 H-pyrazol-3-yl]phenyl}-N,N-dimethylurea |
| Example 130 | 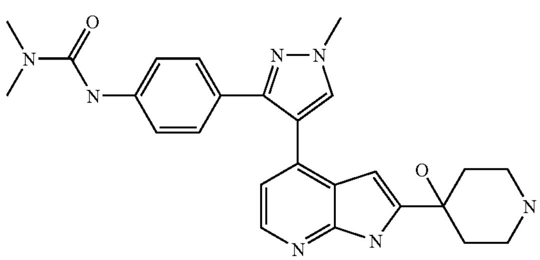 | N'-(4-{4-[2-(4-hydroxy-4-piperidinyl)-1 H-pyrrolo[2,3-b]pyridin-4-yl]-1-methyl-1 H-pyrazol-3-yl}phenyl)-N,N-dimethylurea |
| Example 131 | 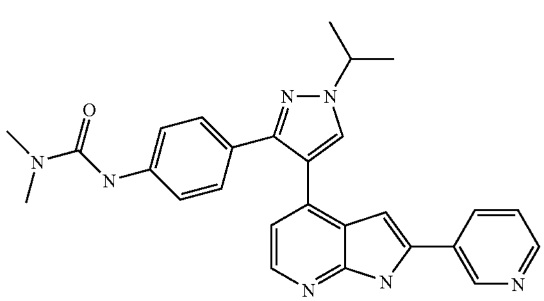 | N,N-dimethyl-N'-(4-{1-(1-methylethyl)-4-[2-(3-pyridinyl)-1 H-pyrrolo[2,3-b]pyridin-4-yl]-1 H-pyrazol-3-yl}phenyl)urea |

-continued

| Example # | Structure | Name |
|---|---|---|
| Example 132 | 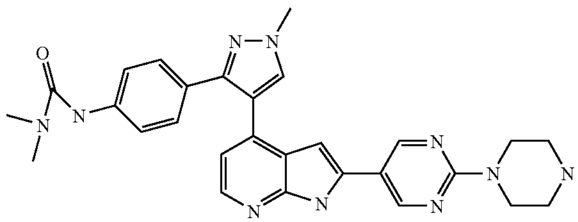 | N,N-dimethyl-N'-[4-(1-methyl-4-{2-[2-(1-piperazinyl)-5-pyrimidinyl]-1 H-pyrrolo[2,3-b]pyridin-4-yl}-1 H-pyrazol-3-yl)phenyl]urea |
| Example 133 | 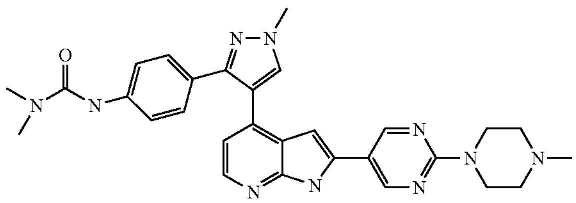 | N,N-dimethyl-N'-[4-(1-methyl-4-{2-[2-(4-methyl-1-piperazinyl)-5-pyrimidinyl]-1 H-pyrrolo[2,3-b]pyridin-4-yl}-1 H-pyrazol-3-yl)phenyl]urea |
| Example 134 | 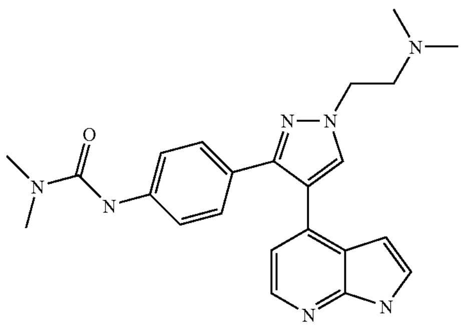 | N'-{4-[1-[2-(dimethylamino)ethyl]-4-(1 H-pyrrolo[2,3-b]pyridin-4-yl)-1 H-pyrazol-3-yl]phenyl}-N,N-dimethylurea |

Example 1

Preparation of N-{4-[1-ethyl-4-(1H-pyrrolo[2,3-b]pyridin-4-yl)-1H-pyrazol-3-yl]phenyl}-N'-phenylurea A solution of 4-[1-ethyl-4-(1H-pyrrolo[2,3-b]pyridin-4-yl)-1H-pyrazol-3-yl]aniline (2.2 mmol) in pyridine (4 mL) was treated with phenyl isocyanate (2.4 mmol) and stirred for 1 h at room temperature. The reaction mixture was concentrated in vacuo and purification of the residue by flash chromatography (80-100% ethyl acetate/hexanes) provided the title product as a white powder (50%). ESMS [M+H]$^+$: 423.2

Example 2

Preparation of N-{4-[1-ethyl-4-(1H-pyrrolo[2,3-b]pyridin-4-yl)-1H-pyrazol-3-yl]phenyl}-N'-(1-methylethyl)urea A solution of 4-[1-ethyl-4-(1H-pyrrolo[2,3-b]pyridin-4-yl)-1H-pyrazol-3-yl]aniline (0.19 mmol) in dichloromethane (1 mL) was treated with pyridine (0.39 mmol) and isopropyl isocyanate (0.39 mmol). The reaction mixture was stirred for 18 h at room temperature and poured into water (1 mL), followed by extraction with (3×3 mL) ethyl acetate. The combined organic layers were dried over sodium sulfate and concentrated in vacuo. Purification of the residue by Gilson reverse phase HPLC provided the title product as a white powder (45%). ESMS [M+H]$^+$: 389.2

Example 3

Preparation of N-{4-[1-ethyl-4-(1H-pyrrolo[2,3-b]pyridin-4-yl)-1H-pyrazol-3-yl]phenyl}-4-morpholinecarboxamide A solution of 4-[1-ethyl-4-(1H-pyrrolo[2,3-b]pyridin-4-yl)-1H-pyrazol-3-yl]aniline (0.19 mmol) in dichloromethane (1 mL) was treated with triethylamine (0.39 mmol) and 4-morpholinecarbonyl chloride (0.39 mmol). The reaction mixture was stirred for 18 h at 50° C. and poured into water (1 mL), followed by extraction with (3×3 mL) ethyl acetate. The combined organic layers were dried over sodium sulfate and concentrated in vacuo. Purification of the residue by Gilson reverse phase HPLC provided the title product as a yellow powder (50%). ESMS [M+H]$^+$: 417.4

Example 4a

Preparation of N-{4-[1-ethyl-4-(1H-pyrrolo[2,3-b]pyridin-4-yl)-1H-pyrazol-3-yl]phenyl}-1-pyrrolidinecarboxamide A solution of 4-[1-ethyl-4-(1H-pyrrolo[2,3-b]pyridin-4-yl)-1H-pyrazol-3-yl]aniline (0.26 mmol) in pyridine (1 mL) was treated with 1-pyrrolidinecarbonyl chloride (0.29 mmol). The reaction stirred for 18 h at room temperature and was then concentrated. Purification of the residue by Gilson reverse phase HPLC provided the title product as a white powder (52%). ESMS [M+H]$^+$: 401.2

Example 4b

Preparation of N'-{4-[1-ethyl-4-(1H-pyrrolo[2,3-b]pyridin-4-yl)-1H-pyrazol-3-yl]phenyl}-N,N-dimethylurea Following the procedure described in Example 4a with dimethylcarbamoyl chloride provided the title product. ESMS [M+H]$^+$: 375.0

Example 4c

Preparation of N-{4-[1-ethyl-4-(1H-pyrrolo[2,3-b]pyridin-4-yl)-1H-pyrazol-3-yl]phenyl}-1-methyl-1H-pyrrole-2-carboxamide Following the procedure described in Example 4a with 1-methyl-1H-pyrrole-2-carbonyl chloride provided the title product. ESMS [M+H]$^+$: 411.2

Example 4d

Preparation of N-{4-[1-ethyl-4-(1H-pyrrolo[2,3-b]pyridin-4-yl)-1H-pyrazol-3-yl]phenyl}-2-(methyloxy)acetamide Following the procedure described in Example 4a with (methyloxy)acetyl chloride provided the title product. ESMS [M+H]$^+$: 376.2

Example 4e

Preparation of N-cyclopropyl-N'-{4-[1-ethyl-4-(1H-pyrrolo[2,3-b]pyridin-4-yl)-1H-pyrazol-3-yl]phenyl}urea Following the procedure described in Example 4a with cyclopropanecarbonyl chloride provided the title product. ESMS [M+H]$^+$: 387.2

Example 5a

Preparation of N-3-biphenylyl-N'-{4-[1-ethyl-4-(1H-pyrrolo[2,3-b]pyridin-4-yl)-1H-pyrazol-3-yl]phenyl}urea A solution of 4-[1-ethyl-4-(1H-pyrrolo[2,3-b]pyridin-4-yl)-1H-pyrazol-3-yl]aniline (0.23 mmol) in tetrahydrofuran (1 mL) was treated with triethylamine (0.23 mmol) and 4-nitrophenyl chloroformate (0.23 mmol). The reaction stirred for 1 h at room temperature and was then treated with 3-biphenylamine (5 eq). After stirring 18 h at room temperature the reaction was poured into water (1 mL), and extracted with (3×1 mL) ethyl acetate. The combined organic layers were washed with 1N sodium hydroxide (3×1 mL), brine (1×1 mL), dried over sodium sulfate and concentrated in vacuo. Purification of the residue by Gilson reverse phase HPLC provided the title product as a white powder (45%). ESMS [M+H]$^+$: 499.2

Example 5b

Preparation of N-{4-[1-ethyl-4-(1H-pyrrolo[2,3-b]pyridin-4-yl)-1H-pyrazol-3-yl]phenyl}-N'-2-pyridinylurea Following the procedure described in Example 5a with 2-pyridinamine provided the title product. ESMS [M+H]$^+$: 424.2

Example 5c

Preparation of N-{4-[1-ethyl-4-(1H-pyrrolo[2,3-b]pyridin-4-yl)-1H-pyrazol-3-yl]phenyl}-N'-3-pyridinylurea Following the procedure described in Example 5a with 3-pyridinamine provided the title product. ESMS [M+H]$^+$: 424.2

Example 5d

Preparation of N-{4-[1-ethyl-4-(1H-pyrrolo[2,3-b]pyridin-4-yl)-1H-pyrazol-3-yl]phenyl}-3-hydroxy-1-pyrrolidinecarboxamide Following the procedure described in Example 5a with 3-pyrrolidinol provided the title product. ESMS [M+H]$^+$: 417.2

Example 5e

Preparation of N-{4-[1-ethyl-4-(1H-pyrrolo[2,3-b]pyridin-4-yl)-1H-pyrazol-3-yl]phenyl}-N'-1,3-thiazol-2-ylurea Following the procedure described in Example 5a with 1,3-thiazol-2-amine provided the title product. ESMS [M+H]$^+$: 430.2

Example 5f

Preparation of N-{4-[1-ethyl-4-(1H-pyrrolo[2,3-b]pyridin-4-yl)-1H-pyrazol-3-yl]phenyl}-N'-2-thienylurea Following the procedure described in Example 5a with 2-thienylamine provided the title product. ESMS [M+H]$^+$: 429.2

Example 5g

Preparation of N-{4-[1-ethyl-4-(1H-pyrrolo[2,3-b]pyridin-4-yl)-1H-pyrazol-3-yl]phenyl}-N'-4-pyridinylurea Following the procedure described in Example 5a with 4-pyridinamine provided the title product. ESMS [M+H]$^+$: 424.2

Example 5h

Preparation of N-(2-cyanophenyl)-N'-{4-[1-ethyl-4-(1H-pyrrolo[2,3-b]pyridin-4-yl)-1H-pyrazol-3-yl]phenyl}urea Following the procedure described in Example 5a with 2-aminobenzonitrile and stirring at 50° C. provided the title product. ESMS [M+H]$^+$: 448.2

Example 5i

Preparation of N-(3-cyanophenyl)-N'-{4-[1-ethyl-4-(1H-pyrrolo[2,3-b]pyridin-4-yl)-1H-pyrazol-3-yl]phenyl}urea Following the procedure described in Example 5a with 3-aminobenzonitrile and stirring at 50° C. provided the title product. ESMS [M+H]$^+$: 448.2

Example 5j

Preparation of N-(2-aminophenyl)-N'-{4-[1-ethyl-4-(1H-pyrrolo[2,3-b]pyridin-4-yl)-1H-pyrazol-3-yl]phenyl}urea Following the procedure described in Example 5a with (2-aminophenyl)amine and stirring at 50° C. provided the title product. ESMS [M+H]$^+$: 438.2

Example 5k

Preparation of N-(3-aminophenyl)-N'-{4-[1-ethyl-4-(1H-pyrrolo[2,3-b]pyridin-4-yl)-1H-pyrazol-3-yl]phenyl}urea Following the procedure described in Example 5a with (3-aminophenyl)amine and stirring at 50° C. provided the title product. ESMS [M+H]$^+$: 438.2

Example 5l

Preparation of N-{4-[1-ethyl-4-(1H-pyrrolo[2,3-b]pyridin-4-yl)-1H-pyrazol-3-yl]phenyl}-N'-[2-(trifluoromethyl)phenyl]urea Following the procedure described in Example 5a with (2-trifluoromethyl)aniline and stirring at 50° C. provided the title product. ESMS [M+H]$^+$: 491.2

Example 5m

Preparation of N-{4-[1-ethyl-4-(1H-pyrrolo[2,3-b]pyridin-4-yl)-1H-pyrazol-3-yl]phenyl}-N'-[3-(trifluoromethyl)phenyl]urea Following the procedure described in Example 5a with (3-trifluoromethyl)aniline and stirring at 50° C. provided the title product. ESMS [M+H]$^+$: 491.2

Example 5n

Preparation of N-{2-[(dimethylamino)methyl]phenyl}-N'-{4-[1-ethyl-4-(1H-pyrrolo[2,3-b]pyridin-4-yl)-1H-pyrazol-3-yl]phenyl}urea Following the procedure described in Example 5a with 2-[(dimethylamino)methyl]aniline and stirring at 50° C. provided the title product. ESMS [M+H]$^+$: 480.2

Example 5o

Preparation of N-{3-[(dimethylamino)methyl]phenyl}-N'-{4-[1-ethyl-4-(1H-pyrrolo[2,3-b]pyridin-4-yl)-1H-pyrazol-3-yl]phenyl}urea Following the procedure described in Example 5a with 3-[(dimethylamino)methyl]aniline and stirring at 50° C. provided the title product. ESMS [M+H]$^+$: 480.2

Example 5p

Preparation of N-{4-[1-ethyl-4-(1H-pyrrolo[2,3-b]pyridin-4-yl)-1H-pyrazol-3-yl]phenyl}-N'-(3-fluorophenyl)urea Following the procedure described in Example 5a with 3-fluoroaniline and stirring at 50° C. provided the title product. ESMS [M+H]$^+$: 441.2

Example 5q

Preparation of N-(4-cyanophenyl)-N'-{4-[1-ethyl-4-(1H-pyrrolo[2,3-b]pyridin-4-yl)-1H-pyrazol-3-yl]phenyl}urea Following the procedure described in Example 5a with 4-aminobenzonitrile and stirring at 50° C. provided the title product. ESMS [M+H]$^+$: 448.2

Example 5r

Preparation of N-{4-[1-ethyl-4-(1H-pyrrolo[2,3-b]pyridin-4-yl)-1H-pyrazol-3-yl]phenyl}-N'-[4-(trifluoromethyl)phenyl]urea Following the procedure described in Example 5a with 4-(trifluoromethyl)aniline and stirring at 50° C. provided the title product. ESMS [M+H]$^+$: 491.2

Example 5s

Preparation of N-{4-[1-ethyl-4-(1H-pyrrolo[2,3-b]pyridin-4-yl)-1H-pyrazol-3-yl]phenyl}-N'-(2-methylphenyl)urea Following the procedure described in Example 5a with 2-methylaniline and stirring at 50° C. provided the title product. ESMS [M+H]$^+$: 437.2

Example 5t

Preparation of N-{4-[1-ethyl-4-(1H-pyrrolo[2,3-b]pyridin-4-yl)-1H-pyrazol-3-yl]phenyl}-N'-(3-methylphenyl)urea Following the procedure described in Example 5a with 3-methylaniline and stirring at 50° C. provided the title product. ESMS [M+H]$^+$: 437.2

Example 5u

Preparation of N-{4-[1-ethyl-4-(1H-pyrrolo[2,3-b]pyridin-4-yl)-1H-pyrazol-3-yl]phenyl}-N'-(4-fluorophenyl)urea Following the procedure described in Example 5a with 4-fluoroaniline and stirring at 50° C. provided the title product. ESMS [M+H]$^+$: 441.2

Example 5v

Preparation of N-{4-[1-ethyl-4-(1H-pyrrolo[2,3-b]pyridin-4-yl)-1H-pyrazol-3-yl]phenyl}-N'-(4-chlorophenyl)urea Following the procedure described in Example 5a with 4-chloroaniline and stirring at 50° C. provided the title product. ESMS [M+H]$^+$: 457.2

Example 5w

Preparation of N-{4-[1-ethyl-4-(1H-pyrrolo[2,3-b]pyridin-4-yl)-1H-pyrazol-3-yl]phenyl}-N'-(2-fluorophenyl)urea Following the procedure described in Example 5a with 2-fluoroaniline and stirring at 50° C. provided the title product. ESMS [M+H]$^+$: 441.2

Example 5x

Preparation of N'-{4-[1-ethyl-4-(1H-pyrrolo[2,3-b]pyridin-4-yl)-1H-pyrazol-3-yl]phenyl}-N-methyl-N-phenylurea Following the procedure described in Example 5a with N-methylaniline and stirring at 50° C. provided the title product. ESMS [M+H]$^+$: 437.2

Example 6

Preparation of N-{4-[1-ethyl-4-(1H-pyrrolo[2,3-b]pyridin-4-yl)-1H-pyrazol-3-yl]phenyl}-N-methyl-N'-phenylurea A solution of {4-[1-ethyl-4-(1H-pyrrolo[2,3-b]pyridin-4-yl)-1H-pyrazol-3-yl]phenyl}methylamine (0.16 mmol) in tetrahydrofuran (1 mL) was treated with triethylamine (0.17 mmol), and phenyl isocyanate (0.17 mmol). After stirring 18 h at room temperature the reaction was poured into water (1 mL), and extracted with (3×1 mL) ethyl acetate. The combined organic layers were washed with water (2×1 mL), brine (1×1 mL) dried over sodium sulfate and concentrated in vacuo. Purification of the residue by Gilson reverse phase HPLC provided the title product as a white powder (42%). ESMS [M+H]$^+$: 437.2

Example 7a

Preparation of N-ethyl-N'-{4-[1-ethyl-4-(5-fluoro-1H-pyrrolo[2,3-b]pyridin-4-yl)-1H-pyrazol-3-yl]phenyl}urea Following the procedure described in Example 1 using 4-[1-ethyl-4-(5-fluoro-1H-pyrrolo[2,3-b]pyridin-4-yl)-1H-pyrazol-3-yl]aniline and ethyl isocyanate afforded the title compound. ESMS [M+H]$^+$: 393.4

Example 7b

Preparation of N-{4-[1-ethyl-4-(5-fluoro-1H-pyrrolo[2,3-b]pyridin-4-yl)-1H-pyrazol-3-yl]phenyl}-N'-phenylurea Following the procedure described in Example 1 with 4-[1-ethyl-4-(5-fluoro-1H-pyrrolo[2,3-b]pyridin-4-yl)-1H-pyrazol-3-yl]aniline provided the title compound. ESMS [M+H]$^+$: 480.2

Example 8

Preparation of N'-{4-[1-ethyl-4-(5-fluoro-1H-pyrrolo[2,3-b]pyridin-4-yl)-1H-pyrazol-3-yl]phenyl}-N,N-dimethylurea Following the procedure described in Example 5a with 4-[1-ethyl-4-(5-fluoro-1H-pyrrolo[2,3-b]pyridin-4-yl)-1H-pyrazol-3-yl]aniline and 2M dimethylamine in tetrahydrofuran afforded the title compound. ESMS [M+H]$^+$: 393.4

Example 9a

Preparation of N-ethyl-N'-{4-[1-ethyl-4-(5-methyl-1H-pyrrolo[2,3-b]pyridin-4-yl)-1H-pyrazol-3-yl]phenyl}urea Following the procedure described in Example 1 with 4-[1-ethyl-4-(5-methyl-1H-pyrrolo[2,3-b]pyridin-4-yl)-1H-pyrazol-3-yl]aniline and ethyl isocyanate afforded the title compound. ESMS [M+H]$^+$: 389.2

Example 9b

Preparation of N-{4-[1-ethyl-4-(5-methyl-1H-pyrrolo[2,3-b]pyridin-4-yl)-1H-pyrazol-3-yl]phenyl}-N'-phenylurea Following the procedure described in Example 1 with 4-[1-ethyl-4-(5-methyl-1H-pyrrolo[2,3-b]pyridin-4-yl)-1H-pyrazol-3-yl]aniline provided the title compound. ESMS[M+H]$^+$: 437.4

Example 10

Preparation of N'-{4-[1-ethyl-4-(5-methyl-1H-pyrrolo[2,3-b]pyridin-4-yl)-1H-pyrazol-3-yl]phenyl}-N,N-dimethylurea Following the procedure described in Example 5a with 4-[1-ethyl-4-(5-methyl-1H-pyrrolo[2,3-b]pyridin-4-yl)-1H-pyrazol-3-yl]aniline and 2M dimethylamine in tetrahydrofuran afforded the title compound. ESMS[M+H]$^+$: 389.4

Example 11

Preparation of N-(4-{1-ethyl-4-[2-(1,2,3,6-tetrahydro-4-pyridinyl)-1H-pyrrolo[2,3-b]pyridin-4-yl]-1H-pyrazol-3-yl}phenyl)-N'-phenylurea 1,1-dimethylethyl 4-{4-[1-ethyl-3-(4-{[(phenylamino)carbonyl]amino}phenyl)-1H-pyrazol-4-yl]-1H-pyrrolo[2,3-b]pyridin-2-yl}-3,6-dihydro-1(2H)-pyridinecarboxylate (0.362 mmol) was treated with 4N hydrogen chloride in 1,4-dioxane (2 mL). The suspension was stirred vigorously for 2 h, then concentrated under reduced pressure. Purification of the residue by reverse phase HPLC afforded the title compound as a yellow solid (42%). ESMS [M+H]$^+$: 504.4

Example 12a

Preparation of methyl {4-[1-ethyl-4-(1H-pyrrolo[2,3-b]pyridin-4-yl)-1H-pyrazol-3-yl]phenyl}carbamate To a solution of 4-[1-ethyl-4-(1H-pyrrolo[2,3-b]pyridin-4-yl)-1H-pyrazol-3-yl]aniline (0.18 mmol) in pyridine (1.5 mL) was added methyl chloroformate (0.18 mmol). After 3.5 h, the reaction mixture was quenched with methanol and concentrated in vacuo. Purification of the residue by Gilson reverse phase HPLC provided the title product as a pale yellow powder (40%). ESMS [M+H]$^+$: 362.2

Example 12b

Preparation of ethyl {4-[1-ethyl-4-(1H-pyrrolo[2,3-b]pyridin-4-yl)-1H-pyrazol-3-yl]phenyl}carbamate Following the procedure described in Example 12a with ethyl chloroformate provided the title product. ESMS [M+H]$^+$: 376.2

Example 12c

Preparation of N-{4-[1-ethyl-4-(1H-pyrrolo[2,3-b]pyridin-4-yl)-1H-pyrazol-3-yl]phenyl}-N'-[4-(methyloxy)phenyl]urea Following the procedure described in Example 12a with 4-methoxy-phenyl isocyanate provided the title product. ESMS [M+H]$^+$: 453.2

Example 12d

Preparation of N-{4-[1-ethyl-4-(1H-pyrrolo[2,3-b]pyridin-4-yl)-1H-pyrazol-3-yl]phenyl}-N'-methylurea Following the procedure described in Example 12a with methyl isocyanate provided the title product. ESMS [M+H]$^+$: 361.2

Example 12e

Preparation of N-{4-[1-ethyl-4-(1H-pyrrolo[2,3-b]pyridin-4-yl)-1H-pyrazol-3-yl]phenyl}-N'-[3-(methyloxy)phenyl]urea Following the procedure described in Example 12a with 3-methoxy-phenyl isocyanate provided the title product. ESMS [M+H]$^+$: 453.2

Example 13

Preparation of N-{4-[1-{[4-(methyloxy)phenyl]methyl}-4-(1H-pyrrolo[2,3-b]pyridin-4-yl)-1H-pyrazol-3-yl]phenyl}-N'-phenylurea Following the procedure described in Example 1 with crude 4-[1-{[4-(methyloxy)phenyl]methyl}-4-(1H-pyrrolo[2,3-b]pyridin-4-yl)-1H-pyrazol-3-yl]aniline and phenyl isocyanate provided the title product. ESMS [M+H]$^+$: 515.4

Example 14

Preparation of N-phenyl-N'-{4-[4-(1H-pyrrolo[2,3-b]pyridin-4-yl)-1H-pyrazol-3-yl]phenyl}urea To a solution of 4-[4-(1H-pyrrolo[2,3-b]pyridin-4-yl)-1H-pyrazol-3-yl]aniline (0.13 mmol) and triethylamine (0.20 mmol) in tetrahydrofuran (1.5 mL) was added phenyl isocyanate (0.13 mmol). After 14 h, the reaction mixture was concentrated in vacuo and the residue was purified by Gilson reverse phase HPLC to provide the title compound. ESMS [M+H]$^+$: 395.2

Example 15a

Preparation of N-(2-hydroxyethyl)-2-[3-(4-{[(phenylamino)carbonyl]amino}phenyl)-4-(1H-pyrrolo[2,3-b]pyridin-4-yl)-1H-pyrazol-1-yl]acetamide To a solution of [3-(4-{[(phenylamino)carbonyl]amino}phenyl)-4-(1H-pyrrolo[2,3-b]pyridin-4-yl)-1H-pyrazol-1-yl]acetic acid (0.13 mmol) in anhydrous N,N-dimethylformamide (4 mL) was added 1,1'-carbonyldiimidazole (0.156 mmol). The reaction mixture was stirred at room temperature for 30 minutes and then ethanolamine (0.195 mmol) was added. The reaction mixture was stirred for another 3 h and concentrated in vacuo. Purification of the residue by Gilson reverse phase HPLC afforded recovered starting material and the title compound as a white solid (9%). ESMS [M+H]$^+$: 496.4

Example 15b

Preparation of N-{4-[1-[2-(4-morpholinyl)-2-oxoethyl]-4-(1H-pyrrolo[2,3-b]pyridin-4-yl)-1H-pyrazol-3-yl]phenyl}-N'-phenylurea Following the procedure described in Example 15a with morpholine afforded the title compound. ESMS [M+H]$^+$: 522.4

Example 16a

Preparation of N-[3-(methyloxy)phenyl]-2-[3-(4-{[(phenylamino)carbonyl]amino}phenyl)-4-(1H-pyrrolo[2,3-b]pyridin-4-yl)-1H-pyrazol-1-yl]acetamide To a solution of [3-(4-{[(phenylamino)carbonyl]amino}phenyl)-4-(1H-pyrrolo[2,3-b]pyridin-4-yl)-1H-pyrazol-1-yl]acetic acid (0.166 mmol), 1-ethyl-3-(3-dimethylaminopropyl)carbodiimide (0.249 mmol), 4-dimethylaminopyridine (0.249 mmol) and N,N-dimethylformamide (3.2 mL) at room temperature was added m-anisidine (0.415 mmol). The reaction mixture was stirred overnight at room temperature, concentrated in vacuo, taken up in ethyl acetate (10 mL) and washed with saturated aqueous sodium bicarbonate (10 mL). The organic layer was dried over sodium sulfate and concentrated in vacuo. Purification by Gilson reverse phase HPLC afforded the title compound as a white solid (26%). ESMS [M+H]$^+$: 558.4

Example 16b

Preparation of N-ethyl-2-[3-(4-{[(phenylamino)carbonyl]amino}phenyl)-4-(1H-pyrrolo[2,3-b]pyridin-4-yl)-1H-pyrazol-1-yl]acetamide Following the procedure described in Example 15a with ethylamine provided the title product (40%). ESMS [M+H]⁺: 480.2

Example 17

Preparation of 2-[3-(4-{[(phenylamino)carbonyl]amino}phenyl)-4-(1H-pyrrolo[2,3-b]pyridin-4-yl)-1H-pyrazol-1-yl]acetamide To a cooled (0° C.) solution of [3-(4-{[(phenylamino)carbonyl]amino}phenyl)-4-(1H-pyrrolo[2,3-b]pyridin-4-yl)-1H-pyrazol-1-yl]acetic acid (0.166 mmol) in anhydrous tetrahydrofuran (3.3 mL) was added triethylamine (0.25 mmol) and ethylchloroformate (0.18 mmol). After 30 minutes at 0° C., ammonium hydroxide (50 uL) was added and the reaction stirred at room temperature for 1 h. Concentration in vacuo followed by Gilson reverse phase HPLC furnished the title compound as a white solid (13%). ESMS [M+H]⁺: 452.4

Example 18

Preparation of N-phenyl-N'-{4-[4-(1H-pyrrolo[2,3-b]pyridin-4-yl)-1-(tetrahydro-2-furanylmethyl)-1H-pyrazol-3-yl]phenyl}urea A mixture of N-{4-[4-bromo-1-(tetrahydro-2-furanylmethyl)-1H-pyrazol-3-yl]phenyl}-N'-phenylurea (0.147 mmol), 1-(phenylsulfonyl)-4-(4,4,5,5-tetramethyl-1,3,2-dioxaborolan-2-yl)-1H-pyrrolo[2,3-b]pyridine (0.162 mmol), N,N-dimethylformamide (1.5 mL), saturated aqueous sodium bicarbonate (0.44 mL) and tetrakis(triphenylphosphine)palladium(0) (0.007 mmol) in a sealed tube was stirred at 100° C. for 18 hrs. The solution was cooled to room temperature, filtered though Celite and concentrated in vacuo. The residue was dissolved in methanol (5 mL) and 6.0N aqueous sodium hydroxide (1 mL) and stirred at 70° C. for 6 h. The reaction mixture was concentrated in vacuo, dissolved in water (10 mL) and extracted with ethyl acetate (3×10 mL). The combined organic extracts were dried over magnesium sulfate and concentrated in vacuo. Purification of the residue by Gilson reverse phase HPLC afforded the title compound as a white solid (11%). ESMS [M+H]⁺: 479.4

Example 19

Preparation of N-phenyl-N'-{4-[4-(1H-pyrrolo[2,3-b]pyridin-4-yl)-1-(2,2,2-trifluoroethyl)-1H-pyrazol-3-yl]phenyl}urea A mixture of N-{4-[4-bromo-1-(2,2,2-trifluoroethyl)-1H-pyrazol-3-yl]phenyl}-N'-phenylurea (0.059 mmol), 4-(4,4,5,5-tetramethyl-1,3,2-dioxaborolan-2-yl)-1H-pyrrolo[2,3-b]pyridine (0.059 mmol), tetrakis(triphenylphosphine)palladium(0) (0.003 mmol), saturated sodium bicarbonate (0.177 mL) and anhydrous N,N-dimethylformamide (1 mL) was stirred at 100° C. in a sealed tube for 4 h and cooled to room temperature. Filtration through a pad of Celite, concentration in vacuo and Gilson reverse phase HPLC purification furnished the title compound as a white solid (35%). ESMS [M+H]⁺: 477.2

Example 20

Preparation of N-{4-[1-(2-hydroxyethyl)-4-(1H-pyrrolo[2,3-b]pyridin-4-yl)-1H-pyrazol-3-yl]phenyl}-N'-phenylurea Following the procedure described in Example 19 with N-{4-[4-bromo-1-(2-{[(1,1-dimethylethyl)(dimethyl)silyl]oxy}ethyl)-1H-pyrazol-3-yl]phenyl}-N'-phenylurea provided the title product. ESMS[M+H]⁺: 439.4

Example 21

Preparation of N-{4-[1-ethyl-4-(1H-pyrrolo[2,3-b]pyridin-4-yl)-1H-pyrazol-5-yl]phenyl}-N'-phenylurea Following the procedure in Example 19 with N-[4-(4-bromo-1-ethyl-1H-pyrazol-5-yl)phenyl]-N'-phenylurea provided the title compound. ESMS [M+H]⁺: 423.2

Example 22

Preparation of N-{4-[1-(1,1-dimethylethyl)-4-(1H-pyrrolo[2,3-b]pyridin-4-yl)-1H-pyrazol-3-yl]phenyl}-N'-phenylurea Following the procedure in Example 19 with N-{4-[4-bromo-1-(1,1-dimethylethyl)-1H-pyrazol-3-yl]phenyl}-N'-phenylurea provided the title compound. ESMS [M+H]⁺: 451.4

Example 23

Preparation of N-{4-[1-(1,1-dimethylethyl)-4-(1H-pyrrolo[2,3-b]pyridin-4-yl)-1H-pyrazol-5-yl]phenyl}-N'-phenylurea Following the procedure described for Intermediate 31, substituting 4-[1-(1,1-dimethylethyl)-5-(4-nitrophenyl)-1H-pyrazol-4-yl]-1H-pyrrolo[2,3-b]pyridine for 4-[1-ethyl-3-(4-nitrophenyl)-1H-pyrazol-4-yl]-1H-pyrrolo[2,3-b]pyridine, provided the title compound. ESMS [M+H]⁺: 451.2

Example 24

Preparation of N-phenyl-N'-{4-[1-(2-propen-1-yl)-4-(1H-pyrrolo[2,3-b]pyridin-4-yl)-1H-pyrazol-3-yl]phenyl}urea Following the procedure described for Intermediate 31 with 4-[3-(4-nitrophenyl)-1-(2-propen-1-yl)-1H-pyrazol-4-yl]-1H-pyrrolo[2,3-b]pyridine provided the title product. ESMS [M+H]⁺: 435.4

Example 25

Preparation of N-{4-[1-(3-hydroxypropyl)-4-(1H-pyrrolo[2,3-b]pyridin-4-yl)-1H-pyrazol-3-yl]phenyl}-N'-phenylurea Following the procedure described for Example 19 with 3-[3-(4-nitrophenyl)-4-(1H-pyrrolo[2,3-b]pyridin-4-yl)-1H-pyrazol-1-yl]-1-propanol, provided the title compound. ESMS [M+H]⁺: 453.2

Example 26

Preparation of N-{4-[1-(2,3-dihydroxypropyl)-4-(1H-pyrrolo[2,3-b]pyridin-4-yl)-1H-pyrazol-3-yl]phenyl}-N'-phenylurea To a solution of N-phenyl-N'-{4-[1-(2-propen-1-yl)-4-(1H-pyrrolo[2,3-b]pyridin-4-yl)-1H-pyrazol-3-yl]phenyl}urea (0.18 mmol) in 5:1 acetone:water (1.2 mL) was added N-methylmorpholine N-oxide (0.276 mmol) followed by a 2.5% solution of osmium tetroxide in t-butanol (93.5 mg). The reaction mixture was stirred at room temperature for 18 h. The reaction was quenched with saturated aqueous sodium sulfate (11 mL), filtered through a pad of celite (rinsing with ethyl acetate) and concentrated in vacuo. The residue was purified by Gilson reverse phase HPLC to afford the title compound as a white solid (14%). ESMS [M+H]$^+$: 469.2

Example 27a

Preparation of N-phenyl-N'-{4-[2-(1H-pyrrolo[2,3-b]pyridin-4-yl)-3-thienyl]phenyl}urea Following the procedure described in Example 1 with 4-[2-(1H-pyrrolo[2,3-b]pyridin-4-yl)-3-thienyl]aniline provided the title compound. ESMS [M+H]$^+$: 411.2

Example 27b

Preparation of N-ethyl-N'-{4-[2-(1H-pyrrolo[2,3-b]pyridin-4-yl)-3-thienyl]phenyl}urea Following the procedure described in Example 1 with 4-[2-(1H-pyrrolo[2,3-b]pyridin-4-yl)-3-thienyl]aniline and ethyl isocyanate provided the title compound. ESMS [M+H]$^+$: 363.2

Example 28

Preparation of N,N-dimethyl-N'-{4-[2-(1H-pyrrolo[2,3-b]pyridin-4-yl)-3-thienyl]phenyl}urea Following the procedure described in Example 5a with 4-[2-(1H-pyrrolo[2,3-b]pyridin-4-yl)-3-thienyl]aniline and 2M dimethylamine in tetrahydrofuran provided title compound. ESMS [M+H]$^+$: 363.2

Example 29

Preparation of N-{4-[2-methyl-5-(1H-pyrrolo[2,3-b]pyridine-4-yl)-1,3-thiazol-4-yl]phenyl}-N'-phenylurea Following the procedure described in Intermediate 21 with N-[4-(2-methyl-5-{1-[(4-methylphenyl)sulfonyl]-1H-pyrrolo[2,3-b]pyridine-4-yl}-1,3-thiazol-4-yl)phenyl]-N'-phenylurea gave the title compound. ESMS [M+H]$^+$: 426.2

Example 30

Preparation of N-ethyl-N'-{4-[2-methyl-5-(1H-pyrrolo[2,3-b]pyridin-4-yl)-1,3-thiazol-4-yl]phenyl}urea Following the procedure in Intermediate 21 with N-[4-(2-methyl-5-{1-[(4-methylphenyl)sulfonyl]-1H-pyrrolo[2,3-b]pyridin-4-yl}-1,3-thiazol-4-yl)phenyl]-N'-phenylurea, provided the title compound. ESMS [M+H]$^+$: 378.2

Example 31

Preparation of N,N-dimethyl-N'-{4-[2-methyl-5-(1H-pyrrolo[2,3-b]pyridin-4-yl)-1-thiazol-4-yl]phenyl}urea Following the procedure in Intermediate 21 with N,N-dimethyl-N'-[4-(2-methyl-5-{1-[(4-methylphenyl)sulfonyl]-1H-pyrrolo[2,3-b]pyridin-4-yl}-1,3-thiazol-4-yl)phenyl]urea, provided the title compound. ESMS [M+H]$^+$: 378.2

Example 32

Preparation of N-{4-[2-methyl-5-(1H-pyrrolo[2,3-b]pyridin-4-yl)-1,3-oxazol-4-yl]phenyl}-N'-phenylurea Following the procedure described in Intermediate 21 with N-[4-(2-methyl-5-{1-[(4-methylphenyl)sulfonyl]-1H-pyrrolo[2,3-b]pyridin-4-yl}-1,3-oxazol-4-yl)phenyl]-N'-phenylurea provided the title product. ESMS [M+H]$^+$: 410.0

Example 33

Preparation of N-ethyl-N'-{4-[2-methyl-5-(1H-pyrrolo[2,3-b]pyridin-4-yl)-1,3-oxazol-4-yl]phenyl}urea Following the procedure described in Intermediate 21 with N-ethyl-N'-[4-(2-methyl-5-{1-[(4-methylphenyl)sulfonyl]-1H-pyrrolo[2,3-b]pyridin-4-yl}-1,3-oxazol-4-yl)phenyl]urea provided the title product. ESMS [M+H]$^+$: 362.2

Example 34

Preparation of N,N-dimethyl-N'-{4-[2-methyl-5-(1H-pyrrolo[2,3-b]pyridin-4-yl)-1-oxazol-4-yl]phenyl}urea Following the procedure described in Intermediate 21 with N,N-dimethyl-N'-[4-(2-methyl-5-{1-[(4-methylphenyl)sulfonyl]-1H-pyrrolo[2,3-b]pyridin-4-yl}-1,3-oxazol-4-yl)phenyl]urea provided the title product. ESMS [M+H]$^+$: 362.2

Example 35

Preparation of N-{4-[4-(6-chloro-1H-pyrrolo[2,3-b]pyridin-4-yl)-1-ethyl-1H-pyrazol-3-yl]phenyl}-N'-phenylurea Following the procedure described in Example 1 with {4-[4-(6-chloro-1H-pyrrolo[2,3-b]pyridin-4-yl)-1-ethyl-1H-pyrazol-3-yl]phenyl}amine provided the title compound. ESMS [M+H]$^+$: 457.2

Example 36

Preparation of N-{4-[4-(6-{4-[(dimethylamino)methyl]phenyl}-1H-pyrrolo[2,3-b]pyridin-4-yl)-1-ethyl-1H-pyrazol-3-yl]phenyl}-N'-phenylurea Following the procedure described in Example 1 with [(4-{4-[3-(4-aminophenyl)-1-ethyl-1H-pyrazol-4-yl]-1H-pyrrolo[2,3-b]pyridin-6-yl}phenyl)methyl]dimethylamine provided the title compound. ESMS [M+H]$^+$: 556.4

Example 37

Preparation of 4-[1-ethyl-3-(4-{[(phenylamino)carbonyl]amino}phenyl)-1H-pyrazol-4-yl]-N-[2-(4-morpholinyl)ethyl]-1H-pyrrolo[2,3-b]pyridine-2-carboxamide Following the procedure described in Example 1 with 4-[3-(4-aminophenyl)-1-ethyl-1H-pyrazol-4-yl]-N-[2-(4-morpholinyl)ethyl]-1H-pyrrolo[2,3-b]pyridine-2-carboxamide provided the title product. ESMS [M+H]$^+$: 579.6

Example 38

Preparation of 4-[1-ethyl-3-(4-{[(phenylamino)carbonyl]amino}phenyl)-1H-pyrazol-4-yl]-N-[2-(4-methyl-1-piperazinyl)ethyl]-1H-pyrrolo[2,3-b]pyridine-2-carboxamide Following the procedure described in Example 1 with 4-[3-(4-aminophenyl)-1-ethyl-1H-pyrazol-4-yl]-N-[2-(4-methyl-1-piperazinyl)ethyl]-1H-pyrrolo[2,3-b]pyridine-2-carboxamide provided the title compound. ESMS [M+H]$^+$: 592.4

Example 39

Preparation of 4-[1-ethyl-3-(4-{[(phenylamino)carbonyl]amino}phenyl)-1H-pyrazol-4-yl]-N-[2-(methylthio)ethyl]-1H-pyrrolo[2,3-b]pyridine-2-carboxamide Following the procedure described in Example 1 with 4-[3-(4-aminophenyl)-1-ethyl-1H-pyrazol-4-yl]-N-[2-(methylthio)ethyl]-1H-pyrrolo[2,3-b]pyridine-2-carboxamide provided the title compound. ESMS [M+H]$^+$: 540.4

Example 40

Preparation of N-(4-{1-ethyl-4-[2-({[2-(4-morpholinyl)ethyl]amino}methyl)-1H-pyrrolo[2,3-b]pyridin-4-yl]-1H-pyrazol-3-yl}phenyl)-N'-phenylurea Following the procedure described in Intermediate 21 with N-(4-{1-ethyl-4-[2-({[2-(4-morpholinyl)ethyl]amino}methyl)-1-(phenylsulfonyl)-1H-pyrrolo[2,3-b]pyridin-4-yl]-1H-pyrazol-3-yl}phenyl)-N'-phenylurea provided the title compound. ESMS [M+H]$^+$: 565.4

Example 41

Preparation of N-(4-{4-[2-({[2-(dimethylamino)ethyl]amino}methyl)-1H-pyrrolo[2,3-b]pyridin-4-yl]-1-ethyl-1H-pyrazol-3-yl}phenyl)-N'-phenylurea Following the procedure described in Intermediate 21 with N-(4-{4-[2-({[2-(dimethylamino)ethyl]amino}methyl)-1-(phenylsulfonyl)-1H-pyrrolo[2,3-b]pyridin-4-yl]-1-ethyl-1H-pyrazol-3-yl}phenyl)-N'-phenylurea provided the title compound. ESMS [M+H]$^+$: 523.4

Example 42

Preparation of N-(4-{1-ethyl-4-[2-({[2-(methylsulfonyl)ethyl]amino}methyl)-1H-pyrrolo[2,3-b]pyridin-4-yl]-1H-pyrazol-3-yl}phenyl)-N'-phenylurea Following the procedure described in Intermediate 21 with N-(4-{1-ethyl-4-[2-({[2-(methylsulfonyl)ethyl]amino}methyl)-1-(phenylsulfonyl)-1H-pyrrolo[2,3-b]pyridin-4-yl]-1H-pyrazol-3-yl}phenyl)-N'-phenylurea provided the title compound. ESMS [M+H]$^+$: 558.4

Example 43

Preparation of N-[4-(4-{2-[(dimethylamino)methyl]-1H-pyrrolo[2,3-b]pyridin-4-yl}-1-ethyl-1H-pyrazol-3-yl)phenyl]-N'-phenylurea Following the procedure described in Intermediate 21 with N-(4-{4-[2-[(dimethylamino)methyl]-1-(phenylsulfonyl)-1H-pyrrolo[2,3-b]pyridin-4-yl]-1-ethyl-1H-pyrazol-3-yl}phenyl)-N'-phenylurea provided the title compound. ESMS [M+H]$^+$: 480.4

Example 44

Preparation of N-{4-[1-ethyl-4-(2-{[(2-hydroxyethyl)amino]methyl}-1H-pyrrolo[2,3-b]pyridin-4-yl)-1H-pyrazol-3-yl]phenyl}-N'-phenylurea Following the procedure described in Intermediate 21 with N-(4-{1-ethyl-4-[2-{[(2-hydroxyethyl)amino]methyl}-1-(phenylsulfonyl)-1H-pyrrolo[2,3-b]pyridin-4-yl]-1H-pyrazol-3-yl}phenyl)-N'-phenylurea provided the title compound. ESMS [M+H]$^+$: 496.4

Example 45

Preparation of N-(4-{1-ethyl-4-[2-({[3-(4-methyl-1-piperazinyl)propyl]amino}methyl)-1H-pyrrolo[2,3-b]pyridin-4-yl]-1H-pyrazol-3-yl}phenyl)-N'-phenylurea Following the procedure described in Intermediate 21 with N-(4-{1-ethyl-4-[2-({[3-(4-methyl-1-piperazinyl)propyl]amino}methyl)-1-(phenylsulfonyl)-1H-pyrrolo[2,3-b]pyridin-4-yl]-1H-pyrazol-3-yl}phenyl)-N'-phenylurea provided the title compound. ESMS [M+H]$^+$: 592.4

Example 46a

Preparation of N-{4-[1-Ethyl-4-(1H-pyrrolo[2,3-b]pyridin-4-yl)-1H-pyrazol-3-yl]phenyl}-2-(2-thienyl)acetamide Following the procedure described in Example 1 with 4-[1-ethyl-4-(1H-pyrrolo[2,3-b]pyridin-4-yl)-1H-pyrazol-3-yl]aniline and thiophene-2-acetyl chloride provided the title compound. ESMS [M+H]$^+$: 428.4

Example 46b

Preparation of N-{4-[1-Ethyl-4-(1H-pyrrolo[2,3-b]pyridin-4-yl)-1H-pyrazol-3-yl]phenyl}cyclohexanecarboxamide Following the procedure described in Example 1 with 4-[1-ethyl-4-(1H-pyrrolo[2,3-b]pyridin-4-yl)-1H-pyrazol-3-yl]aniline and cyclohexanecarbonyl chloride provided the title compound. ESMS [M+H]$^+$: 414.4

Example 46c

Preparation of N-{4-[1-Ethyl-4-(1H-pyrrolo[2,3-b]pyridin-4-yl)-1H-pyrazol-3-yl]phenyl}cyclopentanecarboxamide Following the procedure described in Example 1 with 4-[1-ethyl-4-(1H-pyrrolo[2,3-b]pyridin-4-yl)-1H-pyrazol-3-yl]aniline and cyclopentancarbonyl chloride provided the title compound. ESMS [M+H]$^+$: 400.4

Example 46d

Preparation of N-{4-[1-Ethyl-4-(1H-pyrrolo[2,3-b]pyridin-4-yl)-1H-pyrazol-3-yl]phenyl}-2-phenylacetamide Following the procedure described in Example 1 with 4-[1-ethyl-4-(1H-pyrrolo[2,3-b]pyridin-4-yl)-1H-pyrazol-3-yl]aniline and phenylacetyl chloride provided the title compound. ESMS [M+H]$^+$: 422.2

Example 46e

Preparation of N-{4-[1-Ethyl-4-(1H-pyrrolo[2,3-b]pyridin-4-yl)-1H-pyrazol-3-yl]phenyl}benzamide Following the procedure described in Example 1 with 4-[1-ethyl-4-(1H-pyrrolo[2,3-b]pyridin-4-yl)-1H-pyrazol-3-yl]aniline and benzoyl chloride provided the title compound. ESMS [M+H]$^+$: 408.2

Example 46f

Preparation of N-(3-Chlorophenyl)-N'-{4-[1-ethyl-4-(1H-pyrrolo[2,3-b]pyridin-4-yl)-1H-pyrazol-3-yl]phenyl}urea Following the procedure described in Example 1 with 4-[1-ethyl-4-(1H-pyrrolo[2,3-b]pyridin-4-yl)-1H-pyrazol-3-yl]aniline and 3-chlorophenyl isocyanate provided the title compound. ESMS [M+H]$^+$: 457.2

Example 46g

Preparation of N-Cyclohexyl-N'-{4-[1-ethyl-4-(1H-pyrrolo[2,3-b]pyridin-4-yl)-1H-pyrazol-3-yl]phenyl}urea Following the procedure described in Example 1 with 4-[1-ethyl-4-(1H-pyrrolo[2,3-b]pyridin-4-yl)-1H-pyrazol-3-yl]aniline and cyclohexyl isocyanate provided the title compound. ESMS [M+H]$^+$: 429.2

Example 46h

Preparation of N-Cyclopentyl-N'-{4-[1-ethyl-4-(1H-pyrrolo[2,3-b]pyridin-4-yl)-1H-pyrazol-3-yl]phenyl}urea Following the procedure described in Example 47a with 4-[1-ethyl-4-(1H-pyrrolo[2,3-b]pyridin-4-yl)-1H-pyrazol-3-yl]aniline and cyclopentyl isocyanate provided the title compound. ESMS [M+H]$^+$: 415.2

Example 46i

Preparation of N-Ethyl-N'-{4-[1-ethyl-4-(1H-pyrrolo[2,3-b]pyridin-4-yl)-1H-pyrazol-3-yl]phenyl}urea Following the procedure described in Example 1 with 4-[1-ethyl-4-(1H-pyrrolo[2,3-b]pyridin-4-yl)-1H-pyrazol-3-yl]aniline and ethyl isocyanate provided the title compound. ESMS [M+H]$^+$: 375.2

Example 46j

Preparation of N-(1,1-Dimethylethyl)-N'-{4-[1-ethyl-4-(1H-pyrrolo[2,3-b]pyridin-4-yl)-1H-pyrazol-3-yl]phenyl}urea Following the procedure described in Example 1 with 4-[1-ethyl-4-(1H-pyrrolo[2,3-b]pyridin-4-yl)-1H-pyrazol-3-yl]aniline and tert-butyl isocyanate provided the title compound. ESMS [M+H]$^+$: 403.2

Example 46k

Preparation of N-{4-[1-Ethyl-4-(1H-pyrrolo[2,3-b]pyridin-4-yl)-1H-pyrazol-3-yl]phenyl}-N'-(phenylmethyl)urea Following the procedure described in Example 1 with 4-[1-ethyl-4-(1H-pyrrolo[2,3-b]pyridin-4-yl)-1H-pyrazol-3-yl]aniline and benzyl isocyanate provided the title compound. ESMS [M+H]$^+$: 437.2

Example 47

Preparation of N'-{4-[4-(2-{3-[(dimethylamino)methyl]phenyl}-1H-pyrrolo[2,3-b]pyridin-4-yl)-1-ethyl-1H-pyrazol-3-yl]phenyl}-N,N-dimethylurea To a stirred solution of 4-[3-(4-aminophenyl)-1-ethyl-1H-pyrazol-4-yl]-2-[3-(dimethylaminomethyl)phenyl]-1H-pyrrolo[2,3-b]pyridine (1.0 mmol) in tetrahydrofuran (15 mL) was added p-nitrophenylchloroformate (1.1 mmol). After stirring for 1 h at room temperature a solution of 2.0 M dimethylamine in tetrahydrofuran (14 mmol) was added. The reaction was stirred an additional 1 h at room temperature then concentrated under vacuum. The residue which remained was triturated with aqueous sodium hydroxide, filtered, washed with cold water, and dried under vacuum. Purification by Gilson reverse phase HPLC afforded title compound as an off-white solid (46%). ESMS (M+H)$^+$: 508.4

Example 48

Preparation of 4-[3-(4-N-phenylcarbamylaminophenyl)-1-ethyl-1H-pyrazol-4-yl]-2-[3-(dimethylaminomethyl)phenyl]-1H-pyrrolo[2,3-b]pyridine To a stirred solution of 4-[3-(4-aminophenyl)-1-ethyl-1H-pyrazol-4-yl]-2-[3-(dimethylaminomethyl)phenyl]-1H-pyrrolo[2,3-b]pyridine (0.34 mmol) in tetrahydrofuran (5 mL) was added phenyl isocyanate (0.41 mmol) and two drops of Et$_3$N. The reaction was stirred at room temperature for 1 h and concentrated to dryness under vacuum. The remaining solid was triturated with (1:1) diethyl ether:petroleum ether, filtered, and dried under vacuum. Purification by Gilson reverse phase HPLC gave the title compound as an off-white solid (44%). ESMS (M+H)$^+$: 556.4

Example 49

Preparation of 4-[3-(4-N-ethylcarbamylaminophenyl)-1-ethyl-1H-pyrazol-4-yl]-2-[3-(dimethylaminomethyl)phenyl]-1H-pyrrolo[2,3-b]pyridine Following the procedure described in Example 48 with ethyl isocyanate and stirring at rt for 2 days provided the title product. ESMS[M+H]$^+$: 508.4

Example 50

Preparation of 4-[3-(4-N,N-dimethylcarbamylaminophenyl)-1-ethyl-1H-pyrazol-4-yl]-2-[3-(N-morpholinylmethyl)phenyl]-1H-pyrrolo[2,3-b]pyridine Following the procedure described in Example 47 using 4-[3-(4-aminophenyl)-1-ethyl-1H-pyrazol-4-yl]-2-[3-(N-morpholinylmethyl)phenyl]-1H-pyrrolo[2,3-b]pyridine provided the title compound. ESMS (M+H)$^+$: 550.4

Example 51

Preparation of 4-[3-(4-N-phenylcarbamylaminophenyl)-1-ethyl-1H-pyrazol-4-yl]-2-[3-(N-morpholinylmethyl)phenyl]-1H-pyrrolo[2,3-b]pyridine Following the procedure described in Example 48 using 4-[3-(4-aminophenyl)-1-ethyl-1H-pyrazol-4-yl]-2-[3-(N-morpholinylmethyl)phenyl]-1H-pyrrolo[2,3-b]pyridine provided the title compound. ESMS (M+H)$^+$: 598.6

Example 52

Preparation of 4-[3-(4-N-ethylcarbamylaminophenyl)-1-ethyl-1H-pyrazol-4-yl]-2-[3-(N-morpholinylmethyl)phenyl]-1H-pyrrolo[2,3-b]pyridine Following the procedure described in Example 48 using 4-[3-(4-aminophenyl)-1-ethyl-1H-pyrazol-4-yl]-2-[3-(N-morpholinylmethyl)phenyl]-1H-pyrrolo[2,3-b]pyridine and ethyl isocyanate provided the title compound. ESMS (M+H)$^+$: 550.6

Example 53

Preparation of 4-[3-(4-N-phenylcarbamylaminophenyl)-1-ethyl-1H-pyrazol-4-yl]-2-(4-acetamidophenyl)-1H-pyrrolo[2,3-b]pyridine To a stirred solution of 4-[3-(4-N-phenylcarbamylaminophenyl)-1-ethyl-1H-pyrazol-4-yl]-2-(4-acetamidophenyl)-1-phenylsulfonyl-1H-pyrrolo[2,3-b]pyridine (0.30 mmol) in methanol (5 mL) was added aqueous 6.0 N sodium hydroxide (0.66 mmol). The reaction was stirred at 70° C. for 8 h, and cooled to room temperature. The cloudy suspension was diluted with cold water (25 mL), filtered, rinsed with cold water and dried under vacuum to give the title product as a white solid (66%). ESMS (M+H)$^+$: 556.4

Example 54

Preparation of 4-[3-(4-N-phenylcarbamylaminophenyl)-1-ethyl-1H-pyrazol-4-yl]-2-(3-acetamidophenyl)-1H-pyrrolo[2,3-b]pyridine Following the procedure described in Intermediate 21 using 4-[3-(4-N-phenylcarbamylaminophenyl)-1-ethyl-1H-pyrazol-4-yl]-2-(3-acetamidophenyl)-1-phenylsulfonyl-1H-pyrrolo[2,3-b]pyridine provided the title compound. ESMS (M+H)$^+$: 556.4

Example 55

Preparation of 4-[3-(4-N-ethylcarbamylaminophenyl)-1-ethyl-1H-pyrazol-4-yl]-2-(3-acetamidophenyl)-1H-pyrrolo[2,3-b]pyridine Following the procedure described in Example 53 using 4-[3-(4-N-ethylcarbamylaminophenyl)-1-ethyl-1H-pyrazol-4-yl]-2-(3-acetamidophenyl)-1-phenylsulfonyl-1H-pyrrolo[2,3-b]pyridine provided the title compound. ESMS (M+H)$^+$: 508.4

Example 56

Preparation of 4-[3-(4-N,N-dimethylcarbamylaminophenyl)-1-ethyl-1H-pyrazol-4-yl]-2-[4-(dimethylaminomethyl)phenyl]-1H-pyrrolo[2,3-b]pyridine Following the procedure described in Example 47 using 4-[3-(4-aminophenyl)-1-ethyl-1H-pyrazol-4-yl]-2-[4-(dimethylaminomethyl)phenyl]-1H-pyrrolo[2,3-b]pyridine provided the title compound. ESMS (M+H)$^+$: 508.4

Example 57

Preparation of 4-[3-(4-N-phenylcarbamylaminophenyl)-1-ethyl-1H-pyrazol-4-yl]-2-[4-(dimethylaminomethyl)phenyl]-1H-pyrrolo[2,3-b]pyridine Following the procedure described in Example 48 using 4-[3-(4-aminophenyl)-1-ethyl-1H-pyrazol-4-yl]-2-[4-(dimethylaminomethyl)phenyl]-1H-pyrrolo[2,3-b]pyridine provided the title compound. ESMS (M+H)$^+$: 556.4

Example 58

Preparation of 4-[3-(4-N-ethylcarbamylaminophenyl)-1-ethyl-1H-pyrazol-4-yl]-2-[4-(dimethylaminomethyl)phenyl]-1H-pyrrolo[2,3-b]pyridine Following the procedure described in Example 48 using 4-[3-(4-aminophenyl)-1-ethyl-1H-pyrazol-4-yl]-2-[4-(dimethylaminomethyl)phenyl]-1H-pyrrolo[2,3-b]pyridine and ethyl isocyanate provided the title compound. ESMS (M+H)$^+$: 508.4

Example 59

Preparation of 4-[3-(4-N,N-dimethylcarbamylaminophenyl)-1-ethyl-1H-pyrazol-4-yl]-2-[4-(N-morpholinylmethyl)phenyl]-1H-pyrrolo[2,3-b]pyridine Following the procedure described in Example 47 using 4-[3-(4-aminophenyl)-1-ethyl-1H-pyrazol-4-yl]-2-[4-(N-morpholinylmethyl)phenyl]-1H-pyrrolo[2,3-b]pyridine provided the title compound. ESMS (M+H)$^+$: 550.4

Example 60

Preparation of 4-[3-(4-N-phenylcarbamylaminophenyl)-1-ethyl-1H-pyrazol-4-yl]-2-[4-(N-morpholinylmethyl)phenyl]-1H-pyrrolo[2,3-b]pyridine Following the procedure described in Example 48 using 4-[3-(4-aminophenyl)-1-ethyl-1H-pyrazol-4-yl]-2-[4-(N-morpholinylmethyl)phenyl]-1H-pyrrolo[2,3-b]pyridine provided the title compound. ESMS (M+H)$^+$: 598.4

Example 61

Preparation of 4-[3-(4-N-ethylcarbamylaminophenyl)-1-ethyl-1H-pyrazol-4-yl]-2-[4-(N-morpholinylmethyl)phenyl]-1H-pyrrolo[2,3-b]pyridine Following the procedure described in Example 48 using 4-[3-(4-aminophenyl)-1-ethyl-1H-pyrazol-4-yl]-2-[4-(N-morpholinylmethyl)phenyl]-1H-pyrrolo[2,3-b]pyridine and ethyl isocyanate provided the title compound. ESMS (M+H)$^+$: 550.4

Example 62

Preparation of 4-[3-(4-N-phenylcarbamylaminophenyl)-1-ethyl-1H-pyrazol-4-yl]-2-[2-(ethoxycarbonyl)-1-ethyl]-1H-pyrrolo[2,3-b]pyridine Following the procedure described in Example 48 using 4-[3-(4-aminophenyl)-1-ethyl-1H-pyrazol-4-yl]-2-[2-(ethoxycarbonyl)-1-ethyl]-1H-pyrrolo[2,3-b]pyridine provided the title compound. ESMS (M+H)$^+$: 523.4

Example 63

Preparation of 4-[3-(4-N-phenylcarbamylaminophenyl)-1-ethyl-1H-pyrazol-4-yl]-2-[2-carboxy-1-ethyl]-1H-pyrrolo[2,3-b]pyridine To a stirred solution of 4-[3-(4-N-phenylcarbamylaminophenyl)-1-ethyl-1H-pyrazol-4-yl]-2-[2-(ethoxycarbonyl)-1-ethyl]-1H-pyrrolo[2,3-b]pyridine (0.2 mmol) in 1,4-dioxane (4 mL) was added aqueous 1 N sodium hydroxide (1 mL). The reaction was stirred at room temperature for 18 h, neutralized with aqueous 1 N hydrochloric acid (1 mL), and concentrated under vacuum. The remaining residue was triturated with cold water, filtered, washed with water, and dried under vacuum to give the title compound as a white solid (85%). ESMS (M+H)$^+$: 495.4

Example 64

Preparation of 4-[3-(4-N-phenylcarbamylaminophenyl)-1-ethyl-1H-pyrazol-4-yl]-2-{2-[N'(N-methylpiperazinyl)carbonyl]-1-ethyl}-1H-pyrrolo[2,3-b]pyridine To 4-[3-(4-N-phenylcarbamylaminophenyl)-1-ethyl-1H-pyrazol-4-yl]-2-[2-carboxy-1-ethyl]-1H-pyrrolo[2,3-b]pyridine (0.12 mmol) in N,N-dimethylformamide (2 mL) was added N-methylpiperazine (0.13 mmol) and 1-ethyl-3-(3-dimethylaminopropyl)carbodiimide (0.14 mmol). The reaction was stirred at room temperature for 18 h and evaporated to dryness. Purification by reverse phase Gilson HPLC gave the title compound as a white solid (25%). ESMS (M+H)$^+$: 577.4

Example 65

Preparation of N-ethyl-N'-[4-(1-ethyl-4-{2-[4-(1-pyrrolidinylmethyl)phenyl]-1H-pyrrolo[2,3-b]pyridin-4-yl}-1H-pyrazol-3-yl)phenyl]urea Following the procedure described in Example 48 4-(1-ethyl-4-{2-[4-(1-pyrrolidinylmethyl)phenyl]-1H-pyrrolo[2,3-b]pyridin-4-yl}-1H-pyrazol-3-yl)aniline and ethyl isocyanate provided the title compound. ESMS [M+H]$^+$: 534.4

Example 66

Preparation of N'-[4-(1-ethyl-4-{2-[4-(1-pyrrolidinylmethyl)phenyl]-1H-pyrrolo[2,3-b]pyridin-4-yl}-1H-pyrazol-3-yl)phenyl]-N,N-dimethylurea Following the procedure described in Example 47 using 4-(1-ethyl-4-{2-[4-(1-pyrrolidinylmethyl)phenyl]-1H-pyrrolo[2,3-b]pyridin-4-yl}-1H-pyrazol-3-yl)aniline provided the title compound. ESMS [M+H]$^+$: 534.4

Example 67

Preparation of N-[4-(1-ethyl-4-{2-[1-(4-morpholinylcarbonyl)-1,2,3,6-tetrahydro-4-pyridinyl]-1H-pyrrolo[2,3-b]pyridin-4-yl}-1H-pyrazol-3-yl)phenyl]-N'-phenylurea Following the procedures described in Intermediate 124 and then Example 1 using 4-(1-ethyl-4-{2-[1-(4-morpholinylcarbonyl)-1,2,3,6-tetrahydro-4-pyridinyl]-1H-pyrrolo[2,3-b]pyridin-4-yl}-1H-pyrazol-3-yl)aniline provided the title compound. ESMS [M+H]$^+$: 617.4

Example 68

Preparation of N'-[4-(1-ethyl-4-{2-[1-(4-morpholinylcarbonyl)-1,2,3,6-tetrahydro-4-pyridinyl]-1H-pyrrolo[2,3-b]pyridin-4-yl}-1H-pyrazol-3-yl)phenyl]-N,N-dimethylurea Following the procedure described in Example 47 using 4-(1-ethyl-4-{2-[1-(4-morpholinylcarbonyl)-1,2,3,6-tetrahydro-4-pyridinyl]-1H-pyrrolo[2,3-b]pyridin-4-yl}-1H-pyrazol-3-yl)aniline provided the title compound. ESMS [M+H]$^+$: 569.6

Example 69

Preparation of N-[4-(4-{2-[1-(N,N-dimethylglycyl)-1,2,3,6-tetrahydro-4-pyridinyl]-1H-pyrrolo[2,3-b]pyridin-4-yl}-1-ethyl-1H-pyrazol-3-yl)phenyl]-N'-phenylurea To a solution of N-(4-{1-ethyl-4-[2-(1,2,3,6-tetrahydro-4-pyridinyl)-1H-pyrrolo[2,3-b]pyridin-4-yl]-1H-pyrazol-3-yl}phenyl)-N'-phenylurea (0.23 mmol) was in N,N-dimethylformamide (3.0 mL) was added EDC (0.39 mmol), HOBt (0.39 mmol), triethylamine (1.38 mmol) followed by N,N dimethylglycine (0.39 mmol). The reaction stirred at room temp for 16 h. The reaction was poured into ethyl acetate and washed saturated sodium bicarbonate (2×10 mL). The organic layer was evaporated and purification of the residue by Gilson reverse phase HPLC provided the title product. ESMS [M+H]$^+$: 589.4

Example 70

Preparation of N'-(4-{1-ethyl-4-[2-(1,2,3,6-tetrahydro-4-pyridinyl)-1H-pyrrolo[2,3-b]pyridin-4-yl]-1H-pyrazol-3-yl}phenyl)-N,N-dimethylurea Following the procedures described in Examples 47 and Example 11 with 1,1-dimethylethyl 4-{4-[3-(4-aminophenyl)-1-ethyl-1H-pyrazol-4-yl]-1H-pyrrolo[2,3-b]pyridin-2-yl}-3,6-dihydro-1(2H)-pyridinecarboxylate provided the title product. ESMS [M+H]$^+$: 456.4

Example 71a

Preparation of N-[4-(1-ethyl-4-{2-[4-(4-morpholinylmethyl)phenyl]-1H-pyrrolo[2,3-b]pyridin-4-yl}-1H-pyrazol-3-yl)phenyl]-2,2-dimethylpropanamide A solution of [4-(1-ethyl-4-{2-[4-(4-morpholinylmethyl)phenyl]-1H-pyrrolo[2,3-b]pyridin-4-yl}-1H-pyrazol-3-yl)phenyl]amine (0.104 mmol) in methylene chloride (5 mL) was treated with triethylamine (0.3 mmol), DMAP (0.01 mmol) and pivalyl chloride (0.15 mmol). The reaction was stirred for 3 h at room temperature and concentrated. The residue was dissolved in ethyl acetate (10 mL) and washed with water (2×5 mL). The organic layer was concentrated and the residue purified by Gilson reverse phase HPLC to provide the title product as a white powder (82%). ESMS [M+H]$^+$: 563.2

Example 71b

Preparation of N-[4-(1-ethyl-4-{2-[4-(4-morpholinylmethyl)phenyl]-1H-pyrrolo[2,3-b]pyridin-4-yl}-1H-pyrazol-3-yl)phenyl]-2-methylpropanamide Following the procedure described in Example 71a with dimethyl acetyl chloride provided the title product. ESMS [M+H]$^+$: 549.2

Example 72

Preparation of N$^1$-[4-(1-ethyl-4-{2-[4-(4-morpholinylmethyl)phenyl]-1H-pyrrolo[2,3-b]pyridin-4-yl}-1H-pyrazol-3-yl)phenyl]-N$^2$,N$^2$-dimethylglycinamide A solution of [4-(1-ethyl-4-{2-[4-(4-morpholinylmethyl)phenyl]-1H-pyrrolo[2,3-b]pyridin-4-yl}-1H-pyrazol-3-yl)phenyl]amine (0.104 mmol) in N,N-dimethylformamide (1 mL) was treated with diisopropylethylamine (0.4 mmol) and then pentafluorophenyl-N,N-dimethylglycinate (0.104 mmol). The reaction was stirred 18 h and purified directly on the Gilson reverse phase HPLC which provided the title product as a yellow solid (57%). ESMS [M+H]$^+$: 564.2

Example 73a

Preparation of N-[4-(1-ethyl-4-{2-[4-(4-morpholinylmethyl)phenyl]-1H-pyrrolo[2,3-b]pyridin-4-yl}-1H-pyrazol-3-yl)phenyl]-1-pyrrolidinecarboxamide A solution of [4-(1-ethyl-4-{2-[4-(4-morpholinylmethyl)phenyl]-1H-pyrrolo[2,3-b]pyridin-4-yl}-1H-pyrazol-3-yl)phenyl]amine (0.204 mmol) in tetrahydrofuran (1 mL) was treated with triethylamine (0.8 mmol) and isopropenyl chloroformate (0.3 mmol). The reaction was stirred for 3 h then pyrrolidine (2 mmol) was added and the reaction heated at 50° C. for 18 h. The reaction was concentrated in vacuo and redissolved in methylene chloride (20 mL) and washed with water (2×10 mL). The methylene chloride was evaporated to give the crude produce which was purified using a Gilson reverse phase HPLC to provide the title product (37%). ESMS [M+H]$^+$: 576.2

Example 73b

Preparation of N-[4-(1-ethyl-4-{2-[4-(4-morpholinylmethyl)phenyl]-1H-pyrrolo[2,3-b]pyridin-4-yl}-1H-pyrazol-3-yl)phenyl]-1-piperidinecarboxamide Following the procedure described in Example 73a with piperidine provided the title product (33%). ESMS [M+H]$^+$: 590.2

Example 73c

Preparation of N-[4-(1-ethyl-4-{2-[4-(4-morpholinylmethyl)phenyl]-1H-pyrrolo[2,3-b]pyridin-4-yl}-1H-pyrazol-3-yl)phenyl]-4-morpholinecarboxamide Following the procedure described in Example 73a with morpholine provided the title product (33%). ESMS [M+H]$^+$: 592.2

Example 73d

Preparation of N-[4-(1-ethyl-4-{2-[4-(4-morpholinylmethyl)phenyl]-1H-pyrrolo[2,3-b]pyridin-4-yl}-1H-pyrazol-3-yl)phenyl]-4-methyl-1-piperazinecarboxamide Following the procedure described in Example 73a with 1-methyl piperazine provided the title product (34%). ESMS [M+H]$^+$: 605.2

Example 73e

Preparation of N-[4-(1-ethyl-4-{2-[4-(4-morpholinylmethyl)phenyl]-1H-pyrrolo[2,3-b]pyridin-4-yl}-1H-pyrazol-3-yl)phenyl]-4-thiomorpholinecarboxamide Following the procedure described in Example 73a with thiomorpholine provided the title product (32%). ESMS [M+H]$^+$: 608.2.

Example 74a

Preparation of N-(4-{4-[3-(4-{[(dimethylamino)carbonyl]amino}phenyl)-1-ethyl-1H-pyrazol-4-yl]-1H-pyrrolo[2,3-b]pyridin-2-yl}phenyl)methanesulfonamide Following the procedure described in Intermediate 21 with N-{4-[4-[3-(4-{[(dimethylamino)carbonyl]amino}phenyl)-1-ethyl-1H-pyrazol-4-yl]-1-(phenylsulfonyl)-1H-pyrrolo[2,3-b]pyridin-2-yl]phenyl}methanesulfonamide provided the title product. ESMS [M+H]$^+$: 544.4

Example 74b

Preparation of N-(3-{4-[3-(4-{[(dimethylamino)carbonyl]amino}phenyl)-1-ethyl-1H-pyrazol-4-yl]-1H-pyrrolo[2,3-b]pyridin-2-yl}phenyl)methanesulfonamide Following the procedure described in Intermediate 21 with N-{3-[4-[3-(4-{[(dimethylamino)carbonyl]amino}phenyl)-1-ethyl-1H-pyrazol-4-yl]-1-(phenylsulfonyl)-1H-pyrrolo[2,3-b]pyridin-2-yl]phenyl}methanesulfonamide provided the title product. ESMS [M+H]$^+$: 544.4

Example 74c

Preparation of N'-[4-(1-ethyl-4-{2-[3-(4-morpholinyl)phenyl]-1H-pyrrolo[2,3-b]pyridin-4-yl}-1H-pyrazol-3-yl)phenyl]-N,N-dimethylurea Following the procedure described in Intermediate 21 with N'-(4-{1-ethyl-4-[2-[3-(4-morpholinyl)phenyl]-1-(phenylsulfonyl)-1H-pyrrolo[2,3-b]pyridin-4-yl]-1H-pyrazol-3-yl}phenyl)-N,N-dimethylurea provided the title product. ESMS [M+H]$^+$: 536.4

Example 74d

Preparation of N'-[4-(1-ethyl-4-{2-[4-(4-morpholinyl)phenyl]-1H-pyrrolo[2,3-b]pyridin-4-yl}-1H-pyrazol-3-yl)phenyl]-N,N-dimethylurea Following the procedure described in Intermediate 21 with N'-(4-{1-ethyl-4-[2-[4-(4-morpholinyl)phenyl]-1-(phenylsulfonyl)-1H-pyrrolo[2,3-b]pyridin-4-yl]-1H-pyrazol-3-yl}phenyl)-N,N-dimethylurea provided the title product. ESMS [M+H]$^+$: 536.4

Example 74e

Preparation of N'-[4-(4-{2-[3-(dimethylamino)phenyl]-1H-pyrrolo[2,3-b]pyridin-4-yl}-1-ethyl-1H-pyrazol-3-yl)phenyl]-N,N-dimethylurea Following the procedure described in Intermediate 21 with N'-(4-{4-[2-[3-(dimethylamino)phenyl]-1-(phenylsulfonyl)-1H-pyrrolo[2,3-b]pyridin-4-yl]-1-ethyl-1H-pyrazol-3-yl}phenyl)-N,N-dimethylurea provided the title product. ESMS [M+H]$^+$: 494.4

Example 74f

Preparation of N'-[4-(4-{2-[4-(dimethylamino)phenyl]-1H-pyrrolo[2,3-b]pyridin-4-yl}-1-ethyl-1H-pyrazol-3-yl)phenyl]-N,N-dimethylurea Following the procedure described in Intermediate 21 with N'-(4-{4-[2-[4-(dimethylamino)phenyl]-1-(phenylsulfonyl)-1H-pyrrolo[2,3-b]pyridin-4-yl]-1-ethyl-1H-pyrazol-3-yl}phenyl)-N,N-dimethylurea provided the title product. ESMS [M+H]$^+$: 494.4

Example 74g

Preparation of N'-[4-(1-ethyl-4-{2-[6-(4-morpholinyl)-3-pyridinyl]-1H-pyrrolo[2,3-b]pyridin-4-yl}-1H-pyrazol-3-yl)phenyl]-N,N-dimethylurea Following the procedure described in Intermediate 21 with N'-(4-{1-ethyl-4-[2-[6-(4-morpholinyl)-3-pyridinyl]-1-(phenylsulfonyl)-1H-pyrrolo[2,3-b]pyridin-4-yl]-1H-pyrazol-3-yl}phenyl)-N,N-dimethylurea provided the title product. ESMS [M+H]$^+$: 537.4

Example 75

Preparation of 4-[3-(4-N,N-dimethylcarbamylaminophenyl)-1-(2-hydroxyethyl)-1H-pyrazol-4-yl]-2-[4-(N-morpholinylmethyl)phenyl]-1H-pyrrolo[2,3-b]pyridine Following the procedure described in Example 47 using 4-[3-(4-aminophenyl)-1-ethyl-1H-pyrazol-4-yl]-2-[3-(dimethylaminomethyl)phenyl]-1H-pyrrolo[2,3-b]pyridine provided the title compound. ESMS [M+H]$^+$: 566.4

Example 76

Preparation of 4-[3-(4-N,N-dimethylcarbamylaminophenyl)-1-ethyl-1H-pyrazol-4-yl]-2-[3-(N-pyrrolidinylmethyl)phenyl]-1H-pyrrolo[2,3-b]pyridine Following the procedure described in Example 47 using 4-[3-(4-aminophenyl)-1-ethyl-1H-pyrazol-4-yl]-2-[3-(dimethylaminomethyl)phenyl]-1H-pyrrolo[2,3-b]pyridine provided the title compound. ESMS [M+H]$^+$: 534.4

Example 77

Preparation of N'-{4-[4-(2-{4-[(dimethylamino)methyl]phenyl}-1H-pyrrolo[2,3-b]pyridin-4-yl)-1-methyl-1H-pyrazol-3-yl]phenyl}-N,N-dimethylurea Following the procedure described in Intermediate 100 and then Intermediate 21 using N,N-dimethyl-1-{4-[1-(phenylsulfonyl)-4-(4,4,5,5-tetramethyl-1,3,2-dioxaborolan-2-yl)-1H-pyrrolo[2,3-b]pyridin-2-yl]phenyl}methanamine and N'-[4-(4-bromo-1-methyl-1H-pyrazol-3-yl)phenyl]-N,N-dimethylurea provided the title compound. ESMS [M+H]$^+$: 494.6

Example 78

Preparation of N'-{4-[4-(2-{4-[(dimethylamino)methyl]phenyl}-1H-pyrrolo[2,3-b]pyridin-4-yl)-1-(1-methylethyl)-1H-pyrazol-3-yl]phenyl}-N,N-dimethylurea Following the procedure described in Intermediate 100 and then Intermediate 21 using N,N-dimethyl-1-{4-[1-(phenylsulfonyl)-4-(4,4,5,5-tetramethyl-1,3,2-dioxaborolan-2-yl)-1H-pyrrolo[2,3-b]pyridin-2-yl]phenyl}methanamine and N'-{4-[4-bromo-1-(1-methylethyl)-1H-pyrazol-3-yl]phenyl}-N,N-dimethylurea provided the title compound. ESMS [M+H]$^+$: 522.6

141

Example 79

Preparation of N-{4-[4-(2-{4-[(dimethylamino)methyl]phenyl}-1H-pyrrolo[2,3-b]pyridin-4-yl)-1-methyl-1H-pyrazol-3-yl]phenyl}-1-pyrrolidinecarboxamide Following the procedure described for Example 5a using pyrrolidine and [(4-{4-[3-(4-aminophenyl)-1-methyl-1H-pyrazol-4-yl]-1H-pyrrolo[2,3-b]pyridin-2-yl}phenyl)methyl]dimethylamine provided the title compound. ESMS [M+H]$^+$: 520.2

Example 80

Preparation of N-{4-[4-(2-{4-[(dimethylamino)methyl]phenyl}-1H-pyrrolo[2,3-b]pyridin-4-yl)-1-(1-methylethyl)-1H-pyrazol-3-yl]phenyl}-1-pyrrolidinecarboxamide Following the procedure described for Example 5a using pyrrolidine and [(4-{4-[3-(4-aminophenyl)-1-(1-methylethyl)-1H-pyrazol-4-yl]-1H-pyrrolo[2,3-b]pyridin-2-yl}phenyl)methyl]dimethylamine provided the title compound. ESMS [M+H]$^+$: 547.4

Example 81

Preparation of N-[4-(1-ethyl-4-{2-[4-(4-morpholinylmethyl)phenyl]-1H-pyrrolo[2,3-b]pyridin-4-yl}-1H-pyrazol-3-yl)phenyl]-4-thiomorpholinecarboxamide 1,1-dioxide To a solution of 4-(1-ethyl-4-{2-[4-(4-morpholinylmethyl)phenyl]-1H-pyrrolo[2,3-b]pyridin-4-yl}-1H-pyrazol-3-yl)aniline (0.25 mmol) in anhydrous THF (2 mL) cooled to 5° C., was added triethylamine (4 mmol) and isopropenyl chloroformate (0.5 mmol). The reaction mixture was stirred overnight at room temperature. Thiomorpholine 1,1-dioxide (2.5 mmol) was added and the reaction heated at 50° C. for three days. The crude reaction was purified by reverse phase chromatography to give the title product (30%). ESMS [M+H]$^+$: 640.0.

Example 82

Preparation of N-{4-[4-(2-{3-[(dimethylamino)methyl]phenyl}-1H-pyrrolo[2,3-b]pyridin-4-yl)-1-ethyl-1H-pyrazol-3-yl]phenyl}-N'-phenylurea Following the procedure described in Example 48 using [4-(1-ethyl-4-{2-[3-(1-pyrrolidinylmethyl)phenyl]-1H-pyrrolo[2,3-b]pyridin-4-yl}-1H-pyrazol-3-yl)phenyl]amine provided the title compound (166 mg, 66%) as an off-white solid. ESMS [M+H]+: 582.7

Example 83

Preparation of N-{4-[4-(2-{3-[(dimethylamino)methyl]phenyl}-1H-pyrrolo[2,3-b]pyridin-4-yl)-1-ethyl-1H-pyrazol-3-yl]phenyl}-N'-ethylurea Following the procedure described in Example 48 using [4-(1-ethyl-4-{2-[3-(1-pyrrolidinylmethyl)phenyl]-1H-pyrrolo[2,3-b]pyridin-4-yl}-1H-pyrazol-3-yl)phenyl]amine and ethyl isocyanate provided the title compound. ESMS [M+H]+: 534.5

142

Example 84

N-[4-(1-ethyl-4-{2-[3-(1-pyrrolidinylmethyl)phenyl]-1H-pyrrolo[2,3-b]pyridin-4-yl}-1H-pyrazol-3-yl)phenyl]-2-methylpropanamide Prepared as described in Example 95 using 4-(1-ethyl-4-{2-[3-(1-pyrrolidinylmethyl)phenyl]-1H-pyrrolo[2,3-b]pyridin-4-yl}-1H-pyrazol-3-yl)aniline provided the title compound. ESMS [M+H]$^+$: 533.0.

Example 85

Preparation of N'-(4-{1-ethyl-4-[2-(1,2,3,4-tetrahydro-7-isoquinolinyl)-1H-pyrrolo[2,3-b]pyridin-4-yl]-1H-pyrazol-3-yl}phenyl)-N,N-dimethylurea Following the procedure described in Example 11 using N'-(4-{4-[2-(2-acetyl-1,2,3,4-tetrahydro-7-isoquinolinyl)-1H-pyrrolo[2,3-b]pyridin-4-yl]-1-ethyl-1H-pyrazol-3-yl}phenyl)-N,N-dimethylurea in ethanol at 100° C. provided the title compound. ESMS [M+H]$^+$: 507.4

Example 86

Preparation of N'-(4-{4-[2-(2-acetyl-1,2,3,4-tetrahydro-7-isoquinolinyl)-1H-pyrrolo[2,3-b]pyridin-4-yl]-1-ethyl-1H-pyrazol-3-yl}phenyl)-N,N-dimethylurea Following the procedure described in Intermediate 21 using N'-(4-{4-[2-(2-acetyl-1,2,3,4-tetrahydro-7-isoquinolinyl)-1-(phenylsulfonyl)-1H-pyrrolo[2,3-b]pyridin-4-yl]-1-ethyl-1H-pyrazol-3-yl}phenyl)-N,N-dimethylurea provided the title compound. ESMS [M+H]$^+$: 549.4

Example 87

Preparation of N,N-dimethyl-N'-[4-(1-methyl-4-{2-[4-(1-pyrrolidinylmethyl)phenyl]-1H-pyrrolo[2,3-b]pyridin-4-yl}-1H-pyrazol-3-yl)phenyl]urea Following the procedure described for Intermediate 101 using N'-(4-{4-[2-(4-formylphenyl)-1H-pyrrolo[2,3-b]pyridin-4-yl]-1-methyl-1H-pyrazol-3-yl}phenyl)-N,N-dimethylurea and pyrrolidine provided the title compound. ESMS [M+H]+: 520.4.

Example 88

Preparation of N'-(4-{4-[2-(4-{[ethyl(2-hydroxyethyl)amino]methyl}phenyl)-1H-pyrrolo[2,3-b]pyridin-4-yl]-1-methyl-1H-pyrazol-3-yl}phenyl)-N,N-dimethylurea Following the procedure described for Intermediate 101 using N'-(4-{4-[2-(4-formylphenyl)-1H-pyrrolo[2,3-b]pyridin-4-yl]-1-methyl-1H-pyrazol-3-yl}phenyl)-N,N-dimethylurea and 2-(ethylamino)ethanol provided the title compound. ESMS [M+H]+: 538.4

Example 89

Preparation of N,N-diethyl-N'-{4-[1-ethyl-4-(2-{4-[(methylamino)methyl]phenyl}-1H-pyrrolo[2,3-b]pyridin-4-yl)-1H-pyrazol-3-yl]-phenyl}urea Following the procedure in Example 96 using [(4-{4-[3-(4-aminophenyl)-1-ethyl-1H-pyrazol-4-yl]-1H-pyrrolo[2,3-b]pyridin-2-yl}phenyl)methyl]dimethylamine provided the title compound. ESMS [M+H]+: 536.4

Example 90

Preparation of N,N-dimethyl-N'-[4-(4-{2-[4-(1-pyrrolidinylmethyl)phenyl]-1H-pyrrolo[2,3-b]pyridin-4-yl}-1H-pyrazol-3-yl)phenyl]urea Following the procedure described for Intermediate 101 using N'-(4-{4-[2-(4-formylphenyl)-1H-pyrrolo[2,3-b]pyridin-4-yl]-1H-pyrazol-3-yl}phenyl)-N,N-dimethylurea and pyrrolidine provided the title compound. ESMS [M+H]+: 506.4

Example 91

Preparation of N'-(4-{1-ethyl-4-[2-(2-methyl-1,2,3,4-tetrahydro-7-isoquinolinyl)-1H-pyrrolo[2,3-b]pyridin-4-yl]-1H-pyrazol-3-yl}phenyl)-N,N-dimethylurea Following the procedure described in Intermediate 21 using N'-(4-{1-ethyl-4-[2-(2-methyl-1,2,3,4-tetrahydro-7-isoquinolinyl)-1-(phenylsulfonyl)-1H-pyrrolo[2,3-b]pyridin-4-yl]-1H-pyrazol-3-yl}phenyl)-N,N-dimethylurea provided the title compound. ESMS [M+H]$^+$: 520.6

Example 92

Preparation of N'-{4-[1-ethyl-4-(2-{4-[2-(1-pyrrolidinyl)ethyl]-phenyl}-1H-pyrrolo[2,3-b]pyridin-4-yl)-1H-pyrazol-3-yl]phenyl}-N,N-dimethylurea Following the procedure described for Intermediate 21 using N'-{4-[1-ethyl-4-(1-(phenylsulfonyl)-2-{4-[2-(1-pyrrolidinyl)ethyl]phenyl}-1H-pyrrolo[2,3-b]pyridin-4-yl)-1H-pyrazol-3-yl]phenyl}-N,N-dimethylurea provided the title compound. ESMS [M+H]$^+$: 548.4.

Example 93

Preparation of N-{4-[4-(2-{5-[(dimethylamino)methyl]-2-methylphenyl}-1H-pyrrolo[2,3-b]pyridin-4-yl)-1-ethyl-1H-pyrazol-3-yl]phenyl}-N'-phenylurea Following the procedure describe din Example 48 using [(3-{4-[3-(4-aminophenyl)-1-ethyl-1H-pyrazol-4-yl]-1H-pyrrolo[2,3-b]pyridin-2-yl}-4-methylphenyl)methyl]dimethylamine provided the title compound. ESMS [M+H]+: 570.4

Example 94

Preparation of N'-(4-{4-(2-{4-[(dimethylamino)methyl]phenyl}-1H-pyrrolo[2,3-b]pyridin-4-yl)-1-[2-(methylamino)ethyl]-1H-pyrazol-3-yl}phenyl)-N,N-dimethylurea Following the procedure described in Example 47 using 1,1-dimethylethyl {2-[3-(4-aminophenyl)-4-(2-{4-[(dimethylamino)methyl]phenyl}-1H-pyrrolo[2,3-b]pyridin-4-yl)-1H-pyrazol-1-yl]ethyl}methylcarbamate and then Boc deprotection by treatment with 50% TFA in CH$_2$Cl$_2$ (20 mL) for 30 minutes. Concentration and purification of the residue by Gilson HPLC provided the title compound (49%) as a yellow solid. ESMS [M+H]+: 537.4.

Example 95

Preparation of N-[4-(1-ethyl-4-{2-[4-(1-pyrrolidinylmethyl)phenyl]-1H-pyrrolo[2,3-b]pyridin-4-yl}-1H-pyrazol-3-yl)phenyl]-2-methylpropanamide To a cloudy orange mixture of 4-(1-ethyl-4-{2-[4-(1-pyrrolidinylmethyl)phenyl]-1H-pyrrolo[2,3-b]pyridin-4-yl}-1H-pyrazol-3-yl)aniline (280 mg, 0.61 mmol) in dry CH$_2$Cl$_2$ (6 mL) was added TEA (253 uL, 1.82 mmol), DMAP (4 mg, 0.03 mmol) and 2-methylpropanoyl chloride (77 uL, 0.73 mmol). The reaction was stirred for 15 min at room temperature, quenched with water and diluted with CH$_2$Cl$_2$ and brine. The aqueous layer was extracted with CH$_2$Cl$_2$ followed by 1% MeOH in CH$_2$Cl$_2$ and the combined extracts were dried (Na$_2$SO$_4$), filtered and concentrated under reduced pressure. The residue was purified by Gilson reverse phase HPLC (MeCN/H$_2$O with 0.1% TFA). The clean fractions were neutralized with aqueous NaHCO$_3$, extracted with three portions of CH$_2$Cl$_2$ followed by 1% MeOH in CH$_2$Cl$_2$, dried (Na$_2$SO$_4$), filtered and concentrated under reduced pressure to give 139 mg (43%) of the title product as a yellow solid. ESMS [M+H]$^+$: 533.4.

Example 96

N,N-diethyl-N'-[4-(1-ethyl-4-{2-[4-(1-pyrrolidinylmethyl)phenyl]-1H-pyrrolo[2,3-b]pyridin-4-yl}-1H-pyrazol-3-yl)phenyl]urea To a cloudy mixture of 4-(1-ethyl-4-{2-[4-(1-pyrrolidinylmethyl)phenyl]-1H-pyrrolo[2,3-b]pyridin-4-yl}-1H-pyrazol-3-yl)aniline (350 mg, 0.76 mmol) in dry THF (8 mL) was added 4-nitrophenyl chloroformate (168 mg, 0.83 mmol). The resultant slurry was stirred at room temperature for 45 min and diethylamine (0.32 mL, 3.03 mmol) was added. After 1 h, the reaction was concentrated under reduced pressure and diluted with 1N NaOH and EtOAc. The aqueous layer was extracted with three portions of EtOAc followed by 5% MeOH in EtOAc and the combined extracts were dried (Na$_2$SO$_4$), filtered and concentrated under reduced pressure. The residue was purified by Gilson reverse phase HPLC (MeCN/H$_2$O with 0.1% TFA) to provide 159 mg (32%) of the title product as a bis-TFA salt (yellow solid). ESMS [M+H]$^+$: 562.4

Example 97

Preparation of N N-diethyl-N'-[4-(1-ethyl-4-{2-[3-fluoro-4-(1-pyrrolidinylmethyl)phenyl]-1H-pyrrolo[2,3-b]pyridin-4-yl}-1H-pyrazol-3-yl)phenyl]urea Following the procedure described for Example 96 using [4-(1-ethyl-4-{2-[3-fluoro-4-(1-pyrrolidinylmethyl)phenyl]-1H-pyrrolo[2,3-b]pyridin-4-yl}-1H-pyrazol-3-yl)phenyl] amine provided the title compound. ESMS [M+H]+: 580.6

Example 98

Preparation of N,N-diethyl-N'-[4-(1-ethyl-4-{2-[4-fluoro-3-(1-pyrrolidinylmethyl)phenyl]-1H-pyrrolo[2,3-b]pyridin-4-yl}-1H-pyrazol-3-yl)phenyl]urea Following the procedure described in Example 96 using [4-(1-ethyl-4-{2-[4-fluoro-3-(1-pyrrolidinylmethyl)phenyl]-1H-pyrrolo[2,3-b]pyridin-4-yl}-1H-pyrazol-3-yl)phenyl] amine provided the title compound. ESMS [M+H]+: 580.6

Example 99

Preparation of N-{4-[4-[2-(4-{[4-(2-hydroxyethyl)-1-piperazinyl]methyl}phenyl)-1H-pyrrolo[2,3-b]pyridin-4-yl]-1-(1-methylethyl)-1H-pyrazol-3-yl]phenyl}-2-methylpropanamide Following the procedure described in Example 95 using 2-{4-[(4-{4-[3-(4-aminophenyl)-1-(1-methylethyl)-1H-pyrazol-4-yl]-1H-pyrrolo[2,3-b]pyridin-2-yl}phenyl)methyl]-1-piperazinyl}ethanol provided the title compound. ESMS [M+H]+: 606.6

Example 100

Preparation of N'-[4-(1-ethyl-4-{2-[3-(hydroxymethyl)phenyl]-1H-pyrrolo[2,3-b]pyridin-4-yl}-1H-pyrazol-3-yl)phenyl]-N,N-dimethylurea Following the procedure described in Example 47 using (3-{4-[3-(4-aminophenyl)-1-ethyl-1H-pyrazol-4-yl]-1H-pyrrolo[2,3-b]pyridin-2-yl}phenyl)methanol provided the title compound. ESMS [M+H]+: 481.4

Example 101

Preparation of: N-[4-(1-ethyl-4-{2-[4-(1-pyrrolidinylmethyl)phenyl]-1H-pyrrolo[2,3-b]pyridin-4-yl}-1H-pyrazol-3-yl)phenyl]-2,2-dimethylpropanamide Following the procedure described in Example 95 using trimethylacetyl chloride provided the title compound. ESMS [M+H]+: 547.4

Example 102

N'-(4-{1-ethyl-4-[2-(4-{[ethyl(2-hydroxyethyl)amino]methyl}phenyl)-1H-pyrrolo[2,3-b]pyridin-4-yl]-1H-pyrazol-3-yl}phenyl)-N,N-dimethylurea Following the procedure described in Example 47 with 2-[({4-[3-(4-aminophenyl)-1-ethyl-1H-pyrazol-4-yl]-1H-pyrrolo[2,3-b]pyridin-2-yl}methyl)(ethyl)amino]ethanol and 2 M dimethylamine in THF provided the title compound. ESMS (M+H)+: 552.4

Example 103

Preparation of N,N-diethyl-N'-(4-{1-ethyl-4-[2-(4-{[ethyl(2-hydroxyethyl)amino]methyl}phenyl)-1H-pyrrolo[2,3-b]pyridin-4-yl]-1H-pyrazol-3-yl}phenyl)urea Following the procedure described in Example 96 with 2-[({4-[3-(4-aminophenyl)-1-ethyl-1H-pyrazol-4-yl]-1H-pyrrolo[2,3-b]pyridin-2-yl}methyl)(ethyl)amino]ethanol and diethylamine provided the title compound. ESMS (M+H)+: 580.4

Example 104

Preparation of N-(4-{1-ethyl-4-[2-(4-{[ethyl(2-hydroxyethyl)amino]methyl}phenyl)-1H-pyrrolo[2,3-b]pyridin-4-yl]-1H-pyrazol-3-yl}phenyl)-1-pyrrolidinecarboxamide Following the procedure described in Example 47 with 2-[({4-[3-(4-aminophenyl)-1-ethyl-1H-pyrazol-4-yl]-1H-pyrrolo[2,3-b]pyridin-2-yl}methyl)(ethyl)amino]ethanol and pyrrolidine provided the title compound. ESMS (M+H)+: 578.4

Example 105

Preparation of N'-{4-[1-ethyl-4-(2-{3-[2-(1-pyrrolidinyl)ethyl]phenyl}-1H-pyrrolo[2,3-b]pyridin-4-yl)-1H-pyrazol-3-yl]phenyl}-N,N-dimethylurea To a stirred solution of N'-[4-(1-ethyl-4-{2-[3-(2-hydroxyethyl)phenyl]-1H-pyrrolo[2,3-b]pyridin-4-yl}-1H-pyrazol-3-yl)phenyl]-N,N-dimethylurea (210 mg, 0.42 mMol) in CH$_2$Cl$_2$ (15 mL) was added at 0° C. Et$_3$N (120 uL, 0.86 mmol) and methanesulfonyl lchloride (40 uL, 0.52 mmol). After stirring for 3 h, pyrrolidine (2 mL, 24 mmol) was added. The reaction was allowed to warm to RT, stirred for 18 h, and evaporated to dryness under vacuum. Purification by Gilson HPLC provided the title compound (25%) as a pale yellow solid. ESMS [M+H]+: 548.4.

Example 106

Preparation of N-[4-(1-ethyl-4-{2-[4-(1-pyrrolidinylmethyl)phenyl]-1H-pyrrolo[2,3-b]pyridin-4-yl}-1H-pyrazol-3-yl)phenyl]-1-pyrrolidinecarboxamide Following the procedure described for Example 47 using [4-(1-ethyl-4-{2-[4-(1-pyrrolidinylmethyl)phenyl]-1H-pyrrolo[2,3-b]pyridin-4-yl}-1H-pyrazol-3-yl)phenyl]amine and pyrrolidine provided the title compound. ESMS [M+H]+: 560.4.

Example 107

N'-{4-[4-[2-(4-{[ethyl(2-hydroxyethyl)amino]methyl}phenyl)-1H-pyrrolo[2,3-b]pyridin-4-yl]-1-(1-methylethyl)-1H-pyrazol-3-yl]phenyl}-N,N-dimethylurea Following the procedure described in Example 47 using 2-[[(4-{4-[3-(4-aminophenyl)-1-(1-methylethyl)-1H-pyrazol-4-yl]-1H-pyrrolo[2,3-b]pyridin-2-yl}phenyl)methyl](ethyl)amino]ethanol provided the title compound. ESMS [M+H]+: 566.4

Example 108

Preparation of N-(4-{4-[2-(4-{[4-(2-hydroxyethyl)-1-piperazinyl]methyl}phenyl)-1H-pyrrolo[2,3-b]pyridin-4-yl]-1-methyl-1H-pyrazol-3-yl}phenyl)-1-pyrrolidinecarboxamide Following the procedure described in Example 47 using 2-{4-[(4-{4-[3-(4-aminophenyl)-1-methyl-1H-pyrazol-4-yl]-1H-pyrrolo[2,3-b]pyridin-2-yl}phenyl)methyl]-1-piperazinyl}ethanol and pyrrolidine provided the title compound. ESMS [M+H]+: 605.6

Example 109

Preparation of N,N-diethyl-N'-(4-{4-[2-(4-{[4-(2-hydroxyethyl)-1-piperazinyl]methyl}phenyl)-1H-pyrrolo[2,3-b]pyridin-4-yl]-1-methyl-1H-pyrazol-3-yl}phenyl)urea Following the procedure described in Example 96 using 2-{4-[(4-{4-[3-(4-aminophenyl)-1-methyl-1H-pyrazol-4-yl]-1H-pyrrolo[2,3-b]pyridin-2-yl}phenyl)methyl]-1-piperazinyl}ethanol provided the title compound. ESMS [M+H]+: 607.6

Example 110

Preparation of N'-(4-{4-[2-(4-{[4-(2-hydroxyethyl)-1-piperazinyl]methyl}phenyl)-1H-pyrrolo[2,3-b]pyridin-4-yl]-1-methyl-1H-pyrazol-3-yl}phenyl)-N,N-dimethylurea Following the procedure described in Example 47 using 2-{4-[(4-{4-[3-(4-aminophenyl)-1-methyl-1H-pyrazol-4-yl]-1H-pyrrolo[2,3-b]pyridin-2-yl}phenyl)methyl]-1-piperazinyl}ethanol provided the title compound. ESMS [M+H]+: 579.6

Example 111

N,N-diethyl-N'-{4-[4-[2-(4-{[ethyl(2-hydroxyethyl)amino]methyl}phenyl)-1H-pyrrolo[2,3-b]pyridin-4-yl]-1-(1-methylethyl)-1H-pyrazol-3-yl]phenyl}urea Following the procedure described in Example 96 using 2-[[(4-{4-[3-(4-aminophenyl)-1-(1-methylethyl)-1H-pyrazol-4-yl]-1H-pyrrolo[2,3-b]pyridin-2-yl}phenyl)methyl](ethyl)amino]ethanol and N,N-diethylamine afforded the title compound. ESMS [M+H]+: 594.6

Example 112

Preparation of N,N-diethyl-N'-{4-[4-[2-(4-{[4-(2-hydroxyethyl)-1-piperazinyl]methyl}phenyl)-1H-pyrrolo[2,3-b]pyridin-4-yl]-1-(1-methylethyl)-1H-pyrazol-3-yl]phenyl}urea Following the procedure described in Example 96 using 2-{4-[(4-{4-[3-(4-aminophenyl)-1-(1-methylethyl)-1H-pyrazol-4-yl]-1H-pyrrolo[2,3-b]pyridin-2-yl}phenyl)methyl]-1-piperazinyl}ethanol provided the title compound. ESMS [M+H]+: 635.6.

Example 113

Preparation of N'-{4-[4-[2-(4-{[4-(2-hydroxyethyl)-1-piperazinyl]methyl}phenyl)-1H-pyrrolo[2,3-b]pyridin-4-yl]-1-(1-methylethyl)-1H-pyrazol-3-yl]phenyl}-N,N-dimethylurea Following the procedure described in Example 47 using dimethylamine and 2-{4-[(4-{4-[3-(4-aminophenyl)-1-(1-methylethyl)-1H-pyrazol-4-yl]-1H-pyrrolo[2,3-b]pyridin-2-yl}phenyl)methyl]-1-piperazinyl}ethanol provided the title compound. ESMS [M+H]+: 607.7

Example 114

Preparation of N,N-diethyl-N'-[4-(1-(1-methylethyl)-4-{2-[4-(1-pyrrolidinylmethyl)phenyl]-1H-pyrrolo[2,3-b]pyridin-4-yl}-1H-pyrazol-3-yl)phenyl]urea Following the procedure in Example 96 using 4-(1-(1-methylethyl)-4-{2-[4-(1-pyrrolidinylmethyl)phenyl]-1H-pyrrolo[2,3-b]pyridin-4-yl}-1H-pyrazol-3-yl)aniline provided the title compound. ESMS [M+H]+=576.4

Example 115

Preparation of N-(4-{4-[2-(4-{[ethyl(2-hydroxyethyl)amino]methyl}phenyl)-1H-pyrrolo[2,3-b]pyridin-4-yl]-1-methyl-1H-pyrazol-3-yl}phenyl)-1-pyrrolidinecarboxamide Following the procedure described for Intermediate 21 using N-(4-{4-[2-(4-{[ethyl(2-hydroxyethyl)amino]methyl}phenyl)-1-(phenylsulfonyl)-1H-pyrrolo[2,3-b]pyridin-4-yl]-1-methyl-1H-pyrazol-3-yl}phenyl)-1-pyrrolidinecarboxamide and stirring for 30 minutes provided the title compound. ESMS [M+H]+: 564.3

Example 116

N,N-diethyl-N'-(4-{1-ethyl-4-[2-(4-{[4-(2-hydroxyethyl)-1-piperazinyl]methyl}phenyl)-1H-pyrrolo[2,3-b]pyridin-4-yl]-1H-pyrazol-3-yl}phenyl)urea Following the procedure described in Example 96 with 2-{4-[(4-{4-[3-(4-aminophenyl)-1-ethyl-1H-pyrazol-4-yl]-1H-pyrrolo[2,3-b]pyridin-2-yl}phenyl)methyl]-1-piperazinyl}ethanol and diethylamine provided the title compound. ESMS (M+H)+: 551.4

Example 117

Preparation of N,N-diethyl-N'-(4-{4-[2-(4-{[ethyl(2-hydroxyethyl)amino]methyl}phenyl)-1H-pyrrolo[2,3-b]pyridin-4-yl]-1-methyl-1H-pyrazol-3-yl}phenyl)urea Following the procedure described in Example 96 using 2-[[(4-{4-[3-(4-aminophenyl)-1-methyl-1H-pyrazol-4-yl]-1H-pyrrolo[2,3-b]pyridin-2-yl}phenyl)methyl](ethyl)amino]ethanol provided the title compound. ESMS [M+H]+: 566.4.

Example 118

N,N-dimethyl-N'-[4-(1-(1-methylethyl)-4-{2-[4-(1-pyrrolidinylmethyl)phenyl]-1H-pyrrolo[2,3-b]pyridin-4-yl}-1H-pyrazol-3-yl)phenyl]urea Following the procedure described in Example 47 using 4-(1-(1-methylethyl)-4-{2-[4-(1-pyrrolidinylmethyl)phenyl]-1H-pyrrolo[2,3-b]pyridin-4-yl}-1H-pyrazol-3-yl)aniline provided the title compound. ESMS [M+H]$^+$=548.4

Example 119

2-methyl-N-[4-(1-(1-methylethyl)-4-{2-[4-(1-pyrrolidinylmethyl)phenyl]-1H-pyrrolo[2,3-b]pyridin-4-yl}-1H-pyrazol-3-yl)phenyl]propanamide Following the procedure described in Example 95 using 4-(1-(1-methylethyl)-4-{2-[4-(1-pyrrolidinylmethyl)phenyl]-1H-pyrrolo[2,3-b]pyridin-4-yl}-1H-pyrazol-3-yl)aniline provided the title compound. [M+H]$^+$=547.4

Example 120

Preparation of N-{4-[4-[2-(4-{[4-(2-hydroxyethyl)-1-piperazinyl]methyl}phenyl)-1H-pyrrolo[2,3-b]pyridin-4-yl]-1-(1-methylethyl)-1H-pyrazol-3-yl]phenyl}-1-pyrrolidinecarboxamide Following the procedure described in Example 47 using 2-{4-[(4-{4-[3-(4-aminophenyl)-1-(1-methylethyl)-1H-pyrazol-4-yl]-1H-pyrrolo[2,3-b]pyridin-2-yl}phenyl)methyl]-1-piperazinyl}ethanol and pyrrolidine provided the title compound. ESMS [M+H]+: 633.7

Example 121

Preparation of N'-[4-(1-ethyl-4-{2-[3-(2-hydroxyethyl)phenyl]-1H-pyrrolo[2,3-b]pyridin-4-yl}-1H-pyrazol-3-yl)phenyl]-N,N-dimethylurea Following the procedure described in Example 47 using 2-(3-{4-[3-(4-aminophenyl)-1-ethyl-1H-pyrazol-4-yl]-1H-pyrrolo[2,3-b]pyridin-2-yl}phenyl)ethanol-provided the title compound. [M+H]+: 495.4

Example 122

Preparation of N'-(4-{1-ethyl-4-[2-(3-formylphenyl)-1H-pyrrolo[2,3-b]pyridin-4-yl]-1H-pyrazol-3-yl}phenyl)-N,N-dimethylurea Following the procedure described for Intermediate 102 and then for Example 47 using 3-[4-[1-ethyl-3-(4-nitrophenyl)-1H-pyrazol-4-yl]-1-(phenylsulfonyl)-1H-pyrrolo[2,3-b]pyridin-2-yl]benzaldehyde provided the title compound. ESMS[M+H]$^+$: 479.0

Example 123

N'-{4-[1-ethyl-4-(2-{3-[(methylamino)methyl]phenyl}-1H-pyrrolo[2,3-b]pyridin-4-yl)-1H-pyrazol-3-yl]phenyl}-N,N-dimethylurea Following the procedure described for Intermediate 101 using N'-(4-{1-ethyl-4-[2-(3-formylphenyl)-1H-pyrrolo[2,3-b]pyridin-4-yl]-1H-pyrazol-3-yl}phenyl)-N,N-dimethylurea and 2M dimethylamine provided the title compound. ESMS [M+H]$^+$: 494.0.

Example 124

Preparation of N'-{4-[4-(2-{4-[(dimethylamino)methyl]phenyl}-1H-pyrrolo[2,3-b]pyridin-4-yl)-1-(1-methylethyl)-1H-pyrazol-3-yl]phenyl}-N,N-diethylurea Following the procedure described in Example 96 using [(4-{4-[3-(4-aminophenyl)-1-(1-methylethyl)-1H-pyrazol-4-yl]-1H-pyrrolo[2,3-b]pyridin-2-yl}phenyl)methyl]dimethylamine provided the title compound. ESMS [M+H]+: 550.4

Example 125

N'-{4-[4-(2-{4-[(dimethylamino)methyl]phenyl}-1H-pyrrolo[2,3-b]pyridin-4-yl)-1-methyl-1H-pyrazol-3-yl]phenyl}-N,N-diethylurea Following the procedure described in Example 96 using [(4-{4-[3-(4-aminophenyl)-1-methyl-1H-pyrazol-4-yl]-1H-pyrrolo[2,3-b]pyridin-2-yl}phenyl)methyl]dimethylamine provided the title compound. MS [M+H]+: 522.3

Example 126

Preparation of N'-(4-{4-(2-{3-[(dimethylamino)methyl]phenyl}-1H-pyrrolo[2,3-b]pyridin-4-yl)-1-[2-(methylamino)ethyl]-1H-pyrazol-3-yl}phenyl)-N,N-dimethylurea To 1,1-dimethylethyl {2-[3-(4-{[(dimethylamino)carbonyl]amino}phenyl)-4-(2-{3-[(dimethylamino)methyl]phenyl}-1H-pyrrolo[2,3-b]pyridin-4-yl)-1H-pyrazol-1-yl]ethyl}methylcarbamate (1.05 g, 1.65 mmol) was added 25% TFA in CH$_2$Cl$_2$ (25 mL). The reaction was stirred at RT for 1 h and evaporated to dryness under vacuum. Trituration with (1:1) Et$_2$O/Pet. Ether, filtration, and drying under vacuum gave the title compound (1.39 g, 95%) as a yellow solid. ESMS [M+H]+: 537.3

Example 127

Preparation of N'-(4-{4-{2-[3-(hydroxymethyl)phenyl]-1H-pyrrolo[2,3-b]pyridin-4-yl}-1-[2-(methylamino)ethyl]-1H-pyrazol-3-yl}phenyl)-N,N-dimethylurea Following the procedure described in Example 47 using 1,1-dimethylethyl [2-(3-(4-aminophenyl)-4-{2-[3-(hydroxymethyl)phenyl]-1H-pyrrolo[2,3-b]pyridin-4-yl}-1H-pyrazol-1-yl)ethyl]methylcarbamate provided the title compound. ESMS [M+H]+: 510.3

Example 128

Preparation of N-{2-[3-(4-{[(dimethylamino)carbonyl]amino}phenyl)-4-(2-{3-[(dimethylamino)methyl]phenyl}-1H-pyrrolo[2,3-b]pyridin-4-yl)-1H-pyrazol-1-yl]ethyl}-N-methylacetamide To N'-(4-{4-(2-{3-[(dimethylamino)methyl]phenyl}-1H-pyrrolo[2,3-b]pyridin-4-yl)-1-[2-(methylamino)ethyl]-1H- pyrazol-3-yl}phenyl)-N,N-dimethylurea.3TFA (300 mg, 0.34 mMol) in MeOH (10 mL) was added with stirring at RT, aq. 1 N NaOH and Ac$_2$O (40 uL, 0.42 mMol). After stirring for 30 min. the reaction was diluted with water, basified with aq. 1 N NaOH (0.4 mL), extracted with (9:1) CHCl$_3$/iPrOH, dried (Na$_2$SO$_4$), filtered, and evaporated to dryness under vacuum. Trituration with (1:1) Et$_2$O and petroleum ether, filtration and drying under vacuum gave the title compound (177 mg, 90%) as an off-white solid. ESMS [M+H]+: 579.7.

Example 129

Preparation of N'-{4-[1-[2-(dimethylamino)ethyl]-4-(2-{3-[(dimethylamino)methyl]phenyl}-1H-pyrrolo[2,3-b]pyridin-4-yl)-1H-pyrazol-3-yl]phenyl}-N,N-dimethylurea To N'-(4-{4-(2-{3-[(dimethylamino)methyl]phenyl}-1H-pyrrolo[2,3-b]pyridin-4-yl)-1-[2-(methylamino)ethyl]-1H-pyrazol-3-yl}phenyl)-N,N-dimethylurea.3TFA (300 mg, 0.34 mMol) in MeOH (10 mL) was added with stirring at RT aq. 1 N NaOH (1.1 mL, 1.1 mMol), 37 wt. % CH$_2$O in water (50 uL, 0.67 mMol) and 20% Pd(OH)$_2$/C (Pearlman's catalyst) (~10 mg). A balloon of H$_2$ was attached and the reaction stirred at RT for 3 days. The reaction was evaporated to dryness under vacuum, taken up in (9:1) CHCl$_3$/iPrOH (15 mL) and treated with excess methyl isatoic anhydride polystyrene resin (~500 mg, >1.8 mMol/g). After stirring at RT for 4 h the reaction was filtered, rinsed with (9:1) CHCl$_3$/iPrOH, and the filtrate concentrated to dryness under vacuum. Purification by Gilson HPLC provided the title compound (56.6 mg, 30%) as a white solid. ESMS [M+H]+: 551.6

Example 130

Preparation of N'-(4-{4-[2-(4-hydroxy-4-piperidinyl)-1H-pyrrolo[2,3-b]pyridin-4-yl]-1-methyl-1H-pyrazol-3-yl}phenyl)-N,N-dimethylurea Following the procedure described in Example 47 using 1,1-dimethylethyl 4-{4-[3-(4-aminophenyl)-1-methyl-1H-pyrazol-4-yl]-1H-pyrrolo[2,3-b]pyridin-2-yl}-4-hydroxy-1-piperidinecarboxylate provided the title compound. ESMS [M+H]$^+$: 460.2

Example 131

Preparation of N,N-dimethyl-N'-(4-{1-(1-methylethyl)-4-[2-(3-pyridinyl)-1H-pyrrolo[2,3-b]pyridin-4-yl]-1H-pyrazol-3-yl}phenyl)urea Following the procedure described in Example 47 using 4-{1-(1-methylethyl)-4-[2-(3-pyridinyl)-1H-pyrrolo[2,3-b]pyridin-4-yl]-1H-pyrazol-3-yl}aniline provided the title compound ESMS [M+H]$^+$: 466.2

Example 132

Preparation of N,N-dimethyl-N'-[4-(1-methyl-4-{2-[2-(1-piperazinyl)-5-pyrimidinyl]-1H-pyrrolo[2,3-b]pyridin-4-yl}-1H-pyrazol-3-yl)phenyl]urea To a solution of 1,1-dimethylethyl 4-(5-{4-[3-(4-{[(dimethylamino)carbonyl]amino}phenyl)-1-methyl-1H-pyrazol-4-yl]-1H-pyrrolo[2,3-b]pyridin-2-yl}-2-pyrimidinyl)-1-piperazinecarboxylate (0.0883 mmol) in dichloromethane (20 ml) was added trifluoroacetic acid (1 ml) and the resulting solution stirred at room temperature for 4 hours. Concentration and purification by reverse-phase HPLC provided the title compound as a yellow solid (43%). ESMS [M+H]$^+$: 523.2

Example 133

Preparation of N,N-dimethyl-N'-[4-(1-methyl-4-{2-[2-(4-methyl-1-piperazinyl)-5-pyrimidinyl]-1H-pyrrolo[2,3-b]pyridin-4-yl}-1H-pyrazol-3-yl)phenyl]urea Following the procedure described in Example 47 using [4-(1-methyl-4-{2-[2-(4-methyl-1-piperazinyl)-5-pyrimidinyl]-1H-pyrrolo[2,3-b]pyridin-4-yl}-1H-pyrazol-3-yl)phenyl]amine provided the title compound. ESMS [M+H]$^+$: 537.2

Example 134

Preparation of N'-{4-[1-[2-dimethylamino)ethyl]-4-(1H-pyrrolo[2,3-b]pyridine-4-yl)-1H-pyrazol-3-yl]phenyl}-N,N-dimethylurea Following the procedure described for Intermediate 102 using N,N-dimethyl-2-{3-(4-nitrophenyl)-4-[1-(phenylsulfonyl)-1H-pyrrolo[2,3-b]pyridine-4-yl]-1H-pyrazol-1-yl}ethanamine and then following the procedure described for Example 47 provided the title compound. ESMS [M+H]$^+$: 418.2

Example 135

Alternative Preparation of N'-{4-[4-(2-{3-[(dimethylamino)methyl]phenyl}-1H-pyrrolo[2,3-b]pyridin-4-yl)-1-ethyl-1H-pyrazol-3-yl]phenyl}-N,N-dimethylurea The compound of Example 47 was also prepared as follows:

a). {3-[4-bromo-1-(phenylsulfonyl)-1H-pyrrolo[2,3-b]pyridin-2-yl]phenyl}methanol

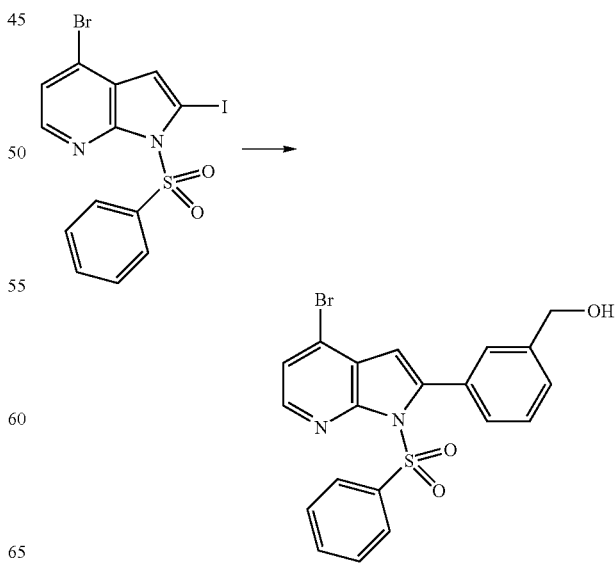

In a large pressure bottle (~1 L) was added 4-bromo-2-iodo-1-(phenylsulfonyl)-1H-pyrrolo[2,3-b]pyridine (10 g of a reported 90% pure lot from CiVenti, 19.4 mMol), 3-(hydroxymethyl)benzeneboronic acid (3.3 g, 21.7 mMol), dioxane (200 mL), aq. sat. NaHCO₃ (50 mL) and Pd(PPh₃)₄ (1.0 g, 0.86 mMol). The reaction was purged with N₂, capped and stirred at 110° C. for 18 h. After cooling to RT the reaction was concentrated under vacuum, taken up in EtOAc, washed with H₂O, brine, dried (Mg₂SO₄), filtered and evaporated to dryness under vacuum.

The above reaction was repeated two more times with 4-bromo-2-iodo-1-phenylsulfonyl-1H-pyrrolo[2,3-b]pyridine (15 g of a reported 90% pure lot from CiVenti, 29.1 mMol) and 3-(hydroxymethyl)benzeneboronic acid (4.0 g, 26.3 mMol the first time, then 3.7 g, 24.3 mMol the second time). In both reactions dioxane (300 mL), aq. sat. NaHCO₃ (75 mL), and (1.0 g, 0.86 mMol) of Pd(PPh₃)₄ was used. The amount of a bis-coupled side product was reduced from 26% to 15% and 13% respectively (by LCMS) in each of the reactions. All three reaction products (derived from a total of 40 g of 4-bromo-2-iodo-1-phenylsulfonyl-1H-pyrrolo[2,3-b]pyridine, 90% pure lot from CiVenti=36 g, 77.7 mMol) were combined and purified by flash chromatography by silica gel (10 to 15% EtOAc/CH₂Cl₂) to give the title compound (22.77 g, 66%) as a white solid: MS (ES) m/e 443.2 (M+H)⁺; ¹H NMR (400 MHz, DMSO-d₆) δ 8.27 (d, J=5.1 Hz, 1H), 7.85-7.91 (m, 2H), 7.70 (t, J=7.5 Hz, 1H), 7.63 (d, J=5.3 Hz, 1H), 7.59 (app. t, J=7.8 Hz, 2H), 7.53 (s, 1H), 7.44-7.50 (m, 3H), 6.75 (s, 1H), 5.35 (t, J=5.8 Hz, 1H), 4.62 (d, J=5.8 Hz, 2H).

b). {3-[4-[1-ethyl-3-(4-nitrophenyl)-1H-pyrazol-4-yl]-1-(phenylsulfonyl)-1H-pyrrolo[2,3-b]pyridin-2-yl]phenyl}methanol

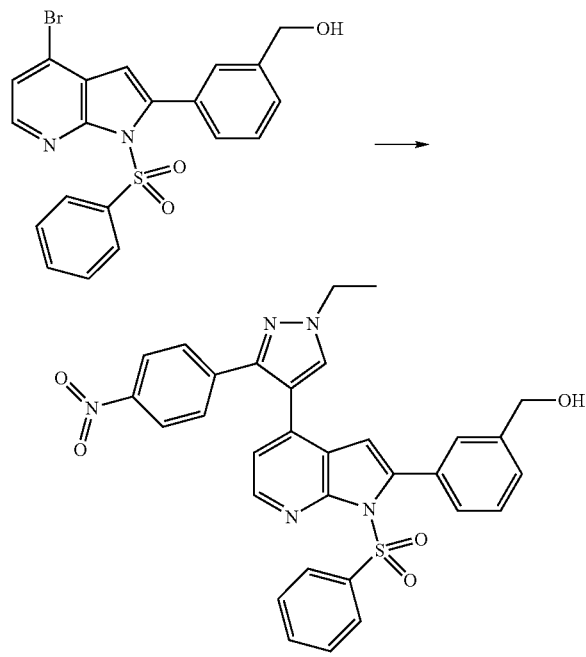

In a large pressure bottle (~1 L) was added {3-[4-bromo-1-(phenylsulfonyl)-1H-pyrrolo[2,3-b]pyridin-2-yl]phenyl}methanol (22.75 g, 51.3 mMol), 1-ethyl-3-(4-nitrophenyl)-4-(4,4,5,5-tetramethyl-1,3,2-dioxaborolan-2-yl)-1H-pyrazole (21.0 g of a ~85% pure lot, 52.0 mMol, Intermediate 5), dioxane (400 mL), aq. sat. NaHCO₃ (120 mL), and Pd(PPh₃)₄ (1.5 g, 1.3 mMol). The reaction was purged with N₂, capped, and stirred at 110° C. for 16 h. After cooling to RT the reaction was concentrated under vacuum, taken up in EtOAc, washed with H₂O, brine, dried (Mg₂SO₄), filtered, and evaporated to dryness under vacuum. Purification by flash chromatography by silica gel (20 to 30% EtOAc/CH₂Cl₂) gave the title compound (26.90 g, 90%) as a yellow solid: MS (ES) m/e 580.4 (M+H)⁺; ¹H NMR (400 MHz, DMSO-d₆) δ 8.34 (s, 1H), 8.32 (d, J=5.1 Hz, 1H), 8.15 (app. d, 2H), 7.89 (d, J=7.3 Hz, 2H), 7.74 (t, J=7.5 Hz, 1H), 7.61 (app. t, J=7.8 Hz, 2H), 7.54 (app. d, 2H), 7.39-7.43 (m, 2H), 7.32-7.36 (m, 2H), 7.06 (d, J=5.1 Hz, 1H), 6.52 (s, 1H), 5.31 (t, J=5.6 Hz, 1H), 4.57 (d, J=5.3 Hz, 2H), 4.26 (q, J=7.2 Hz, 2H), 1.47 (t, J=7.3 Hz, 3H).

c). (3-{4-[3-(4-aminophenyl)-1-ethyl-1H-pyrazol-4-yl]-1H-pyrrolo[2,3-b]pyridin-2-yl}phenyl)methanol

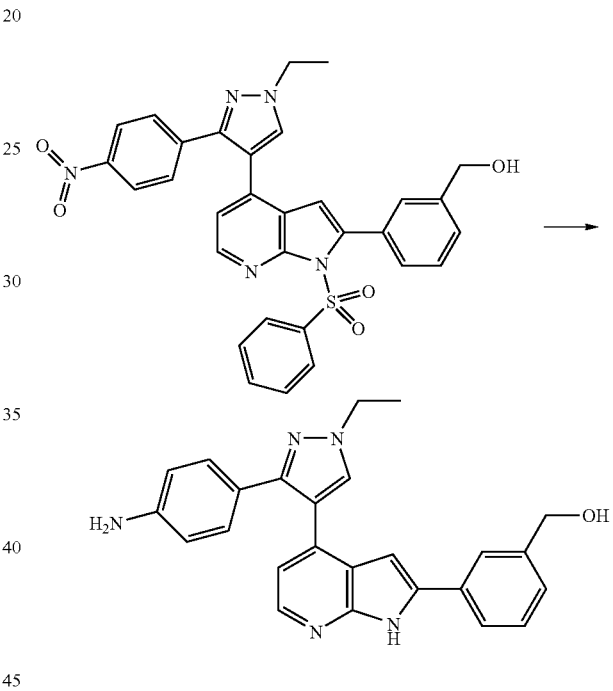

To {3-[4-[1-ethyl-3-(4-nitrophenyl)-1H-pyrazol-4-yl]-1-(phenylsulfonyl)-1H-pyrrolo[2,3-b]pyridin-2-yl]phenyl}methanol (26.90 g, 46.4 mMol) in MeOH (400 mL) was added 20% Pd(OH)₂/C (Pearlman's catalyst) (~3.0 g). Two balloons of H₂ were attached and the reaction stirred overnight at RT. (LCMS of the reaction mixture showed 31% of the desired aniline (M+H)⁺=550.3, 50% of the hydroxylamine intermediate (M+H)⁺=566.2 and 20% of the starting material and nitroso intermediate (M+H)⁺=580.4 and 564.1.) Another 3.0 g of the Pearlman's catalyst was added and the reaction stirred under H₂ for an additional 24 h. (LCMS showed that the reaction had gone to >90% complete. The same reaction was later shown to go to completion, under 50 psi H₂, in the Parr reactor overnight at RT.) The reaction was filtered through a pad of Celite®, rinsed with MeOH and concentrated under vacuum. The remaining residue was taken up in MeOH (300 mL) and treated with aq. 6 N NaOH (25 mL, 150 mMol). The reaction was stirred and heated at 70° C. for 8 h, cooled to RT and concentrated to near dryness under vacuum. The slurry was triturated with cold water, filtered, washed with cold water, and dried under vacuum. Purification by flash chromatography on silica gel (5 to 15%

MeOH/CHCl₃) (product slow to dissolve on the column) gave the title compound (16.19 g, 85%) as a yellow solid: MS (ES) m/e 410.4 (M+H)⁺; ¹H NMR (400 MHz, DMSO-d₆) δ 12.11 (d, J=1.8 Hz, 1H), 8.21 (s, 1H), 8.05 (d, J=5.1 Hz, 1H), 7.84 (s, 1H), 7.78 (d, J=7.8 Hz, 1H), 7.41 (t, J=7.7 Hz, 1H), 7.31 (d, J=7.6 Hz, 1H), 7.08 (d, J=8.6 Hz, 2H), 6.81 (d, J=2.3 Hz, 1H), 6.80 (d, J=5.1 Hz, 1H), 6.49 (d, J=8.6 Hz, 2H), 5.27 (t, J=5.8 Hz, 1H), 5.14 (s, 2H), 4.56 (d, J=5.8 Hz, 2H), 4.24 (q, J=7.2 Hz, 2H), 1.49 (t, J=7.3 Hz, 3H).

d) N'-[4-(1-ethyl-4-{2-[3-(hydroxymethyl)phenyl]-1H-pyrrolo[2,3-b]pyridin-4-yl}-1H-pyrazol-3-yl)phenyl]-N,N-dimethylurea

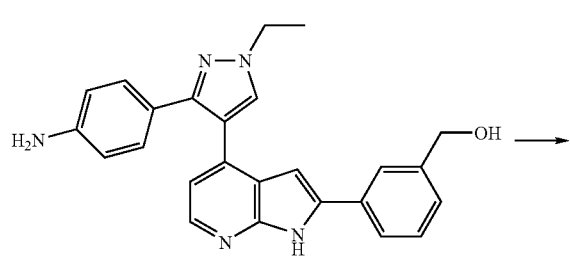

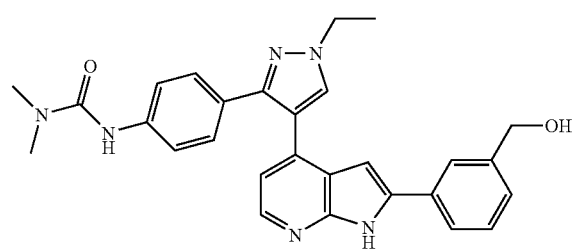

To a vigorously stirred solution of (3-{4-[3-(4-aminophenyl)-1-ethyl-1H-pyrazol-4-yl]-1H-pyrrolo[2,3-b]pyridin-2-yl}phenyl)methanol (16.13 g, 39.4 mMol) in THF (400 mL) was added NMM (4.5 mL, 40.9 mMol) followed by p-nitrophenylchloroformate (7.9 g, 39.2 mMol). (The reaction quickly became a fine suspension.) After stirring for 1 h at RT, a solution of 2.0 M dimethylamine in THF (200 mL, 400 mMol) was added. The reaction was stirred an additional 1 h at RT then concentrated to dryness under vacuum. The residue which remained was triturated with a cold solution of aq. 1 N NaOH (100 mL) in ice water (200 mL), filtered, washed with cold water (100 mL), and dried under vacuum. Purification by flash chromatography on silica gel (2 to 10% MeOH/CHCl₃) gave the title product (16.67 g, 85% pure containing ~15% starting aniline by LCMS, 75%) as a yellow solid: MS (ES) m/e 481.4 (M+H)⁺; ¹H NMR (400 MHz, DMSO-d₆) δ 12.14 (d, J=1.8 Hz, 1H), 8.31 (s, 1H), 8.26 (s, 1H), 8.07 (d, J=4.8 Hz, 1H), 7.83 (s, 1H), 7.77 (d, J=7.8 Hz, 1H), 7.42 (d, J=8.6 Hz, 2H), 7.41 (m, 1H), 7.29 (m, 1H), 7.28 (d, J=8.6 Hz, 2H), 6.79 (s, 1H), 6.78 (d, J=4.8 Hz, 1H), 5.26 (t, J=5.7 Hz, 1H), 4.56 (d, J=5.6 Hz, 2H), 4.27 (q, J=7.3 Hz, 2H), 2.91 (s, 6H), 1.51 (t, J=7.3 Hz, 3H).

e) N'-(4-{1-ethyl-4-[2-(3-formylphenyl)-1H-pyrrolo[2,3-b]pyridin-4-yl]-1H-pyrazol-3-yl}phenyl)-N,N-dimethylurea

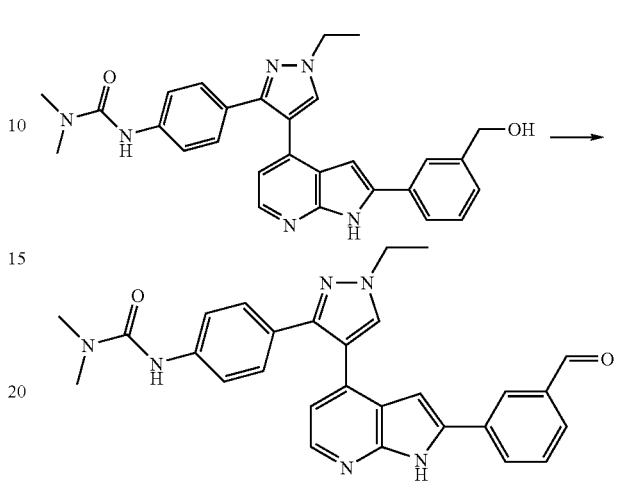

To a stirred solution of N'-[4-(1-ethyl-4-{2-[3-(hydroxymethyl)phenyl]-1H-pyrrolo[2,3-b]pyridin-4-yl}-1H-pyrazol-3-yl)phenyl]-N,N-dimethylurea (16.67 g, 85% pure, 29.5 mMol) in CHCl₃ (700 mL) was added activated MnO₂ (33 g, 380 mMol). The reaction was stirred and refluxed (70° C. oil bath) for 6 h, cooled to RT, filtered through a pad of Celite®, rinsed with CHCl₃, and evaporated to dryness under vacuum. Purification by flash chromatography on silica gel (5 to 15% MeOH in (1:1) EtOAc/CHCl₃) gave the title product (11.45 g, 81%) as a yellow solid (>95% pure by HPLC): MS (ES) m/e 479.3 (M+H)⁺; ¹H NMR (400 MHz, DMSO-d₆) δ 12.33 (d, J=1.3 Hz, 1H), 10.07 (s, 1H), 8.44 (s, 1H), 8.31 (s, 1H), 8.29 (s, 1H), 8.22 (d, J=8.1 Hz, 1H), 8.11 (d, J=5.1 Hz, 1H), 7.86 (d, J=7.8 Hz, 1H), 7.69 (t, J=7.7 Hz, 1H), 7.43 (d, J=8.6 Hz, 2H), 7.28 (d, J=8.6 Hz, 2H), 6.95 (d, J=2.0 Hz, 1H), 6.81 (d, J=5.1 Hz, 1H), 4.28 (q, J=7.2 Hz, 2H), 2.91 (s, 6H), 1.52 (t, J=7.3 Hz, 3H).

f) N'-{4-[4-(2-{3-[(dimethylamino)methyl]phenyl}-1H-pyrrolo[2,3-b]pyridin-4-yl) 1-ethyl-1H-pyrazol-3-yl]phenyl}-N,N-dimethylurea

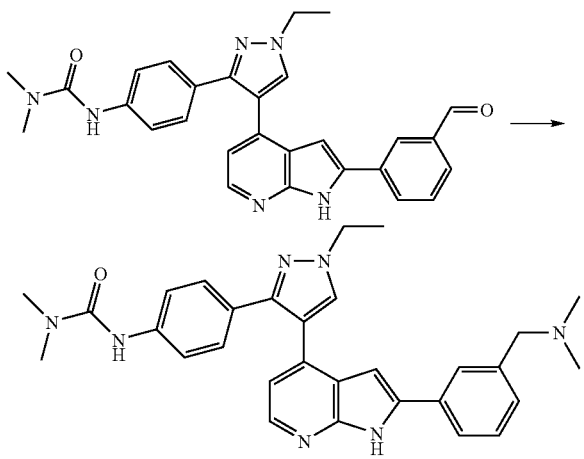

To N'-(4-{1-ethyl-4-[2-(3-formylphenyl)-1H-pyrrolo[2,3-b]pyridin-4-yl]-1H-pyrazol-3-yl}phenyl)-N,N-dimethylurea (11.45 g, 23.9 mMol) was added a solution of 2 M dimethylamine in THF (24 mL, 48 mMol). The slurry was rinsed down with THF (150 mL) and treated with NaBH(OAc)$_3$ (8.6 g, 40.6 mMol). (Gentle gas evolution was seen and the reaction got slightly warm to the touch.) The reaction was stirred at RT for 1 h (started out as a thick suspension that slowly became a homogeneous fine suspension) and concentrated to dryness under vacuum. The residue that remained was basified with aq. 1 N Na$_2$CO$_3$, (200 mL) and aq. 1 N NaOH (25 mL), extracted with CHCl$_3$ (300 mL) washed with brine, dried (Na$_2$SO$_4$), filtered, and evaporated to dryness under vacuum. Trituration with (1:1) Et$_2$O/pet. ether, filtration, and drying under vacuum gave the title compound (11.20 g, 92%) as a yellow solid (>95% pure by HPLC): MS (ES) m/e 508.2 (M+H)$^+$; $^1$H NMR (400 MHz, DMSO-d$_6$) δ 12.14 (d, J=1.8 Hz, 1H), 8.31 (s, 1H), 8.27 (s, 1H), 8.07 (d, J=4.8 Hz, 1H), 7.78 (d, J=8.1 Hz, 1H), 7.77 (s, 1H), 7.43 (d, J=8.6 Hz, 2H), 7.39 (d, J=8.1 Hz, 1H), 7.27 (d, J=8.6 Hz, 2H), 7.27 (dd, 1H), 6.79 (d, J=5.1 Hz, 1H), 6.76 (d, J=2.0 Hz, 1H), 4.27 (q, J=7.3 Hz, 2H), 3.43 (s, 2H), 2.18 (s, 6H), 1.51 (t, J=7.2 Hz, 3H).

The intermediates used in the preparation of the exemplified compounds can be prepared as shown or substantially as shown by the following procedures:

Intermediate 1

5-(4-nitrophenyl)-1H-pyrazole

A solution of 1-(4-nitrophenyl)ethanone (605.5 mmol) and bis(methyloxy)methanamine (726 mmol) in N,N-dimethylformamide (1000 mL) was stirred for 1 h at 80° C. The reaction was concentrated in vacuo, the residue was dissolved in ethanol (1000 mL) and treated with hydrazine monohydrate (1816 mmol). After the reaction stirred 2 h at 70° C. it was cooled to room temperature and poured into ice-water (2000 mL). Product precipitated out of solution, which was filtered, washed with water (4×500 mL) and dried to provide the title product as a yellow powder (98%). ESMS [M+H]$^+$: 190.2

Intermediate 2

4-bromo-3-(4-nitrophenyl)-1H-pyrazole

A solution of 5-(4-nitrophenyl)-1H-pyrazole (595 mmol) in N,N-dimethylformamide (1000 mL) was treated with N-bromosuccinimide (654 mmol). The reaction stirred for 30 min at room temperature and was poured into ice-water (1000 mL). Product precipitated out of solution, was filtered, washed with water (4×500 mL) and dried to provide the title product as an off-white powder (90%). ESMS [M+H]$^+$: 269.2

Intermediate 3

4-bromo-1-ethyl-3-(4-nitrophenyl)-1H-pyrazole

A 0° C. solution of 4-bromo-3-(4-nitrophenyl)-1H-pyrazole (485 mmol) in N,N-dimethylformamide (1000 mL) was slowly treated with sodium hydride (485 mmol) and then iodoethane (582 mmol). The reaction mixture was stirred for 30 minutes at room temperature and then poured into ice-water (1000 mL). Product precipitated out of solution and was collected by filtration, washed with water (4×500 mL) and dried to provide the title product as a light brown powder (94%). ESMS [M+H]$^+$: 297.2

Intermediate 4

1-ethyl-5-(4-nitrophenyl)-1H-pyrazole

Following the procedure described for Intermediate 3, the title product was provided as a light brown powder (6%). ESMS [M+H]$^+$: 438.2

Intermediate 5

1-ethyl-3-(4-nitrophenyl)-4-(4,4,5,5-tetramethyl-1,3,2-dioxaborolan-2-yl)-1H-pyrazole A solution of 4-bromo-1-ethyl-3-(4-nitrophenyl)-1H-pyrazole (27 mmol), 4,4,4',4',5,5,5',5'-octamethyl-2,2'-bi-1,3,2-dioxaborolane (30 mmol), potassium acetate (81 mmol), and bis(triphenylphosphine)palladium(II) dichloride (1.08 mmol) in 1,4-dioxane (30 mL) was stirred for 3 h at 100° C. in a sealed tube. After the reaction cooled to room temperature it was diluted with ethyl acetate (200 mL), filtered though a silica-gel plug and concentrated. Purification of the residue by Gilson reverse phase HPLC provided the title product as an off-white powder (42%). ESMS [M+H]$^+$: 344.2

Intermediate 6

4-[1-ethyl-3-(4-nitrophenyl)-1H-pyrazol-4-yl]-1H-pyrrolo[2,3-b]pyridine

A solution of 1-ethyl-3-(4-nitrophenyl)-4-(4,4,5,5-tetramethyl-1,3,2-dioxaborolan-2-yl)-1H-pyrazole (7.5 mmol), 4-bromo-1H-pyrrolo[2,3-b]pyridine (Ref Org. Lett. 5(26), 5023-5024, 2003) (6.3 mmol), and tetrakis(triphenylphosphine)palladium(0) (0.25 mmol) in a 1:1 solution of 1,4-dioxane (12 mL):2M potassium carbonate (12 mL) was stirred for 18 h at 100° C. in a sealed tube. Upon cooling to room temperature, product precipitated out of solution which was filtered and dried to provide the title product as a light yellow powder (80%). ESMS [M+H]$^+$: 334.2

Intermediate 7

4-[1-ethyl-4-(1H-pyrrolo[2,3-b]pyridin-4-yl)-1H-pyrazol-3-yl]aniline

A solution of 4-[1-ethyl-3-(4-nitrophenyl)-1H-pyrazol-4-yl]-1H-pyrrolo[2,3-b]pyridine (59 mmol) in glacial acetic acid (25 mL) was treated with zinc dust (41 mmol) and stirred for 1 h at room temperature. The reaction was then filtered and concentrated in vacuo. The resultant residue was suspended in a 1:1 solution of ethyl acetate (10 mL) and saturated sodium bicarbonate (10 mL) and stirred 30 minutes. The organic layer was separated, filtered, washed with brine (1×5 mL), dried over sodium sulfate, and concentrated. Purification of the residue by flash chromatography (80-100% ethyl acetate/hexanes) provided the title product as a white powder (85%). ESMS [M+H]$^+$: 304.2

Intermediate 8

4-[1-ethyl-4-(1H-pyrrolo[2,3-b]pyridin-4-yl)-1H-pyrazol-3-yl]phenyl}formamide

A solution of 4-[1-ethyl-4-(1H-pyrrolo[2,3-b]pyridin-4-yl)-1H-pyrazol-3-yl]aniline (0.49 mmol) in tetrahydrofuran (1 mL) was treated with triethylamine (1.20 mmol) and 4-nitrophenyl formate (0.54 mmol). After stirring 18 h at room temperature the reaction was poured into water (1 mL), and extracted with (3×1 mL) ethyl acetate. The combined organic layers were washed with 1N sodium hydroxide (3×1 mL), brine (1×1 mL) dried over sodium sulfate and concentrated in vacuo. Purification of the residue by silica gel flash chromatography (0-10% methanol/dichloromethane) provided the title product as a white powder (50%). ESMS [M+H]$^+$: 332.2

Intermediate 9

{4-[1-ethyl-4-(1H-pyrrolo[2,3-b]pyridin-4-yl)-1H-pyrazol-3-yl]-phenyl}methylamine A solution of {4-[1-ethyl-4-(1H-pyrrolo[2,3-b]pyridin-4-yl)-1H-pyrazol-3-yl]phenyl}formamide (0.17 mmol) in tetrahydrofuran (1 mL) was slowly treated with lithium aluminum hydride, 95%, (0.51 mmol). After stirring 18 h at 50° C. the reaction was poured into water (1 mL), and extracted with (3×1 mL) ethyl acetate. The combined organic layers were washed with saturated sodium sulfate solution (2×1 mL), brine (1×1 mL) dried over sodium sulfate and concentrated in vacuo. The resulting yellow solid was used directly in the next reaction without further purification. ESMS [M+H]$^+$: 318.2

Intermediate 10

1-acetyl-5-fluoro-4-iodo-1H-pyrrolo[2,3-b]pyridine

A microwave vial was charged with 4-chloro-5-fluoro-1-[tris(1-methylethyl)silyl]-1H-pyrrolo[2,3-b]pyridine (3.06 mmol, prepared as described in *Tetrahedron Lett.* 2004, 45, 2317-2319), sodium iodide (4.90 mmol), acetyl chloride (6.43 mmol) and dry acetonitrile (8 mL). The reaction tube was sealed, and heated in a microwave reactor at 150° C. for 15 minutes. Upon cooling to room temperature, the resultant precipitate was collected by filtration and washed with a minimal amount of cold acetonitrile. Drying under high vacuum provided the title compound as a yellow powder which was used without further purification. ESMS [M+H]$^+$: 305.2

Intermediate 11

4-[1-ethyl-3-(4-nitrophenyl)-1H-pyrazol-4-yl]-5-fluoro-1H-pyrrolo[2,3-b]pyridine A mixture of 1-acetyl-5-fluoro-4-iodo-1H-pyrrolo[2,3-b]pyridine (0.822 mmol), 1-ethyl-3-(4-nitrophenyl)-4-(4,4,5,5-tetramethyl-1,3,2-dioxaborolan-2-yl)-1H-pyrazole (1.15 mmol), tetrakis(triphenylphosphine)palladium(0) (0.041 mmol), sodium bicarbonate (2.47 mmol), water (2 mL) and N,N-dimethylformamide (6 mL) were heated to 100° C. in a sealed tube for 16 h. The reaction mixture was quenched with water (5 mL) and extracted with ethyl acetate (3×10 mL). The combined extracts were dried over sodium sulfate filtered and concentrated under reduced pressure. The residue was purified by silica gel chromatography (50% ethyl acetate/hexanes) to give the title compound as a yellow solid (80%). ESMS [M+H]$^+$: 352.2

Intermediate 12

4-[1-ethyl-4-(5-fluoro-1H-pyrrolo[2,3-b]pyridin-4-yl)-1H-pyrazol-3-yl]aniline

To a suspension of 4-[1-ethyl-3-(4-nitrophenyl)-1H-pyrazol-4-yl]-5-fluoro-1H-pyrrolo[2,3-b]pyridine (0.655 mmol) in ethanol (3.5 mL) was added tin(0) powder (3.28 mmol) and 6N aqueous hydrochloric acid (3.5 mL) and the mixture was heated to 70° C. for 1 h. The reaction mixture was allowed to cool to room temperature, filtered through a pad of celite. The filtrate was diluted with ethyl acetate (10 mL) and washed with 1N sodium hydroxide (5 mL). The aqueous layer was extracted with ethyl acetate (3×10 mL) and the combined extracts were dried over sodium sulfate, filtered through a pad of celite and concentrated under reduced pressure to give the title compound as a yellow solid which was used without further purification. ESMS [M+H]$^+$: 322

Intermediate 13

4-chloro-5-methyl-1-[tris(1-methylethyl)silyl]-1H-pyrrolo[2,3-b]pyridine

To a cold −78° C. solution of 4-chloro-1-[tris(1-methylethyl)silyl]-1H-pyrrolo[2,3-b]pyridine (3.24 mmol, prepared as described in *Tetrahedron Lett.* 2004, 45, 2317-2319), in dry tetrahydrofuran (22 mL) was added 1.4M sec-BuLi in hexanes (7.12 mmol) dropwise over 5 min. After 30 min, methyliodide (10.5 mmol) was added. After 45 min, the reaction mixture was quenched with saturated aqueous ammonium chloride (25 mL) and diluted with ethyl acetate (25 mL). The extracts were dried over sodium sulfate, filtered, concentrated under reduced pressure and the residue was purified by silica gel chromatography (100% hexanes) to give the title product as a white solid (86%). ESMS [M+H]$^+$: 323.2

Intermediate 14

1-acetyl-4-iodo-5-methyl-1H-pyrrolo[2,3-b]pyridine

Following the procedure described for Intermediate 10 using 4-chloro-5-methyl-1-[tris(1-methylethyl)silyl]-1H-pyrrolo[2,3-b]pyridine afforded title compound. ESMS [M+H]$^+$: 301.2

Intermediate 15

4-[1-ethyl-3-(4-nitrophenyl)-1H-pyrazol-4-yl]-5-methyl-1H-pyrrolo[2,3-b]pyridine Following the procedure described for Intermediate 11 using 1-acetyl-4-iodo-5-methyl-1H-pyrrolo[2,3-b]pyridine afforded the title compound. ESMS [M+H]$^+$: 348.2

Intermediate 16

4-[1-ethyl-4-(5-methyl-1H-pyrrolo[2,3-b]pyridin-4-yl)-1H-pyrazol-3-yl]aniline

Following the procedure described for Intermediate 12 with 4-[1-ethyl-3-(4-nitrophenyl)-1H-pyrazol-4-yl]-5-methyl-1H-pyrrolo[2,3-b]pyridine (0.559 mmol) gave the title compound. ESMS [M+H]$^+$: 318

Intermediate 17

1,1-dimethylethyl 4-[4-bromo-1-(phenylsulfonyl)-1H-pyrrolo[2,3-b]pyridin-2-yl]-3,6-dihydro-1(2H)-pyridinecarboxylate Following the procedure described for Intermediate 99 with 4-bromo-2-iodo-1-(phenylsulfonyl)-1H-pyrrolo[2,3-b]pyridine and 1,1-dimethylethyl 4-(4,4,5,5-tetramethyl-1,3,2-

Intermediate 18

1,1-dimethylethyl 4-[4-[1-ethyl-3-(4-nitrophenyl)-1H-pyrazol-4-yl]-1-(phenylsulfonyl)-1H-pyrrolo[2,3-b]pyridin-2-yl]-3,6-dihydro-1(2H)-pyridinecarboxylate Following the procedure described for Intermediate 11 with 4-[4-bromo-1-(phenylsulfonyl)-1H-pyrrolo[2,3-b]pyridin-2-yl]-3,6-dihydro-1(2H)-pyridinecarboxylate and 1-ethyl-3-(4-nitrophenyl)-4-(4,4,5,5-tetramethyl-1,3,2-dioxaborolan-2-yl)-1H-pyrazole gave the title compound. ESMS [M+H]$^+$: 655.4

Intermediate 19

1,1-dimethylethyl 4-[4-[3-(4-aminophenyl)-1-ethyl-1H-pyrazol-4-yl]-1-(phenylsulfonyl)-1H-pyrrolo[2,3-b]pyridin-2-yl]-3,6-dihydro-1(2H)-pyridinecarboxylate A solution of 1,1-dimethylethyl 4-[4-[1-ethyl-3-(4-nitrophenyl)-1H-pyrazol-4-yl]-1-(phenylsulfonyl)-1H-pyrrolo[2,3-b]pyridin-2-yl]-3,6-dihydro-1(2H)-pyridinecarboxylate (0.46 mmol) in ethyl acetate (5 mL) was purged with nitrogen and palladium(II) hydroxide/Carbon (30 mg of 20 wt. % palladium) added. The reaction was purged with hydrogen gas and allowed to stir vigorously under 1 atm of hydrogen. After 16 h, the reaction was purged with nitrogen and filtered though a pad of Celite (rinsing with ethyl acetate). The filtrate was concentrated under reduced pressure to give the title compound as a yellow foam which was used without further purification. ESMS [M+H]$^+$: 625.6

Intermediate 20

1,1-dimethylethyl 4-[4-[1-ethyl-3-(4-{[(phenylamino)carbonyl]amino}phenyl)-1H-pyrazol-4-yl]-1-(phenylsulfonyl)-1H-pyrrolo[2,3-b]pyridin-2-yl]-3,6-dihydro-1(2H)-pyridinecarboxylate Following the procedure described in Example 1 with 1,1-dimethylethyl 4-[4-[3-(4-aminophenyl)-1-ethyl-1H-pyrazol-4-yl]-1-(phenylsulfonyl)-1H-pyrrolo[2,3-b]pyridin-2-yl]-3,6-dihydro-1(2H)-pyridinecarboxylate afforded the title compound. ESMS [M+H]$^+$: 744.4

Intermediate 21

1,1-dimethylethyl 4-{4-[1-ethyl-3-(4-{[(phenylamino)carbonyl]amino}phenyl)-1H-pyrazol-4-yl]-1H-pyrrolo[2,3-b]pyridin-2-yl}-3,6-dihydro-1(2H)-pyridinecarboxylate To a solution of 1,1-dimethylethyl 4-[4-[1-ethyl-3-(4-{[(phenylamino)carbonyl]amino}phenyl)-1H-pyrazol-4-yl]-1-(phenylsulfonyl)-1H-pyrrolo[2,3-b]pyridin-2-yl]-3,6-dihydro-1(2H)-pyridinecarboxylate (0.38 mmol) in methanol (3.8 mL) was added 6N sodium hydroxide (1.14 mmol). The reaction mixture was refluxed for 5 h, cooled to room temperature and concentrated under reduced pressure. The solid residue was suspended in water, stirred vigorously and collected by filtration to give the title compound as an orange solid which was used without further purification (95%). Alternatively, the solid residue was purified by Gilson reverse phase HPLC to afford the title compound. ESMS [M+H]$^+$: 604.4

Intermediate 22

4-bromo-1-{[4-(methyloxy)phenyl]methyl}-3-(4-nitrophenyl)-1H-pyrazole

Following the procedure described for Intermediate 3 with 4-bromo-3-(4-nitrophenyl)-1H-pyrazole and p-methoxybenzylchloride provided the title product. ESMS [M+H]$^+$: 388.2

Intermediate 23

1-{[4-(methyloxy)phenyl]methyl}-3-(4-nitrophenyl)-4-(4,4,5,5-tetramethyl-1,3,2-dioxaborolan-2-yl)-1H-pyrazole Following the procedure described for Intermediate 5 with 4-bromo-1-{[4-(methyloxy)phenyl]methyl}-3-(4-nitrophenyl)-1H-pyrazole provided the title compound. ESMS [M+H]$^+$: 435.4

Intermediate 24

4-[1-{[4-(methyloxy)phenyl]methyl}-3-(4-nitrophenyl)-1H-pyrazol-4-yl]-1H-pyrrolo[2,3-b]pyridine Following the procedure described for Intermediate 6 with 4-bromo-1H-pyrrolo[2,3-b]pyridine and 1-{[4-(methyloxy)phenyl]methyl}-3-(4-nitrophenyl)-4-(4,4,5,5-tetramethyl-1,3,2-dioxaborolan-2-yl)-1H-pyrazole provided the title compound. ESMS [M+H]$^+$: 426.2

Intermediate 25

4-[1-{[4-(methyloxy)phenyl]methyl}-4-(1H-pyrrolo[2,3-b]pyridin-4-yl)-1H-pyrazol-3-yl]aniline Following the procedure described for Intermediate 7 with 4-[1-{[4-(methyloxy)phenyl]methyl}-3-(4-nitrophenyl)-1H-pyrazol-4-yl]-1H-pyrrolo[2,3-b]pyridine provided the title compound. ESMS [M+H]$^+$: 396.2

Intermediate 26

4-[3-(4-nitrophenyl)-1H-pyrazol-4-yl]-1H-pyrrolo[2,3-b]pyridine

A solution of 4-[1-{[4-(methyloxy)phenyl]methyl}-3-(4-nitrophenyl)-1H-pyrazol-4-yl]-1H-pyrrolo[2,3-b]pyridine (0.22 mmol) in trifluoroacetic acid (0.75 mL) was heated at 74° C. for 1.5 h. The reaction mixture was diluted with water (4 mL) and extracted with (3×5 mL) ethyl acetate. The combined organic layers were dried over sodium sulfate and were concentrated. Purification of the residue by Gilson reverse phase HPLC afforded the title product as a yellow solid (64%). ESMS [M+H]$^+$: 306.4

Intermediate 27

4-[4-(1H-pyrrolo[2,3-b]pyridin-4-yl)-1H-pyrazol-3-yl]aniline

Following the procedure described for Intermediate 12 with 4-[3-(4-nitrophenyl)-1H-pyrazol-4-yl]-1H-pyrrolo[2,3-b]pyridine provided the title compound. ESMS [M+H]$^+$: 276.2

Intermediate 28

1,1-dimethylethyl [4-bromo-3-(4-nitrophenyl)-1H-pyrazol-1-yl]acetate

Following the procedure described for Intermediate 3 with 4-bromo-3-(4-nitrophenyl)-1H-pyrazole and dimethylethyl bromoacetate furnished the title compound. ESMS [M+H]$^+$: 382.0

Intermediate 29

1,1-dimethylethyl [3-(4-nitrophenyl)-4-(4,4,5,5-tetramethyl-1,3,2-dioxaborolan-2-yl)-1H-pyrazol-1-yl]acetate

Following the procedure described for Intermediate 5 with 1,1-dimethylethyl [4-bromo-3-(4-nitrophenyl)-1H-pyrazol-1-yl]acetate yielded the title compound. ESMS [M+H]$^+$: 430.2

Intermediate 30

[3-(4-nitrophenyl)-4-(1H-pyrrolo[2,3-b]pyridin-4-yl)-1H-pyrazol-1-yl]acetic acid

Following the procedure described for Intermediate 6 with 1,1-dimethylethyl [3-(4-nitrophenyl)-4-(4,4,5,5-tetramethyl-1,3,2-dioxaborolan-2-yl)-1H-pyrazol-1-yl]acetate afforded the title compound. ESMS [M+H]$^+$: 364.

Intermediate 31

[3-(4-{[(phenylamino)carbonyl]amino}phenyl)-4-(1H-pyrrolo[2,3-b]pyridin-4-yl)-1H-pyrazol-1-yl]acetic acid

A heterogeneous mixture of [3-(4-nitrophenyl)-4-(1H-pyrrolo[2,3-b]pyridin-4-yl)-1H-pyrazol-1-yl]acetic acid (31.0 mmol), elemental tin dust (5.30 mmol), 6.0N aqueous hydrochloric acid (5.3 mL) and absolute ethanol (5.3 mL) was stirred at 70° C. for 1 h. The solution was filtered through Celite and concentrated in vacuo. The resulting aniline was dissolved in anhydrous pyridine (10 mL) and phenyl isocyanate (11.17 mmol) added dropwise. The reaction mixture was stirred at room temperature for 4 h. After concentration in vacuo, purification by Gilson reverse phase HPLC afforded the title compound as a white solid (93%). ESMS [M+H]$^+$: 453.2

Intermediate 32

1-(phenylsulfonyl)-4-(4,4,5,5-tetramethyl-1,3,2-dioxaborolan-2-yl)-1H-pyrrolo[2,3-b]pyridine

In a sealed tube was combined 4-bromo-1-(phenylsulfonyl)-1H-pyrrolo[2,3-b]pyridine (11.48 mmol; WO03/000690A1), potassium acetate (34.43 mmol), bis(pinacolato)diboron (13.77 mmol), 1,1'-bis(diphenylphosphino)ferrocenepalladium(II) dichloride dichloromethane complex (0.46 mmol) followed by anhydrous 1,4-dioxane (115 mL). The reaction mixture was stirred at 100° C. for 45 minutes then cooled to room temperature. After dilution with ethyl acetate (50 mL) and filtration through a pad of Celite, the filtrate was concentrated in vacuo. The residue was purified by silica gel chromatography (Analogix, 20-50% ethyl acetate/hexanes) to provide the title product as a white solid (92%). ESMS [M+H]$^+$: 384.0

Intermediate 33

N-[4-(4-bromo-1H-pyrazol-3-yl)phenyl]-N'-phenylurea

Following the procedure described for Intermediate 31 using 4-bromo-3-(4-nitrophenyl)-1H-pyrazole afforded the title compound. ESMS [M+H]$^+$: 357.0

Intermediate 34

N-{4-[4-bromo-1-(tetrahydro-2-furanylmethyl)-1H-pyrazol-3-yl]phenyl}-N'-phenylurea

To a solution of N-[4-(4-bromo-1H-pyrazol-3-yl)phenyl]-N'-phenylurea (0.28 mmol) in anhydrous N,N-dimethylformamide (6 mL) cooled to 0° C. was added 1.0M potassium tert-butoxide in tetrahydrofuran (1.12 mmol) dropwise. The reaction mixture was stirred for a further 15 minutes in the cold before dropwise addition of tetrahydrofuryl bromide (0.28 mmol). The reaction mixture was stirred at room temperature for 18 h, followed by quenching with saturated aqueous ammonium chloride (1 mL). The reaction mixture was diluted with water (3 mL) and extracted with ethyl acetate (3×5 mL). The combined organic layers were dried over magnesium sulfate and concentrated in vacuo. Gilson reverse phase HPLC afforded the title compound (53%). ESMS [M+H]$^+$: 441.4

Intermediate 35

4-(4,4,5,5-tetramethyl-1,3,2-dioxaborolan-2-yl)-1H-pyrrolo[2,3-b]pyridine

Following the procedure described in Intermediate 32 with 4-bromo-1H-pyrrolo[2,3-b]pyridine provided the title compound. ESMS: [M-(CH$_3$)$_2$CC(CH$_3$)$_2$+2H]+: 302.2; HNMR (400 MHz, d$_6$-DMSO) δ 11.63 (s, 1H), 8.2 (d, 1H), 7.5 (d, 1H), 7.27 (d, 1H), 6.66 (d, 1H), 1.32 (s, 12H)

Intermediate 36

N-{4-[4-bromo-1-(2,2,2-trifluoroethyl)-1H-pyrazol-3-yl]phenyl}-N'-phenylurea

Following the procedure described for Intermediate 34 with trifluoromethanesulfonic acid 2,2,2-trifluoroethylester provided the title product. ESMS [M+H]$^+$: 439.2

Intermediate 37

N-{4-[4-bromo-1-(2-{[(1,1-dimethylethyl)(dimethyl)silyl]oxy}ethyl)-1H-pyrazol-3-yl]phenyl}-N'-phenylurea

Following the procedure described for Intermediate 34 with (2-bromoethoxy)-t-butyldimethylsilane provided the title product. ESMS[M+H]$^+$: 515.4

Intermediate 38

N-[4-(4-bromo-1-ethyl-1H-pyrazol-5-yl)phenyl]-N'-phenylurea

Following the procedure described for Intermediate 31 with 4-bromo-1-ethyl-5-(4-nitrophenyl)-1H-pyrazole, provided the title compound. ESMS [M+H]$^+$: 385.3, 387.2

Intermediate 39

1-(1,1-dimethylethyl)-5-(4-nitrophenyl)-1H-pyrazole

Following the procedure described for Intermediate 1 with t-butylhydrazine hydrochloride, provided the title compound as the major isomer (80%). ESMS (M-C(CH$_3$)$_3$+2H): 190.0; HNMR (400 MHz, d$_6$-DMSO) δ 8.32 (d, 2H), 7.7 (d, 2H), 7.48 (d, 1H), 6.25 (d, 1H), 1.42 (s, 9H)

Intermediate 40

1-(1,1-dimethylethyl)-3-(4-nitrophenyl)-1H-pyrazole

Following the procedure described for Intermediate 1 with t-butylhydrazine hydrochloride, provided the title compound as the minor isomer. ESMS (M-C(CH$_3$)$_3$+2H): 190.0; HNMR (400 MHz, d$_6$-DMSO) δ 8.20 (d, 2H), 7.86 (d, 2H), 7.7 (d, 1H), 6.55 (d, 1H), 1.25 (s, 9H)

Intermediate 41

4-bromo-1-(1,1-dimethylethyl)-3-(4-nitrophenyl)-1H-pyrazole

Following the procedure described for Intermediate 2 with 1-(1,1-dimethylethyl)-5-(4-nitrophenyl)-1H-pyrazole provided the title compound. ESMS [M-C(CH$_3$)$_3$+2H]: +: 268.0, 270.0; HNMR (400 MHz, d$_6$-DMSO) δ 8.35 (d, 2H), 8.2 (s, 1H), 8.15 (d, 2H), 1.4 (s, 9H)

Intermediate 42

N-{4-[4-bromo-1-(1,1-dimethylethyl)-1H-pyrazol-3-yl]phenyl}-N'-phenylurea

Following the procedure described for Intermediate 31 with 4-bromo-3-(4-nitrophenyl)-1H-pyrazole provided the title compound. ESMS [M+H]$^+$: 415.4

Intermediate 43

4-bromo-1-(1,1-dimethylethyl)-5-(4-nitrophenyl)-1H-pyrazole

Following the procedure described for Intermediate 2 with 1-(1,1-dimethylethyl)-5-(4-nitrophenyl)-1H-pyrazole for provided the title compound. ESMS [M-C(CH$_3$)$_3$+2H]: +: 268.0, 270.0, HNMR (400 MHz, d$_6$-DMSO) δ 8.38 (d, 2H), 7.7 (m, 3H), 1.4 (s, 9H)

Intermediate 44

1-(1,1-dimethylethyl)-5-(4-nitrophenyl)-4-(4,4,5,5-tetramethyl-1,3,2-dioxaborolan-2-yl)-1H-pyrazole Following the procedure described for Intermediate 5 with 4-bromo-1-(1,1-dimethylethyl)-5-(4-nitrophenyl)-1H-pyrazole provided the title compound. ESMS[M-C(CH3)3+H]+: 315.2. HNMR (400 MHz, d$_6$-DMSO) δ 8.28 (d, 2H), 7.65 (m, 3H), 1.42 (s, 9H), 1.05 (s, 12H)

Intermediate 45

4-[1-(1,1-dimethylethyl)-5-(4-nitrophenyl)-1H-pyrazol-4-yl]-1H-pyrrolo[2,3-b]pyridine Following the procedure described for Intermediate 6 with 1-(1,1-dimethylethyl)-5-(4-nitrophenyl)-4-(4,4,5,5-tetramethyl-1,3,2-dioxaborolan-2-yl)-1H-pyrazole for 1-ethyl-3-(4-nitrophenyl)-4-(4,4,5,5-tetramethyl-1,3,2-dioxaborolan-2-yl)-1H-pyrazole, provided the title compound. ESMS [M+H]$^+$: 362.2

Intermediate 46

4-bromo-3-(4-nitrophenyl)-1-(2-propen-1-yl)-1H-pyrazole

Following the procedure described for Intermediate 3 using allylbromide provided the title compound. ESMS [M+H]$^+$: 308.2

Intermediate 47

3-(4-nitrophenyl)-1-(2-propen-1-yl)-4-(4,4,5,5-tetramethyl-1,3,2-dioxaborolan-2-yl)-1H-pyrazole Following the procedure described for Intermediate 5 with 4-bromo-3-(4-nitrophenyl)-1-(2-propen-1-yl)-1H-pyrazole provided the title compound. ESMS [M+H]$^+$: 356.2

Intermediate 48

4-[3-(4-nitrophenyl)-1-(2-propen-1-yl)-1H-pyrazol-4-yl]-1H-pyrrolo[2,3-b]pyridine Following the procedure described for Intermediate 6 with 3-(4-nitrophenyl)-1-(2-propen-1-yl)-4-(4,4,5,5-tetramethyl-1,3,2-dioxaborolan-2-yl)-1H-pyrazole provided the title compound. ESMS [M+H]$^+$: 346.2

Intermediate 49

4-[3-(4-nitrophenyl)-1-(2-propen-1-yl)-1H-pyrazol-4-yl]-1-(phenylsulfonyl)-1H-pyrrolo[2,3-b]pyridine Following the procedure described for Intermediate 6 using 4-bromo-3-(4-nitrophenyl)-1-(2-propen-1-yl)-1H-pyrazole and (1-phenylsulfonyl)-4-(4,4,5,5-tetramethyl-1,3,2-dioxaborolan-2-yl)-1H-pyrrolo[2,3-b]pyridine provided the title compound. ESMS [M+H]$^+$: 486.2

Intermediate 50

3-{3-(4-nitrophenyl)-4-[1-(phenylsulfonyl)-1H-pyrrolo[2,3-b]pyridin-4-yl]-1H-pyrazol-1-yl}-1-propanol To a solution of 0.5M 9-borabicyclo[3.3.1]nonane in tetrahydrofuran (6.16 mL) cooled to 0° C. was added a solution of 4-[3-(4-nitrophenyl)-1-(2-propen-1-yl)-1H-pyrazol-4-yl]-1-(phenylsulfonyl)-1H-pyrrolo[2,3-b]pyridine (2.06 mmol) in tetrahydrofuran (14 mL). The reaction mixture was stirred at room temperature under an inert atmosphere for 4.5 h and then re-cooled to 0° C. followed by quenching with water (1.7 mL). After 15 minutes of stirring at 0° C., 6N aqueous sodium hydroxide (1.24 mL) was added dropwise followed by 30% aqueous hydrogen peroxide (0.865 mL). The reaction mixture was stirred for 1.5 h at 0° C., neutralized with 6N aqueous hydrochloric acid and concentrated in vacuo. Water (10 mL) was added to the residue and the solution extracted with ethyl acetate (3×15 mL), the combined organic layers dried over magnesium sulfate and concentrated in vacuo to afford the title compound (84%). ESMS [M+H]+: 504.2

Intermediate 51

3-[3-(4-nitrophenyl)-4-(1H-pyrrolo[2,3-b]pyridin-4-yl)-1H-pyrazol-1-yl]-1-propanol Following the procedure described for Intermediate 21 with 3-{3-(4-nitrophenyl)-4-[1-(phenylsulfonyl)-1H-pyrrolo[2,3-b]pyridin-4-yl]-1H-pyrazol-1-yl}-1-propanol afforded the title compound. ESMS [M+H]+: 364.2

Intermediate 53

4-(3-bromo-2-thienyl)-1-[(4-methylphenyl)sulfonyl]-1H-pyrrolo[2,3-b]pyridine

Following the procedure described for Intermediate 6 with 1-[(4-methylphenyl)sulfonyl]-4-(4,4,5,5-tetramethyl-1,3,2-dioxaborolan-2-yl)-1H-pyrrolo[2,3-b]pyridine and 2,5-dibromothiophene gave the title compound. ESMS [M+H]+: 434.2

Intermediate 54

1,1-dimethylethyl {4-[2-(1H-pyrrolo[2,3-b]pyridin-4-yl)-3-thienyl]phenyl}carbamate To a solution of 4-(3-bromo-2-thienyl)-1-[(4-methylphenyl)sulfonyl]-1H-pyrrolo[2,3-b]pyridine (5.3 mmol) in 40 mL of 1,2-dimethoxyethane was added 4-(N-Boc-amino)phenyl boronic acid (13.8 mmol), tetrakis(triphenylphosphine)palladium(0), (0.17 mmol), water (16 mL) and barium hydroxide (21.2 mmol). The reaction was heated at 80° C. for 36 h. The 1,2-dimethoxyethane was evaporated and the residue taken up in ethyl acetate and washed with water (50 mL). The crude product was purified by silica gel chromatography (0-50% ethyl acetate/hexanes) to give the title compound (40%). ESMS [M+H]+: 392.2

Intermediate 55

4-[2-(1H-pyrrolo[2,3-b]pyridin-4-yl)-3-thienyl]aniline

Following the procedure described for Intermediate 21 and then Example 11 with 1,1-dimethylethyl {4-[2-(1H-pyrrolo[2,3-b]pyridin-4-yl)-3-thienyl]phenyl}provided the title compound. ESMS [M+H]+: 292.2.

Intermediate 56

2-methyl-4-(4-nitrophenyl)-1,3-thiazole

A solution of 3-bromo-(4-nitrophenyl)-ethanone (2.5 mmol) and thioacetamide (3 mmol) in N,N-dimethylformamide (20 mL) was heated at 65° C. for 8 h. Ethyl acetate (40 mL) was added and the solution was washed with water (3×20 mL). The product was purified by crystallization from ether to give the title product (80%). ESMS [M+H]+: 221.2

Intermediate 57

5-bromo-2-methyl-4-(4-nitrophenyl)-1,3-thiazole

Bromine (6 mmol) was added dropwise to a solution of 2-methyl-4-(4-nitrophenyl)-1,3-thiazole (5 mmol) in chloroform (20 mL) and the solution refluxed for 4 h. The solvent was evaporated and the product purified by crystallization from ether to afford the title compound (60%). ESMS [M+H]+: 300.2

Intermediate 58

4-[2-methyl-4-(4-nitrophenyl)-1,3-thiazol-5-yl]-1-[(4-methylphenyl)sulfonyl]-1H-pyrrolo[2,3-b]pyridine Following the procedure described for Intermediate 6 with 5-bromo-2-methyl-4-(4-nitrophenyl)-1,3-thiazole and [(4-methylphenyl)sulfonyl]-4-(4,4,5,5-tetramethyl-1,3,2-dioxaborolan-2-yl)-1H-pyrrolo[2,3-b]pyridine provided title compound. ESMS [M+H]+: 491.2

Intermediate 59

4-(2-methyl-5-{1-[(4-methylphenyl)sulfonyl]-1H-pyrrolo[2,3-b]pyridin-4-yl}-1,3-thiazol-4-yl)aniline Following the procedure described for Intermediate 7 with 4-[2-methyl-4-(4-nitrophenyl)-1,3-thiazol-5-yl]-1-[(4-methylphenyl)sulfonyl]-1H-pyrrolo[2,3-b]pyridine afforded the title compound. ESMS [M+H]+: 461.2

Intermediate 60

N-[4-(2-methyl-5-{1-[(4-methylphenyl)sulfonyl]-1H-pyrrolo[2,3-b]pyridine-4-yl}-1,3-thiazol-4-yl)phenyl]-N'-phenylurea Following the procedure described in Example 1 with 4-(2-methyl-5-{1-[(4-methylphenyl)sulfonyl]-1H-pyrrolo[2,3-b]pyridine-4-yl}-1,3-thiazol-4-yl)aniline provided the title product. ESMS [M+H]+: 581.2

Intermediate 61

N-ethyl-N'-[4-(2-methyl-5-{1-[(4-methylphenyl)sulfonyl]-1H-pyrrolo[2,3-b]pyridin-4-yl}-1,3-thiazol-4-yl)phenyl]urea Following the procedure described in Example 1 with 4-(2-methyl-5-{1-[(4-methylphenyl)sulfonyl]-1H-pyrrolo[2,3-b]pyridin-4-yl}-1,3-thiazol-4-yl)aniline and ethyl isocyanate provided the title product. ESMS [M+H]+: 532.2

Intermediate 62

N,N-dimethyl-N'-[4-(2-methyl-5-{1-[(4-methylphenyl)sulfonyl]-1H-pyrrolo[2,3-b]pyridin-4-yl}-1,3-thiazol-4-yl)phenyl]urea Following the procedure in Example 5a with 4-(2-methyl-5-{1-[(4-methylphenyl)sulfonyl]-1H-pyrrolo[2,3-b]pyridin-4-yl}-1,3-thiazol-4-yl)aniline and 2M dimethylamine in tetrahydrofuran provided the title compound. ESMS [M+H]+: 532.2

Intermediate 63

5-bromo-2-methyl-4-(4-nitrophenyl)-1,3-oxazole

Following the procedures described in the literature: *Synthetic Communications* 2003, 33(9), 1611-14; *J. Org. Chem.* 1977, 42(8), 1476; *Synlett* 2001, 10, 1563; *Organic Letters* 2003, 5(16), 2911-14 with 4-nitrophenylacetophenone (commercially available) provided the title compound. ESMS [M+H]$^+$: 284

Intermediate 64

4-[2-methyl-4-(4-nitrophenyl)-1,3-oxazol-5-yl]-1-[(4-methylphenyl)sulfonyl]-1H-pyrrolo[2,3-b]pyridine Following the procedure described for Intermediate 6 with 5-bromo-2-methyl-4-(4-nitrophenyl)-1,3-oxazole and [(4-methylphenyl)sulfonyl]-4-(4,4,5,5-tetramethyl-1,3,2-dioxaborolan-2-yl)-1H-pyrrolo[2,3-b]pyridine provided the title compound. ESMS [M+H]$^+$: 476.2

Intermediate 65

4-(2-methyl-5-{1-[(4-methylphenyl)sulfonyl]-1H-pyrrolo[2,3-b]pyridin-4-yl}-1,3-oxazol-4-yl)aniline Following the procedure described for Intermediate 7 with 4-[2-methyl-4-(4-nitrophenyl)-1,3-oxazol-5-yl]-1-[(4-methylphenyl)sulfonyl]-1H-pyrrolo[2,3-b]pyridine and provided the title product. ESMS [M+H]$^+$: 445.2

Intermediate 66

N-[4-(2-methyl-5-{1-[(4-methylphenyl)sulfonyl]-1H-pyrrolo[2,3-b]pyridin-4-yl}-1,3-oxazol-4-yl)phenyl]-N'-phenylurea Following the procedure described for Intermediate 31 with 4-(2-methyl-5-{1-[(4-methylphenyl)sulfonyl]-1H-pyrrolo[2,3-b]pyridin-4-yl}-1,3-oxazol-4-yl)aniline provided the title product. ESMS [M+H]$^+$: 564.0

Intermediate 67

N-ethyl-N'-[4-(2-methyl-5-{1-[(4-methylphenyl)sulfonyl]-1H-pyrrolo[2,3-b]pyridin-4-yl}-1,3-oxazol-4-yl)phenyl]urea Following the procedure described for Intermediate 31 with 4-(2-methyl-5-{1-[(4-methylphenyl)sulfonyl]-1H-pyrrolo[2,3-b]pyridin-4-yl}-1,3-oxazol-4-yl)aniline and ethyl isocyanate provided the title compound. ESMS [M+H]$^+$: 516.2

Intermediate 68

N,N-dimethyl-N'-[4-(2-methyl-5-{1-[(4-methylphenyl)sulfonyl]-1H-pyrrolo[2,3-b]pyridin-4-yl}-1,3-oxazol-4-yl)phenyl]urea Following the procedure described for Intermediate 31 with 4-(2-methyl-5-{1-[(4-methylphenyl)sulfonyl]-1H-pyrrolo[2,3-b]pyridin-4-yl}-1,3-oxazol-4-yl)aniline and dimethylcarbamoyl chloride provided the title product. ESMS [M+H]$^+$: 516.2

Intermediate 69

4-bromo-1H-pyrrolo[2,3-b]pyridine 7-oxide

To a solution of 4-bromo-1H-pyrrolo[2,3-b]pyridine (25 mmol) in diethyl ether (400 mL) under nitrogen at room temperature was added m-chloroperbenzoic acid (40 mmol). The reaction was stirred for 2.5 h. The resultant precipitate was filtered and washed with cold ether (50 mL) to give the title compound as an off-white solid (87%). ESMS[M+H]$^+$: 213.2

Intermediate 70

4-bromo-6-chloro-1H-pyrrolo[2,3-b]pyridine

To a suspension of the 4-bromo-1H-pyrrolo[2,3-b]pyridine 7-oxide (27 mmol) in N,N-dimethylformamide (57 mL) at 50° C. was added methanesulfonyl chloride (67.5 mmol) under nitrogen. Upon completion of the addition, the reaction was stirred at 75° C. for 1 hour. The reaction was cooled to room temperature and quenched with water (60 mL). Then, it was cooled to 5° C. and 6N sodium hydroxide solution was added to raise the pH to 7. The ice bath was removed and the resulting slurry was stirred at room temperature for 3 h. The precipitate was filtered, washed with water (50 mL), and dried under high vacuum to give the title product as a white solid (89%). ESMS [M+H]$^+$: 231.0

Intermediate 71

6-chloro-4-[1-ethyl-3-(4-nitrophenyl)-1H-pyrazol-4-yl]-1H-pyrrolo[2,3-b]pyridine Following the procedure described for Intermediate 6 with 4-bromo-6-chloro-1H-pyrrolo[2,3-b]pyridine and 1-ethyl-3-(4-nitrophenyl)-4-(4,4,5,5-tetramethyl-1,3,2-dioxaborolan-2-yl)-1H-pyrazole afforded the title compound. ESMS [M+H]$^+$: 368.2

Intermediate 72

{4-[4-(6-chloro-1H-pyrrolo[2,3-b]pyridin-4-yl)-1-ethyl-1H-pyrazol-3-yl]phenyl}amine Following the procedure described for Intermediate 7 with 6-chloro-4-[1-ethyl-3-(4-nitrophenyl)-1H-pyrazol-4-yl]-1H-pyrrolo[2,3-b]pyridine provided the title compound. ESMS [M+H]$^+$: 338.4

Intermediate 73

[4-(4-bromo-1-ethyl-1H-pyrazol-3-yl)phenyl]amine

Following the procedure described for Intermediate 7 using 4-bromo-1-ethyl-3-(4-nitrophenyl)-1H-pyrazole provided the title compound. ESMS [M+H]$^+$: 266.0

Intermediate 74

[(4-{4-[1-ethyl-3-(4-nitrophenyl)-1H-pyrazol-4-yl]-1H-pyrrolo[2,3-b]pyridin-6-yl}phenyl)methyl]dimethylamine Following the procedure described for Intermediate 6 using 6-chloro-4-[1-ethyl-3-(4-nitrophenyl)-1H-pyrazol-4-yl]-1H-pyrrolo[2,3-b]pyridine and N,N-dimethylaminom-

Intermediate 75

[(4-{4-[3-(4-aminophenyl)-1-ethyl-1H-pyrazol-4-yl]-1H-pyrrolo[2,3-b]pyridin-6-yl}phenyl)methyl]dimethylamine Following the procedure described for Intermediate 12 with [(4-{4-[1-ethyl-3-(4-nitrophenyl)-1H-pyrazol-4-yl]-1H-pyrrolo[2,3-b]pyridin-6-yl}phenyl)methyl]dimethylamine afforded title compound. ESMS [M+H]$^+$: 437.4

Intermediate 76

4-[1-ethyl-3-(4-nitrophenyl)-1H-pyrazol-4-yl]-1H-pyrrolo[2,3-b]pyridine-2-carboxylic acid Following the procedure described for Intermediate 6 with ethyl 4-bromo-1H-pyrrolo[2,3-b]pyridine-2-carboxylic acid and 1-ethyl-3-(4-nitrophenyl)-4-(4,4,5,5-tetramethyl-1,3,2-dioxaborolan-2-yl)-1H-pyrazole provided title compound. ESMS [M+H]$^+$: 378.2

Intermediate 77

4-[1-ethyl-3-(4-nitrophenyl)-1H-pyrazol-4-yl]-N-[2-(4-morpholinyl)ethyl]-1H-pyrrolo[2,3-b]pyridine-2-carboxamide Following the procedure described in Example 15a using 4-[1-ethyl-3-(4-nitrophenyl)-1H-pyrazol-4-yl]-1H-pyrrolo[2,3-b]pyridine-2-carboxylic acid and 4-(2-aminoethyl)-morpholine afforded the title compound. ESMS [M+H]$^+$: 490.4

Intermediate 78

4-[3-(4-aminophenyl)-1-ethyl-1H-pyrazol-4-yl]-N-[2-(4-morpholinyl)ethyl]-1H-pyrrolo[2,3-b]pyridine-2-carboxamide Following the procedure described for Intermediate 12 with 4-[1-ethyl-3-(4-nitrophenyl)-1H-pyrazol-4-yl]-N-[2-(4-morpholinyl)ethyl]-1H-pyrrolo[2,3-b]pyridine-2-carboxamide provided the title compound. ESMS [M+H]$^+$: 460.4

Intermediate 79

4-[1-ethyl-3-(4-nitrophenyl)-1H-pyrazol-4-yl]-N-[2-(4-methyl-1-piperazinyl)ethyl]-1H-pyrrolo[2,3-b]pyridine-2-carboxamide A solution of 4-[1-ethyl-3-(4-nitrophenyl)-1H-pyrazol-4-yl]-1H-pyrrolo[2,3-b]pyridine-2-carboxylic acid (0.331 mmol), 2-(4-methyl-piperazin-1-yl)-ethylamine (0.993 mmol), and N-(3-dimethylaminopropyl)-N'-ethylcarbodiimide hydrochloride (0.397 mmol) in N,N-dimethylformamide (1 mL) under nitrogen was stirred for 17 h at room temperature. The reaction was concentrated in vacuo and purification by Gilson reverse phase HPLC afforded the title compound as a solid (20%). ESMS [M+H]$^+$: 503.4

Intermediate 80

4-[3-(4-aminophenyl)-1-ethyl-1H-pyrazol-4-yl]-N-[2-(4-methyl-1-piperazinyl)ethyl]-1H-pyrrolo[2,3-b]pyridine-2-carboxamide Following the procedure described for Intermediate 12 with 4-[1-ethyl-3-(4-nitrophenyl)-1H-pyrazol-4-yl]-N-[2-(4-methyl-1-piperazinyl)ethyl]-1H-pyrrolo[2,3-b]pyridine-2-carboxamide provided the title compound. ESMS [M+H]$^+$: 473.4

Intermediate 81

4-[1-ethyl-3-(4-nitrophenyl)-1H-pyrazol-4-yl]-N-[2-(methylthio)ethyl]-1H-pyrrolo[2,3-b]pyridine-2-carboxamide Following the procedure described for Intermediate 79 with 2-(methylthio)ethylamine provided the title compound. ESMS [M+H]$^+$: 451.2

Intermediate 82

4-[3-(4-aminophenyl)-1-ethyl-1H-pyrazol-4-yl]-N-[2-(methylthio)ethyl]-1H-pyrrolo[2,3-b]pyridine-2-carboxamide Following the procedure described for Intermediate 12 with 4-[1-ethyl-3-(4-nitrophenyl)-1H-pyrazol-4-yl]-N-[2-(methylthio)ethyl]-1H-pyrrolo[2,3-b]pyridine-2-carboxamide provided the title compound. ESMS [M+H]$^+$: 421.2

Intermediate 83

4-bromo-1-(phenylsulfonyl)-1H-pyrrolo[2,3-b]pyridine-2-carbaldehyde n-Butyllithium (2.5M in hexanes, 3.56 mmol) was added dropwise to a solution of diisopropylamine (3.56 mmol) in anhydrous tetrahydrofuran (5 mL) at −78° C. under nitrogen. The reaction was stirred for 30 minutes at −78° C. and then a solution of 4-bromo-1-(phenylsulfonyl)-1H-pyrrolo[2,3-b]pyridine (2.97 mmol) in anhydrous tetrahydrofuran (1 mL) was added dropwise via syringe. The resulting reaction was stirred at −78° C. for 2 h and then a solution of N,N-dimethylformamide (11.88 mmol) in tetrahydrofuran (1 mL) was added dropwise by syringe. The reaction was stirred at −78° C. for 2 h and then quenched with saturated aqueous ammonium chloride solution (10 mL). The mixture was extracted with ethyl acetate (2×20 mL), and the combined organic layers were dried over magnesium sulfate and concentrated in vacuo. Purification by silica gel chromatography (Analogix IF280, 70-100% CH$_2$Cl$_2$/hexanes) afforded the title compound as a white solid (66%). ESMS [M+H]$^+$: 365.0

Intermediate 84

1-(phenylsulfonyl)-4-(4,4,5,5-tetramethyl-1,3,2-dioxaborolan-2-yl)-1H-pyrrolo[2,3-b]pyridine-2-carbaldehyde Following the procedure described for Intermediate 32 with 4-bromo-1-(phenylsulfonyl)-1H-pyrrolo[2,3-b]pyridine-2-carbaldehyde provided title compound. ESMS [M+H]$^+$: 330.2

Intermediate 85

N-(4-{4-[2-formyl-1-(phenylsulfonyl)-1H-pyrrolo[2,3-b]pyridin-4-yl]-1-ethyl-1H-pyrazol-3-yl}phenyl)-N'-phenylurea Following the procedure described in Intermediate 100 with N-[4-(4-bromo-1-ethyl-1H-pyrazol-3-yl)phenyl]-N'-phenylurea and 1-(phenylsulfonyl)-4-(4,4,5,5-tetramethyl-1,3,2-dioxaborolan-2-yl)-1H-pyrrolo[2,3-b]pyridine-2-carbaldehyde provided the title compound. ESMS [M+H]$^+$: 591.4

Intermediate 86

N-(4-{1-ethyl-4-[2-({[2-(4-morpholinyl)ethyl]amino}methyl)-1-(phenylsulfonyl)-1H-pyrrolo[2,3-b]pyridin-4-yl]-1H-pyrazol-3-yl}-phenyl)-N'-phenylurea A solution of N-(4-{4-[2-formyl-1-(phenylsulfonyl)-1H-pyrrolo[2,3-b]pyridin-4-yl]-1-ethyl-1H-pyrazol-3-yl}phenyl)-N'-phenylurea (0.1 mmol), 4-(2-aminoethyl)-morpholine (0.2 mmol), and sodium triacetoxyborohydride (0.2 mmol) in dichloromethane (1 mL) and acetic acid (0.25 mL) under nitrogen was stirred at room temperature for 30 minutes. The reaction was quenched with 1N sodium hydroxide solution (5 mL) and extracted with ethyl acetate (3×5 mL). The combined organic layers were washed with brine (5 mL), dried over magnesium sulfate, and concentrated in vacuo to give the title compound as the crude product. ESMS [M+H]$^+$: 705.6

Intermediate 87

N-(4-{4-[2-({[2-(dimethylamino)ethyl]amino}methyl)-1-(phenylsulfonyl)-1H-pyrrolo[2,3-b]pyridin-4-yl]-1-ethyl-1H-pyrazol-3-yl}phenyl)-N'-phenylurea Following the procedure described for Intermediate 86 with (2-aminoethyl)dimethylamine provided the title compound. ESMS [M+H]$^+$: 663.4

Intermediate 88

N-{[4-bromo-1-(phenylsulfonyl)-1H-pyrrolo[2,3-b]pyridin-2-yl]methyl}-2-(methylsulfonyl)ethanamine Following the procedure described for Intermediate 86 using 2-aminoethylmethylsulfone hydrochloride and purification by silica gel chromatography (Analogix IF280, 25-80% ethyl acetate/hexanes) afforded the title product as a solid (34%). ESMS [M+H]$^+$: 472.2

Intermediate 89

N-(4-{1-ethyl-4-[2-({[2-(methylsulfonyl)ethyl]amino}methyl)-1-(phenylsulfonyl)-1H-pyrrolo[2,3-b]pyridin-4-yl]-1H-pyrazol-3-yl}phenyl)-N'-phenylurea Following the procedure described for Intermediate 32 with N-{[4-bromo-1-(phenylsulfonyl)-1H-pyrrolo[2,3-b]pyridin-2-yl]methyl}-2-(methylsulfonyl)ethanamine. Using this product crude and following the procedure described in Intermediate 100 provided the title compound. ESMS [M+H]$^+$: 698.4

Intermediate 90

{[4-bromo-1-(phenylsulfonyl)-1H-pyrrolo[2,3-b]pyridin-2-yl]methyl}dimethylamine

Following the procedure described for Intermediate 86 using dimethylamine (2M solution in tetrahydrofuran) and purification by silica gel chromatography (Analogix IF280, 0-10% methanol/dichloromethane with 10% ammonium hydroxide) afforded the title product as a solid (46%). ESMS [M+H]$^+$: 394.0

Intermediate 91

N-(4-{4-[2-[(dimethylamino)methyl]-1-(phenylsulfonyl)-1H-pyrrolo[2,3-b]pyridin-4-yl]-1-ethyl-1H-pyrazol-3-yl}phenyl)-N'-phenylurea Following the procedure described for Intermediate 32 with {[4-bromo-1-(phenylsulfonyl)-1H-pyrrolo[2,3-b]pyridin-2-yl]methyl}dimethylamine. Using this product crude and following the procedure described in Intermediate 100 provided the title compound. ESMS [M+H]$^+$: 620.6

Intermediate 92

2-({[4-bromo-1-(phenylsulfonyl)-1H-pyrrolo[2,3-b]pyridin-2-yl]methyl}amino)ethanol Following the procedure described for Intermediate 86 using ethanolamine provided the title product as a solid. ESMS [M+H]$^+$: 409.2

Intermediate 93

N-(4-{1-ethyl-4-[2-{[(2-hydroxyethyl)amino]methyl}-1-(phenylsulfonyl)-1H-pyrrolo[2,3-b]pyridin-4-yl]-1H-pyrazol-3-yl}phenyl)-N'-phenylurea Following the procedure described for Intermediate 32 with 2-({[4-bromo-1-(phenylsulfonyl)-1H-pyrrolo[2,3-b]pyridin-2-yl]methyl}amino)ethanol. Using this product crude and following the procedure described in Intermediate 100 provided the title compound. ESMS [M+H]$^+$: 636.4

Intermediate 94

N-{[4-bromo-1-(phenylsulfonyl)-1H-pyrrolo[2,3-b]pyridin-2-yl]methyl}-3-(4-methyl-1-piperazinyl)-1-propanamine Following the procedure described for Intermediate 86 using 1-(3-aminopropyl)-4-methylpiperazine and purification by silica gel chromatography (Analogix IF280, 0-10% methanol/dichloromethane with 10% ammonium hydroxide) afforded the title compound. ESMS [M+H]$^+$: 505.4

Intermediate 95

N-(4-{1-ethyl-4-[2-({[3-(4-methyl-1-piperazinyl)propyl]amino}methyl)-1-(phenylsulfonyl)-1H-pyrrolo[2,3-b]pyridin-4-yl]-1H-pyrazol-3-yl}phenyl)-N'-phenylurea Following the procedure described for Intermediate 32 with N-{[4-bromo-1-(phenylsulfonyl)-1H-pyrrolo[2,3-b]pyridin-2-yl]methyl}-3-(4-methyl-1-piperazinyl)-1-propanamine. Using this product crude following the procedure described in Intermediate 100 provided the title compound. ESMS [M+H]+: 732.4

Intermediate 99

4-Bromo-2-(3-formylphenyl)-1-phenylsulfonyl-1H-pyrrolo[2,3-b]pyridine

In a sealed pressure tube was added 4-bromo-2-iodo-1-phenylsulfonyl-1H-pyrrolo[2,3-b]pyridine (2.1 mmol; preparation disclosed in WO03/000690A1), 3-formylbenzeneboronic acid (2.1 mmol), N,N-dimethylformamide (15 mL), aqueous saturated sodium bicarbonate (5 mL) and tetrakis(triphenylphosphine)palladium(0) (0.1 mmol). The reaction was purged with nitrogen, capped and stirred at 100° C. for 16 h. After cooling to room temperature the reaction was concentrated under vacuum, taken up in ethyl acetate, washed with water, brine, dried over sodium sulfate, filtered and evaporated to dryness under vacuum. Purification by flash chromatography by silica gel (0-4% ethyl acetate in methylene chloride) gave the title compound as a white solid (77%). ESMS [M+H]+: 441.2

Intermediate 100

4-[3-(4-nitrophenyl)-1-ethyl-1H-pyrazol-4-yl]-2-(3-formylphenyl)-1-phenylsulfonyl-1H-pyrrolo[2,3-b]pyridine In a sealed pressure tube was added 4-bromo-2-(3-formylphenyl)-1-phenylsulfonyl-1H-pyrrolo[2,3-b]pyridine (1.6 mmol), 3-(4-nitrophenyl)-1-ethyl-4-(4,4,5,5-tetramethyl-1,3,2-dioxaborolan-2-yl)-1H-pyrazole (1.7 mmol), N,N-dimethylformamide (15 mL), aqueous saturated sodium bicarbonate (4 mL) and tetrakis(triphenylphosphine)palladium(0) (0.09 mmol). The reaction was purged with nitrogen, capped, and stirred at 100° C. for 8 h. After cooling to room temperature, the reaction was concentrated under vacuum, taken up in ethyl acetate, washed with water, brine, dried over sodium sulfate, filtered, and evaporated to dryness under vacuum. Purification by silica gel flash chromatography (5-10% ethyl acetate/methylene chloride) gave the title compound as a yellow solid (81%). ESMS [M+H]+: 578.3

Intermediate 101

4-[3-(4-nitrophenyl)-1-ethyl-1H-pyrazol-4-yl]-2-[3-(dimethylaminomethyl)phenyl]-1-phenylsulfonyl-1H-pyrrolo[2,3-b]pyridine To a stirred solution of 4-[3-(4-nitrophenyl)-1-ethyl-1H-pyrazol-4-yl]-2-(3-formylphenyl)-1-phenylsulfonyl-1H-pyrrolo[2,3-b]pyridine (1.3 mmol) in tetrahydrofuran (20 mL) was added a solution of 2 M dimethylamine in tetrahydrofuran (2.0 mmol) followed by sodium triacetoxyborohydride (1.9 mmol). The reaction was stirred at room temperature for 4 h and concentrated to dryness under vacuum. The residue was taken up in ethyl acetate, washed with brine, dried (sodium sulfate), filtered, and evaporated under vacuum. Purification by flash chromatography on silica gel (0-5% (5% ammonium hydroxide, methanol)/methylene chloride) gave the title compound as a yellow solid (87%). ESMS [M+H]+: 607.4

Intermediate 102

4-[3-(4-aminophenyl)-1-ethyl-1H-pyrazol-4-yl]-2-[3-(dimethylaminomethyl)phenyl]-1H-pyrrolo[2,3-b]pyridine To a stirred solution of 4-[3-(4-nitrophenyl)-1-ethyl-1H-pyrazol-4-yl]-2-[3-(dimethylaminomethyl)phenyl]-1-phenylsulfonyl-1H-pyrrolo[2,3-b]pyridine (1.1 mmol) in HOAc (20 mL) was added portionwise zinc dust (8.0 mmol) over 5 minutes. The reaction was stirred at room temperature for 1 h, filtered through a pad of Celite, rinsed with acetic acid, and concentrated to dryness under vacuum. The residue was re-evaporated several times from methanol/toluene to remove the excess acetic acid, taken up in methanol (35 mL) and treated with 6 N sodium hydroxide (1.5 mL). The reaction mixture was stirred and heated at 70° C. for 8 h. After cooling to room temperature the reaction was concentrated under vacuum, triturated with cold water, filtered, washed with water, and dried under vacuum to give the crude product as a pale orange solid: ESMS [M+H]+: 437.2

Intermediate 103

4-[3-(4-nitrophenyl)-1-ethyl-1H-pyrazol-4-yl]-2-[3-(N-morpholinylmethyl)phenyl]-1-phenylsulfonyl-1H-pyrrolo[2,3-b]pyridine Following the procedure describe in Intermediate 101 using morpholine and stirring over the weekend provided the title compound. ESMS [M+H]+: 649.6

Intermediate 104

4-[3-(4-aminophenyl)-1-ethyl-1H-pyrazol-4-yl]-2-[3-(N-morpholinylmethyl)phenyl]-1H-pyrrolo[2,3-b]pyridine Following the procedure describe for Intermediate 102 using 4-[3-(4-nitrophenyl)-1-ethyl-1H-pyrazol-4-yl]-2-[3-(N-morpholinylmethyl)phenyl]-1-phenylsulfonyl-1H-pyrrolo[2,3-b]pyridine gave the title compound. ESMS [M+H]+: 479.4

Intermediate 105

4-bromo-2-(4-acetamidophenyl)-1-phenylsulfonyl-1H-pyrrolo[2,3-b]pyridine

Following the procedure described for Intermediate 99 using 4-acetamidophenylboronic acid provided the title compound. ESMS [M+H]+: 470.2

Intermediate 106

4-[3-(4-nitrophenyl)-1-ethyl-1H-pyrazol-4-yl]-2-(4-acetamidophenyl)-1-phenylsulfonyl-1H-pyrrolo[2,3-b]pyridine Following the procedure described for Intermediate 100 using 4-bromo-2-(4-acetamidophenyl)-1-phenylsulfonyl-1H-pyrrolo[2,3-b]pyridine for 4-bromo-2-(3-formylphenyl)-1-phenylsulfonyl-1H-pyrrolo[2,3-b]pyridine gave the title compound. ESMS [M+H]+: 607.4

Intermediate 107

4-[3-(4-aminophenyl)-1-ethyl-1H-pyrazol-4-yl]-2-(4-acetamidophenyl)-1-phenylsulfonyl-1H-pyrrolo[2,3-b]pyridine A stirred solution of 4-[3-(4-nitrophenyl)-1-ethyl-1H-pyrazol-4-yl]-2-(4-acetamidophenyl)-1-phenylsulfonyl-1H-pyrrolo[2,3-b]pyridine (0.8 mmol) and 20% palladium(II) hydroxide on carbon (0.1 g) was hydrogenated with a balloon of hydrogen for 3 days at room temperature. The reaction was filtered through a pad of Celite, rinsed with ethyl acetate and concentrated under vacuum to give the title product as an off-white solid (52%). ESMS [M+H]$^+$: 577.4

Intermediate 108

4-[3-(4-N-phenylcarbamylaminophenyl)-1-ethyl-1H-pyrazol-4-yl]-2-(4-acetamidophenyl)-1-phenylsulfonyl-1H-pyrrolo[2,3-b]pyridine Following the procedure described in Example 1 using 4-[3-(4-aminophenyl)-1-ethyl-1H-pyrazol-4-yl]-2-(4-acetamidophenyl)-1-phenylsulfonyl-1H-pyrrolo[2,3-b]pyridine gave the title compound. ESMS [M+H]$^+$: 696.4

Intermediate 109

4-bromo-2-(3-acetamidophenyl)-1-phenylsulfonyl-1H-pyrrolo[2,3-b]pyridine

Following the procedure described for Intermediate 99 using 3-acetamidophenylboronic acid afforded the title compound. ESMS [M+H]$^+$: 470.2

Intermediate 110

4-[3-(4-nitrophenyl)-1-ethyl-1H-pyrazol-4-yl]-2-(3-acetamidophenyl)-1-phenylsulfonyl-1H-pyrrolo[2,3-b]pyridine Following the procedure described for Intermediate 100 using 4-bromo-2-(3-acetamidophenyl)-1-phenylsulfonyl-1H-pyrrolo[2,3-b]pyridine provided the title compound. ESMS [M+H]$^+$: 607.4

Intermediate 111

4-[3-(4-aminophenyl)-1-ethyl-1H-pyrazol-4-yl]-2-(3-acetamidophenyl)-1-phenylsulfonyl-1H-pyrrolo[2,3-b]pyridine Following the procedure described for Intermediate 107 using 4-[3-(4-nitrophenyl)-1-ethyl-1H-pyrazol-4-yl]-2-(3-acetamidophenyl)-1-phenylsulfonyl-1H-pyrrolo[2,3-b]pyridine provided the title product. ESMS [M+H]$^+$: 577.4

Intermediate 112

4-[3-(4-N-phenylcarbamylaminophenyl)-1-ethyl-1H-pyrazol-4-yl]-2-(3-acetamidophenyl)-1-phenylsulfonyl-1H-pyrrolo[2,3-b]pyridine Following the procedure described in Example 1 using 4-[3-(4-aminophenyl)-1-ethyl-1H-pyrazol-4-yl]-2-(3-acetamidophenyl)-1-phenylsulfonyl-1H-pyrrolo[2,3-b]pyridine provided the title product. ESMS [M+H]$^+$: 696.4

Intermediate 113

4-[3-(4-N-ethylcarbamylaminophenyl)-1-ethyl-1H-pyrazol-4-yl]-2-(3-acetamidophenyl)-1-phenylsulfonyl-1H-pyrrolo[2,3-b]pyridine Following the procedure described in Example 48 using 4-[3-(4-aminophenyl)-1-ethyl-1H-pyrazol-4-yl]-2-(3-acetamidophenyl)-1-phenylsulfonyl-1H-pyrrolo[2,3-b]pyridine and ethyl isocyanate obtained the title compound. ESMS [M+H]$^+$: 648.6

Intermediate 114

4-bromo-2-[4-(dimethylaminomethyl phenyl]-1-phenylsulfonyl-1H-pyrrolo[2,3-b]pyridine Following the procedure described for Intermediate 99 using 4-[(N,N-dimethylamino)methyl]phenyl boronic acid afforded the title compound. ESMS [M+H]$^+$: 470.0

Intermediate 115

4-[3-(4-nitrophenyl)-1-ethyl-1H-pyrazol-4-yl]-2-[4-(dimethylaminomethyl)phenyl]-1-phenylsulfonyl-1H-pyrrolo[2,3-b]pyridine Following the procedure described for Intermediate 100 using 4-bromo-2-[4-(dimethylaminomethyl)phenyl]-1-phenylsulfonyl-1H-pyrrolo[2,3-b]pyridine provided the title compound. ESMS [M+H]$^+$: 607.6

Intermediate 116

4-[3-(4-aminophenyl)-1-ethyl-1H-pyrazol-4-yl]-2-[4-(dimethylaminomethyl)phenyl]-1H-pyrrolo[2,3-b]pyridine Following the procedure described for Intermediate 102 using 4-[3-(4-nitrophenyl)-1-ethyl-1H-pyrazol-4-yl]-2-[4-(dimethylaminomethyl)phenyl]-1-phenylsulfonyl-1H-pyrrolo[2,3-b]pyridine provided the title compound. ESMS [M+H]$^+$: 437.4

Intermediate 117

4-bromo-2-[4-(N-morpholinylmethyl)phenyl]-1-phenylsulfonyl-1H-pyrrolo[2,3-b]pyridine Following the procedure described for Intermediate 99 using 4-[4-(4,4,5,5-tetramethyl-1,3,2-dioxaborolan-2-yl)benzyl]morpholine provided the title compound. ESMS [M+H]$^+$: 512.2

Intermediate 118

4-[3-(4-nitrophenyl)-1-ethyl-1H-pyrazol-4-yl]-2-[4-(N-morpholinylmethyl)phenyl]-1-phenylsulfonyl-1H-pyrrolo[2,3-b]pyridine Following the procedure described for Intermediate 100 using 4-bromo-2-[4-(N-morpholinylmethyl)phenyl]-1-phenylsulfonyl-1H-pyrrolo[2,3-b]pyridine provided the title compound. ESMS [M+H]$^+$: 649.2.

Intermediate 119

4-[3-(4-aminophenyl)-1-ethyl-1H-pyrazol-4-yl]-2-[4-(N-morpholinylmethyl)phenyl]-1H-pyrrolo[2,3-b]pyridine Following the procedure described for Intermediate 102 using 4-[3-(4-nitrophenyl)-1-ethyl-1H-pyrazol-4-yl]-2-[4-(N-morpholinylmethyl)phenyl]-1-phenylsulfonyl-1H-pyrrolo[2,3-b]pyridine provided the title compound. ESMS [M+H]$^+$: 479.4

Intermediate 120

4-bromo-2-[2-(ethoxycarbonyl)-ethyl-1-ene]-1-phenylsulfonyl-1H-pyrrolo[2,3-b]pyridine In a sealed pressure tube was added 4-bromo-2-iodo-1-phenylsulfonyl-1H-pyrrolo[2,3-b]pyridine (5.4 mmol), ethyl acrylate (7.6 mmol), propionitrile (25 mL), diisopropylamine (8.0 mmol), and palladium(II)diacetate (0.11 mmol). The reaction was purged with nitrogen, capped and stirred at 100° C. for 16 h. After cooling to room temperature the reaction was concentrated under vacuum, taken up in ethyl acetate, washed with water, brine, dried sodium sulfate, filtered and evaporated to dryness under vacuum. Purification by flash chromatography by silica gel (0-5% ethyl acetate/methylene chloride) gave the title compound as a white solid (22%). ESMS [M+H]$^+$: 435.0

Intermediate 121

4-[3-(4-nitrophenyl)-1-ethyl-1H-pyrazol-4-yl]-2-[2-(ethoxycarbonyl)-ethyl-1-ene]-1-phenylsulfonyl-1H-pyrrolo[2,3-b]pyridine Following the procedure described for Intermediate 100 using 4-bromo-2-[2-(ethoxycarbonyl)-ethyl-1-ene]-1-phenylsulfonyl-1H-pyrrolo[2,3-b]pyridine provided the title compound. ESMS [M+H]$^+$: 572.4

Intermediate 122

4-[3-(4-aminophenyl)-1-ethyl-1H-pyrazol-4-yl]-2-[2-(ethoxycarbonyl)-1-ethyl]-1H-pyrrolo[2,3-b]pyridine To a stirred solution of 4-[3-(4-nitrophenyl)-1-ethyl-1H-pyrazol-4-yl]-2-[2-(ethoxycarbonyl)-ethyl-1-ene]-1-phenylsulfonyl-1H-pyrrolo[2,3-b]pyridine (0.77 mmol) in acetic acid (15 mL) was added zinc dust (6.1 mmol). After stirring for 18 h an additional quantity of zinc dust (6.1 mmol) was added and the reaction stirred at 40° C. for 24 h. After cooling to room temperature the reaction was filtered through a pad of Celite, rinsed with acetic acid, and evaporated to dryness under vacuum. The residue was taken up in methylene chloride (50 mL), washed with aqueous 1 N sodium carbonate, brine, dried sodium sulfate, filtered, and concentrated to dryness under vacuum. Following the procedure described in Intermediate 21 afforded the title compound. ESMS [M+H]$^+$: 404.4

Intermediate 123

4-[1-ethyl-3-(4-nitrophenyl)-1H-pyrazol-4-yl]-1-(phenylsulfonyl)-2-[4-(1-pyrrolidinylmethyl)phenyl]-1H-pyrrolo[2,3-b]pyridine To a solution of 4-[4-[1-ethyl-3-(4-nitrophenyl)-1H-pyrazol-4-yl]-1-(phenylsulfonyl)-1H-pyrrolo[2,3-b]pyridin-2-yl]benzaldehyde (0.52 mmol) in tetrahydrofuran (5 mL) was added pyrrolidine (2.08 mmol) followed by sodium triacetoxyborohydride (2.08 mmol). After 1 h, the reaction mixture was quenched with water (5 mL) and diluted with ethyl acetate (5 mL). The aqueous layer was extracted with ethyl acetate (4×10 mL) and the combined extracts were dried over sodium sulfate, filtered, and concentrated under reduced pressure. The residue was purified by silica gel chromatography (5% methanol/methylene chloride with 5% concentrated ammonium hydroxide) to give the desired compound as a golden solid (93%). ESMS [M+H]$^+$: 633.4

Intermediate 124

4-(1-ethyl-4-{2-[4-(1-pyrrolidinylmethyl)phenyl]-1H-pyrrolo[2,3-b]pyridin-4-yl}-1H-pyrazol-3-yl)aniline To a solution of 4-[1-ethyl-3-(4-nitrophenyl)-1H-pyrazol-4-yl]-1-(phenylsulfonyl)-2-[4-(1-pyrrolidinylmethyl)phenyl]-1H-pyrrolo[2,3-b]pyridine (0.487 mmol) in glacial acetic acid (4 mL) was added zinc powder (3.41 mmol). After 1 h, the reaction was filtered and the zinc residue was rinsed with acetic acid. The filtrate was concentrated under reduced pressure and azeotroped five times with 1:1 methanol/toluene to remove residual acetic acid. The crude aniline was dissolved in methanol, treated with 6N NaOH (1.46 mmol) and heated to 70° C. After 5 h, the reaction mixture was concentrated under reduced pressure and the residue was suspended in cold water and stirred vigorously. The precipitate was collected by filtration and dried to constant weight under high vacuum to give title compound. ESMS [M+H]$^+$: 463.4

Intermediate 125

4-[1-ethyl-3-(4-nitrophenyl)-1H-pyrazol-4-yl]-2-[1-(4-morpholinylcarbonyl)-1,2,3,6-tetrahydro-4-pyridinyl]-1-(phenylsulfonyl)-1H-pyrrolo[2,3-b]pyridine A solution of 1,1-dimethylethyl 4-[4-[1-ethyl-3-(4-nitrophenyl)-1H-pyrazol-4-yl]-1-(phenylsulfonyl)-1H-pyrrolo[2,3-b]pyridin-2-yl]-3,6-dihydro-1(2H)-pyridinecarboxylate (0.38 mmol) methylene chloride (1 mL) was treated with 4N hydrochloric acid in dioxane (1 mL) and stirred for 1 h at room temperature. The reaction was concentrated in vacuo and evaporated one time from methylene chloride. The resultant residue was suspended in pyridine (5 mL) and treated with 4-morpholine carbonyl chloride (3.00 mmol) and stirred 48 h. The reaction was concentrated and purification of the residue by Gilson reverse phase HPLC provided the title compound (55%). ESMS [M+H]$^+$: 668.4

Intermediate 126

N'-[4-(4-bromo-1-ethyl-1H-pyrazol-3-yl)phenyl]-N,N-dimethylurea

Following the procedure described in Example 5a with 4-(4-bromo-1-ethyl-1H-pyrazol-3-yl)aniline and 2 M dimethylamine in tetrahydrofuran provided the title compound. ESMS [M+H]$^+$: 337.2

Intermediate 127

N-{4-[4-bromo-1-(phenylsulfonyl)-1H-pyrrolo[2,3-b]pyridin-2-yl]phenyl}methanesulfonamide Following the procedure described for Intermediate 99 with (4-methylsulfonylaminophenyl)boronic acid provided the title product. ESMS [M+H]+: 506.2

Intermediate 128

N-{3-[4-bromo-1-(phenylsulfonyl)-1H-pyrrolo[2,3-b]pyridin-2-yl]phenyl}methanesulfonamide Following the procedure described for Intermediate 99 with N-[3-(4,4,5,5-tetramethyl-1,3,2-dioxaborolan-2-yl)-phenyl]methanesulfonamide provided the title product. ESMS [M+H]+: 506.2

Intermediate 129

4-bromo-2-[3-(4-morpholinyl)phenyl]-1-(phenylsulfonyl)-1H-pyrrolo[2,3-b]pyridine Following the procedure described for Intermediate 99 with 3-(morpholino)phenylboronic acid provided the title product. ESMS [M+H]+: 498.4

Intermediate 130

4-bromo-2-[4-(4-morpholinyl)phenyl]-1-(phenylsulfonyl)-1H-pyrrolo[2,3-b]pyridine Following the procedure described for Intermediate 99 with 4-(morpholino)phenylboronic acid provided the title product. ESMS [M+H]+: 498.4

Intermediate 131

{3-[4-bromo-1-(phenylsulfonyl)-1H-pyrrolo[2,3-b]pyridin-2-yl]phenyl}dimethylamine Following the procedure described for Intermediate 99 with 3-(dimethylamino)phenylboronic acid provided the title product. ESMS [M+H]+: 456.2

Intermediate 132

{4-[4-bromo-1-(phenylsulfonyl)-1H-pyrrolo[2,3-b]pyridin-2-yl]phenyl}dimethylamine Following the procedure described for Intermediate 99 with 4-(dimethylamino)phenylboronic acid provided the title product. ESMS [M+H]+: 456.2

Intermediate 133

4-bromo-2-[6-(4-morpholinyl)-3-pyridinyl]-1-(phenylsulfonyl)-1H-pyrrolo[2,3-b]pyridine Following the procedure described for Intermediate 99 with 4-[5-(4,4,5,5-tetramethyl-1,3,2-dioxaborolan-2-yl)-2-pyridinyl]morpholine provided the title product. ESMS [M+H]+: 499.2

Intermediate 134

N-{4-[4-[3-(4-{[(dimethylamino)carbonyl]amino}phenyl)-1-ethyl-1H-pyrazol-4-yl]-1-(phenylsulfonyl)-1H-pyrrolo[2,3-b]pyridin-2-yl]phenyl}methanesulfonamide Following the procedure described for Intermediate 32 with N-{4-[4-bromo-1-(phenylsulfonyl)-1H-pyrrolo[2,3-b]pyridin-2-yl]phenyl}methanesulfonamide. Using this product crude and following the procedure described in Intermediate 100 with N'-[4-(4-bromo-1-ethyl-1H-pyrazol-3-yl)phenyl]-N,N-dimethylurea provided the title product. ESMS [M+H]+: 684.6

Intermediate 135

N-{3-[4-[3-(4-{[(dimethylamino)carbonyl]amino}phenyl)-1-ethyl-1H-pyrazol-4-yl]-1-(phenylsulfonyl)-1H-pyrrolo[2,3-b]pyridin-2-yl]phenyl}methanesulfonamide Following the procedure described for Intermediate 32 with N-{3-[4-bromo-1-(phenylsulfonyl)-1H-pyrrolo[2,3-b]pyridin-2-yl]phenyl}methanesulfonamide. Using this product crude and following the procedure described in Intermediate 100 using N'-[4-(4-bromo-1-ethyl-1H-pyrazol-3-yl)phenyl]-N,N-dimethylurea provided the title product. ESMS [M+H]+: 684.4

Intermediate 136

N'-(4-{1-ethyl-4-[2-[3-(4-morpholinyl)phenyl]-1-(phenylsulfonyl)-1H-pyrrolo[2,3-b]pyridin-4-yl]-1H-pyrazol-3-yl}phenyl)-N,N-dimethylurea Following the procedure described for Intermediate 32 with 4-bromo-2-[3-(4-morpholinyl)phenyl]-1-(phenylsulfonyl)-1H-pyrrolo[2,3-b]pyridine. Using this product crude and following the procedure in Intermediate 100 using N'-[4-(4-bromo-1-ethyl-1H-pyrazol-3-yl)phenyl]-N,N-dimethylurea provided the title product. ESMS [M+H]+: 676.4

Intermediate 137

N'-(4-{1-ethyl-4-[2-[4-(4-morpholinyl)phenyl]-1-(phenylsulfonyl)-1H-pyrrolo[2,3-b]pyridin-4-yl]-1H-pyrazol-3-yl}phenyl)-N,N-dimethylurea Following the procedure described for Intermediate 32 with 4-bromo-2-[4-(4-morpholinyl)phenyl]-1-(phenylsulfonyl)-1H-pyrrolo[2,3-b]pyridine. Using this product crude and following the procedure described in Intermediate 100 using N'-[4-(4-bromo-1-ethyl-1H-pyrazol-3-yl)phenyl]-N,N-dimethylurea provided the title product. ESMS [M+H]+: 676.4

Intermediate 138

N'-(4-{2-[3-(dimethylamino)phenyl]-1-(phenylsulfonyl)-1H-pyrrolo[2,3-b]pyridin-4-yl]-1-ethyl-1H-pyrazol-3-yl}phenyl)-N,N-dimethylurea Following the procedure described for Intermediate 32 with {3-[4-bromo-1-(phenylsulfonyl)-1H-pyrrolo[2,3-b]pyridin-2-yl]phenyl}dimethylamine. Using this product crude and following the procedure described in Intermediate 100 using N'-[4-(4-bromo-1-ethyl-1H-pyrazol-3-yl)phenyl]-N,N-dimethylurea provided the title product. ESMS [M+H]+: 634.6

Intermediate 139

N'-(4-{4-[2-[4-(dimethylamino)phenyl]-1-(phenylsulfonyl)-1H-pyrrolo[2,3-b]pyridin-4-yl]-1-ethyl-1H-pyrazol-3-yl}phenyl)-N,N-dimethylurea Following the procedure described for Intermediate 32 with {4-[4-bromo-1-(phenylsulfonyl)-1H-pyrrolo[2,3-b]pyridin-2-yl]phenyl}dimethylamine. Using this product crude and following the procedure described in Intermediate 100 using N'-[4-(4-bromo-1-ethyl-1H-pyrazol-3-yl)phenyl]-N,N-dimethylurea provided the title product. ESMS [M+H]+: 634.6

Intermediate 140

N'-(4-{1-ethyl-4-[2-[6-(4-morpholinyl)-3-pyridinyl]-1-(phenylsulfonyl)-1H-pyrrolo[2,3-b]pyridin-4-yl]-1H-pyrazol-3-yl}phenyl)-N,N-dimethylurea Following the procedure described for Intermediate 32 with 4-bromo-2-[6-(4-morpholinyl)-3-pyridinyl]-1-(phenylsulfonyl)-1H-pyrrolo[2,3-b]pyridine. Using this product crude and following the procedure described in Intermediate 100 using N'-[4-(4-bromo-1-ethyl-1H-pyrazol-3-yl)phenyl]-N,N-dimethylurea provided the title product. ESMS [M+H]+: 677.4

Intermediate 141

3-(4-nitrophenyl)-1-(2-hydroxyethyl)-4-(4,4,5,5-tetramethyl-1,3,2-dioxaborolan-2-yl)-1H-pyrazole In a sealed pressure tube was added 3-(4-nitrophenyl)-1-(2-hydroxyethyl)-4-bromo-1H-pyrazole (11.1 mmol), bis(pinacolato)diboron (13.8 mmol), potassium acetate (35.6 mmol), dichlorobis(triphenylphosphine)palladium(II) (0.5 mmol), and dioxane (60 mL). The reaction was purged with nitrogen, capped, stirred and heated to 100° C. for 8 h. After cooling to room temperature the reaction was evaporated to dryness under vacuum, taken up in ethyl acetate, filtered to remove insolubles, and concentrated under vacuum. Purification by flash chromatography on silica gel (75% ethyl acetate, n-hexane) gave the title compound as an off-white solid (45%). ESMS [M+H]+: 359.2

Intermediate 142

4-[3-(4-nitrophenyl)-1-(2-hydroxyethyl)-1H-pyrazol-4-yl]-2-[4-(N-morpholinylmethyl)phenyl]-1-phenylsulfonyl-1H-pyrrolo[2,3-b]pyridine Following the procedure for Intermediate 100 using 4-bromo-2-[4-(N-morpholinylmethyl)phenyl]-1-phenylsulfonyl-1H-pyrrolo[2,3-b]pyridine and 3-(4-nitrophenyl)-1-(2-hydroxyethyl)-4-(4,4,5,5-tetramethyl-1,3,2-dioxaborolan-2-yl)-1H-pyrazole provided the title compound. ESMS [M+H]+: 665.2

Intermediate 143

4-[3-(4-aminophenyl)-1-(2-hydroxyethyl)-1H-pyrazol-4-yl]-2-[4-(N-morpholinylmethyl)phenyl]-1H-pyrrolo[2,3-b]pyridine Following the procedure described for Intermediate 102 using 4-[3-(4-nitrophenyl)-1-(2-hydroxyethyl)-1H-pyrazol-4-yl]-2-[4-(N-morpholinylmethyl)phenyl]-1-phenylsulfonyl-1H-pyrrolo[2,3-b]pyridine provided the title compound. ESMS [M+H]+: 495.4

Intermediate 144

4-[3-(4-nitrophenyl)-1-ethyl-1H-pyrazol-4-yl]-2-[3-(N-pyrrolidinylmethyl)phenyl]-1-phenylsulfonyl-1H-pyrrolo[2,3-b]pyridine Following the procedure described for Intermediate 101 using pyrrolidine provided the title compound. ESMS [M+H]+: 633.6

Intermediate 145

4-[3-(4-aminophenyl)-1-ethyl-1H-pyrazol-4-yl]-2-[3-(N-pyrrolidinylmethyl)phenyl]-1H-pyrrolo[2,3-b]pyridine Following the procedure described for Intermediate 102 using 4-[3-(4-nitrophenyl)-1-ethyl-1H-pyrazol-4-yl]-2-[3-(N-pyrrolidinylmethyl)phenyl]-1-phenylsulfonyl-1H-pyrrolo[2,3-b], furnished the title compound. ESMS [M+H]+: 463.4

Intermediate 146

N,N-dimethyl-1-{4-[1-(phenylsulfonyl)-4-(4,4,5,5-tetramethyl-1,3,2-dioxaborolan-2-yl)-1H-pyrrolo[2,3-b]pyridin-2-yl]phenyl}methanamine Following the described for Intermediate 32 using ({4-[4-bromo-1-(phenylsulfonyl)-1H-pyrrolo[2,3-b]pyridin-2-yl]phenyl}methyl)dimethylamine provided the title compound. ESMS [M+H]+: 518.4; [M-(CH$_3$)$_2$CC(CH$_3$)$_2$+3H]: 436.2

Intermediate 147

4-bromo-1-methyl-3-(4-nitrophenyl)-1H-pyrazole

Following the procedure described for Intermediate 3 using methyliodide provided the titled compound as a light yellow solid. ESMS [M+H]+: 282.0

Intermediate 148

[4-(4-bromo-1-methyl-1H-pyrazol-3-yl)phenyl]amine

Following the procedure described for Intermediate 7 using 4-bromo-1-methyl-3-(4-nitrophenyl)-1H-pyrazole provided the title compound. ESMS [M+H]+: 252.0

Intermediate 149

N'-[4-(4-bromo-1-methyl-1H-pyrazol-3-yl)phenyl]-N,N-dimethylurea

Following the procedure described for Example 5a using [4-(4-bromo-1-methyl-1H-pyrazol-3-yl)phenyl]amine and 2M dimethylamine in tetrahydrofuran provided the title compound. ESMS [M+H]+: 323.2

Intermediate 150

4-bromo-1-(1-methylethyl)-3-(4-nitrophenyl)-1H-pyrazole

Following the procedure described for Intermediate 3 using isopropyliodide provided the title compound. ESMS [M+H]$^+$: 310.

Intermediate 151

{4-[4-bromo-1-(1-methylethyl)-1H-pyrazol-3-yl]phenyl}amine

Following the procedure described for Intermediate 7 using 4-bromo-1-(1-methylethyl)-3-(4-nitrophenyl)-1H-pyrazole provided the title compound. ESMS [M+H]$^+$: 280.2

Intermediate 152

N'-{4-[4-bromo-1-(1-methylethyl)-1H-pyrazol-3-yl]phenyl}-N,N-dimethylurea

Following the procedure described in Example 5a using {4-[4-bromo-1-(1-methylethyl)-1H-pyrazol-3-yl]phenyl}amine and 2M dimethylamine in tetrahydrofuran provided the title compound. ESMS [M+H]$^+$: 351.2

Intermediate 153

N,N-dimethyl-1-(4-{4-[1-methyl-3-(4-nitrophenyl)-1H-pyrazol-4-yl]-1H-pyrrolo[2,3-b]pyridin-2-yl}phenyl)methanamine Following the procedure described in Intermediate 100 and Intermediate 21 using N,N-dimethyl-1-{4-[1-(phenylsulfonyl)-4-(4,4,5,5-tetramethyl-1,3,2-dioxaborolan-2-yl)-1H-pyrrolo[2,3-b]pyridin-2-yl]phenyl}methanamine and 4-bromo-1-methyl-3-(4-nitrophenyl)-1H-pyrazole provided the title compound. ESMS [M+H]$^+$: 453.2.

Intermediate 154

[(4-{4-[3-(4-aminophenyl)-1-methyl-1H-pyrazol-4-yl]-1H-pyrrolo[2,3-b]pyridin-2-yl}phenyl)methyl]dimethylamine Following the procedure described for Intermediate 7 using N,N-dimethyl-1-(4-{4-[1-methyl-3-(4-nitrophenyl)-1H-pyrazol-4-yl]-1H-pyrrolo[2,3-b]pyridin-2-yl}phenyl)methanamine provided the title compound. ESMS [M+H]$^+$: 423.4

Intermediate 155

N,N-dimethyl-1-(4-{4-[1-(1-methylethyl)-3-(4-nitrophenyl)-1H-pyrazol-4-yl]-1H-pyrrolo[2,3-b]pyridin-2-yl}phenyl)methanamine Following the procedure described in Intermediate 100 and Intermediate 21 using N,N-dimethyl-1-{4-[1-(phenylsulfonyl)-4-(4,4,5,5-tetramethyl-1,3,2-dioxaborolan-2-yl)-1H-pyrrolo[2,3-b]pyridin-2-yl]phenyl}methanamine and 4-bromo-1-(1-methylethyl)-3-(4-nitrophenyl)-1H-pyrazole provided the title compound. ESMS [M+H]$^+$: 481.4

Intermediate 156

[(4-{4-[3-(4-aminophenyl)-1-(1-methylethyl)-1H-pyrazol-4-yl]-1H-pyrrolo[2,3-b]pyridin-2-yl}phenyl)methyl]dimethylamine Following the procedure described for Intermediate 7 using N,N-dimethyl-1-(4-{4-[1-(1-methylethyl)-3-(4-nitrophenyl)-1H-pyrazol-4-yl]-1H-pyrrolo[2,3-b]pyridin-2-yl}phenyl)methanamine provided the title compound. ESMS [M+H]$^+$: 451.4.

Intermediate 157

1-methyl-3-(4-nitrophenyl)-4-(4,4,5,5-tetramethyl-1,3,2-dioxaborolan-2-yl)-1H-pyrazole Following the procedure described for Intermediate 5 using 4-bromo-1-methyl-3-(4-nitrophenyl)-1H-pyrazole provided the title compound. ESMS [M+]+: 329.4

Intermediate 158

1-(1-methylethyl)-3-(4-nitrophenyl)-4-(4,4,5,5-tetramethyl-1,3,2-dioxaborolan-2-yl)-1H-pyrazole Following the procedure described for Intermediate 5 using 4-bromo-1-(1-methylethyl)-3-(4-nitrophenyl)-1H-pyrazole provided the title compound. ESMS [M]+: 357.2.

Intermediate 159

4-[4-bromo-1-(phenylsulfonyl)-1H-indol-2-yl]benzaldehyde

Following the procedure described for Intermediate 99 using (4-formylphenyl)boronic acid provided the title compound. ESMS [M+]: 441.2.

Intermediate 160

4-[4-[1-ethyl-3-(4-nitrophenyl)-1H-pyrazol-4-yl]-1-(phenylsulfonyl)-1H-indol-2-yl]benzaldehyde Following the procedure described for Intermediate 100 using 1-ethyl-3-(4-nitrophenyl)-4-(4,4,5,5-tetramethyl-1,3,2-dioxaborolan-2-yl)-1H-pyrazole and 4-[4-bromo-1-(phenylsulfonyl)-1H-indol-2-yl]benzaldehyde provided the title compound. ESMS [M+H]+:

Intermediate 161

4-[4-[1-methyl-3-(4-nitrophenyl)-1H-pyrazol-4-yl]-1-(phenylsulfonyl)-1H-indol-2-yl]benzaldehyde Following the procedure described for Intermediate 100 using 4-[4-bromo-1-(phenylsulfonyl)-1H-indol-2-yl]benzaldehyde and 1-methyl-3-(4-nitrophenyl)-4-(4,4,5,5-tetramethyl-1,3,2-dioxaborolan-2-yl)-1H-pyrazole provided the title compound. ESMS [M+H]+: 564.2.

Intermediate 162

4-[4-[1-(1-methylethyl)-3-(4-nitrophenyl)-1H-pyrazol-4-yl]-1-(phenylsulfonyl)-1H-indol-2-yl]benzaldehyde Following the procedure for Intermediate 100 using 4-[4-bromo-1-(phenylsulfonyl)-1H-indol-2-yl]benzaldehyde and 1-(1-methylethyl)-3-(4-nitrophenyl)-4-(4,4,5,5-tetramethyl-1,3,2-dioxaborolan-2-yl)-1H-pyrazole provided the title compound. ESMS [M+H]+: 592.4.

Intermediate 163

2-(ethyl{[4-[1-ethyl-3-(4-nitrophenyl)-1H-pyrazol-4-yl]-1-(phenylsulfonyl)-1H-pyrrolo[2,3-b]pyridin-2-yl]methyl}amino)ethanol Following the procedure described in Intermediate 101 using 4-[1-ethyl-3-(4-nitrophenyl)-1H-pyrazol-4-yl]-1-(phenylsulfonyl)-1H-pyrrolo[2,3-b]pyridine-2-carbaldehyde and 2-(ethylamino)ethanol provided the title compound as a yellow solid. ESMS [M+H]$^+$: 651.4.

Intermediate 164

2-[({4-[3-(4-aminophenyl)-1-ethyl-1H-pyrazol-4-yl]-1H-pyrrolo[2,3-b]pyridin-2-yl}methyl)(ethyl)amino]ethanol Following the procedure described for Intermediate 102 using 2-(ethyl{[4-[1-ethyl-3-(4-nitrophenyl)-1H-pyrazol-4-yl]-1-(phenylsulfonyl)-1H-pyrrolo[2,3-b]pyridin-2-yl]methyl}amino)ethanol the title compound. ESMS [M+H]$^+$: 481.2.

Intermediate 165

2-[4-({4-[4-[1-ethyl-3-(4-nitrophenyl)-1H-pyrazol-4-yl]-1-(phenylsulfonyl)-1H-pyrrolo[2,3-b]pyridin-2-yl]phenyl}methyl)-1-piperazinyl]ethanol Following the procedure described in Intermediate 101 using 4-[1-ethyl-3-(4-nitrophenyl)-1H-pyrazol-4-yl]-1-(phenylsulfonyl)-1H-pyrrolo[2,3-b]pyridine-2-carbaldehyde and 2-(1-piperazinyl)ethanol provided the title compound. ESMS (M+H)$^+$: 692.4.

Intermediate 166

2-{4-[(4-{4-[3-(4-aminophenyl)-1-ethyl-1H-pyrazol-4-yl]-1H-pyrrolo[2,3-b]pyridin-2-yl}phenyl)methyl]-1-piperazinyl}ethanol Following the procedure described in Intermediate 102 with 2-[4-({4-[4-[1-ethyl-3-(4-nitrophenyl)-1H-pyrazol-4-yl]-1-(phenylsulfonyl)-1H-pyrrolo[2,3-b]pyridin-2-yl]phenyl}methyl)-1-piperazinyl]ethanol provided the title compound. ESMS (M+H)$^+$: 522.4.

Intermediate 167

4-{1-ethyl-4-[2-[4-(4-morpholinylmethyl)phenyl]-1-(phenylsulfonyl)-1H-pyrrolo[2,3-b]pyridin-4-yl]-1H-pyrazol-3-yl}aniline Following the procedure described for Intermediate 102 using 4-[1-ethyl-3-(4-nitrophenyl)-1H-pyrazol-4-yl]-2-[4-(4-morpholinylmethyl)phenyl]-1H-pyrrolo[2,3-b]pyridine provided the title compound. ESMS [M+H]$^+$: 479.0

Intermediate 168

4-[1-ethyl-3-(4-nitrophenyl)-1H-pyrazol-4-yl]-1-(phenylsulfonyl)-2-[3-(1-pyrrolidinylmethyl)phenyl]-1H-pyrrolo[2,3-b]pyridine Following the procedure described for Intermediate 101 using 3-[4-[1-ethyl-3-(4-nitrophenyl)-1H-pyrazol-4-yl]-1-(phenylsulfonyl)-1H-pyrrolo[2,3-b]pyridin-2-yl]benzaldehyde and pyrrolidine provided the title compound. ESMS [M+H]$^+$: 633.0.

Intermediate 169

4-(1-ethyl-4-{2-[3-(1-pyrrolidinylmethyl)phenyl]-1H-pyrrolo[2,3-b]pyridin-4-yl}-1H-pyrazol-3-yl)aniline Following the procedure described for Intermediate 102 using 4-[1-ethyl-3-(4-nitrophenyl)-1H-pyrazol-4-yl]-1-(phenylsulfonyl)-2-[3-(1-pyrrolidinylmethyl)phenyl]-1H-pyrrolo[2,3-b]pyridine provided the title compound. ESMS [M+H]$^+$: 463.0

Intermediate 170

4-[1-(1-methylethyl)-3-(4-nitrophenyl)-1H-pyrazol-4-yl]-1-(phenylsulfonyl)-2-[4-(1-pyrrolidinylmethyl)phenyl]-1H-pyrrolo[2,3-b]pyridine Following the procedure described for Intermediate 101 using 4-[4-[1-(1-methylethyl)-3-(4-nitrophenyl)-1H-pyrazol-4-yl]-1-(phenylsulfonyl)-1H-pyrrolo[2,3-b]pyridin-2-yl]benzaldehyde and pyrrolidine provided the title compound. ESMS [M+H]$^+$=647.6.

Intermediate 171

4-(1-(1-methylethyl)-4-{2-[4-(1-pyrrolidinylmethyl)phenyl]-1H-pyrrolo[2,3-b]pyridin-4-yl}-1H-pyrazol-3-yl)aniline Following the procedure described in Intermediate 102 using 4-[1-(1-methylethyl)-3-(4-nitrophenyl)-1H-pyrazol-4-yl]-1-(phenylsulfonyl)-2-[4-(1-pyrrolidinylmethyl)phenyl]-1H-pyrrolo[2,3-b]pyridine provided the title compound. ESMS [M+H]$^+$=477.3.

Intermediate 172

3-bromo-4-methylbenzaldehyde

To a stirred solution of 3-bromo-4-methylbenzyl alcohol (4.43 g, 22 mMol) in CHCl$_3$ (100 mL) was added MnO$_2$ (15 g, 172 mMol). The reaction was stirred and refluxed (70° C. oil bath) for 18 h, cooled to RT, filtered through Celite®, rinsed with CHCl$_3$, and concentrated to dryness under vacuum. Purification by flash chromatography on silica gel (10% EtOAc, hexanes) gave the title product (3.0 g, 68%). $^1$H NMR (400 MHz, CDCl$_3$) δ 9.98 (s, 1H), 7.75 (d, J=1.5 Hz, 1 H), 7.73 (d, J=8.1 Hz, 1 H), 7.57 (dd, J=8.1, 1.5 Hz, 1 H), 7.28 (s, 1 H), 2.50 (s, 3 H).

Intermediate 173

4-methyl-3-(4,4,5,5-tetramethyl-1,3,2-dioxaborolan-2-yl)benzaldehyde

Following the procedure described for Intermediate 5 using 3-bromo-4-methylbenzaldehyde provided the title compound. ESMS [M+H]+: 246.4.

Intermediate 174

3-[4-bromo-1-(phenylsulfonyl)-1H-pyrrolo[2,3-b]pyridin-2-yl]-4-methylbenzaldehyde Following the procedure described in Intermediate 99 using 4-methyl-3-(4,4,5,5-tetramethyl-1,3,2-dioxaborolan-2-yl)benzaldehyde and 3-formyl-6-methyl-phenylboronate pinacolato ester provided the title compound. ESMS [M+H]+: 455.0.

Intermediate 175

3-[4-[1-ethyl-3-(4-nitrophenyl)-1H-pyrazol-4-yl]-1-(phenylsulfonyl)-1H-pyrrolo[2,3-b]pyridin-2-yl]-4-methylbenzaldehyde Following the procedure described for Intermediate 100 using 3-[4-bromo-1-(phenylsulfonyl)-1H-pyrrolo[2,3-b]pyridin-2-yl]-4-methylbenzaldehyde provided the title compound. ESMS [M+H]+: 592.4.

Intermediate 176

({3-[4-[1-ethyl-3-(4-nitrophenyl)-1H-pyrazol-4-yl]-1-(phenylsulfonyl)-1H-pyrrolo[2,3-b]pyridin-2-yl]-4-methylphenyl}methyl)dimethylamine Following the procedure described for Intermediate 101 using 3-[4-[1-ethyl-3-(4-nitrophenyl)-1H-pyrazol-4-yl]-1-(phenylsulfonyl)-1H-pyrrolo[2,3-b]pyridin-2-yl]-4-methylbenzaldehyde provided the title compound. ESMS [M+H]+: 621.6.

Intermediate 177

[(3-{4-[3-(4-aminophenyl)-1-ethyl-1H-pyrazol-4-yl]-1H-pyrrolo[2,3-b]pyridin-2-yl}-4-methylphenyl)methyl]dimethylamine Following the procedure described for Intermediate 102 using ({3-[4-[1-ethyl-3-(4-nitrophenyl)-1H-pyrazol-4-yl]-1-(phenylsulfonyl)-1H-pyrrolo[2,3-b]pyridin-2-yl]-4-methylphenyl}methyl)dimethylamine provided the title compound. ESMS [M+H]+: 451.4.

Intermediate 178

1,1-dimethylethyl (2-{4-bromo-3-[(1E,2Z)-1-ethylidene-4-nitro-2,4-pentadien-1-yl]-1H-pyrazol-1-yl}ethyl)methylcarbamate Following the procedure described for Intermediate 3 using 2-(N-t-butoxycarbonyl-N-methylamino)ethylbromide provided the title compound. ESMS [M+H]+: 425.2.

Intermediate 179

1,1-dimethylethyl {2-[3-[(1E,2Z)-1-ethylidene-4-nitro-2,4-pentadien-1-yl]-4-(4,4,5,5-tetramethyl-1,3,2-dioxaborolan-2-yl)-1H-pyrazol-1-yl]ethyl}methylcarbamate Following the procedure described for Intermediate 5 using 1,1-dimethylethyl (2-{4-bromo-3-[(1E,2Z)-1-ethylidene-4-nitro-2,4-pentadien-1-yl]-1H-pyrazol-1-yl}ethyl)methylcarbamate provided the title compound. ESMS [M+H]+: 472.2.

Intermediate 180

1,1-dimethylethyl {2-[4-[2-{4-[(dimethylamino)methyl]phenyl}-1-(phenylsulfonyl)-1H-pyrrolo[2,3-b]pyridin-4-yl]-3-(4-nitrophenyl)-1H-pyrazol-1-yl]ethyl}methylcarbamate Following the procedure described for Intermediate 100 using 1,1-dimethylethyl {2-[3-[(1E,2Z)-1-ethylidene-4-nitro-2,4-pentadien-1-yl]-4-(4,4,5,5-tetramethyl-1,3,2-dioxaborolan-2-yl)-1H-pyrazol-1-yl]ethyl}methylcarbamate and ({4-[4-bromo-1-(phenylsulfonyl)-1H-pyrrolo[2,3-b]pyridin-2-yl]phenyl}methyl)dimethylamine provided the title compound. ESMS [M+H]+: 736.4.

Intermediate 181

1,1-dimethylethyl (2-{3-(4-aminophenyl)-4-[2-{4-[(dimethylamino)methyl]phenyl}-1-(phenylsulfonyl)-1H-pyrrolo[2,3-b]pyridin-4-yl]-1H-pyrazol-1-yl}ethyl)methylcarbamate Following the procedure described for Intermediate 102 using 1,1-dimethylethyl {2-[4-[2-{4-[(dimethylamino)methyl]phenyl}-1-(phenylsulfonyl)-1H-pyrrolo[2,3-b]pyridin-4-yl]-3-(4-nitrophenyl)-1H-pyrazol-1-yl]ethyl}methylcarbamate provided the title compound. ESMS [M+H]+: 566.6.

Intermediate 182

4-[4-bromo-1-(phenylsulfonyl)-1H-pyrrolo[2,3-b]pyridin-2-yl]-2-fluorobenzaldehyde Following the procedure described for Intermediate 99 using (3-fluoro-4-formylphenyl)boronic acid provided the title compound. ESMS [M+H]+: 459.2.

Intermediate 183

4-[4-[1-ethyl-3-(4-nitrophenyl)-1H-pyrazol-4-yl]-1-(phenylsulfonyl)-1H-pyrrolo[2,3-b]pyridin-2-yl]-2-fluorobenzaldehyde Following the procedure described for Intermediate 100 using 4-[4-bromo-1-(phenylsulfonyl)-1H-pyrrolo[2,3-b]pyridin-2-yl]-2-fluorobenzaldehyde provided the title compound. ESMS[M+H]+: 596.2.

Intermediate 184

4-[1-ethyl-3-(4-nitrophenyl)-1H-pyrazol-4-yl]-2-[3-fluoro-4-(1-pyrrolidinylmethyl)phenyl]-1-(phenylsulfonyl)-1H-pyrrolo[2,3-b]pyridine Following the procedure described for Intermediate 101 using 4-[4-[1-ethyl-3-(4-nitrophenyl)-1H-pyrazol-4-yl]-1-(phenylsulfonyl)-1H-pyrrolo[2,3-b]pyridin-2-yl]-2-fluorobenzaldehyde and pyrrolidine provided the title compound. ESMS[M+H]+: 651.4.

Intermediate 185

4-(1-ethyl-4-{2-[3-fluoro-4-(1-pyrrolidinylmethyl) phenyl]-1H-pyrrolo[2,3-b]pyridin-4-yl}-1H-pyrazol-3-yl)phenyl]amine Following the procedure described for Intermediate 102 using 4-[1-ethyl-3-(4-nitrophenyl)-1H-pyrazol-4-yl]-2-[3-fluoro-4-(1-pyrrolidinylmethyl)phenyl]-1-(phenylsulfonyl)-1H-pyrrolo[2,3-b]pyridine provided the title compound. ESMS [M+H]+: 481.4.

Intermediate 186

5-[4-bromo-1-(phenylsulfonyl)-1H-pyrrolo[2,3-b] pyridin-2-yl]-2-fluorobenzaldehyde Following the procedure described for Intermediate 99 using (4-fluoro-3-formylphenyl)boronic acid provided the title compound. ESMS [M+H]+: 459.2.

Intermediate 187

5-[4-[1-ethyl-3-(4-nitrophenyl)-1H-pyrazol-4-yl]-1-(phenylsulfonyl)-1H-pyrrolo[2,3-b]pyridin-2-yl]-2-fluorobenzaldehyde Following the procedure described for Intermediate 100 using 5-[4-bromo-1-(phenylsulfonyl)-1H-pyrrolo[2,3-b]pyridin-2-yl]-2-fluorobenzaldehyde provided the title compound. ESMS [M+H]+: 596.2.

Intermediate 188

4-[1-ethyl-3-(4-nitrophenyl)-1H-pyrazol-4-yl]-2-[4-fluoro-3-(1-pyrrolidinylmethyl)phenyl]-1-(phenylsulfonyl)-1H-pyrrolo[2,3-b]pyridine Following the procedure described for Intermediate 101 using 5-[4-[1-ethyl-3-(4-nitrophenyl)-1H-pyrazol-4-yl]-1-(phenylsulfonyl)-1H-pyrrolo[2,3-b]pyridin-2-yl]-2-fluorobenzaldehyde provided the title compound. ESMS [M+H]+: 651.4.

Intermediate 189

[4-(1-ethyl-4-{2-[4-fluoro-3-(1-pyrrolidinylmethyl) phenyl]-1H-pyrrolo[2,3-b]pyridin-4-yl}-1H-pyrazol-3-yl)phenyl]amine Following the procedure described for Intermediate 102 using 4-[1-ethyl-3-(4-nitrophenyl)-1H-pyrazol-4-yl]-2-[4-fluoro-3-(1-pyrrolidinylmethyl)phenyl]-1-(phenylsulfonyl)-1H-pyrrolo[2,3-b]pyridine provided the title compound. ESMS [M+H]+: 481.4.

Intermediate 190

{3-[4-bromo-1-(phenylsulfonyl)-1H-pyrrolo[2,3-b] pyridin-2-yl]phenyl}methanol

Following the procedure described for Intermediate 99 using [3-(hydroxymethyl)phenyl]boronic acid provided the title compound. ESMS [M+H]+: 443.2.

Intermediate 191

{3-[4-[1-ethyl-3-(4-nitrophenyl)-1H-pyrazol-4-yl]-1-(phenylsulfonyl)-1H-pyrrolo[2,3-b]pyridin-2-yl] phenyl}methanol Following the procedure described for Intermediate 100 using {3-[4-bromo-1-(phenylsulfonyl)-1H-pyrrolo[2,3-b] pyridin-2-yl]phenyl}methanol provided the title compound. ESMS [M+H]+: 580.4.

Intermediate 192

(3-{4-[3-(4-aminophenyl)-1-ethyl-1H-pyrazol-4-yl]-1H-pyrrolo[2,3-b]pyridin-2-yl}phenyl)methanol Following the procedure described for Intermediate 102 using {3-[4-[1-ethyl-3-(4-nitrophenyl)-1H-pyrazol-4-yl]-1-(phenylsulfonyl)-1H-pyrrolo[2,3-b]pyridin-2-yl] phenyl}methanol provided the title compound. ESMS [M+H]+: 410.4.

Intermediate 193

2-[3-(4,4,5,5-tetramethyl-1,3,2-dioxaborolan-2-yl) phenyl]ethanol

Following the procedure described for Intermediate 5 using 2-(3-bromophenyl)ethanol provided the title compound. ESMS [M+H]+: 249.4.

Intermediate 194

2-{3-[4-bromo-1-(phenylsulfonyl)-1H-pyrrolo[2,3-b] pyridin-2-yl]phenyl}ethanol

Following the procedure described for Intermediate 99 using 2-[3-(4,4,5,5-tetramethyl-1,3,2-dioxaborolan-2-yl) phenyl]ethanol provided the title compound. ESMS [M+H]+: 457.2.

Intermediate 195

2-{3-[4-[1-ethyl-3-(4-nitrophenyl)-1H-pyrazol-4-yl]-1-(phenylsulfonyl)-1H-pyrrolo[2,3-b]pyridin-2-yl] phenyl}ethanol Following the procedure described for Intermediate 100 using 2-{3-[4-bromo-1-(phenylsulfonyl)-1H-pyrrolo[2,3-b] pyridin-2-yl]phenyl}ethanol provided the title compound. ESMS [M+H]+: 594.4.

Intermediate 196

2-(3-{4-[3-(4-aminophenyl)-1-ethyl-1H-pyrazol-4-yl]-1H-pyrrolo[2,3-b]pyridin-2-yl}phenyl)ethanol Following the procedure described for Intermediate 102 using 2-{3-[4-[1-ethyl-3-(4-nitrophenyl)-1H-pyrazol-4-yl]-1-(phenylsulfonyl)-1H-pyrrolo[2,3-b]pyridin-2-yl] phenyl}ethanol provided the title compound. ESMS [M+H]+: 424.2.

Intermediate 197

1,1-dimethylethyl {2-[4-[2-[3-(hydroxymethyl)phenyl]-1-(phenylsulfonyl)-1H-pyrrolo[2,3-b]pyridin-4-yl]-3-(4-nitrophenyl)-1H-pyrazol-1-yl]ethyl}methylcarbamate Following the procedure described for Intermediate 100 using {3-[4-bromo-1-(phenylsulfonyl)-1H-pyrrolo[2,3-b]pyridin-2-yl]phenyl}methanol and 1,1-dimethylethyl {2-[3-[(2E,2Z)-1-ethylidene-4-nitro-2,4-pentadien-1-yl]-4-(4,4,5,5-tetramethyl-1,3,2-dioxaborolan-2-yl)-1H-pyrazol-1-yl]ethyl}methylcarbamate provided the title compound. ESMS [M+H]+: 709.2.

Intermediate 198

1,1-dimethylethyl [2-(3-(4-aminophenyl)-4-{2-[3-(hydroxymethyl)phenyl]-1H-pyrrolo[2,3-b]pyridin-4-yl}-1H-pyrazol-1-yl)ethyl]methylcarbamate Following the procedure described for Intermediate 102 using 1,1-dimethylethyl {2-[4-[2-[3-(hydroxymethyl)phenyl]-1-(phenylsulfonyl)-1H-pyrrolo[2,3-b]pyridin-4-yl]-3-(4-nitrophenyl)-1H-pyrazol-1-yl]ethyl}methylcarbamate provided the title compound. ESMS [M+H]+: 539.5.

Intermediate 199

1,1-dimethylethyl (2-{3-(4-{[(dimethylamino)carbonyl]amino}phenyl)-4-[2-(3-formylphenyl)-1H-pyrrolo[2,3-b]pyridin-4-yl]-1H-pyrazol-1-yl}ethyl)methylcarbamate To a stirred solution of 1,1-dimethylethyl [2-(3-(4-{[(dimethylamino)carbonyl]amino}phenyl)-4-{2-[3-(hydroxymethyl)phenyl]-1H-pyrrolo[2,3-b]pyridin-4-yl}-1H-pyrazol-1-yl)ethyl]methylcarbamate (1.24 g, 2.0 mMol) in CHCl$_3$ (100 mL) was added activated MnO$_2$ (2.5 g, 28.7 mMol). The reaction was stirred and refluxed (70° C. oil bath) for 8 h, cooled to RT, filtered through a pad of Celite®, rinsed with CHCl$_3$, and evaporated to dryness under vacuum. Purification by flash chromatography on silica gel (5 to 10% MeOH in (1:1) EtOAc/CHCl$_3$) provided the title compound (0.94 g, 77%) as a pale yellow solid. ESMS [M+H]+: 608.6.

Intermediate 200

1,1-dimethylethyl {2-[3-(4-{[(dimethylamino)carbonyl]amino}phenyl)-4-(2-{3-[(dimethylamino)methyl]phenyl}-1H-pyrrolo[2,3-b]pyridin-4-yl)-1H-pyrazol-1-yl]ethyl}methylcarbamate Following the procedure described for Intermediate 101 using 1,1-dimethylethyl (2-{3-(4-{[(dimethylamino)carbonyl]amino}phenyl)-4-[2-(3-formylphenyl)-1H-pyrrolo[2,3-b]pyridin-4-yl]-1H-pyrazol-1-yl}ethyl)methylcarbamate provided the title compound. ESMS [M+H]+: 637.5.

Intermediate 201

4-[1-(phenylsulfonyl)-4-(4,4,5,5-tetramethyl-1,32-dioxaborolan-2-yl)-1H-pyrrolo[2,3-b]pyridin-2-yl]benzaldehyde Following the procedure described for Intermediate 5 using 4-[4-bromo-1-(phenylsulfonyl)-1H-pyrrolo[2,3-b]pyridin-2-yl]benzaldehyde and dichloro[1,1'-bis(diphenylphosphino)ferrocene]palladium(II) provided the title compound. ESMS [M+H]: 488.4.

Intermediate 202

N'-(4-{4-[2-(4-formylphenyl)-1H-pyrrolo[2,3-b]pyridin-4-yl]-1-methyl-1H-pyrazol-3-yl}phenyl)-N,N-dimethylurea Following the procedure described for Intermediate 6 and then Intermediate 21 using 4-[1-(phenylsulfonyl)-4-(4,4,5,5-tetramethyl-1,3,2-dioxaborolan-2-yl)-1H-pyrrolo[2,3-b]pyridin-2-yl]benzaldehyde and N'-[4-(4-bromo-1-methyl-1H-pyrazol-3-yl)phenyl]-N,N-dimethylurea provided the title compound. ESMS [M+H]+: 465.4.

Intermediate 203

4-bromo-1-(methylsulfonyl)-3-(4-nitrophenyl)-1H-pyrazole

Following the procedure described for Intermediate 3 using methanesulfonyl chloride provided the title compound. ESMS [M+H]+: 347.8/345.8.

Intermediate 204

N'-{4-[4-bromo-1-(methylsulfonyl)-1H-pyrazol-3-yl]phenyl}-N,N-dimethylurea

Following the procedures described for Intermediate 7 using 4-bromo-1-(methylsulfonyl)-3-(4-nitrophenyl)-1H-pyrazole and then for Example 47 using dimethylamine provided the title compound. ESMS [M]+: 387.2.

Intermediate 205

N'-(4-{4-[2-(4-formylphenyl)-1H-pyrrolo[2,3-b]pyridin-4-yl]-1H-pyrazol-3-yl}phenyl)-N,N-dimethylurea Following the procedure described for Intermediate 6 and then Intermediate 21 using 4-[1-(phenylsulfonyl)-4-(4,4,5,5-tetramethyl-1,3,2-dioxaborolan-2-yl)-1H-pyrrolo[2,3-b]pyridin-2-yl]benzaldehyde and N'-{4-[4-bromo-1-(methylsulfonyl)-1H-pyrazol-3-yl]phenyl}-N,N-dimethylurea provided the title compound. ESMS [M+H]+: 380.2.

Intermediate 206

Preparation of 2-{4-[(4-{4-[3-(4-aminophenyl)-1-(1-methylethyl)-1H-pyrazol-4-yl]-1H-pyrrolo[2,3-b]pyridin-2-yl}phenyl)methyl]-1-piperazinyl}ethanol Following the procedure described for Intermediate 101 and then Intermediate 102 using 4-{4-[1-(1-methylethyl)-3-(4-nitrophenyl)-1H-pyrazol-4-yl]-1H-pyrrolo[2,3-b]pyridin-2-yl}benzaldehyde and 2-(1-piperazinyl)ethanol provided the title compound. ESMS [M+H]+: 536.4.

Intermediate 207

2-acetyl-7-(4,4,5,5-tetramethyl-1,3,2-dioxaborolan-2-yl)-1,2,3,4-tetrahydroisoquinoline Following the procedure described for Intermediate 32 using 7-bromo-1,2,3,4-tetrahydroisoquinoline hydrochloride (Ennova MedChem Group, Inc) provided the title compound. ESMS [M+H]$^+$: 301.4.

Intermediate 208

2-acetyl-7-[4-bromo-1-(phenylsulfonyl)-1H-pyrrolo[2,3-b]pyridin-2-yl]-1,2,3,4-tetrahydroisoquinoline Following the procedure described for Intermediate 99 using 2-acetyl-7-(4,4,5,5-tetramethyl-1,3,2-dioxaborolan-2-yl)-1,2,3,4-tetrahydroisoquinoline provided the title compound. ESMS [M+H]$^+$: 510.2.

Intermediate 209

N'-(4-{4-[2-(2-acetyl-1,2,3,4-tetrahydro-7-isoquinolinyl)-1-(phenylsulfonyl)-1H-pyrrolo[2,3-b]pyridin-4-yl]-1-ethyl-1H-pyrazol-3-yl}phenyl)-N,N-dimethylurea Following the procedure described for Intermediate 32 with 2-acetyl-7-[4-bromo-1-(phenylsulfonyl)-1H-pyrrolo[2,3-b]pyridin-2-yl]-1,2,3,4-tetrahydroisoquinoline. Using this product crude and following the procedure described in Intermediate 100 using N'-[4-(4-bromo-1-ethyl-1H-pyrazol-3-yl)phenyl]-N,N-dimethylurea and stirring for 4.5 hours provided the title compound. ESMS [M+H]$^+$: 688.6.

Intermediate 210

7-bromo-2-methyl-1,2,3,4-tetrahydroisoquinoline

Following the procedure described for Intermediate 3 using 7-bromo-1,2,3,4-tetrahydroisoquinoline hydrochloride and iodomethane provided the title compound. ESMS [M+H]$^+$: 226.0.

Intermediate 211

2-methyl-7-(4,4,5,5-tetramethyl-1,3,2-dioxaborolan-2-yl)-1,2,3,4-tetrahydroisoquinoline Following the procedure described for Intermediate 32 using 7-bromo-2-methyl-1,2,3,4-tetrahydroisoquinoline provided the title compound. ESMS [M+H]$^+$: 273.4.

Intermediate 212

7-[4-bromo-1-(phenylsulfonyl)-1H-pyrrolo[2,3-b]pyridin-2-yl]-2-methyl-1,2,3,4-tetrahydroisoquinoline Following the procedure described for Intermediate 99 using 2-methyl-7-(4,4,5,5-tetramethyl-1,3,2-dioxaborolan-2-yl)-1,2,3,4-tetrahydroisoquinoline provided the title compound. ESMS [M+H]$^+$: 482.2.

Intermediate 213

N'-(4-{1-ethyl-4-[2-(2-methyl-1,2,3,4-tetrahydro-7-isoquinolinyl)-1-(phenylsulfonyl)-1H-pyrrolo[2,3-b]pyridin-4-yl]-1H-pyrazol-3-yl}phenyl)-N,N-dimethylurea Following the procedure described for Intermediate 32 with 7-[4-bromo-1-(phenylsulfonyl)-1H-pyrrolo[2,3-b]pyridin-2-yl]-2-methyl-1,2,3,4-tetrahydroisoquinoline. Using this product crude and following the procedure described for Intermediate 100 using N'-[4-(4-bromo-1-ethyl-1H-pyrazol-3-yl)phenyl]-N,N-dimethylurea and stirring for 4.5 hours provided the title compound. ESMS [M+H]$^+$: 660.6.

Intermediate 214

1-[2-(4-bromophenyl)ethyl]pyrrolidine

To a solution of 4-bromophenethyl alcohol (2.54 mmol) and p-toluenesulfonyl chloride (2.74 mmol) in anhydrous dichloromethane (5 mL) under nitrogen was added triethylamine (2.74 mmol) dropwise by syringe at room temperature. The reaction was stirred for 16 hours at room temperature. A white precipitate formed. 1N HCl solution (5 mL) was added to the suspension and the reaction became clear. The layers were separated and the organic layer was washed with saturated aqueous sodium bicarbonate solution (5 mL), dried over magnesium sulfate and concentrated in vacuo to give a white solid. To this crude product was added pyrrolidine (1 mL) under nitrogen and the reaction was stirred at 50° C. for 90 minutes. The reaction was cooled to room temperature and concentrated in vacuo. The resulting residue was dissolved in ethyl acetate (20 mL) and washed successively with water (20 mL) and saturated aqueous sodium bicarbonate solution (20 mL), dried over magnesium sulfate and concentrated in vacuo. Purification by silica gel chromatography (20-100% ethyl acetate/hexanes) afforded the title compound as a white solid (80%). ESMS [M+H]$^+$: 254.2.

Intermediate 215

1-{2-[4-(4,4,5,5-tetramethyl-1,3,2-dioxaborolan-2-yl)phenyl]ethyl}pyrrolidine

Following the procedure described for Intermediate 32 using 1-[2-(4-bromophenyl)ethyl]pyrrolidine provided the title compound. ESMS [M+H]$^+$: 301.4.

Intermediate 216

4-bromo-1-(phenylsulfonyl)-2-{4-[2-(1-pyrrolidinyl)ethyl]phenyl}-1H-pyrrolo[2,3-b]pyridine Following the procedure described for Intermediate 99 using 1-{2-[4-(4,4,5,5-tetramethyl-1,3,2-dioxaborolan-2-yl)phenyl]ethyl}pyrrolidine provided the title compound. ESMS [M+H]$^+$: 510.2.

Intermediate 217

N'-{4-[1-ethyl-4-(1-(phenylsulfonyl)-2-{4-[2-(1-pyrrolidinyl)ethyl]phenyl}-1H-pyrrolo[2,3-b]pyridin-4-yl)-1H-pyrazol-3-yl]phenyl}-N,N-dimethylurea Following the procedure described for Intermediate 32 using 4-bromo-1-(phenylsulfonyl)-2-{4-[2-(1-pyrrolidinyl)ethyl]phenyl}-1H-pyrrolo[2,3-b]pyridine and then following the procedure described for Intermediate 100 using N'-[4-(4-bromo-1-ethyl-1H-pyrazol-3-yl)phenyl]-N,N-dimethylurea and stirring for 4.5 hours provided the title compound. ESMS [M+H]$^+$: 688.6.

Intermediate 218

2-[4-({4-[4-[1-methyl-3-(4-nitrophenyl)-1H-pyrazol-4-yl]-1-(phenylsulfonyl)-1H-pyrrolo[2,3-b]pyridin-2-yl]phenyl}methyl)-1-piperazinyl]ethanol Following the procedure described for Intermediate 101 using 4-[4-[1-methyl-3-(4-nitrophenyl)-1H-pyrazol-4-yl]-1-(phenylsulfonyl)-1H-pyrrolo[2,3-b]pyridin-2-yl]benzaldehyde and 2-(1-piperazinyl)ethanol provided the title compound. ESMS [M+H]$^+$: 678.4.

Intermediate 219

2-{4-[(4-{4-[3-(4-aminophenyl)-1-methyl-1H-pyrazol-4-yl]-1H-pyrrolo[2,3-b]pyridin-2-yl}phenyl)methyl]-1-piperazinyl}ethanol Following the procedure described for Intermediate 102 using 2-[4-({4-[4-[1-methyl-3-(4-nitrophenyl)-1H-pyrazol-4-yl]-1-(phenylsulfonyl)-1H-pyrrolo[2,3-b]pyridin-2-yl]phenyl}methyl)-1-piperazinyl]ethanol provided the title compound. ESMS [M+H]$^+$: 508.4.

Intermediate 220

N-[4-(4-bromo-1-methyl-1H-pyrazol-3-yl)phenyl]-1-pyrrolidinecarboxamide

Following the procedures described in Example 47 using [4-(4-bromo-1-methyl-1H-pyrazol-3-yl)phenyl]amine and pyrrolidine provided the title compound. ESMS [M+H]$^+$: 349.2.

Intermediate 221

N-(4-{4-[2-(4-formylphenyl)-1-(phenylsulfonyl)-1H-pyrrolo[2,3-b]pyridin-4-yl]-1-methyl-1H-pyrazol-3-yl}phenyl)-1-pyrrolidinecarboxamide Following the procedure described for Intermediate 32 using 4-[4-bromo-1-(phenylsulfonyl)-1H-pyrrolo[2,3-b]pyridin-2-yl]benzaldehyde and then following the procedure described for Intermediate 100 with N-[4-(4-bromo-1-methyl-1H-pyrazol-3-yl)phenyl]-1-pyrrolidinecarboxamide provided the title compound. ESMS [M+H]$^+$: 631.4.

Intermediate 222

N-(4-{4-[2-(4-{[ethyl(2-hydroxyethyl)amino]methyl}phenyl)-1-(phenylsulfonyl)-1H-pyrrolo[2,3-b]pyridin-4-yl]-1-methyl-1H-pyrazol-3-yl}-phenyl)-1-pyrrolidinecarboxamide Following the procedure described in Intermediate 101 using N-(4-{4-[2-(4-formylphenyl)-1-(phenylsulfonyl)-1H-pyrrolo[2,3-b]pyridin-4-yl]-1-methyl-1H-pyrazol-3-yl}phenyl)-1-pyrrolidinecarboxamide and 2-(ethylamino)ethanol in dichloroethane (instead of dichloromethane) provided the title compound. ESMS [M+H]$^+$: 704.6.

Intermediate 223

2-[ethyl({4-[4-[1-(1-methylethyl)-3-(4-nitrophenyl)-1H-pyrazol-4-yl]-1-(phenylsulfonyl)-1H-indol-2-yl]phenyl}methyl)amino]ethanol Following the procedure described for Intermediate 101 using 4-[4-[1-(1-methylethyl)-3-(4-nitrophenyl)-1H-pyrazol-4-yl]-1-(phenylsulfonyl)-1H-indol-2-yl]benzaldehyde and 2-(ethylamino)ethanol (18.8 mmol) provided the title compound. ESMS [M+H]$^+$: 665.4.

Intermediate 224

2-[[(4-{4-[3-(4-aminophenyl)-1-(1-methylethyl)-1H-pyrazol-4-yl]-1H-pyrrolo[2,3-b]pyridin-2-yl}phenyl)methyl](ethyl)amino]ethanol Following the procedure described for Intermediate 102 using 2-[ethyl({4-[4-[1-(1-methylethyl)-3-(4-nitrophenyl)-1H-pyrazol-4-yl]-1-(phenylsulfonyl)-1H-indol-2-yl]phenyl}methyl)amino]ethanol provided the title compound. ESMS [M+H]$^+$: 495.4.

Intermediate 225

4-bromo-1-(phenylsulfonyl)-2-(3-pyridinyl)-1H-pyrrolo[2,3-b]pyridine

A solution of 4-bromo-2-iodo-1-(phenylsulfonyl)-2-(3-pyridinyl)-1H-pyrrolo[2,3-b]pyridine (0.44 mmol), 3-pyridinyl boronic acid (0.35 mmol) and tetrakis(triphenylphosphine) palladium(0) (0.013 mmol) in a 4:1 solution of 1,4-dioxane (4 mL):saturated sodium carbonate (1 mL) was stirred for 18 h at 100° C. in a sealed tube. After concentrated in vacuo, the residue was partitioned between ethyl acetate (5 mL) and water (5 mL). The organic layer was washed with brine (1×5 mL), dried over magnesium sulfate, and concentrated. Purification by flash chromatography (0-20% ethyl acetate/dichloromethane) provided the title compound as a yellow oil (50%). ESMS [M+H]$^+$: 414.8.

Intermediate 226

4-[1-(1-methylethyl)-3-(4-nitrophenyl)]-1-(phenylsulfonyl)-2-(3-pyridinyl)-1H-pyrrolo[2,3-b]pyridine Following the procedure described for Intermediate 100 using 1-isopropyl-3-(4-nitrophenyl)-4-(4,4,5,5-tetramethyl-1,3,2-dioxaborolan-2-yl)-1H-pyrazole and 4-bromo-1-(phenylsulfonyl)-2-pyridin-3-yl-1H-pyrrolo[2,3-b]pyridine provided the title compound. ESMS [M+H]$^+$: 565.2.

Intermediate 227

4-{1-(1-methylethyl)-4-[2-(3-pyridinyl)-1H-pyrrolo[2,3-b]pyridin-4-yl]-1H-pyrazol-3-yl}aniline Following the procedure described for Intermediate 102 using 4-[1-(1-methylethyl)-3-(4-nitrophenyl)]-1-(phenylsulfonyl)-2-(3-pyridinyl)-1H-pyrrolo[2,3-b]pyridine provided the title compound. ESMS [M+H]$^+$: 395.1.

Intermediate 228

N,N-dimethyl-2-[3-(4-nitrophenyl)-1H-pyrazol-1-yl]ethanamine

Following the procedure described for Intermediate 3 using 3-(4-nitrophenyl)-1H-pyrazol (2.4 mmol) and 2-chloro-N,N-dimethylethanamine hydrochloride provided the title compound. ESMS [M+H]$^+$: 261.2.

Intermediate 229

2-[4-bromo-(3-(4-nitrophenyl)-1H-pyrazol-1-yl]-N,N-dimethylethanamine

A solution of N,N-dimethyl-2-[3-(4-nitrophenyl)-1H-pyrazol-1-yl]ethanamine (1.9 mmol) and bromine (2.9 mmol) in chloroform (10 mL) was stirred for 2 h at room temperature. After concentration in vacuo, the residue was partitioned between ethyl acetate (5 mL) and a 1:1 solution of sodium bicarbonate (5 mL):sodium thiosulfate (5 mL). The organic layer was washed with brine (1×5 mL), dried over magnesium sulfate and concentrated. Trituration with hexanes and filtration provided the title compound (89%). ESMS [M+H]$^+$: 339.0/341.0.

Intermediate 230

N,N-dimethyl-2-{3-(4-nitrophenyl)-4-[1-(phenylsulfonyl)-1H-pyrrolo[2,3-b]pyridine-4-yl]-1H-pyrazol-1-yl}ethanamine Following the procedure described for Intermediate 100 using 1-(phenylsulfonyl)-4-(4,4,5,5-tetramethyl-1,3,2-dioxaborolan-2-yl)-1H-pyrrolo[2,3-b]pyridine and 2-[4-bromo-3-(4-nitrophenyl)-1H-pyrazol-1-yl]-N,N-dimethylethanamine provided the title compound. ESMS [M+H]$^+$: 517.2.

Intermediate 231

1,1-dimethylethyl 4-[4-bromo-1-(phenylsulfonyl)-1H-pyrrolo[2,3-b]pyridin-2-yl]-4-hydroxy-1-piperidinecarboxylate To a solution of isopropylamine (5.5 mmol) in THF (15 mL) cooled to −78° C. was added n-BuLi (2.5 M in hexanes, 5.5 mmol) dropwise. After stirring at −78° C. for 20 min a solution of 4-bromo-1-(phenylsulfonyl)-1H-pyrrolo[2,3-b]pyridine (5.0 mmol) in THF (5.0 mL) was added dropwise. The resulting orange solution was stirred at −78° C. for 2 h, followed by dropwise addition of a solution of 1,1-dimethylethyl-4-oxo-1-piperidinecarboxylate (6.1 mmol) in THF (5.0 mL). After an additional 1.5 h at −78° C., the reaction mixture was warmed to room temperature and quenched with saturated NH$_4$Cl(aq). Extraction with EtOAc (3□), washing with brine, drying (Na$_2$SO$_4$), filtration and concentrated in vacuo provided crude material which was purified by flash chromatography (120 g SiO$_2$, 0-5% EtOAc in CHCl$_3$) to give the title compound as a white solid (85%). ESMS [M+H]$^+$: 536.0.

Intermediate 232

1,1-dimethylethyl 4-hydroxy-4-[4-[1-methyl-3-(4-nitrophenyl)-1H-pyrazol-4-yl]-1-(phenylsulfonyl)-1H-pyrrolo[2,3-b]pyridin-2-yl]-1-piperidinecarboxylate Following the procedure described for Intermediate 100 using 1-methyl-3-(4-nitrophenyl)-4-(4,4,5,5-tetramethyl-1,3,2-dioxaborolan-2-yl)-1H-pyrazole and 1,1-dimethylethyl 4-[4-bromo-1-(phenylsulfonyl)-1H-pyrrolo[2,3-b]pyridin-2-yl]-4-hydroxy-1-piperidinecarboxylate provided the title compound. ESMS [M+H]$^+$: 659.2.

Intermediate 233

1,1-dimethylethyl 4-{4-[3-(4-aminophenyl)-1-methyl-1H-pyrazol-4-yl]-1H-pyrrolo[2,3-b]pyridin-2-yl}-4-hydroxy-1-piperidinecarboxylate Following the procedure described for Intermediate 102 using 1,1-dimethylethyl 4-hydroxy-4-[4-[1-methyl-3-(4-nitrophenyl)-1H-pyrazol-4-yl]-1-(phenylsulfonyl)-1H-pyrrolo[2,3-b]pyridin-2-yl]-1-piperidinecarboxylate provided the title compound. ESMS [M+H]$^+$: 489.2.

Intermediate 234

1,1-dimethylethyl 4-(5-bromo-2-pyrimidinyl)-1-piperazinecarboxylate

A mixture of 5-bromo-2-chloropyrimidine (5.17 mmol) and 1,1-dimethylethyl 1-piperazinecarboxylate (11.4 mmol) in 1,4-dioxane (10 ml) was heated at reflux for 2 hours. After cooling to room temperature, the reaction mixture was diluted with water (100 ml) and ethyl acetate (100 ml). Separation of the organic layer, drying (MgSO$_4$), filtration and concentration in vacuo provided a residue which was purified by silica gel chromatography (40 g silica gel, CHCl$_3$/EtOAc) to give the title compound as a white solid (58%). ESMS [M+H-Boc]$^+$: 245.0/243.0.

Intermediate 235

1,1-dimethylethyl 4-[5-(4,4,5,5-tetramethyl-1,3,2-dioxaborolan-2-yl)-2-pyrimidinyl]-1-piperazinecarboxylate A mixture of 1-dimethylethyl 4-(5-bromo-2-pyrimidinyl)-1-piperazinecarboxylate (3.00 mmol), bis(pinacolato)diboron (3.30 mmol) and potassium acetate (9.00 mmol) was diluted with 1,4-dioxane (10 ml) and degassed with argon for 10 minutes. Dichlorobis(triphenylphosphine) palladium(II) (0.15 mmol) was added and the resulting mixture heated at 95° C. overnight under argon. Upon cooling and dilution with EtOAc (100 ml), the mixture was sonicated for 10 minutes. Filtration through a pad of silica and concentration in vacuo provided a solid residue which was purified on 40 g silica gel (CHCl$_3$/EtOAc w/0.1% MeOH). Recrystallization from diethyl ether/hexanes yielded the title product as white needles (44%). ESMS [M+H]$^+$: 391.2

Intermediate 236

5-bromo-2-(4-methyl-1-piperazinyl)pyrimidine

Following the procedure described for Intermediate 234 using 5-bromo-2-chloropyrimidine and N-methylpiperazine provided the title compound. ESMS [M+H]$^+$: 257.0/259.0.

Intermediate 237

2-(4-methyl-1-piperazinyl)-5-(4,4,5,5-tetramethyl-1, 3,2-dioxaborolan-2-yl)pyrimidine Following the procedure described for Intermediate 235 using 5-bromo-2-(4-methyl-1-piperazinyl)pyrimidine provided the title compound. ESMS [M+H]$^+$: 305.2.

Intermediate 238

4-bromo-1-(phenylsulfonyl)-2-(trimethylsilyl)-1H-pyrrolo[2,3-b]pyridine

A solution of N,N-diisopropylamine (3.6 mmol) in THF (9 ml) was cooled to −78° C. under a nitrogen atmosphere. A solution of n-BuLi (2.5M in hexanes, 3.3 mmol) was added dropwise over 3 minutes. After 30 minutes of stirring, a solution of 4-bromo-1-(phenylsulfonyl)-1H-pyrrolo[2,3-b]pyridine (3.1 mmol) in THF (9 ml) was added dropwise over 9 minutes. After an additional 2 hours of stirring at −78° C., chlorotrimethylsilane (3.1 mmol) was added dropwise over 1 minute. After 1 hour of stirring at −78° C., the reaction was quenched with saturated NH$_4$Cl(aq) (10 ml), warmed to room temperature, and partitioned between water and EtOAc. The aqueous phase was further extracted with EtOAc and the organic layers combined, washed with brine, dried (MgSO$_4$), concentrated, and purified by silica gel chromatography (isocratic CHCl$_3$) to give the title product as a white solid (82%). ESMS [M+H]$^+$: 410.8.

Intermediate 239

4-[1-methyl-3-(4-nitrophenyl)-1H-pyrazol-4-yl]-1-(phenylsulfonyl)-2-(trimethylsilyl)-1H-pyrrolo[2,3-b]pyridine A mixture of 4-bromo-1-(phenylsulfonyl)-2-(trimethylsilyl)-1H-pyrrolo[2,3-b]pyridine (37 mmol) and 1-methyl-3-(4-nitrophenyl)-4-(4,4,5,5-tetramethyl-1,3,2-dioxaborolan-2-yl)-1H-pyrazole (37 mmol) in 1,4-dioxane (300 ml) and saturated NaHCO$_3$(aq) (100 ml) was degassed with N$_2$ for 10 minutes after which time tetrakis(triphenylphosphine) palladium(0) (1.85 mmol) was added and the resulting mixture was heated at 105° C. overnight. The reaction was then concentrated, diluted with CHCl$_3$ (200 ml) and EtOAc (200 ml), sonicated for 10 minutes, filtered through Celite 545, and concentrated to yield a red oil which was purified on 400 g silica gel (CHCl$_3$/EtOAc w/0.1% MeOH) to give the title product as a light yellow foam (36%). ESMS [M+H]$^+$: 532.0.

Intermediate 240

2-iodo-4-[1-methyl-3-(4-nitrophenyl)-1H-pyrazol-4-yl]-1-(phenylsulfonyl)-1H-pyrrolo[2,3-b]pyridine To a solution of ICl (1M in CH$_2$Cl$_2$, 43.3 mmol) in acetonitrile (250 ml) at −10° C. was added a solution of 4-[1-methyl-3-(4-nitrophenyl)-1H-pyrazol-4-yl]-1-(phenylsulfonyl)-2-(trimethylsilyl)-1H-pyrrolo[2,3-b]pyridine (8.67 mmol) in acetonitrile (46 ml) followed by stirring at −10° C. for 5 minutes. The reaction was concentrated to approx. ⅓ total volume and then diluted with EtOAc (500 ml). The solution was washed with saturated NaHCO$_3$(aq) (100 ml), saturated Na$_2$S$_2$O$_3$(aq) (100 ml), brine (100 ml), and dried over MgSO$_4$. Filtration and concentration in vacuo yielded a tan solid which was triturated with hot acetonitrile/Et$_2$O, providing the title product as a light tan solid (53%). ESMS [M+H]$^+$: 586.0.

Intermediate 241

1,1-dimethylethyl 4-{5-[4-[1-methyl-3-(4-nitrophenyl)-1H-pyrazol-4-yl]-1-(phenylsulfonyl)-1H-pyrrolo[2,3-b]pyridin-2-yl]-2-pyrimidinyl}-1-piperazinecarboxylate To a solution of 2-iodo-4-[1-methyl-3-(4-nitrophenyl)-1H-pyrazol-4-yl]-1-(phenylsulfonyl)-1H-pyrrolo[2,3-b]pyridine (0.321 mmol) and 1,1-dimethylethyl 4-[5-(4,4,5,5-tetramethyl-1,3,2-dioxaborolan-2-yl)-2-pyrimidinyl]-1-piperazinecarboxylate (0.353 mmol) in 1,4-dioxane (3 ml) was added saturated NaHCO$_3$(aq) (0.85 ml). After degassing with argon for 10 minutes, dichlorobis(triphenylphosphine) palladium(II) (0.0161 mmol) was added and the resulting mixture was heated at 95° C. overnight. Upon cooling, the reaction was concentrated and partitioned between EtOAc and H$_2$O. The organic layer was washed with brine, dried (MgSO$_4$), filtered and concentrated to yield the title compound as a yellow oil (quant.). ESMS [M+H]$^+$: 722.2.

Intermediate 242

1,1-dimethylethyl 4-{5-[4-[3-(4-aminophenyl)-1-methyl-1H-pyrazol-4-yl]-1-(phenylsulfonyl)-1H-pyrrolo[2,3-b]pyridin-2-yl]-2-pyrimidinyl}-1-piperazinecarboxylate To a solution of ammonium chloride (3.00 mmol) in H$_2$O (5 ml) was added iron powder (1.66 mmol) followed by a solution of 1,1-dimethylethyl 4-{5-[4-[1-methyl-3-(4-nitrophenyl)-1H-pyrazol-4-yl]-1-(phenylsulfonyl)-1H-pyrrolo[2,3-b]pyridin-2-yl]-2-pyrimidinyl}-1-piperazinecarboxylate (0.333 mmol) in methanol (10 ml). The resulting mixture was heated at 70° C. for 2 hours, the hot solution filtered through a pad of celite 545 and concentrated to yield the title product as a yellow solid (quant.) which was used crude in the next step. ESMS [M+H]$^+$: 692.2.

Intermediate 243

1,1-dimethylethyl 4-(5-{4-[3-(4-aminophenyl)-1-methyl-1H-pyrazol-4-yl]-1H-pyrrolo[2,3-b]pyridin-2-yl}-2-pyrimidinyl)-1-piperazinecarboxylate To a solution of 1,1-dimethylethyl 4-{5-[4-[3-(4-aminophenyl)-1-methyl-1H-pyrazol-4-yl]-1-(phenylsulfonyl)-1H-pyrrolo[2,3-b]pyridin-2-yl]-2-pyrimidinyl}-1-piperazinecarboxylate (0.333 mmol) in methanol (20 ml) was added 6M NaOH(aq) (1.5 ml). The resulting solution was heated at 70° C. for 4 hours, concentrated in vacuo and the yellow residue taken up in chloroform. After washing with saturated NH$_4$Cl(aq), the organic layer was dried (MgSO$_4$), filtered and concentrated to yield the title product (99%) as a yellow solid which was used crude in the next step. ESMS [M+H]$^+$: 552.2.

Intermediate 244

1,1-dimethylethyl 4-(5-{4-[3-(4-{[(dimethylamino) carbonyl]amino}phenyl)-1-methyl-1H-pyrazol-4-yl]-1H-pyrrolo[2,3-b]pyridin-2-yl}-2-pyrimidinyl)-1-piperazinecarboxylate To a solution of 1,1-dimethylethyl 4-(5-{4-[3-(4-aminophenyl)-1-methyl-1H-pyrazol-4-yl]-1H-pyrrolo[2,3-b]pyridin-2-yl}-2-pyrimidinyl)-1-piperazinecarboxylate (0.326 mmol) in pyridine (8 ml) under argon at 0° C. was added isopropenyl chloroformate (1.31 mmol) portionwise over 3 hours maintaining the reaction temperature at 0° C. The resulting solution was concentrated, purified by reverse-phase. This intermediate was dissolved in THF (10 ml) and dimethylamine (2M in THF, 20 ml) was added. After heating for 2 hours at 50° C., concentration in vacuo provided the title product (27%) as a yellow solid which was used without further purification. ESMS [M+H]$^+$: 623.2.

Intermediate 245

4-[1-methyl-3-(4-nitrophenyl)-1H-pyrazol-4-yl]-2-[2-(4-methyl-1-piperazinyl)-5-pyrimidinyl]-1-(phenylsulfonyl)-1H-pyrrolo[2,3-b]pyridine Following the procedure described for Intermediate 241 using 2-iodo-4-[1-methyl-3-(4-nitrophenyl)-1H-pyrazol-4-yl]-1-(phenylsulfonyl)-1H-pyrrolo[2,3-b]pyridine and 2-(4-methyl-1-piperazinyl)-5-(4,4,5,5-tetramethyl-1,3,2-dioxaborolan-2-yl)pyrimidine provided the title compound. ESMS [M+H]$^+$: 636.0.

Intermediate 246

(4-{1-methyl-4-[2-[2-(4-methyl-1-piperazinyl)-5-pyrimidinyl]-1-(phenylsulfonyl)-1H-pyrrolo[2,3-b]pyridin-4-yl]-1H-pyrazol-3-yl}phenyl)amine Following the procedure described for Intermediate 242 using 4-[1-methyl-3-(4-nitrophenyl)-1H-pyrazol-4-yl]-2-[2-(4-methyl-1-piperazinyl)-5-pyrimidinyl]-1-(phenylsulfonyl)-1H-pyrrolo[2,3-b]pyridine provided the title compound. ESMS [M+H]$^+$: 606.2.

Intermediate 247

[4-(1-methyl-4-{2-[2-(4-methyl-1-piperazinyl)-5-pyrimidinyl]-1H-pyrrolo[2,3-b]pyridin-4-yl}-1H-pyrazol-3-yl)phenyl]amine Following the procedure described for Intermediate 243 using (4-{1-methyl-4-[2-[2-(4-methyl-1-piperazinyl)-5-pyrimidinyl]-1-(phenylsulfonyl)-1H-pyrrolo[2,3-b]pyridin-4-yl]-1H-pyrazol-3-yl}phenyl)amine provided the title compound. ESMS [M+H]$^+$: 466.2.

The invention claimed is:

1. A composition comprising a) a compound which is N'-{4-[4-(2-{3-[(dimethylamino)methyl]phenyl}-1H-pyrrolo[2,3-b]pyridin-4-yl)-1-ethyl-1H-pyrazol-3-yl]phenyl}-N,N-dimethylurea or a pharmaceutically acceptable salt thereof; and b) at least one pharmaceutically acceptable excipient.

* * * * *